(12) United States Patent
Fanberg

(10) Patent No.: US 12,190,040 B1
(45) Date of Patent: Jan. 7, 2025

(54) USER CONFIGURABLE ELECTRONIC MEDICAL RECORDS BROWSER

(71) Applicant: Victor V. Fanberg, Dublin, OH (US)

(72) Inventor: Victor V. Fanberg, Dublin, OH (US)

(*) Notice: Subject to any disclaimer, the term of this patent is extended or adjusted under 35 U.S.C. 154(b) by 33 days.

(21) Appl. No.: 17/712,813

(22) Filed: Apr. 4, 2022

Related U.S. Application Data

(63) Continuation-in-part of application No. 17/005,429, filed on Aug. 28, 2020, now Pat. No. 11,295,062, which is a continuation-in-part of application No. 16/781,800, filed on Feb. 4, 2020, now Pat. No. 11,288,327.

(60) Provisional application No. 62/918,580, filed on Feb. 5, 2019.

(51) Int. Cl.
| | |
|---|---|
| *G06F 40/106* | (2020.01) |
| *G06F 40/114* | (2020.01) |
| *G06F 40/174* | (2020.01) |
| *G06F 40/258* | (2020.01) |
| *G16H 10/60* | (2018.01) |

(52) U.S. Cl.
CPC .......... *G06F 40/106* (2020.01); *G06F 40/114* (2020.01); *G06F 40/174* (2020.01); *G06F 40/258* (2020.01); *G16H 10/60* (2018.01)

(58) Field of Classification Search
CPC .... G06F 40/106; G06F 40/114; G06F 40/174; G06F 40/259; G16H 10/60
See application file for complete search history.

(56) References Cited

U.S. PATENT DOCUMENTS

| | | | |
|---|---|---|---|
| 2005/0240876 A1* | 10/2005 | Myers | G06F 40/143 715/236 |
| 2014/0039871 A1* | 2/2014 | Crawford | G06F 40/103 704/2 |
| 2016/0092638 A1 | 3/2016 | Padmani et al. | |
| 2016/0321399 A1 | 11/2016 | Ramachandran | |
| 2017/0004124 A1 | 1/2017 | Kyre | |
| 2017/0199964 A1 | 7/2017 | Klocek et al. | |

(Continued)

FOREIGN PATENT DOCUMENTS

| | | | | |
|---|---|---|---|---|
| JP | 2014211916 A | * | 11/2014 | |
| JP | 2021082088 A | * | 5/2021 | |
| WO | WO-2005062198 A1 | * | 7/2005 | G06F 17/2247 |

*Primary Examiner* — Scott T Baderman
*Assistant Examiner* — Seung Woon Jung
(74) *Attorney, Agent, or Firm* — Standley Law Group LLP; Jeffrey S. Standley; Kenny W. Pung

(57) ABSTRACT

Methods for utilizing a document group to generate an output that is formatted for a peripheral output device. The output may be generated by creating output documents, adapting elements from documents of the document group, including or excluding certain elements based on criteria that may be predetermined and/or calculated, and by formatting the included elements to decrease the amount of vertical space used in the formatted output and retain all the significant text, perhaps even using a larger font. For screens, less vertical space may equate to more information fitting on the screen at a time and less scrolling. For printers, less vertical space may equate to less paper to print the same document. Further, the output may be configured to include certain documents and/or document areas based on the content of audit logs that track user-view of an input. Also disclosed are systems and devices for implementing the methods.

27 Claims, 67 Drawing Sheets

---

```
4051 ─── Medical Information Section
4053 ─── Inclusion application for XYZ research.                                        4057
4055 ─── If you agree to participate in our ... : VF
4059 ─── Medical / Psychological History
4061                                                                                     4063
4065 ─── Chronic Health Concerns: Yes        If yes, please describe: Ulcertive Colitis
4067 ─── Prior counseling: After starting college
       ─── Prior Meds: Both                   Please list current medications: Vitamin   4069
                                              B-12, Folic Acid, Xeljanz XR (since age
                                              17)
```

(56) References Cited

U.S. PATENT DOCUMENTS

| | | |
|---|---|---|
| 2017/0287177 A1 | 10/2017 | Wong |
| 2017/0329856 A1* | 11/2017 | Jiang ........................ G06N 7/01 |
| 2018/0189368 A1 | 7/2018 | Atanasiu et al. |
| 2019/0034591 A1 | 1/2019 | Mossin et al. |
| 2019/0042791 A1 | 2/2019 | Dinov et al. |
| 2020/0050845 A1* | 2/2020 | Foncubierta Rodriguez ............... G06V 30/412 |
| 2020/0294640 A1 | 9/2020 | Ginsburg |
| 2021/0097231 A1* | 4/2021 | Downs .................. G06F 40/137 |
| 2021/0150489 A1* | 5/2021 | Haramati .............. G06F 40/177 |
| 2021/0157535 A1* | 5/2021 | Omiya .................. G06F 3/1206 |
| 2021/0240312 A1* | 8/2021 | Wohlstadter .......... G06F 3/0482 |
| 2022/0083195 A1* | 3/2022 | Walcott ............... G06F 3/04186 |

* cited by examiner

```
┌─300─────────────────302─┐304┐─────────────────────────────────────306─┐
│                    LOCATION OF SERVICE (select one)                    │
│  ○ school and child care (all ages through college)    ● temporary home (including friend or family homes, group homes, shelters,
│                                                          apartments, trailers, and other dwellings)
│  ○ community center (e.g., recreation club)              ○ IF A TEMPORARY HOME: PLEASE CHECK THIS BOX IF ANY
│                                                            CHILDREN UNDER AGE 18 LIVE IN THIS HOME.
│  ○ provider site/mental health agency (agency involved with the CCP)   ○ permanent home
│  ○ workplace (workplace of the disaster survivor and/or first responder)   ○ IF A PERMANENT HOME: PLEASE CHECK THIS BOX IF ANY
│                                                            CHILDREN UNDER AGE 18 LIVE IN THIS HOME.
│  ○ disaster recovery center (e.g., Federal Emergency Management         ○ phone counseling (15 minutes or longer)
│    Agency [FEMA], American Red Cross)
│  ○ place of worship (e.g., church, synagogue, mosque)    ○ IF HOTLINE, HELPLINE, or CRISIS LINE, please check here.
│  ○ retail (e.g., restaurant, mall, shopping center, store)   ○ medical center (e.g., doctor, dentist, hospital, mental health specialty center)
│  ○ public place/event (e.g., street, sidewalk, town square, fair, festival,   ○ other (specify in box) [_____]
│    sports)
└──────────────────────────────────────────────308──────────────────────┘
```

Prior art    FIG. 4A 320   322   324

LOCATION OF SERVICE (select one): temporary home (including friend or family homes, group homes, shelters, apartments, trailers, and other dwellings)

FIG. 4B

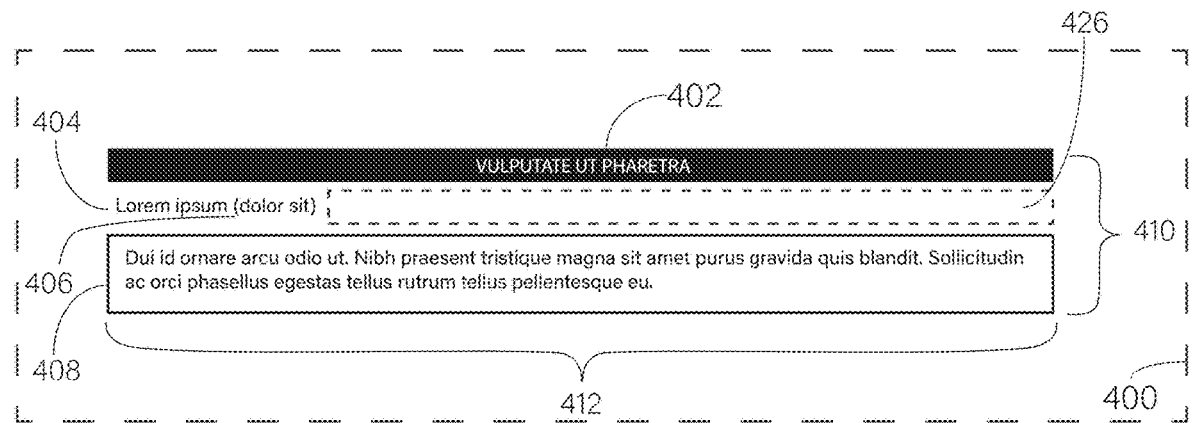
Prior art FIG. 5A
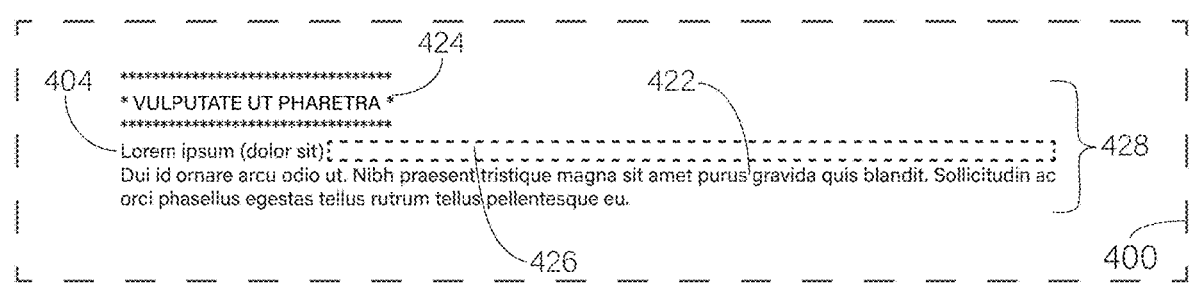
Prior art FIG. 5B
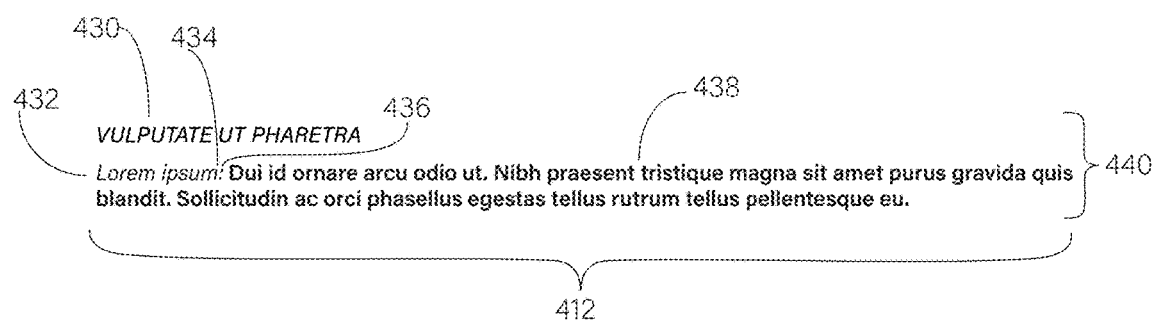
FIG. 5C

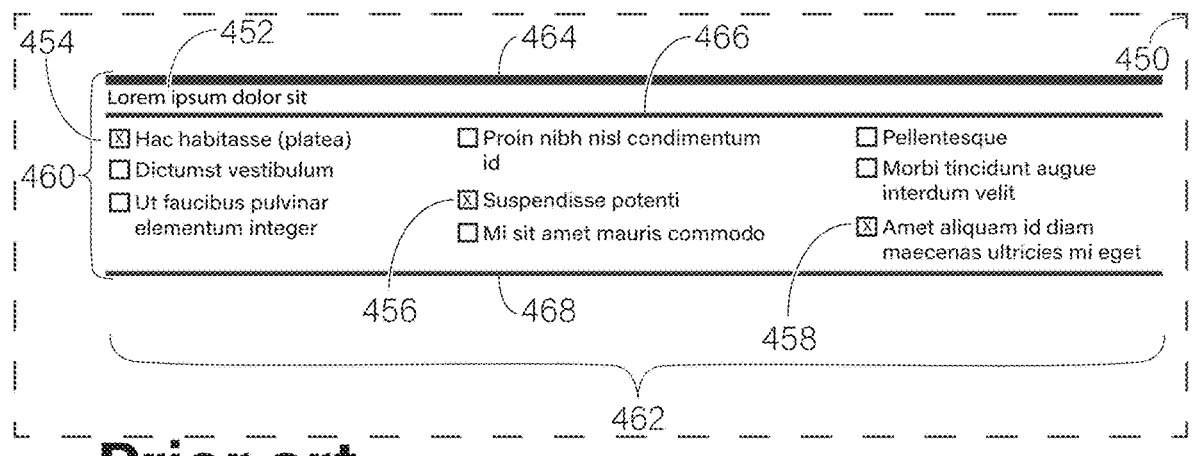
Prior art  FIG. 6A
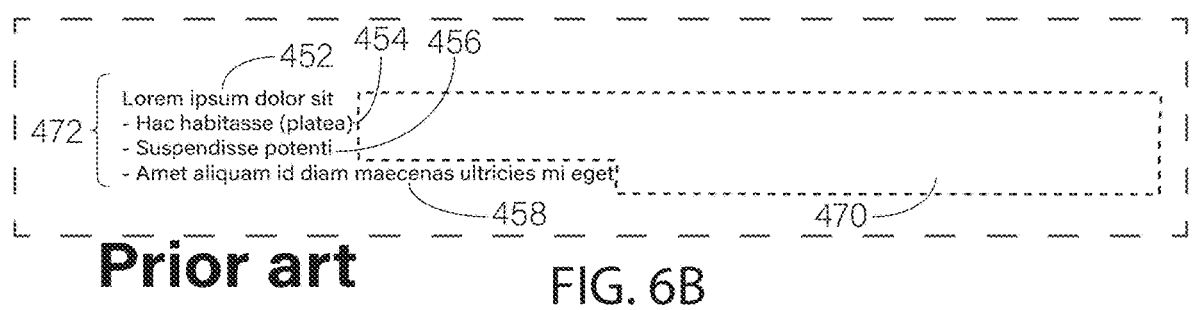
Prior art  FIG. 6B
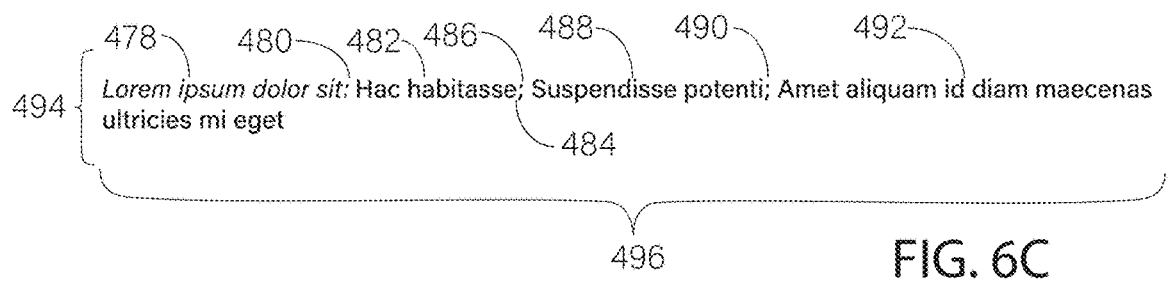
FIG. 6C
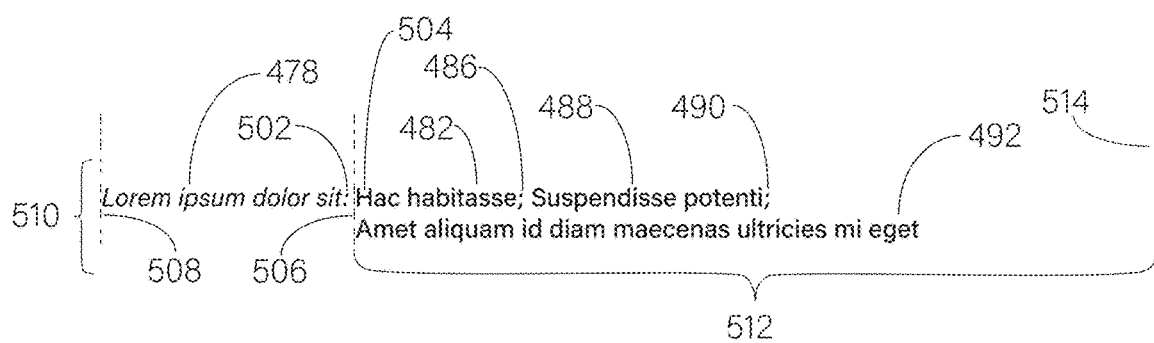
FIG. 6D

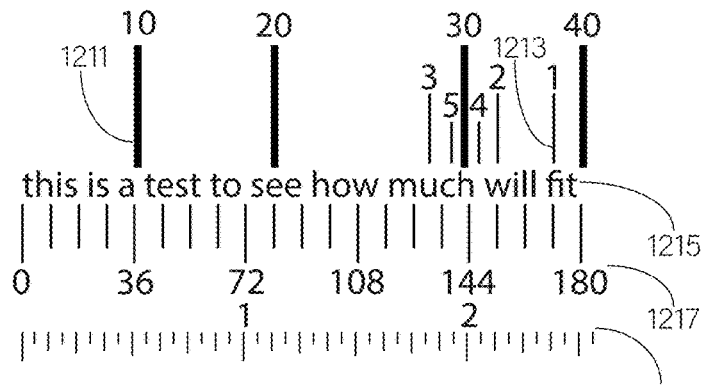
FIG. 15
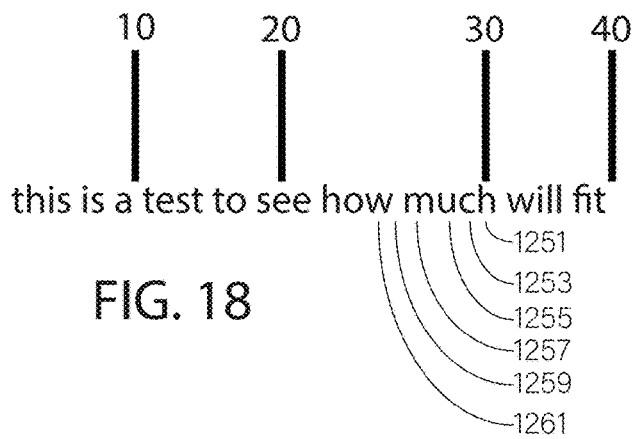
FIG. 18
FIG. 16
| Step No | Computed value |
|---|---|
| 1113 | 9.6 |
| 1115 | 15 |
| 1119 | 60 |
| | Starting | | CurrChar step 1177 | CurrWidth step 1179 | Is too long? Step 1193 | Ending | |
|---|---|---|---|---|---|---|---|
| Pass | minStringChars | maxStringChars | | | | minStringChars step 1195 | maxStringChars step 1197 |
| 1 | 15 | 60 | 37 | 171 | Yes | 15 | 49 |
| 2 | 15 | 49 | 32 | 153 | Yes | 15 | 41 |
| 3 | 15 | 41 | 28 | 131 | No | 21 | 41 |
| 4 | 22 | 41 | 31 | 149 | Yes | 22 | 37 |
| 5 | 22 | 37 | 29 | 138 | Exit at step 1191 | | |
FIG. 17

This is a heading 1346 and is a normal heading ⸺ 1351

This is a heading 1347 and is a top repeat heading ⸺ 1353

This is a heading 1347 and is a lowest repeat heading ⸺ 1355

This is a prompt ⸺ 1357

This is a heading 1347 and is a normal heading ⸺ 1358

This is a heading 1348 and is a normal heading ⸺ 1360

This is a prompt ⸺ 1362

This is a heading 1348 and is a style terminal heading ⸺ 1363

This is a heading 1347 and is a normal heading ⸺ 1364

This is a prompt ⸺ 1366

This is a heading 1346 and is a top repeat heading ⸺ 1367

This is a heading 1346 and is a lowest repeat heading ⸺ 1369

This is a heading 1347 and is a normal heading ⸺ 1372

This is a heading 1348 and is a normal heading ⸺ 1374

This is a prompt ⸺ 1376

This is a heading 1346 and is a normal heading ⸺ 1377

This is a heading 1347 and is a normal heading ⸺ 1379

This is a prompt ⸺ 1381

This is a heading 1346 and is a normal heading ⸺ 1382

This is a heading 1347 and is a normal heading ⸺ 1384

This is a prompt ⸺ 1386

FIG. 19G

|  | | Before current heading | | | |
| --- | --- | --- | --- | --- | --- |
|  | | Heading | Prompt | Start of document marker | End of document marker |
| After current heading | Heading | Repeat heading | Top repeat heading | Top repeat heading | Top repeat heading |
| | Prompt | Lowest repeat heading | Normal heading | Normal heading | Normal heading |
| | Start of document marker | Terminal heading | Terminal heading | Teminal heading | Terminal heading |
| | End of document marker | Terminal heading | Terminal heading | Terminal heading | Terminal heading |

FIG. 19H

Prior art

|  | | Before | | After |
|---|---|---|---|---|
| Pass | Heading | Next heading | HeadingClassification | Next heading |
| 3 | 1417 | #LookForNormalHeading | #NormalHeading | #LookForOtherHeading |
| 4 | 1415 | #LookForOtherHeading | #OtherHeading | #LookForOtherHeading |
| 45 | 1409 | #LookForNormalHeading | #NormalHeading | #LookForOtherHeading |
| 62 | 1403 | #LookForNormalHeading | #NormalHeading | #LookForOtherHeading |
| 63 | 1401 | #LookForOtherHeading | #OtherHeading | #LookForOtherHeading |

FIG. 22A

| Heading | Classification after step 1283 | Classification after step 1285 | Classification after step 1287 | Classification after step 1289 | Classification after step 1290 |
|---|---|---|---|---|---|
| 1401 | #TerminalHeading | #NormalHeading | #RepeatHeading | #TopRepeatHeading | #TopRepeatHeading |
| 1403 | #TerminalHeading | #NormalHeading | #RepeatHeading | #RepeatHeading | #LowestRepeatHeading |
| 1409 | #TerminalHeading | #NormalHeading | #NormalHeading | #NormalHeading | #NormalHeading |
| 1415 | #TerminalHeading | #NormalHeading | #RepeatHeading | #TopRepeatHeading | #TopRepeatHeading |
| 1417 | #TerminalHeading | #NormalHeading | #RepeatHeading | #RepeatHeading | #LowestRepeatHeading |

FIG. 22B

Personal Information Section:

Family Information:

Parent: Morris  Relationship: Father  Age: 62  Occupation: Mechanical Engineer
Education: 4 - Year Degree  Rel. Status: Married  Deceased? No
Parent: Betty  Relationship: Mother  Age: 61  Occupation: Retired
Education: Some College  Rel. Status: Married  Deceased? No

Medical Information Section:

Medical / Psychological History

Chronic Health Concerns: Yes  If yes, please describe: Ulcerative Colitis

FIG. 23

```
#define RECTYPE "RecType"
#define REVERSEAPPTCNT "ReverseApptCnt"
#define LASTVIEWED "LastViewed"
#define RELEVANTDATE "RelevantDate"
#define ALLERGYRECTYPE "AL"
#define MEDLOG1 "ME"
#define MEDLOG2 "M2"                                2961
#define INCLUDE_ALLERGIES -3      2963
#define INCLUDE_RECENT_APPT -4         2965
#define INCLUDE_UNREAD -5         2967
#define INCLUDE_MEDLOG -6              2969
#define INCLUDE_MEDLOG_BY_DRUG -7    2971
#define HIDE_BEFORE_APPT -8            2973
#define HIDE_NOT_VIEWED -9        2975
#define HIDE_VIEWED -10                2977
#define HIDE_OLDER -11            2979
#define EXCLUDE_NOT_VIEWED -12         2981
#define EXCLUDE_VIEWED -13        2983
#define EXCLUDE_OLDER -14              2985
#define EXCLUDE_BEFORE_APPT -15
```

FIG. 28D

```
switch (currNodeTagNo) {
  case INCLUDE_ALLERGIES:
    rtnVal = RECTYPE + "=" + ALLERGYRECTYPE; break;
  case INCLUDE_RECENT_APPT:
  case HIDE_BEFORE_APPT:
    rtnVal = REVERSEAPPTCNT + "BETWEEN 1 AND "
                              + ToString(Qty); break;
  case EXCLUDE_BEFORE_APPT:
    rtnVal = REVERSEAPPTCNT + ">" + ToString(Qty); break;
  case INCLUDE_UNREAD:
  case HIDE_NOT_VIEWED:
  case EXCLUDE_VIEWED:
    rtnVal = LASTVIEWED + " IS NULL"; break;
  case INCLUDE_MEDLOG:
    rtnVal = RECTYPE + "=" + MEDLOG1 ; break;
  case INCLUDE_MEDLOG_BY_DRUG:
    rtnVal = RECTYPE + "=" + MEDLOG2 ; break;
  case HIDE_VIEWED:
  case EXCLUDE_NOT_VIEWED:
    rtnVal = LASTVIEWED + " IS NOT NULL"; break;
  case HIDE_OLDER:
    rtnVal = RELEVANTDATE + "<" + ToString(Date); break;
  case EXCLUDE_OLDER:
    rtnVal = RELEVANTDATE + ">=" + ToString(Date); break;
}
switch (currNodeTagNo) {
  case EXCLUDE_VIEWED:
  case EXCLUDE_NOT_VIEWED:
  case EXCLUDE_OLDER:
  case EXCLUDE_BEFORE_APPT:
    rtnVal = "(" + rtnVal + " AND NeverExclude = 0)"; break;
}
```

Include
    ☐ Appointments
        ☐ Couples
            ☐ Couples initial consultation     *APPT_TYPE: 201*
            ☐ Couples therapy     *APPT_TYPE: 225*
        ☐ Individual
            ☐ Individual initial consultation     *APPT_TYPE: 157*
            ☐ Individual therapy     *APPT_TYPE: 218*
        ☐ Group
            ☐ Group screening     *APPT_TYPE: 125*
            ☐ Group therapy     *APPT_TYPE: 126*
        ☒ Pyschiatry
            ☒ Psychiatry initial contulation     *APPT_TYPE: 131*
            ☒ Ongoing psychiatry     *APPT_TYPE: 140*
    ☐ Authors
        ☒ Psychiatry
            ☒ Gladys Friday, M.D.     *STAFF: 225*
            ☒ Don Key, D.O.     *STAFF: 218*
            ☒ Page Turner, M.D.     *STAFF: 140*
        ☐ Special
            ☐ Client     *STAFF: 50*
            ☐ EMR Generated     *STAFF: 51*
            ☐ Other     *STAFF: 53*
        ☐ Therapy
            ☐ Dr. Rob Berry     *STAFF: 126*
            ☐ Dr. Tim Burr     *STAFF: 300*
            ☐ Dr. Kash Register     *STAFF: 301*
    ☐ Casenote type
        ☐ Brief walkin     *NOTE_TYPE: 289*
        ☐ Initial paperwork     *NOTE_TYPE: 126*
        ☐ Session notes     *NOTE_TYPE: 225*
        ☐ Termination     *NOTE_TYPE: 201*
        ☐ Test results     *NOTE_TYPE: 157*
    Other
        ☐ Include all since last 4 appointments     *SPECIAL: -4*
        ☐ Include everything unread     *SPECIAL: -5*
        ☐ Include medications     *SPECIAL: -6*
        ☐ Include medications in drug order     *SPECIAL: -7*

FIG. 29A

Hide
- ☐ Appointments
    - ☐ Couples
        - ☐ Couples initial consultation — *APPT_TYPE: 201*
        - ☐ Couples therapy — *APPT_TYPE: 225*
    - ☐ Individual
        - ☐ Individual initial consultation — *APPT_TYPE: 157*
        - ☐ Individual therapy — *APPT_TYPE: 218*
    - ☐ Group
        - ☐ Group screening — *APPT_TYPE: 125*
        - ☐ Group therapy — *APPT_TYPE: 126*
    - ☐ Pyschiatry
        - ☐ Psychiatry initial contulation — *APPT_TYPE: 131*
        - ☐ Ongoing psychiatry — *APPT_TYPE: 140*
- ☐ Authors
    - ☐ Psychiatry
        - ☐ Gladys Friday, M.D. — *STAFF: 225*
        - ☐ Don Key, D.O. — *STAFF: 218*
        - ☐ Page Turner, M.D. — *STAFF: 140*
    - ☐ Special
        - ☐ Client — *STAFF: 50*
        - ☐ EMR Generated — *STAFF: 51*
        - ☐ Other — *STAFF: 53*
    - ☐ Therapy
        - ☐ Dr. Rob Berry — *STAFF: 126*
        - ☐ Dr. Tim Burr — *STAFF: 300*
        - ☐ Dr. Kash Register — *STAFF: 301*
- ☐ Casenote type
    - ☐ Brief walkin — *NOTE_TYPE: 289*
    - ☐ Initial paperwork — *NOTE_TYPE: 126*
    - ☐ Session notes — *NOTE_TYPE: 225*
    - 3301 — ☐ Termination — *NOTE_TYPE: 201*
    - ☒ Test results — *NOTE_TYPE: 157* — 3303
- Other
    - ☐ Hide items more then 4 appointments old — *SPECIAL: -8*
    - ☐ Hide items not previously viewed — *SPECIAL: -9*
    - ☐ Hide items previously viewed — *SPECIAL: -10*
    - ☐ Hide items prior to 9/1/2019 — *SPECIAL: -11*

FIG. 29B

Exclude
- ☐ Appointments
  - ☐ Couples
    - ☐ Couples initial consultation — *APPT_TYPE: 201*
    - ☐ Couples therapy — *APPT_TYPE: 225*
  - ☐ Individual
    - ☐ Individual initial consultation — *APPT_TYPE: 157*
    - ☐ Individual therapy — *APPT_TYPE: 218*
  - ☐ Group
    - ☐ Group screening — *APPT_TYPE: 125*
    - ☐ Group therapy — *APPT_TYPE: 126*
  - ☐ Pyschiatry
    - ☐ Psychiatry initial contulation — *APPT_TYPE: 131*
    - ☐ Ongoing psychiatry — *APPT_TYPE: 140*
- ☐ Authors
  - ☐ Psychiatry
    - ☐ Gladys Friday, M.D. — *STAFF: 225*
    - ☐ Don Key, D.O. — *STAFF: 218*
    - ☐ Page Turner, M.D. — *STAFF: 140*
  - ☐ Special
    - ☐ Client — *STAFF: 50*
    - ☐ EMR Generated — *STAFF: 51*
    - ☐ Other — *STAFF: 53*
  - ☐ Therapy
    - ☐ Dr. Rob Berry — *STAFF: 126*
    - ☐ Dr. Tim Burr — *STAFF: 300*
    - ☐ Dr. Kash Register — *STAFF: 301*
- ☐ Casenote type
  - ☐ Brief walkin — *NOTE_TYPE: 289*
  - ☐ Initial paperwork — *NOTE_TYPE: 126*
  - ☐ Session notes — *NOTE_TYPE: 225*
  - ☐ Termination — *NOTE_TYPE: 201*
  - ☐ Test results — *NOTE_TYPE: 157*
- Other
  - ☐ Exclude items not previously viewed — *SPECIAL: -12*
  - 3801 ☐ Exclude items previously viewed — *SPECIAL: -13*
  - ☐ Exclude items prior to 9/1/2019 — *SPECIAL: -14*
  - ☒ Exclude items more than 4 appointments old — *SPECIAL: -15*  — 3803

FIG. 29C

Include
- ☐ Data forms
  - ▲ ☒ Client Information — 3872
    - ☐ General Information
    - ☐ Date of Birth
    - ☐ Preferred First Name — 3871
    - ☐ Gender Identity
    - ☐ Self-identify Gender Identity
    - ☐ Race / Ethnicity
    - ☐ Self-identify Race/Ethnicity
    - ☐ Country of Origin
    - ☐ Sexual Orientation
    - ☐ Relationship Status
    - ☒ Academic Information
    - ☒ Academic Status
    - ☒ GPA
    - ☒ Prior Major
    - ☒ Current Major
    - ☒ International Student — 3879
    - ☒ Transfer Student
    - ☒ College — 3875
    - ☒ First Generation
    - ☐ Appointment information
    - ☐ First Visit
    - ☐ Reason for coming to the Counseling Center — 3877
    - ☐ Health Insurance Carrier
    - ☐ Personal Information Section
    - ☐ Family Information
    - ☐ Parent
    - ☐ Relationship
    - ☐ Occupation
    - ☐ Education
    - ☐ Rel. Status
    - ☐ Deceased
    - ☐ Parent
    - ☐ Relationship
    - ☐ Occupation
    - ☐ Education 3870, 3873, 3883

8/20/2015 Client Information — 3881, 3887

Academic Information:
Academic Status: Junior
GPA: 2.7
Current Major: Biomedical Engineering    International Student: No
Transfer Student: No
College: College of Engineering    First Generation: No

SELECT *, CASE WHEN (NoteType) IN (157) THEN 1 ELSE 0 END AS IsHidden
FROM extractTable                                                    3893
WHERE ((ApptType) IN (131,140) OR (StaffId) IN (225,218,140))
    AND NOT ((ReverseAppointmentCount) > 4 AND (NeverExclude) = 0)
  3891

FIG. 30A

SELECT *, CASE WHEN (NoteType) IN (157) THEN 1 ELSE 0 END AS IsHidden,
    CASE WHEN ((ReverseAppointmentCount) > 4 AND (NeverExclude) = 0)
        THEN 0 ELSE 1 END AS IsVisible
FROM extractTable
WHERE ((ApptType) IN (131,140) OR (StaffId) IN (225,218,140))

FIG. 30B

IS PLACEHOLDER QUERY:
SELECT *
FROM extractTable
WHERE ((ApptType) IN (131,140) OR (StaffId) IN (225,218,140))
    AND NOT ((ReverseAppointmentCount) > 4 AND (NeverExclude) = 0)
    AND (NoteType) IN (157)

IS NORMAL DOCUMENT QUERY:
SELECT *
FROM extractTable
WHERE ((ApptType) IN (131,140) OR (StaffId) IN (225,218,140))
    AND NOT ((ReverseAppointmentCount) > 4 AND (NeverExclude) = 0)
    AND ((NoteType) NOT IN (157))

FIG. 30C

3894
SELECT *, CASE WHEN (NoteType) IN (157) THEN 1 ELSE 0 END AS IsHidden
FROM extractTable
    WHERE (((ApptType) IN (131,140) OR (StaffId) IN (225,218,140)
3891      AND (DocumentId) NOT IN (131))      3893
3892      OR (PrimaryKey) IN (25, 191, 63, 131, 71, 238, 77, 400, 501))
3895    AND NOT ((ReverseAppointmentCount) > 4 AND (NeverExclude) = 0)

FIG. 30D

Wed. 10:30 AM
- Adam Bahm
- Cooky Baker
- Chrystal Ball
- Robin Banks
- Anita Bath
- Rose Bush
- Candy Cain
- Justin Case
- May Flowers
- Clay Potts
- Joy Rider
- April Showers
- Nan Tucket
- Kent Waite

| Couples | Triage | Hospitalization | Medication Log | Last 4 Appointments |
| Settings | Psychiatry | Therapy | Group | Unread Notes | Client Authored |

8/20/2015 [Inventory A Details]

8/20/2015 (Client Information) — 3901

General Information:
Date of Birth: 12/3/1992
Preferred First Name: Eric  — 3902
Gender Identity: Man
Race / Ehtnicity: Bold
Country of Origin: United States
Sexual Orientation: Hetrosexual
Relationship Status: Serious dating or committed relationship

Academic Information:
Academic Status: Junior
GPA: 2.7
Current Major: Biomedical Engineering          International Student: No
                                                   Transfer Student: No
College: College of Engineering                First Generation: No

Appointment Information:
First Visit: No
Reason for coming to the Counseling Center:
Personal | Academic
Health Insurance Carrier: Aetna
                                          3903

Personal Information Section:
Family Information:
Parent: Morris       Relationship: Father              Occupation: Mechanical Engineer
Education: 4 - Year  Rel. Status: Married   Deceased? No
Degree
Parent: Betty        Relationship: Mother
Education: Some      Rel. Status: Married   Deceased? No   3905
College Please provide the names and relationship of ...
Additional Family: Tucker    How related? Brother    Age: 19
Education: Some College
Additional Family: Phyllis   How related? Sister     Age: 16
Education: High School
                                              — 3907

Medical Information Section:
Inclusion application for XYZ research.
If you agree to participate in our research ... : VF
Medical / Psychological History
Chronic Health Concerns: Yes            If yes, please describe: Ulcerative Colitis
Prior Counseling: After starting college
Prior Meds: Both                        Please list current medications:

Close

FIG. 31A

| Primary key | Element type | Default text | Alternate text | Style | Supplemental list id | Answer on new line | Column number | Total Columns | Element starts at | Element ends at | Answer starts at | Answer ends at | Element on new line indicator | Furthest left boundary | Furthest right boundary |
|---|---|---|---|---|---|---|---|---|---|---|---|---|---|---|---|
| | | | | | | | | | | | | Assuming width is 400 | | | |
| 200 | Heading | Medical Information Section | | Section heading | | | 1 | 1 | 1 | 399 | | | Yes | 1 | 399 |
| 201 | Heading | We currently participate in research for XYZ. | Inclusion application for XYZ research. | Text heading | | | 1 | 1 | 1 | 399 | | | Yes | 1 | 399 |
| 202 | Heading | Your participating in the research may benefit others. | | Text heading | | | 1 | 1 | 1 | 399 | | | Yes | 1 | 399 |
| 203 | Heading | You may receive the cost of study related medication for free by participating in the research. | | Text heading | | | 1 | 1 | 1 | 399 | | | Yes | 1 | 399 |
| 204 | Prompt | If you agree to participate in our research, please type your initials here | | Edit box | | No | 1 | 2 | 1 | 99 | 101 | 199 | Yes | 1 | 199 |
| 205 | Heading | Weight information | | Text heading | | | 1 | 1 | 1 | 399 | | | Yes | 1 | 399 |
| 206 | Prompt | What is your current weight (in pounds) if you are coming here for weight treatment | | Numeric | | No | 1 | 2 | 1 | 99 | 101 | 199 | Yes | 1 | 199 |
| 207 | Prompt | Have you had recent, unexplained weight loss or gain? | | Yes / No | | No | 2 | 2 | 201 | 299 | 301 | 399 | No | 201 | 399 |
| 208 | Heading | Medical and Pychological History | Medical / Pychological History | Text heading | | | 1 | 1 | 1 | 399 | | | Yes | 1 | 399 |
| 209 | Prompt | Chronic Health Concerns | | Yes / No | | No | 1 | 2 | 1 | 99 | 101 | 199 | Yes | 1 | 199 |
| 210 | Prompt | If yes, please describe | | Text box | | No | 2 | 2 | 201 | 299 | 301 | 399 | No | 201 | 399 |
| 211 | Prompt | OBSOLETE: Prior counseling | | Dropdown list | 500 | No | 1 | 1 | 1 | 199 | 201 | 399 | Yes | 1 | 399 |
| 212 | Prompt | Prior Meds (only count if taken 30 days or longer) | | Dropdown list | 500 | No | 1 | 2 | 1 | 99 | 101 | 199 | Yes | 1 | 199 |
| 213 | Prompt | Please list current medications | | Text box | | Yes | 2 | 2 | 201 | 399 | 201 | 399 | No | 201 | 399 |
| 214 | Heading | Copyright (C) Acme Road Runner Service 1950 | | Text heading | | | 1 | 1 | 1 | 399 | | | Yes | 1 | 399 |

FIG. 31B

| Primary key | Design Id | Numeric value | Text value |
|---|---|---|---|
| 300 | 204 | | VF |
| 301 | 206 | | |
| 302 | 207 | | |
| 303 | 209 | 1 | |
| 304 | 210 | | Ulcerative Colitis |
| 305 | 211 | 401 | |
| 306 | 212 | 402 | |
| 307 | 213 | | Vitamin B-12, Folic Acid, Xeljanz XR (since age 17) |

Prior art  FIG. 31C

| Primary key | List Id | Text of answer option |
|---|---|---|
| 400 | 500 | Before college (i.e., first college attended) |
| 401 | 500 | After starting college (i.e., first college attended) |
| 402 | 500 | OBSOLETE: Both |

Prior art  FIG. 31D

4001 Medical Information Section

4003 We currently participate in research for XYZ.

4005 Your participating in the research study might benefit others.

4007 You may receive the cost of study related medication for free by participating in the research.

| 4009 If you agree to participate in our research, please type your initials here | 4011 VF |

4013 Weight information

| 4015 What is your current weight (in pounds) if you are coming here for weight reduction | 4017 | 4019 Have you had recent unexplained weight loss or gain? | 4021 ○ Yes   ○ No |

4023 Medical and Psychological History

| 4025 Chronic Health Concerns | 4027 ● Yes   ○ No | 4029 If yes, please describe | 4031 Ulcerative Colitis |
| 4033 OBSOLETE: Prior counseling | | 4035 After starting college (i.e., first college a | |
| 4037 Prior Meds (only counts if taken 30 days or longer) | 4039 OBSOLETE: Both | 4041 Please list current medications | 4043 Vitamin B-12, Folic Acid, Xeljanz XR (since age 17) |

4045 Copyright (C) Acme Road Runner Service 1950

4001 — Medical Information Section
4003 — We currently participate in research for XYZ.
4005 — Your participating in the research study might benefit others.
4007 — You may receive the cost of study related medication for free by participating in the research.
4009 — If you agree to participate in our research, please type your initials here    VF  4011
4013 — Weight information
4015 — What is your current weight (in pounds) if you are coming here for weight reduction    4017
    Have you had recent unexplained weight loss or gain?    ○ Yes  ○ No  4021
    4019
4023 — Medical and Psychological History
4025 — Chronic Health Concerns    ● Yes  ○ No    4027
    4029  If yes, please describe    Ulcerative Colitis  4031
4033 — OBSOLETE: Prior counseling    After starting college (i.e., first college a  4035
4037 — Prior Meds (only counts if taken 30 days or longer)    OBSOLETE: Both    4039
    Please list current medications  4041
    Vitamin B-12, Folic Acid, Xeljanz XR (since age 17)  4043
4045 — Copyright (C) Acme Road Runner Service 1950

Prior art   FIG. 31F

4051 — Medical Information Section
4053 — Inclusion application for XYZ research.    4057
4055 — If you agree to participate in our ... : VF
4059 — Medical / Psychological History    4063
4061 — Chronic Health Concerns: Yes    If yes, please describe: Ulcertive Colitis
4065 — Prior counseling: After starting college
4067 — Prior Meds: Both    Please list current medications: Vitamin B-12, Folic Acid, Xeljanz XR (since age 17)  4069

FIG. 31G

4051 — Medical Information Section
4053 — Inclusion application for XYZ research.    4057
4055 — If you agree to participate in our ... : VF
4059 — Medical / Psychological History    4063
4061 — Chronic Health Concerns: Yes    If yes, please describe: Ulcertive Colitis
4065 — Prior counseling: After starting college
4067 — Prior Meds: Both    Please list current medications: Vitamin B-12, Folic Acid, Xeljanz XR (since age 17)  4071

FIG. 31H

| | DocumentId | RangeFrom | RangeTo |
|---|---|---|---|
| 4682 | Doc #4 | 1 | 38 |
| | Doc #4 | 91 | 168 |
| 4684 | Doc #4 | 72 | 168 |
| | | 4686 | |

Table 4680

| | DocumentId | RangeFrom | RangeTo |
|---|---|---|---|
| 4690 | Doc #4 | 1 | 38 |
| 4692 | Doc #4 | 72 | 168 |

Table 4688

4730

```
IF OBJECT_ID('tempdb..##Tbl') IS NOT NULL DROP TABLE ##Tbl;

WITH RangeCTE AS
(
    SELECT DocumentId, DocTotalLines, RangeFrom, RangeTo
    FROM Ranges

UNION ALL

SELECT Rng.DocumentId, Rng.DocTotalLines, Rng.RangeFrom, RangeCTE.RangeTo
    FROM RangeCTE INNER JOIN Ranges Rng ON (    Rng.RangeFrom BETWEEN RangeCTE.RangeFrom AND RangeCTE.RangeTo + 1
                                             OR RangeCTE.RangeFrom BETWEEN Rng.RangeFrom AND Rng.RangeTo + 1)
    WHERE (Rng.RangeFrom < RangeCTE.RangeFrom)
      AND (Rng.RangeTo < RangeCTE.RangeTo)
      AND (Rng.DocumentId = RangeCTE.DocumentId)
)
SELECT DocumentId, DocTotalLines, RangeFrom, MAX(RangeTo) RangeTo
INTO ##Tbl
FROM RangeCTE
GROUP BY DocumentId, DocTotalLines, RangeFrom SELECT DocumentId, DocTotalLines, MIN(RangeFrom) RangeFrom, RangeTo
FROM ##Tbl
GROUP BY DocumentId, DocTotalLines, RangeTo
ORDER BY DocumentId, RangeFrom, RangeTo
```

FIG. 32G

USER CONFIGURABLE ELECTRONIC MEDICAL RECORDS BROWSER

CROSS-REFERENCE AND PRIORITY CLAIM

This application is a continuation-in-part of U.S. patent application Ser. No. 17/005,429, filed Aug. 28, 2020, which in turn is a continuation-in part of U.S. patent application Ser. No. 16/781,800, filed Feb. 4, 2020, which in turn is a non-provisional of U.S. Provisional Application No. 62/918,580, filed on Feb. 5, 2019. A priority claim is made to U.S. application Ser. Nos. 17/005,429, 16/781,800, and 62/918,580, all of which are incorporated herein by reference in their entirety.

TECHNICAL FIELD

This application relates to methods of displaying a plurality of documents on a screen and, more particularly, displaying electronic medical records on a screen.

BACKGROUND

Record keeping in medical facilities has been migrating to electronic medical record systems (EMR) for the past several years. More and more medical offices, hospitals, college counseling centers, and other providers are now on EMRs. EMRs provide standardized formats to enter information such as electronic data forms and allow for universal retrieval in fractions of a second where old paper chart systems required much longer times to access information.

Traditional EMRs suffer from being designed around a computer model that silos information and expects the display user to follow the way programmers expected the information to be presented. The problem stems from how the data is stored and that programmers have built their navigation systems around the silos of each piece of information in the EMR's database.

The EMR data is stored as records. EMR systems are written to present records with navigation steps necessary to move from one record to another and in the traditional EMR, typically with a requirement to close one record before viewing the next record of the same type (which requires an additional navigation step for each record).

The typical navigation steps of using a traditional EMR to review a client's chart involves the following pattern:

Navigate to a client's master record (requires aiming and clicking)
Navigate to the client's chart (requires aiming and clicking)
Open the first note in the chart (requires aiming and clicking).
Read the document (may require scrolling if the document is taller than the screen height)
Open the first attachment (requires aiming and clicking).
Read the first attachment (may require scrolling if the attachment is taller than the screen height)
Close the first attachment (requires aiming and clicking)
Open the second attachment (requires aiming and clicking).
Read the second attachment (may require scrolling if the attachment is taller than the screen height)
Close the second attachment (requires aiming and clicking)
Close the first note (requires aiming and clicking)
Open the second note (requires aiming and clicking).
Read the document (may require scrolling if the document is taller than the screen height)
Open the first attachment (requires aiming and clicking).
Read the first attachment (may require scrolling if the attachment is taller than the screen height)
Close the first attachment (requires aiming and clicking)
Open the second attachment (requires aiming and clicking).
Read the second attachment (may require scrolling if the attachment is taller than the screen height).
Close the second attachment (requires aiming and clicking).
Close the second note (requires aiming and clicking)
And so on for however many documents were in the chart and however many attachments were in each particular note. There could be hundreds of documents in a client's chart, so even though pointing a mouse and clicking is quick, the process adds up to fatigue on the display user.

Often times it is hard for an EMR to predict exactly how much of a document needs to be presented to the display user because different documents have different space requirements, so it often becomes a matter of having a small window or using the full screen without the display user being able to choose, or if they can, again requiring navigation operations to set the window size each time. Once the full window mode is chosen, obviously, the window eventually has to be closed to navigate elsewhere in the EMR by another mouse aiming and clicking action.

Accordingly, those skilled in the art continue with research and development efforts in the field of EMR systems.

SUMMARY

Disclosed are methods for displaying a plurality of documents, especially documents related to electronic medical records, on a screen.

In an example, provided is a method of selectively displaying entities from a plurality of documents on a screen. The plurality of documents includes a first document and a second document, wherein the first document comprises a first entity and a second entity. The first entity includes an attribute that is text and an element that is a prompt entity. The second entity includes an attribute that can be converted to text and an element that is an answer entity to the prompt entity. The second document includes a third entity that includes an attribute that can be converted to text and an element that is an unanswered prompt entity. The method includes: converting the attribute of the second entity into converted text to yield a converted answer; combining the attribute of the first entity with the converted text of the converted answer to yield a prompt-answer pair; displaying the first document on the screen, wherein the displaying of the first document includes replacing the attribute of the first entity and the attribute of the second entity with the prompt-answer pair; and displaying the second document on the screen, wherein the displaying of the second document includes excluding the attribute of the third entity.

In an example, provided is a method of selectively displaying a plurality of entities from a data form on a screen. The entities define a sequential order based on the arrangement of the entities on the data form. Each entity includes at least one attribute corresponding to the position of the entity in the sequential order and an element that is one of a title entity, a prompt entity, a response entity, and a heading entity. The sequential order includes a first heading-prompt series that includes an initial entity group and a subsequent entity group. The initial entity group includes an entity that includes an element that is a heading. The subsequent entity group includes an entity that includes an element that is an answered prompt. The screen includes a plurality of columns and output lines. The method includes: computing a column number from each entity of the plurality of entities that is one of a title, a prompt, a response, and a heading; computing an element on new line indicator from each entity of the plurality of entities that is one of a title, a prompt, a response, and a heading; selecting a replacement entity for the initial entity group, wherein the replacement entity includes an element that is one of a top repeat heading and a lowest repeat heading; selecting a set of entities from the subsequent entity group to display on the screen, at least one entity of the set of entities includes an element that is an answered prompt; and displaying the first heading-prompt series on the screen in the sequential order, at the column number, and on the line specified by the element on new line indicator. The displaying further includes displaying the replacement entity instead of the initial entity group, followed by the set of entities.

In an example, provided is a method of selectively displaying a plurality of pairs of entities from a document, wherein each pair of the plurality of pairs of entities is displayed between a pair of horizontal boundaries on a screen. Each pair of the plurality of pairs includes a first entity and a second entity. Each first entity includes an attribute that is text and an element that is a prompt entity. Each second entity includes an attribute that can be converted to text and an element that is an answer entity to the prompt entity. The screen defines a horizontal axis comprising an origin point proximate a left periphery of the screen. The first entity defines a left boundary and a right boundary on the screen. The left boundary and the right boundary of the first entity each corresponds to an axis position along the horizontal axis. The second entity defines a left boundary and a right boundary on the screen. The left boundary and the right boundary of the second entity each corresponds to an axis position along the horizontal axis. Each axis position of the left and right boundaries of the first entity and the second entity includes an X-axis value corresponding to the distance between the axis position and the origin point. The method includes: defining an absolute left boundary corresponding to an axis position that includes an X-axis value equal to the lesser of the X-axis value of the left boundary of the first entity and the X-axis value of the left boundary of the second entity; defining an absolute right boundary corresponding to an axis position that includes an X-axis value equal to the greater of the X-axis value of the right boundary of the first entity and the X-axis value of the right boundary of the second entity; converting the attribute of the second entity into converted text to yield a converted answer; combining the attribute of said first entity with a combining string and the converted text of the converted answer to yield a prompt-answer pair; and displaying the prompt-answer pair with combining string, instead of the attribute of the first entity and the attribute of the second entity, on the screen between the absolute left boundary and the absolute right boundary.

In an example, provided is a method of displaying a plurality of documents on a screen that includes a plurality of display tabs. Each document of the plurality of documents includes an attribute of an entity that is a date, and another attribute of an entity that is a document selection attribute. The method includes: selecting a first document criterion and a second document criterion; storing the first document criterion and the second document criterion on a computer readable medium; retrieving the first document criterion and the second document criterion from the computer readable medium; matching the first document criterion with the selection attributes of at least two documents of the plurality of documents to identify a first group of documents; matching the second document criterion with the selection attributes of at least one document of the first group of documents to identify a second group of documents, the remaining documents of the first group of documents being a third group of documents; generating a placeholder for each document of the second group of documents, wherein at least one generated placeholder includes at least one of a field and a pointer link, the pointer link pointing to a different entity that includes a field; and generating a date in at least one of a field of a generated placeholder and a field of an entity pointed to by a pointer link of a generated placeholder, the date being at least one of a default date and the date of the document for which the placeholder was generated; and displaying at least one generated placeholder at least one document of the third group of documents in a predetermined sequential order on a display tab of the plurality of display tabs.

In an example, provided is a tangible, non-transitory, computer readable medium that includes program instructions that cause a computer to execute a method of utilizing a document group to generate an output that is formatted for a peripheral output device. The output includes at least one output document. Each document of the document group includes at least one of a heading and a set theory union of a prompt field and an answer field. The answer field of each union includes an answer status that is either unanswered if the answer field is empty or answered if the answer field is not empty. Each union defines a left boundary and a right boundary. The method includes: generating an output document that includes a plurality of text lines; reproducing the prompt field of a union to yield a reproduced prompt; converting the answer field of the same union into pure text to yield a converted answer; combining the reproduced prompt with the converted answer to yield a prompt-answer pair; including the prompt-answer pair in the text lines of the output document; selecting an answer status of interest between either answered or unanswered; excluding the prompt-answer pair from the output document if the prompt-answer pair includes an answer status that matches the answer status of interest; copying a heading from a document onto the output document; sending an output to the peripheral output device, wherein output includes the output document; calculating the width of available space for the union; and adjusting the width of the prompt-answer pair in the text lines so that it is not wider than the width of available space for the union.

In an example, provided is a method of utilizing a document group to generate an output that is formatted for a peripheral output device. The output includes at least one output document. A plurality of documents of the document group includes at least one of a heading and a set theory union of a prompt field and an answer field. The answer field of each union includes an answer status that is either unanswered if the answer field is empty or answered if the answer field is not empty. Each union defines a left boundary and a right boundary. The method includes: generating an output document that includes a plurality of text lines; reproducing the prompt field of a union from a document of the plurality of documents to yield a reproduced prompt; converting the answer field of the same union into pure text to yield a converted answer; combining the reproduced prompt with the converted answer to yield a prompt-answer pair; including the prompt-answer pair in the text lines of the output document; selecting an answer status of interest between either answered or unanswered; excluding the prompt-answer pair from the output document if the prompt-answer pair includes an answer status that matches the answer status of interest; copying a heading from a document of the plurality of documents onto the output document; sending an output to the peripheral output device, the output comprising the output document; calculating the width of available space for the union; and adjusting the width of the prompt-answer pair in the text lines so that it is not wider than the width of available space for the union.

Other examples of the disclosed methods for displaying a plurality of documents on a screen will become apparent from the following detailed description, the accompanying drawings and the appended claims.

BRIEF DESCRIPTION OF THE DRAWINGS

FIG. 4A is an example of a typical answered prompt field;

FIG. 4B is an example conversion of the answered prompt field of FIG. 4A;

FIG. 5A is an example of a typical answered prompt field where the prompt text is on a separate text line from the answer value;

FIG. 5B is an example of what a display user may see on a paper printout of the answered prompt field of FIG. 5A;

FIG. 5C, is an example of an optimized conversion of the answered prompt field of FIG. 5A;

FIG. 6A is an example of a typical answered multi-select text box;

FIG. 6B is an example of what a display user may see in a printout on paper after answering the multi-select text box of FIG. 6A;

FIG. 6C is an example of an optimized conversion of the answered multi-select text box of FIG. 6A;

FIG. 6D is an example of a further optimization of the answered multi-select text box shown in FIG. 6C where the answer text is split at a concatenation string and left aligned;

FIG. 15 is an example of a string of text being measured in accordance with the procedure of FIG. 13;

FIG. 16 is an overview table showing a number of different values calculated at various steps of the method of FIG. 13;

FIG. 17 is an overview table showing the calculated values at five different passes through the loop of FIG. 14 while processing the string of FIG. 15;

FIG. 18 is the string of text of FIG. 15 being processed through the loops of FIG. 14;

FIG. 19G is an illustration showing sample text that could have created the example of FIG. 19F.

FIG. 19H is a chart showing how to calculate the classification of a heading entity of interest based on the closest significant entities before and after the heading entity of interest.

FIG. 20 is an example portion of a data entry form;

FIG. 21 is an example of how the portion of a data entry form of FIG. 20 may appear after performing step 1271 of the method of FIG. 19A or step 1295 of the method of FIG. 19B or step 1305 of FIG. 19C;

FIG. 22A is an overview table depicting the calculated values from the loop in 1269 of FIG. 19A while processing the data form shown in FIG. 20;

FIG. 22B is an overview table depicting the calculated values for headers from the steps of FIG. 19B while processing the data form shown in FIG. 20;

FIG. 23 is an example of how FIG. 20 may appear after being optimized in accordance with the methods of FIGS. 19A-19C;

FIG. 28D is pseudocode for an example method of generating SQL clauses from leaf nodes when the tag property of the leaf node for special cases is the single integer value currNodeTagNo;

FIG. 29A is an example of a simple Include configuration tree as might appear in one embodiment of a settings screen;

FIG. 29B is an example of a hide configuration tree as might appear in the embodiment of the settings screen of FIG. 29A;

FIG. 29C is an example of an exclude configuration tree as might appear in the embodiment of the settings screen of FIG. 29A;

FIG. 29E is an example of a configuration tree showing selecting sub-leaves of one document (e.g., data form) including a preview, as might appear in the embodiments of the setting screen of FIG. 29A or 29D;

FIG. 30A is an example of a SQL generated for the configuration trees of FIGS. 29A-29D using the methods of FIGS. 27A and 27B, and FIGS. 28A-28D, where the identification of whether a document is hidden is done in a SELECT clause, and the identification of which documents to include and which documents to explicitly exclude is done in a WHERE clause;

FIG. 30B is an example of a SQL generated for the configuration trees of FIGS. 29A-29D using the methods of FIGS. 27A and 27B, and FIGS. 28A-28D, where the identification of whether a document is hidden and the identification of which documents to explicitly exclude is done in a SELECT clause and the identification of which documents to include is done in a WHERE clause;

FIG. 30C is an example of a SQL generated for the configuration trees of FIGS. 29A-29D using the methods of FIGS. 27A and 27B, and FIGS. 28A-28D, where the identification of which documents to include, the identification of which documents to explicitly exclude, and the identification of whether a document is hidden is done in a WHERE clause;

FIG. 30D is an example of a SQL generated for the configuration trees of FIGS. 29A-29E using the methods of FIGS. 27A and 27B, and FIGS. 28A-28D, where the identification of whether a document is hidden is done in a SELECT clause, and the identification of which documents to include, which documents to explicitly exclude and which sub-leaves are included for one document is done in a WHERE clause;

FIG. 31A is an example of two data forms being presented in the context of a tablet computer in accordance with step 2711 of the method of FIG. 26;

FIG. 31B is an example of a portion of the heading entities 51 and prompt entities 52 of FIG. 1 that might be used to calculate document area 3907 of FIG. 31A;

FIG. 31C is an example of a portion of the answer entities 55 of FIG. 1 that might be used to calculate document area 3907 of FIG. 31A;

FIG. 31D is an example of three lookups entities 39 of FIG. 1 used to calculate document area 3907 of FIG. 31A;

FIG. 31E is a layout grid being used by the prompt, heading, answer and lookups entities of FIG. 31B-D used in document area 3907 of FIG. 31A;

FIG. 31F is a view the data entry user 78 of FIG. 1 may see after filling in the data for the current data form and also a copy of FIG. 31E with the layout grid hidden;

FIG. 31G is a reproduction of document area 3907 of FIG. 31A showing the layout grid used by FIG. 31B-D to create document area 3907;

FIG. 31H is an optimized reproduction of document area 3907 of FIG. 31A showing the layout grid used by FIG. 31B-D to create document area 3907;

FIG. 32G is SQL code that demonstrates how to combine and extend overlapping or adjacent document ranges;

DISCLOSURE

Definitions

Figure 1:
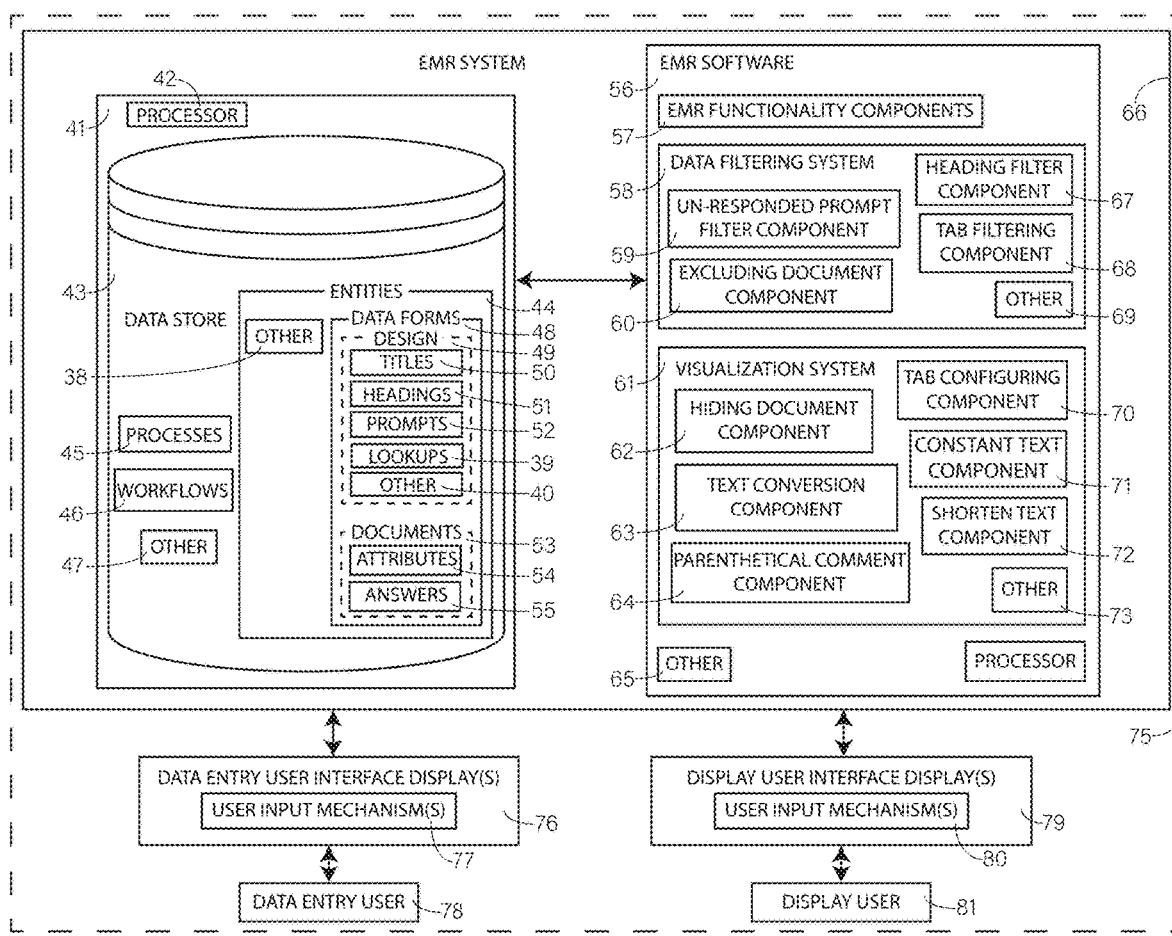
FIG. 1 is a block diagram of one example computer system.

"Absolute horizontal boundaries": The horizontal boundaries for an answered prompt entity expressed as a furthest-left boundary and a furthest-right boundary. The furthest-left boundary of the absolute boundary is the minimum value of the prompt entity's left boundary's X-coordinate and answer entity's left boundary's X-coordinate. The furthest-right boundary of the absolute boundary is the maximum value of the prompt entity's right boundary's X-coordinate and the answer entity's right boundary's X-coordinate. If the coordinate system used by the EMR is based on an origin and a width, then that coordinate system can be converted to the coordinate system that uses X-Y coordinates before calculating the furthest-left and furthest-right boundaries. The terms "attribute" and "column" may be used interchangeably in this specification.

"Answer": values that the data entry user entered when prompted on the screen to enter information. Answer values are generally stored away from the data form design entities with only a reference back to the prompt entity element associated with the answer entities. Answers may include, but are not limited to, text values, numeric values, date and time values, geography values, money values, Boolean values and images. Answers may also be entered by system processes or be default values.

"Access history data set": A data set that includes one or more user-view indications at any point in the lifetime of each user-view indication (either compound document virtual line numbers or individual document area ranges). An access history data set may include a viewing history log, and/or a viewing verification data set, and/or a browser-viewing log, and/or queries that summarize, extract, or process user-view indications and temporary (or permanent) extract tables that include information derived from user-view indications.

"Attribute": a named property (e.g., primary key, entity value, X-position, Y-position, style) of an entity (e.g., titles, heading entities, prompt entities, answer entities, combining strings, concatenation strings, horizontal lines, whole documents), generally the formatting of the texts (e.g., font, colors), paragraphs (e.g., line spacing, indentation), and whole documents (e.g., is the default for this document to display it hidden). The value of an attribute may be defined on various scopes (e.g., a single tab or page, an application instance, a specific user, EMR wide default). Selection attributes (defined elsewhere) may include attributes that are identifying characteristics of an entity. If the entity or attribute are stored encrypted, references in this specification to the attribute refer to either the unencrypted value of the attribute, or the value of the attribute used by the entity to format or display the entity on the screen.

"Available space": the horizontal component of the space provided by a set theory union of a prompt field and an answer field wherein elements (e.g., text) may be included to be displayed on a peripheral output device. It is contemplated that elements may "fit" within an "available space" if they do not overlap other elements that include text (i.e., prompt, answer, heading, title, and the like) and/or extend beyond the boundaries of the peripheral output device.

"Browser-viewing log": a data set that may be used for converting user-view indications received directly from the browser window into a different expression of the same range. The difference can be in terms of precision (i.e., rounding) and/or splitting out a single range into multiple smaller ranges covering the same total area and/or converting (i.e., transforming) an input into one or more individual documents.

"Browser window": an onscreen control of a computer application that allows a display user to see the contents of an input. The computer application may be configured to enable "scrolling" through the input, or in other words, the adjustment of the input position relative to the browser window which allows the user to view individual portions of the whole input. Further, the computer application may also be configured to identify the location coordinates (i.e., from an interval coordinate system) (e.g., virtual line numbers) associated with the browser window at a particular point along the input.

"Candidate text": a smaller text string found within a search text that matches a predetermined pattern. Typical examples of such patterns are matching opening and closing characters (e.g., open and closing parenthesis) that delimit the candidate text, a search text containing a predetermined constant text where the candidate text is the constant text, or a search text that is longer than a predetermined length where the candidate text is the text beyond the predetermined length. The search text may optionally be limited to data form design text or it can include all text of a document.

"Combining string": characters inserted between a prompt text and an answer value to separate the two from one another and/or to format them differently than the other. It may be user definable and can be such values as a colon and/or any other single character or multiple characters. The underlying characters of a combining string may also include encoding strings which do not appear on the screen, but change the formatting of the characters that do appear on the screen (e.g., "<b>" or "<i>" being used to turn on bold formatting or italics formatting, respectively, in HTML; and a "\f1" or "\f2" being used to change the font to the first font or second font, respectively, in the font table of the current document in RTF). Therefore, a combining string may just be a change of format between the prompt text and its related answer value. Some possible combining strings include ":", ": <b>" and just the "<b>" by itself for an HTML encoded document. Whenever there is not an alternate combining string for a document, a combining string for the whole document cannot include any character which forces a new text line every time a prompt text is combined with an answer text, such as text line feed ASCII character hexadecimal 0A or carriage return ASCII character hexadecimal 0D.

It is possible to have an alternate combining string include characters such as a carriage return because an alternate combining string is not applied to the whole document and only applies when a pre-determined condition is met. For example, when the benefit of applying the document's combining string (e.g., to the vertical height) is no better than applying the alternate combining string, smaller advantages of the alternate combining string (e.g., fitting similar formatted text on fewer lines) may outweigh using the whole document's combining string in specific instances.

"Complete document": a document as it was initially presented to the data entry user, with every field available for the data entry user to enter data into. So, there is the potential to provide an answer to every question in a complete document. Not every completed document in an EMR may be a complete document, there may be some documents where individual questions are skipped or complete sections of the document are skipped.

"Concatenation string": the characters inserted between multiple answer values to the same prompt text to separate them from each other. It may be user definable and can be such values as NULL, a space, colon, any other single character or multiple characters. A concatenation string cannot include any character which forces a new text line every time multiple answer values are appended together, such as text line feed ASCII character hexadecimal 0A or carriage return ASCII character hexadecimal 0D.

"Compound document": a document that includes two or more individual documents that have been concatenated together. These individual documents may be concatenated vertically, horizontally, or some combination of both. A compound document may be displayed on a browser window as an input. A compound document may also be included in an output and displayed on a peripheral output device.

"Data entry user": the user who responded to prompt fields on a computer display device such as a screen, typically using keyboard, mouse, touchscreen and like devices where the results of such input were stored back to the answer field of the EMR. It is possible for the data entry user to be a system process or other such non-human data source.

"Data form": a method of controlling the structure of information entered by a data entry user where the data entry user is presented prompt fields for specific pieces of information and is often limited as to the format, length or values that can be placed in the answer fields. The data form design may be stored in the EMR data store as title texts, heading entities, and prompt entities. Completed data form answer fields may be stored as answer entities with reference pointers back to the corresponding prompt entities presented to the data entry user. Completed data form heading fields may also be stored with the answer entities as reference pointers back to the corresponding heading entities to preserve information about which headings were presented to the data entry user.

"Data form design text": all text of a data form that can be made visible by a data entry user by entering and selecting a proper sequence of text and actions to access the data form and any part therein, prior to any data entry user modifying the data form, including any text within the data form hidden on the screen (e.g., values in a dropdown list that has not been selected and therefore is not visible on the screen, text that does not occur until other options are selected, etc.).

"Data form elements": Visual items appearing in a data form, specifically, title text, heading entities, prompt entities and answer entities. While data form design may include other visual items such as lines and extra vertical spacing, these other items may be ignored for purposes of the present invention.

"Data set": A collection of records that have some information in common. For example, a viewing verification data set might contain information about individual users accessing various ranges of document areas. Typical examples of data set components in SQL are tables, views, and queries.

"Display user": the user who looks up or reads information from the EMR, but whose records of which keystrokes, clicks or touches does not update the database with information specifically updating answer entities. The display user's actions may update non-answer, entity specific, information (e.g., a document viewing history log or viewing verification data set).

"Document": A named structural entity that can be stored, retrieved and exchanged among portions of the EMR and users as a separate entity. Document entities contain special purpose attributes called selection attributes which identify characteristics related to the document that a display user might want to select a group of documents using. Each selection attribute is stored in the named structural entity to allow the display user to pick combinations of the various selection attributes. Some examples of selection attributes that documents may contain, but are not limited to, include: document type (e.g., allergy records, appointments, case notes, client information, data forms, diagnoses, client flags, medication histories, staff details, and vital signs), reverse appointment count, indication of whether the current user has viewed the document, indication of whether the client attended any appointment the document was associated with, the date of the document, the appointment type the document was associated with, the case note type that was written for the appointment associated with the document, the type of user the document is associated with (e.g., a therapist, a medical doctor, etc.), and the identities of the users associated with the document (e.g., document signers, practitioners who attended the appointment with client, etc.). While document (e.g., data form) design may include entities other than title, heading, prompt, answer and lookups entities, and start and end of document markers, any other entities (e.g., lines and extra vertical spacing) may be ignored for purposes of the present invention.

"Document area": a contiguous portion of a document. This can include, for example, a region of a document that is viewable on a screen or a printout. Individual document areas that overlap or are immediately adjacent to each other may be combined using a set theory union, which may be useful in the context of a browser-viewing log, a viewing history log or viewing verification data set to indicate that a display user viewed a single larger region rather than several smaller (possibly overlapping or redundant) individual document areas. An individual document area can be as small as a single element or as large as an entire individual document.

"Document criterion": one or more values (including wildcards) that may be used to compare against an attribute or metadata of a selection attribute, a type of comparison operator, and the identity of which document attribute(s) or metadata to check against the value. The values and comparison operator may also be expressed using Regular Expressions, or a like, language. Value types may be expressed as, but are not limited to: numeric, date-time, string, logical, image, and geographical coordinates data. Examples of the comparison operators may include, but are not limited to: equality, inequality, greater than, less than, not greater than, not less than, contains, is contained within, like, is empty, is not empty, etc.

"Element": For data forms which have been responded to by the data entry user, elements include (but are not limited to) heading entities, answered prompt entities and unanswered prompt entities, and start and end of document markers. In the case of an answered prompt entity, this entity can be broken up into a separate prompt entity and a separate answer entity. In the case of an unanswered prompt entity, this entity may not include a separate answer entity in some embodiments (e.g., an unanswered prompt entity may contain a place to store an answer, but a prompt entity may not have a place to store an answer, so there could be slight differences between an unanswered prompt entity and a prompt entity). For data forms which have not been responded to by the data entry user, elements include (but are not limited to) heading entities and prompt entities, and start and end of document markers.

"Element on new line": an indication of whether the current element is to be placed on the same output line as the last element or the next blank output line. The value is calculated, but exact method depends on the layout specification provided by the EMR. For example, if a prompt text was scheduled to be placed on output line number 32 and all answer values on that output line were horizontally aligned with the prompt texts and the next remaining data form element was scheduled to be placed on output line number 40, the element is not to be placed on the same output line as the previous prompt text, so it is to be placed on the next output line number (e.g., output line number 33, since the previous output line number was 32). If a prompt text was scheduled to be placed on output line number 32 and at least one answer value on that output line number was vertically aligned with the prompt text and the next remaining data form element was scheduled to be placed on output line number 40, the element is not to be placed on the same output line number as the previous prompt text, so it is to be placed on the next blank output line number (e.g., output line number 34, since the previous output line number was 32 and output line number 33 already has at least one answer on it).

"Empty": a value that indicates nothing is present in the specified position. This can include such values as a NULL value in a database column; blank space for a converted text; and a zero, NULL or negative value for a foreign key in a database.

"EMR": abbreviation for electronic medical records.

"End of document marker": An indication that there is no more text in the current individual document. Different embodiments may implement this differently. For example, the end of document marker may be an attribute of an element in one embodiment and a separate element in another embodiment. The end of document marker may also be implied by either finding no more characters in a document or by encountering a start of document marker after the first character of a document in an input (where the start of document marker is either an element or an attribute).

"Entity": an object with a predefined structure that holds related pieces of information together. If an entity is stored encrypted, all references to the attributes (e.g., text) of the entity in this specification may refer to the unencrypted values of the attributes. Entities may have default values, typically the text associated with an entity. The value of an instance of a prompt entity without specifying more than "prompt" (e.g., the column number of the prompt) is the text of the prompt entity instance, so the word "prompt" by itself or "prompt entity" where the context indicates it is not the whole object or it is an operation that can be performed on text in this specification refers to the text of the prompt entity instance (e.g., default text 3910 in FIG. 31B). Similarly, in this specification, the value of an answer entity is the text of the answer entity and the value of a heading entity is the text of the heading entity. So, "answer" or "answer entity" where the context indicates the whole object is not in view refers to the text of the answer entity instance. A "heading" where the context indicates the whole object is not in view refers to the text of the heading entity. For example, the term "prompt and related answer" may refer to some concatenation of the text of the prompt entity and the text of the related answer entity, possibly with a combining string between them.

"Exclude": to suppress from being displayed.

"Heading": an entity on the data form that presents text that the data entry user cannot be prompted to enter any information because there are no specifications for a related answer entity and it is not the single title text of the data form. As an entity, it may have a default value of the text associated with the heading entity. Headings can be classified into various heading types. In one classification of headings, "Other headings" are all headings other than a normal heading and a terminal heading. In a second classification of headings, headings may be classified as top repeat headings, repeat headings, lowest repeat headings, normal headings, style terminal headings, and terminal headings, each as defined herein. The EMR may allow the designer of the data form to specify different styles of headings in the EMR, and if so, the different styles of headings are processed as if they ignore the other style headings by the methods of the current invention. For example, if there exists a "section style" and a "text style" in the EMR, and a document had a prompt entity, followed by a section style heading entity, followed by another section style heading entity, followed by a text style heading entity, then a prompt entity, the first section style heading entity would be of classification "top repeat heading" (because it is not proceeded by another heading of the same style and is instead followed by a heading entity of the same style) and the second heading would be of classification "lowest repeat heading". If the same document had a prompt entity, followed by a section style heading entity, followed by a text style heading entity, followed by a prompt entity, then both the section style heading entity and the text style heading entity would be of classification "normal heading" (because, after ignoring the other style heading, each are followed by a prompt entity and not proceeded by another heading entity of the same style).

"Hide": to substitute a placeholder for an individual document. When the placeholder is activated, the individual document appears on the screen.

"Image": an answer entity (e.g., a picture) that cannot be altered to decrease the amount of space it occupies in the display of the EMR by an automated means other than scaling the complete answer entity size, or by creating a link the displays the image when a display user activates that link, thereby hiding portions of the EMR display screen. An image that is converted to a textual form, such as by using OCR, may itself be considered a data form with heading entities, prompt entities and answer entities and possibly a title, if the EMR is programmed to recognize which characters in the OCR image are distinct answer values that were entered by a data entry user and which characters represent individual prompt texts and heading texts.

"Input": either a single document or a concatenation of multiple individual documents that is uploaded, by a user or some entity, to a computer application to be displayed through a browser window. An input may be viewed as a single larger document in a browser window. When displayed on the browser window, it may be the case that only portions of the input are shown (e.g., because the dimensions of the input exceed the dimensions of the browser window). An input area may be converted (i.e., transformed) into one or more individual document areas. The computer application may be configured to identify one or more input areas that are shown on the screen at a given time. It is contemplated that the collection of user-view indications created in this way may be useful for, among other things, a viewing verification data set.

"Interval Coordinate System": system of measurement that utilizes one or more interval scales. An interval coordinate system can be applied to an input so that each point along the input has a location-identifying coordinate or set of coordinates. For example, a computer application that practices the methods of the present disclosure (and any embodiments thereof) may apply an interval coordinate system based on an interval scale of virtual lines. This interval scale of virtual lines may be applied to the vertical dimension of an input, with the uppermost virtual line of the input being the start (i.e., "virtual line 1") of the interval scale. The interval scale may increase downwards from there.

"Invalidate": to delete a line or to mark (e.g., setting a bit to indicate) a line as not being useful for one or more purposes.

"Layout cell": A rectangular constant region on a screen or report that establishes the available size and position in which data will appear on a screen or in a report. The height of the region may vary depending on either the data filling the layout cell or a related cell. In the case of two related layout cells with the same starting horizontal component, the height may be set to the taller of the two related cells. The layout cell width may be predetermined either by a computer application programmer or by a user setting within the computer application. In the case of two related layout cells aligned with the same starting vertical component, the layout cell width may be set to the wider of the two related cells. The line width and starting position (i.e., padding above, below and on each side of the allowable text area within the layout cell) may be predetermined either by the initial computer application programmer or a user setting within the computer application.

"Lowest repeat heading": the last heading entity encountered in a repeat heading series when all elements of the data form design are ignored other than heading entities (of the same style, if the EMR allows multiple styles of heading), and prompt entities.

"Minimum overlap": a threshold degree of overlap between two document areas. The minimum overlap may be the standard by which a computer application practicing the present invention (i.e., any embodiment thereof) determines if a second range received after a first range qualifies to become a user-view indication. As an alternative to being recorded in a separate user-view indication, if a calculated overlap is greater than or equal to the minimum overlap, which should be predetermined, then the first range of the user-view indication may be altered to the set theory union of the first range and the second range. In which case, the second range may be discarded. On the other hand, if the minimum overlap is negative, then any overlap maybe ignored and each range may be recorded in separate user-view indications.

"Minimum time": a period of time between capturing ranges of vertical coordinates. It is, essentially, a time limit that prevents a computer application from continuously updating a browser-viewing log, a viewing history log or a viewing verification data set as a browser window is quickly scrolled. The minimum time can thereby prevent faster computer hardware from generating more user-view indications than slower computer hardware for identical actions on identical documents.

"Normal heading": a heading entity in a document (e.g., data form) that is immediately followed by a prompt entity and not proceeded by another heading entity (of the same style, if the EMR allows multiple styles of heading) when all elements of the document (e.g., data form) design are ignored other than heading and prompt entities.

"Overlap": a common range of vertical coordinates that is shared by two or more ranges of vertical coordinates. For example, if a first range of vertical coordinates includes virtual lines 10-50 and a second range of vertical coordinates includes virtual lines 30-70, the overlap would be vertical lines 30-50.

"Pixel": a screen-dependent unit, standing for "picture element". A pixel is a dot that represents the smallest graphical measurement on a screen.

"Pointer": a variable that holds the address of a data entity.

"Placeholder": any character or combination of characters inserted into the text that a data entry user would not be expected to type, such as "~1~", or certain control characters, etc., that may eventually be replaced with another character string. It can also be a substitute character that a display or data entry user would accept as a replacement for some other character, such as using a square bracket (e.g., "[") as a substitute for a rounded parenthesis (e.g., "(") where the square bracket may later be changed to the corresponding rounded parenthesis.

"Procedure": a block of code that is executed. As used in the present disclosure, "procedure" is used interchangeably with function, process and step.

"Prompt": an entity in a data form that causes the data entry user to be prompted to enter information. The prompt entity may contain restrictions that controls the answer field layout and the acceptable values that are valid to place in the answer field. As an entity, when the word is used in association with the words "heading" or "answer", it may mean just the text of the prompt entity instance whenever the context can support such an interpretation. All prompt entities may have related answer entities, but some of those answer entities may indicate the data entry user did not respond to the prompt field (e.g., blank, null or otherwise empty indicating).

"Range": a sequence of coordinates (e.g., vertical coordinates) related to a particular portion of an input. These coordinates may be reported by a browser window. These coordinates may correlate to particular document area(s) that are visible in a browser window, or to the boundaries of a document area, or to the dimensions of the browser window itself.

"Relevant date": a date that is significant to a document or data form. It may be such values as the date of an appointment; the date when the record was entered, updated, signed, locked, created, or last viewed by the current user.

"Repeat heading": a heading entity in a document (e.g., data form) occurring before the final prompt entity in the document where the previous document element is another heading entity and the following element is another heading entity when all elements of the data form design are ignored other than heading entities (of the same style, if the EMR allows multiple styles of heading) and prompt entities.

"Reverse appointment count": a calculated value which extracts the date of each appointment with the most recent appointment being the value most near a beginning number (e.g., zero), incrementing the count for each new appointment date, then assigning each EMR document one of the reverse appointment count values based on a relevant date for each document. The reverse appointment count is useful as a selection attribute for queries such as "Show me all the EMR data since the last 3 client appointments" or "Show me all the EMR data since my last 2 appointments with the client".

"Scrolling": the act of adjusting the position of an input relative to a browser window. This may be achieved by any capable means such as, for example, user input in the form of mouse movement, arrow keys, normal typing, etc. Scrolling may be vertical, horizontal, and/or any combination thereof. As used herein, unless the context indicates that scrolling is not vertical (e.g., horizontal scrolling), the term "scrolling" should be taken as vertical (or the vertical component of scrolling). Scrolling an input up relative to the browser window allows a display user to see content of the input in the browser window that is further down (i.e., lower) in the input.

"Selection attribute": an attribute or metadata about a document that is used to decide if a document matches a document criterion. Examples may include any one of: record type (e.g., one of the values: allergies, appointments, case notes, client information, data forms, DSM-IV, DSM-V, client flags, medication, and vital signs), associated appointment attribute (e.g., one of the values: reverse appointment count, flag indicating appointment was attended, appointment type, appointment date), document attribute (e.g., one of the values: date document signed, case note type written, staff members identity who attended appointment or wrote notes, type of data form used, viewed date), etc.

"Set theory union": a format for combining two or more collections of objects (that share a common object type, e.g., pixels, whole numbers, etc.) into a single collection of objects (i.e., a "resulting collection"). The format, and thereby the resulting collection, retains every object that occurs at least once in any of the to-be-combined collections. For example, if a first collection contains a list of the numbers 1 and 2, and a second collection contains a list of the numbers 2 and 3, a set theory union of the first and second collections may include a list of the numbers 1, 2, and 3. As another example, if the collections are two regions on a screen for pictures, the objects in this case may be pixels and a set theory union of the collections may include every pixel occurring at least once in either screen region.

If the collections to be combined are adjacent document areas containing text, it is contemplated that pixels may be used as the common object. However, to use pixels in this way it is imperative that any buffering around text characters or lines of text (i.e., that prevent those characters or lines from overlapping each other), as well as blank areas past the end of text, not be excluded. Further, if one adjacent document area is smaller than the other along a shared border, and if there is no text in the way, the shared border of the smaller document area may be expanded to match the dimensions of the larger document.

An alternative for adjacent document areas containing text is to use the layout cells (defined elsewhere) containing the text. Here, the set theory union of two cells would be the area contained within either of the two layout cells. In the event the set theory union of layout cells create two separate areas (e.g., the layout cells are not immediately adjacent), the area between the two cells is also included in the set theory union results creating a single rectangular shaped region.

"Start of document marker": An indication that a new individual document is beginning. Different embodiments may implement this differently. For example, the start of document marker may be an attribute of an element in one embodiment and a separate element in another embodiment. The start of document marker may also be implied by finding the first character in a document, or the first character after an end of document in a compound document (where the end of document marker is either an element or an attribute).

"Style terminal heading": a heading entity in a document that supports multiple styles of headings having no prompt entity occurring between the heading entity and the next heading of a higher-level style. In documents supporting multiple styles of headings, headings are ordered from the highest-level style (typically, the largest and most eye-catching fonts in terms of font weight, color, etc.) to the lowest level (typically either smaller or more subtle fonts). The levels may be inferred from the font characteristics or set by the programmer or user. As a classification of terminal heading, it may be excluded under the same conditions the other classification of terminal heading can be excluded.

"Substitute Classification": In one or more examples, when searching for the next heading entity of the same classification, a normal heading entity may be recognized as being a suitable substitute for a lowest repeat heading entity due to the heading entities sharing a key characteristic in common. That key characteristic may be both heading entities are followed by a prompt entity. In some searching steps detailed in this specification, a normal heading entity may be interchangeable with a lowest repeat heading entity. Such a heading entity may then receive a "substitute classification" (a type of heading classification) designating it as such. Note, that for purposes of finding a suitable substitute and if the EMR supports styles of headings, the style of heading may be ignored when searching for the next heading, but not for the purpose of classifying the basic heading classification attribute (i.e., top repeat heading, repeat heading, lowest repeat heading, normal heading, terminal heading, and, for a different classification system, other heading).

For example, a substitute classification situation may occur when seeking to exclude a lowest repeat heading entity, or when counting prompt entities under a lowest repeat heading entity, and the following sequential order of entities in a document is encountered (when only considering heading and prompt entities): a lowest repeat heading entity immediately followed by one or more prompt entities, followed immediately by a normal heading entity followed immediately by one or more prompt entities. Since both the lowest repeat heading entity and the normal heading entity are both followed by a prompt entity (by definition, the key characteristic the two have in common) and there is a need to identify which prompt entities are under the lowest repeat heading entity by searching for the end of the prompt entities under the lowest repeat heading entity, the normal heading entity may be recognized as a suitable substitute for the lowest repeat heading entity. Thus, the prompt entities under the lowest repeat heading entity (i.e., those being either considered or counted) are those between the lowest repeat heading and the normal heading entities. If all the prompt entities under the lowest repeat heading entity are excluded, some portions of the current invention may also exclude the lowest repeat heading entity.

The above applies despite the fact that lowest repeat heading entities and normal heading entities are not identical-normal heading entities are never immediately preceded by another heading entity, but the element preceding a lowest repeat heading entity is always another heading entity (when only considering heading and prompt entities). It should be noted, however, that the suitability of a substitute for any particular entity, heading entities included, may largely depend on the specific purpose for which the substitute is used. In other words, a key characteristic in common may only be relevant to a specific purpose, and may not be relevant for a different specific purpose. This type of classification may be applied for, but not limited to, exclusionary and counting purposes.

"Summarizing overlapping, redundant or extended ranges": the process of combining a quantity of overlapping, redundant or extended ranges of a single document from either a browser viewing log, a viewing history log or a viewing verification data set into fewer ranges that express the same document areas.

"Tab": a visible structure with a caption and a hotspot located on or near the caption and at least one associated content view page, that allows a display user to press on the hotspot and have the view being displayed switch to the associated content indicated by the tab. If the context indicates a tab control is being used, the term "page" may be used to reference the associated content of the current tab in this specification.

"Terminal heading": a heading entity that occurs after the final prompt entity in a document (e.g., a data form). An alternate definition is a heading entity of interest that does not have a prompt within the scope of the heading entity of interest (see style terminal heading, defined elsewhere).

"Title": a name that identifies a document (in the case of a non-data form) or a data form design. As used in the present disclosure, a title may appear on the first output line of each document to distinguish that document from the previous document and may have the relevant date appended to the field.

"Top repeat heading": a heading entity in a document (e.g., data form) which is immediately followed by a non-terminal heading entity and not proceeded by another heading entity when all elements of the data form design are ignored other than heading entities (of the same style, if the EMR allows multiple styles of heading) and prompt entities.

"Topic": in an electronic medical record system, the person about whom the individual document is written about. In other electronic documentation systems, the person, place or thing which the individual document is written about.

"Twips": screen-independent units to ensure that the proportion of screen elements are the same on all display systems. A twip may be defined as being 1/1440 of an inch.

"Under": if a document does not have different heading styles, an entity of interest is said to be under a first heading entity if and only if the entity of interest occurs after the first heading entity and before the first occurrence of: (1) a second heading entity of the same classification as the first heading entity, (2) a second heading entity classified as a substitute for the first heading entity (e.g., the first heading entity is a lowest repeat heading and the second heading entity is a normal heading), (3) a second heading entity classified as a top repeat heading entity, (4) a second heading entity classified as a terminal heading entity, or (5) an end of document marker.

If a document does have multiple heading styles, an entity of interest is said to be under a first heading entity if and only if the entity of interest occurs after the first heading entity and before the first occurrence of: (1) a second heading entity of a higher level style than the first heading entity, (2) a second heading entity of the same heading style as the first heading entity and the same classification as the first heading entity, (3) a second heading entity of the same heading style as the first heading entity, wherein the second heading entity is classified as a substitute for the first heading entity (e.g., the first heading entity is a lowest repeat heading and the second heading entity is a normal heading), (4) a second heading entity of the same heading style as the first heading entity and classified as a top repeat heading entity, (5) a second heading entity classified as a terminal heading entity, or (6) an end of document marker.

"User identifier": a portion of a user-view indication indicating that a specific user viewed a specific document and/or a document area. A user identifier may include, for example, a primary key to a table that includes textual information about the display user (e.g., name).

"User-view indication": an entry on a record indicating that a specific document area was displayed to a specific user. The user-view indication may also indicate that the document areas was displayed for a prespecified minimum time. This prespecified time may be zero for some situations.

"Viewing history log": A data set that can temporarily include one or more user-view indications until the user-view indications are transferred to a viewing verification data set. Even if the viewing history log were designed to track compound documents rather than individual documents, there may be a need to eventually transform the viewing history information from a virtual line number range of the compound document into an individual document area, before the information in the viewing verification data set can be used. This transforming may occur before the user-view indications are transferred to the viewing verification data set.

"Viewing verification data set": A data set that can include one or more user-view indications. Computer applications adding user-view indications to the viewing verification data set may utilize a viewing history log to accumulate, process and summarize user-view indications prior to adding the user-view indications to the viewing verification data set. A possible use of the viewing verification data set may be to prove a user either did or did not view a particular individual document area. A second possible use of the viewing verification data set may be to allow a display user to determine which individual document areas they haven't yet viewed. In this second use, the prespecified minimum time of each user-view indication may be long enough that a display user might have been able to read some significant portion of the document area and the viewing verification data set may be enhanced with such features as allowing the display user to unmark a section of a document that would not be part of a normal audit log. In the second possible use case, there is nothing that prevents designing the viewing verification data set from including tables totally separate from a normal audit log. Even if the viewing verification data set were designed to track compound documents rather than individual documents, there may be a need to eventually transform the viewing history information from a virtual line number range of the compound document into an individual document area, before the information in the viewing verification data set can be used once the compound document is closed and the display user logged out.

"Virtual line number": a single number that describes a vertical offset from the top of a document being displayed in the browser window. If the document loaded in the browser window is only an individual document, then "document" in this definition means individual document, otherwise it means a compound document.

"Virtual line number range": an expression of a document area that includes multiple virtual line numbers. The virtual line number may be calculated by (and reported by) a control that populates a browser window. If the document with virtual line numbers is a compound document, all the virtual line numbers of the compound document may have a common origin point that may need to be converted to individual document ranges.

DESCRIPTION

The invention of the present disclosure is a method of browsing documents in an EMR environment that has the advantages of (1) fitting more relevant information on the screen at one time with (2) fewer distractions to slow down the display user's comprehension of the information on the screen and (3) quicker navigation through the client's chart. The invention is executable on a desktop or handheld computer in an EMR server environment. The invention may be operated in an off-line mode by downloading an extract file from the EMR server. The communication between the computer and server is likely through a local area network or a wide area network.

In one example, the invention may be configured to fit more relevant information on a screen by using a creative way to utilize what was previously blank, unusable space on the screen. As will be shown further below, the invention can often decrease the amount of vertical space required to present many prompt and heading elements to a display user by a text line or more. The more text lines that are excluded, the more information from further down the data form that used to be off the bottom of the screen becomes visible. Therefore, more information is on the screen at a time and fewer navigation operations are required to obtain information from data forms.

In another example, the invention may be configured to eliminate elements on a screen that can programmatically be determined to be insignificant to a display user. As will be discussed further below, methods of excluding insignificant elements may include, for example, (1) not presenting data to a display user in the same format as it was originally presented to the data entry user, where unselected options do not need to be presented back to the display user; (2) eliminating heading texts when sections they introduce were skipped by the data entry user or multiple heading texts were presented together; (3) excluding certain pre-defined constant text that is presented on the screen as a flag for maintaining forms but are useless and distracting to the display user; (4) shortening certain text to be no more than a pre-specified length, while avoiding shortening text typed by the data entry user; (5) excluding parenthetical comments, again while avoiding excluding anything from text typed by the data entry user and system generated texts and values; (6) excluding unnecessary horizontal and/or vertical lines and other visual distractions.

In yet another example, the invention may include a method for converting records stored in an EMR into what resembles tabs of an internet navigation browser, with the display user in full dynamic control of the document criterion that selects which documents will appear on each page of the browser and the capability to store the configuration settings of each tab. This allows the display user to further customize which information will be displayed and scroll through rather than navigate with mouse clicks for each individual record, opening and closing each before moving on to the next.

The invention may improve the space utilization of the screen so that a larger amount of each underlying data form fits on the screen at a single time. This has an advantage when browsing the screen to review a client's chart, as there are fewer navigation operations necessary because more information was on the screen at a time.

Without being bound by any particular theory, it is believed that by formatting the answer values and the prompt text different from each other, the human eye is more quickly able to distinguish the answer values, and therefore able to more quickly assimilate and use the information. Similarly, it is also believed, without being bound by any particular theory, an answer value stated on one fewer text lines will help the human eye more quickly discern information than an answer value stated on more text lines, all other things (e.g., the text line width, font and line spacing) being equal. Similarly, it is believed, without being bound by any particular theory, that answer values left justified with each other will help the human eye more quickly discern information than answer values that are offset from each other by the width of the prompt and combining string, all other things (e.g., font formatting differences between prompt texts and answer values, formatting an answer value on one fewer lines, and minimizing the vertical height of displaying elements) being equal.

It is generally contemplated that displaying a prompt text with an unanswered field serves only to distract the display viewer's eyes when trying to quickly digest the information on the display screen and can add to the amount of scrolling necessary to view all the information on a data form.

Additionally, some prompt, heading or title texts are excessively long. For example, a terms of service disclosure form can go on for pages with little need for a display user to view the details. It is generally contemplated that once a display user is familiar with information on the data form, the display user should be able to recognize the information on the data form without seeing more than the start of the prompt or heading text.

Additionally, it is further contemplated that if a data entry user skips a section, there may be no reason to display the heading text for that section on the display, thereby further saving vertical space.

Those skilled in the art will appreciate that in an EMR, there is certain information that one generally does not want to view. For example, if a client fills out a data form with their answer values to a scored assessment instrument, it is likely that the display user would want to view only the scored results, not all the individual answer values the client filled in. Even if there were select prompt texts and answer values the display user wanted to view, those would typically be a consistent small subset of all the answers the client provides, and removing the remaining prompt texts and answer values could save significant vertical space.

Depicted in FIG. 1 is a block diagram of one example of an enterprise computing system 75. This system 75 includes an EMR system 66. EMR system 66 illustratively generates one or more user interface displays 76, 79 by using user input mechanisms 77, 80 to interact with a user (e.g., a data entry user 78 and/or a display user 81). Nothing herein is meant to imply the user input mechanisms 77 and 80 are necessarily different devices. To the contrary, they may be the same user input mechanisms, just being used at different times and these times may be separated only by a fraction of the second. Display user 81 may interact with user input mechanisms 80 to control and manipulate EMR system 66. The display user may also be the same individual as the data entry user, just at a different time, also where the time could be as small as a fraction of a second. In one embodiment, the individual may change from a display user 81 into a data entry user 78 by activating a data entry mode, and change back by deactivating the data entry mode. The same individual may also perform a different job function at different times.

EMR system 66 further includes database server 41 and EMR Software 56. The database server includes a database processor 42, and a data store 43. Data store 43 may store, for example, entities 44, processes 45, workflows 46, forms 48, and other EMR system records and/or data 47. Entities 44 may further include form entities 48 and other entities. Form entities may further include data form design entities 49 and form document entities 53 to store answer entities 55 that may be submitted by a data entry user 78. Data form design entities 49 may further be divided into title entities 50, heading entities 51, prompt entities 52, lookup entities 39, and other item entities 40 such as horizontal lines and extra blank space. The prompt entity 52 may include the style and formatting of the expected answers. Data store 43 stores the data associated with the EMR system 66. Further, EMR Software 56 may include, among other items 65, EMR functionality components 57, data filtering system 58, visualization system 61, and the like.

Entities 44 illustratively represent various entities that may be defined within the EMR system 66. Some of the various types of entities that other entities 38 may represent include: an appointment entity, a staff entity, and a client file entity. An appointment entity may describe and define an appointment. A staff entity may describe and define a therapist, medical doctor, and/or front desk worker. A client file entity may describe and define a history of documents, lab reports, evaluations, medications supplied, allergies, and so forth. Those skilled in the art will appreciate that this is a non-limiting set of example entities, and that various other entities may also be used without departing from the scope of the present disclosure. In addition, while the present discussion proceeds with respect to some EMR system records being described as entities, they can be other types of EMR system records as well.

Forms 48 illustratively represents various data (e.g., data form designs 49 and form documents 53) within data store 43, and may be used as a mechanism by which to present the data on a user interface display 76, 79 to a data entry user 78 and/or a display user 81. In some examples, forms 48 may include entities 44 and other data records, and may also include a wide variety of controls, such as text fields, buttons, check boxes, links, icons, navigation elements, etc. Included in these controls may be properties such as the X/Y position for the start of the control on the screen, whether or not the control is visible, the height of the control, the width of the control, etc.

EMR system functionality components 57 illustratively runs various processes 45 and workflows 46, using the data stored in data store 43, to enable a data entry user 78 and/or a display user 81 to perform tasks on the EMR system 66. These EMR system functionality components 57 may be selectively chosen based on the needs of any particular organization deploying the EMR system 66. For example, if the EMR system 66 is being deployed by a medical office, EMR functionality components 57 that may be necessary or otherwise useful for such an organization may include scheduling applications, inventory tracking applications, external provider interaction applications, various audit tracking applications, and the like.

Data filtering system 58 illustratively includes un-responded prompt filter entity component 59, excluding document component 60, heading filter component 67, tab filtering component 68, and other items 69 as well (e.g., document criterion). Un-responded prompt filter entity component 59 may provide and control a process that excludes prompt entities 52 from the data that is returned from the data store 43 during instances when the data entry user 78 did not respond to a prompt entity 52. Excluding document component 60 may exclude whole documents 53 from data returned from the data store 43 that contains specific attributes which may be found in document attributes 54, entities 44 (e.g., staff, client or appointment entities), etc. Heading filter component 67 may analyze documents 53 to find and exclude certain heading entities in their entirety from documents 53. Tab filtering component 68 may select which documents 53 will be included on a tab based on selection attributes 54.

Visualization system 61 may generate user interface displays 76, either by itself, or under the control of other items in EMR system 66, and may include a hiding document component 62, a text conversion component 63, a parenthetical comment component 64, a tab configuring component 70, a constant text component 71, a shorten text component 72, and other items 73 as well. The hiding document component 62 may select which documents 53, amongst the documents 53 that have already been selected, will be visible on a tab based on hide document criterion which matches selection attributes 54, entities 44 (e.g., staff, client or appointment entities), etc. The text conversion component 63 may change prompt entities 52 and their respective answer entities 55 into a text format allowing the characters to be more efficiently positioned on the screen, such that more text may appear on a single page of the screen compared to previously available systems. The text conversion component 63 may exclude everything except title entities 50, heading entities 51, prompt entities 52 and answer entities 55, so that other item entities 40 (e.g., extra output lines and spacing) do not appear on the page even if the other items 40 are encoded into the data form design 49. The parenthetical comment component 64 may exclude from the data returned from the data store 43, the characters between parentheses in headings 51, prompt entities 52, and lookup entities 39. The tab configuring component 70 may select which selection attributes 54 will be active to choose document entities 53 to include, hide and exclude from tabs. The constant text component 71 may exclude from the data returned from the data store 43 pre-specified strings from heading entities 51, prompt entities 52 and certain answer entities 55. The shorten text component 72 may trim from data returned from the data store 43 any text beyond a pre-specified maximum length from heading entities 51, prompt entities 52 and certain answer entities 55.

Figure 2:
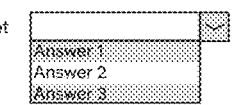
FIG. 2 is an overview table depicting example methods of changing various styles of prompt and answer fields into converted text equivalents.

Referring to FIG. 2, overview table 100 shows common types of prompt and answer fields (each involving a prompt immediately followed by an answer). A data entry user may respond to each prompt field by entering user input (e.g., text, a selection, etc.) [via the data entry user interface 76] into the answer field of an answer. Depending on the prompt and answer restrictions, the answer field may include one or more pre-populated answer values for the data entry user to select and/or one or more [means] for the data entry user to input an answer value of his/her choice. The quantity and arrangement of answer values in an answer field is dictated by a style 3912 of answer restrictions. In other words, the style 3912 of answer restrictions dictates what format the user input must be provided in. If the data entry user has not provided user input (e.g., text, a selection, etc.) to an answer, then that answer is considered to be "empty" (i.e., an "empty answer"). As shown, the left column 130 of the overview table 100 provides the name of each style 3912; the middle column 132 shows how the prompt text and answer fields might appear after a data entry user has entered user input; and the right column 134 shows an example, for each style, of how the prompt text and the answer might appear as converted text. Referring specifically to the right column 134, the prompt text is shown in regular text (e.g., non-bolded) with the answer value in bold; the combining string is a colon (":") followed by a space; and the concatenation string is a space followed by a vertical bar ("|") followed by a space.

The fonts (e.g., font name, boldness, italics, color) and paragraph characteristics (e.g., indentation, hanging indents, text line spacing, paragraph spacing) for each type of element (e.g., title, heading text, prompt text, and answer value), the combining string and the concatenation string are typically options set by the display user, and may vary without departing from the scope of the present disclosure.

Multi-select check boxes 102 may be changed to converted text by presenting the prompt text (in the user defined prompt attributes), followed by the combining string, then each selected answer value (in the user defined answer attributes) with the concatenation string between them. If there is only one selected answer value, then there may be no concatenation string.

Single select option groups 104 may be changed to converted text by presenting the prompt text (in the user defined prompt attributes), followed by the combining string, then the selected answer value (in the user defined answer attributes).

Combo boxes differ only from multi-select dropdown lists 106 in that the latter allows selecting multiple answers. However, it is possible to answer a multi-select dropdown list 106 as if it is just a combo box by only selecting one answer. Combo boxes and multi-select dropdown lists 106 may be changed to converted text by presenting the prompt text (in the user defined prompt attributes), followed by the combining string, then each selected answer value (in the user defined answer attributes) with the concatenation string between them. If there is only one selected answer value, then there may be no concatenation string.

Free text boxes 108 differ only from edit boxes in the length of the expected answer value. Free text boxes 108 and edit boxes may be changed into converted text by presenting the prompt text (in the user defined prompt attributes), followed by the combining string, then the answer value (in the user defined answer attributes).

Likert groups and numeric fields 110 are two example methods of selecting numbers. Likert groups and numeric fields 110 may be changed into converted text by presenting the prompt text (in the user defined prompt attributes), followed by the combining string, then the number (in the user defined answer attributes). It may also be desirable to look up the scale being used in Likert groups and augment one or more values with text the data entry user was prompted with, resulting in such converted text as "Prompt: 1 (Completely disagree)" or "Prompt: 9 (Agree completely)".

Yes/No fields 112 may be changed into converted text by presenting the prompt text (in the user defined prompt attributes), followed by the combining string, then the selected value (in the user defined answer attributes).

Dates may be displayed in many different formats (e.g., standard date 114, "Jul. 1, 1990", "Jul. 1, 1990", "Jul. 1, 1990", etc.). To show a date prompt text with a related answer field in converted text, the prompt text (in the user defined prompt attributes) may be followed by the combining string and the date (in the user defined answer attributes) using whatever date format the display user has selected for dates (e.g., by an operating system setting).

It is also possible to have a field that includes generated information as part of the answer value, such as a date with age calculation 116 that uses the identical formatting for the fields. In this case, it may be necessary to flag one or more optimizations that may exclude characters within all non-data entry user typed parenthetical comments (discussed below) that such processing should ignore this field. One example of a method for doing so includes using a placeholder as a substitute for rounded parenthesis (e.g., using square parentheses in one or more embodiments). This is because the placeholder (e.g., square parentheses) may not be recognized as the usual curved parentheses by the present invention. The other processing (such as excluding characters within all non-data entry user typed parenthetical comments or system generated text and values) may then be performed. If rounded parentheses are desired in the final display, the placeholder can be converted back to rounded parenthesis after completing the optimization that may exclude characters within parenthetical comments. In other examples, the field may be evaluated to determine if the field is a computed field (as shown) before excluding parenthetical comments, and if so, skip excluding the parenthetical comments.

Individual check boxes 118 may be changed into converted text by displaying the prompt text (in the user defined prompt attributes), followed by the combining string, and then the answer value (in the user defined answer attributes). If there are more than one individual check boxes, then each check box may have its own prompt-answer pair. If the data entry user 78 did not select an individual check box 128, then the prompt text with related answer value may be omitted from the displayed text.

In one or more examples, it is also possible to have an individual check box without a prompt 126, which may correspond to the converted text 120 shown. A field with the answer value following the user interface control (e.g., checkbox 124) may have an identical conversion appearance (e.g., display value 122) as the answer value before the user control. There may be an answer field when there is a check box, even if the prompt text is empty. If the prompt text is empty (e.g., missing prompt 136), there is no need to have a combining string (e.g., display value 122) and there is nothing to format in the user defined prompt font attributes (prompt paragraph attributes may still apply to the answer value). The answer value is still formatted using the user defined answer attributes.

In general, regardless of whether the prompt text occurs first, or the answer field occurs first, or the prompt text is above the answer field, or the answer field is above the prompt text, or the answer occurs before the user control, or the answer occurs after the user control, the same converted text is generated (e.g., prompt text 124 and prompt text 126 both resulted in the same format of converted text result).

Figure 3A:
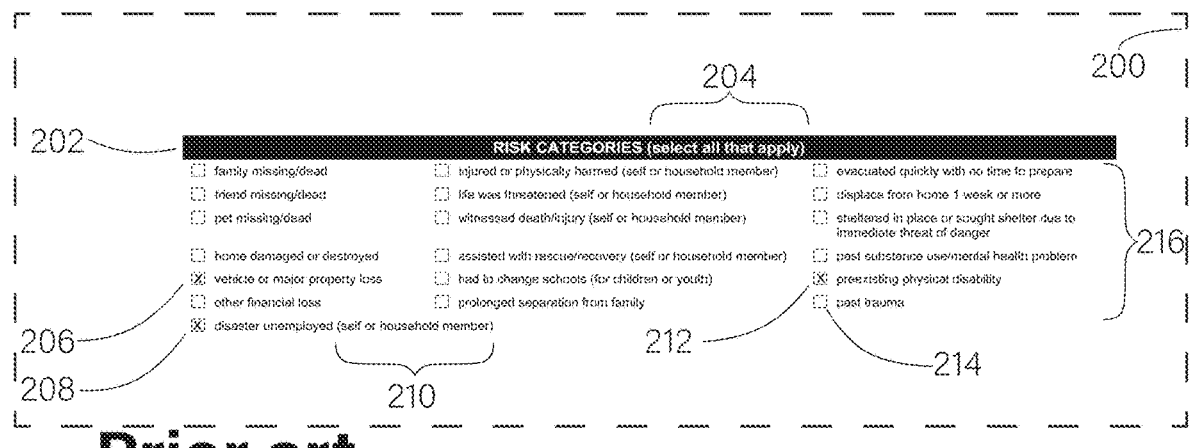
FIG. 3A is an example of a typical multi-select check box.

FIG. 3A depicts an example of how a typical EMR would display a multi-select checkbox 200, which is a type of prompt and answer format, to a user (e.g., a data entry user and/or a display user). The prompt text of the multi-select checkbox 200 has a text 202 with parenthetical comment 204 "(select all that apply)". The answer includes 19 possible selectable answer values in the answer field 216.

In a typical display user interface display, both the prompt text 202 and the answer field 216 would be shown as displayed in FIG. 3A (e.g., identical to the data entry user interface). In this example, there are three selected options 206, 208, and 212 chosen by the data entry user and multiple unselected options (e.g., option 214). A parenthetical comment 210 is shown in the answer field. The total height of the prompt text 202 and answer field 216 in this format is 9 text lines.

Figure 3B:
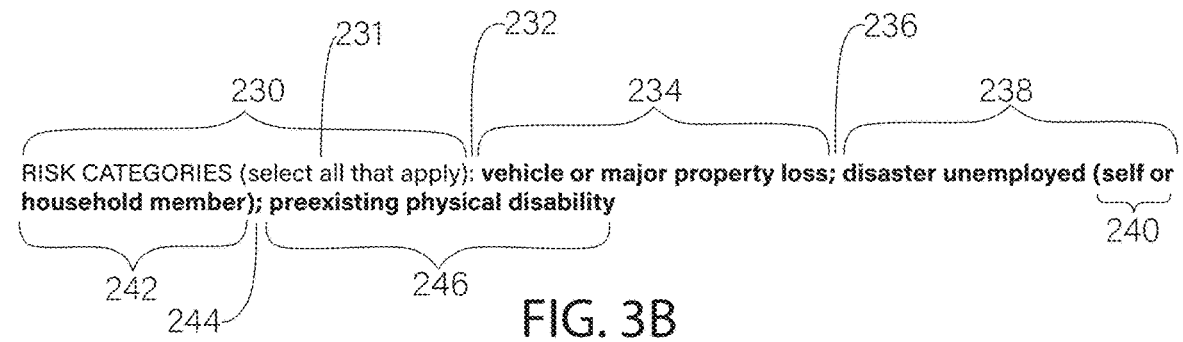
FIG. 3B is a first example of a conversion of the multi-select check box of FIG. 3A.

FIG. 3B shows an embodiment of converting the 9-text line display of 3A into just 2 text lines of converted text. The multi-select checkbox 200 has been changed to a converted text by applying user defined prompt attributes to the prompt text 202 and concatenating the following to it: (1) the combining string 232, (2) the first answer value 234 in user defined answer attributes plus the concatenation string 236, (3) the second answer value 238 plus 242 similarly formatted plus another concatenation string 244, and (4) the third answer value 246 similarly formatted.

Figure 3C:
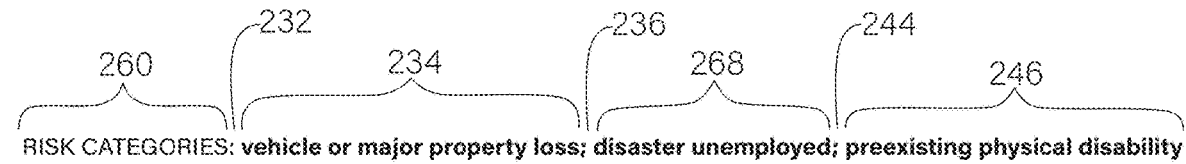
FIG. 3C is a second example of a conversion of the multi-select check box of FIG. 3A excluding parenthetical comments within fields.

Notably, the parenthetical comment 204 in FIG. 3A may either be retained (e.g., in the converted prompt text 230 of the full text conversion of FIG. 3B) or excluded (as will be shown in FIG. 3C). These parenthetical comments may be employed to provide instructions that may assist/instruct the data entry user in responding to the prompt text. Other examples of such instructions may include, for example "(select the top 3 answers)" or "(include subjective and objective info)". For the purposes of the display user 81, these instructions can be excluded from the prompt text without changing the meaning of the prompt text, especially if the display user is familiar with the data form as presented to the data entry user. This translates to fewer words on the screen, which means there may be fewer on-screen distractions to slow the display user's eye from discerning the actually important information on the screen.

Without being bound by any particular theory, it is also believed that by applying separate, application wide user defined attributes to prompt and answer texts, the display user's eye may gravitate to the answer value rather than the prompt text in a way that is tunable to each display user's perceptions, while also keeping the display user oriented to where they are within the document. For example, if a display user determines that light blue prompt text in normal text and bold black answer text in the same font help them see the answers quicker, the display user can set that up in a user application wide setting. If another display user determines that the ideal prompt text for that user is 10 pt Arial Narrow in black and the ideal answer text is 11 pt Arial in bold black, the display user can set it that way. Then, everywhere prompt text and answer text are shown, they will be in their respective fonts and colors for the display user.

Also, the fewer the characters on the screen, the higher the chance of decreasing the quantity of text lines to display the same information, resulting in fewer navigation operations to view an entire document (e.g., data form) or client chart.

There is also a parenthetical comment (240 plus 242) in the second answer value (238 plus 242). Parenthetical comments within potential answer values presented to a data entry user typically help a data entry user 78 discern the bounds of the option by further defining the answer value. But if a display user 81 is familiar with the data form presented to the data entry user 78, the parenthetical comment can be excluded from the answer value for the display user 81. Two exceptions to this rule are: (1) if the parentheses are something that the data entry user typed or (2) the field is in a format that includes some system generated information (such as an age in a date with age calculation 116 field). Furthermore, if a data form designer knows that a display user 81 may need to see any parenthetical information, the data form designer can avoid triggering excluding parenthetical comments by using a placeholder character for the parenthesis or the EMR manufacturer may include a flag that indicates the current field may not have parenthetical comments removed.

FIG. 3C shows another converted text of FIG. 3A but excluding parenthetical comments. In doing so, the same answered prompt field may be shortened by an additional text line, depending on the user defined attributes and the screen size. The prompt text 260 is created by excluding parenthetical comment 204. Similarly, the converted answer value 268 is created by excluding parenthetical comment 210. In an embodiment, a marker may also be left in the field to indicate to the display user 81 that a parenthetical comment had been excluded, such as using "RISK CATEGORIES ( )" for prompt text 260.

As those skilled in the art will appreciate, creating a formatted string, as in FIG. 3C, where one part of the string has one format (e.g., the regular font of texts 260 and 232) and the next portion of the string has a different format (e.g., the bold font of texts 234, 236, 268, 244 and 246), one or more additional encoding strings may be inserted into the underlying string to mark the change. These encoding strings do not appear on the screen (e.g., the characters themselves do not appear and there is no blank space on the screen where the characters appear in the underlying string, they are completely invisible), but encoding strings change the font characteristics. For example, the HTML of FIG. 3C might be "RISK CATEGORIES: <b>vehicle or major property loss; disaster unemployment; preexisting physical disability</b>". In which case, the count of characters in the underlying string (e.g., HTML) has seven more characters then just the count of characters visible on the screen (e.g., the characters "<b>" and "</b>" are added). This same general principle is true of other formatting methods of encoding strings (e.g., RTF), additional invisible characters may be added in the underlying string to mark the font switch. In RTF, there is also additional characters in the document header to specify each font name being referred to by each encoding string.

FIG. 4A depicts an example of a single select option group. Included are the prompt text 302, selected item 304 and unselected option 308 (which may be representative of other unselected options). Ideally, an answer field 306 may be enhanced by changing the wording slightly to take full advantage of the present disclosure, such as by rewording the text as "temporary home with minor children (check this box for a temporary home with children under age 18 in the home)". This would allow excluding parenthetical comments to shorten the text for display user 81. Of course, in doing so, it is generally contemplated that appropriate checks/protocols should also be in place to ensure that the new prompt text completely reflects the intention of the original prompt text.

FIG. 4B shows a text conversion of the information shown in FIG. 4A. The converted text 320 is calculated by concatenating the original prompt text 302, the combining string 322, and the answer value of the selected option 304 (yielding answer value 324), each potentially with their own current user defined prompt attributes. In doing so, the approximately twelve text lines of FIG. 4A was shortened to two text lines, thereby requiring significantly less scrolling to read the client chart.

FIGS. 5A and 5B depict examples of what a data entry user and/or a display user may see in an answered free text box using existing EMR systems. Referring specifically to FIG. 5A, the field includes a heading text 402, a prompt text 404 and an answer field 408. This specific prompt text 404, also includes a parenthetical comment 406. The total height 410 and total width 412 of this specific field are shown. Referring specifically to FIG. 5B, a typical print out from an EMR is shown (e.g., as a display user might see it). The printout includes a heading text 424, a prompt text 404, and an answer value 422. The total height 428 of this format presentation is similar, or slightly less than the height 410 of the original field. Even if the heading 424 was changed to a single line of bolded text, the height would still be 4 lines tall. FIG. 5C depicts an embodiment of the process of the current invention that may be generated from the data shown in FIG. 5A.

Notably, the prompt and answer pair shown in FIGS. 5A and 5B includes unused space 426 defined by the blank areas proximate (e.g., at or near) the text lines of text. Those skilled in the art will appreciate that unused space 426 may be representative of other areas of unused space common to most data presentation formats (be it for EMR documents or otherwise). By employing the process of the present invention, it is possible to utilize the unused space 426, often saving at least one text line to fully reproduce the text of the field (i.e., prompt and answer text).

Further, in one or more examples, the process may also be employed to find text that can generally be excluded safely with minimal impact on the completeness of the information presented on the screen. Since, in the English language, parenthetical comments are generally employed to explain, clarify or qualify something, it is generally contemplated that leaving out the parenthetical comments that are part of the basic data form should still present a substantially complete data form to a display user 81, especially one who is familiar with the form from prior use.

On the other hand, not all parenthetical comments can be excluded. If the data entry user 78 typed the parenthetical comment, the parenthetical comment must be left in because it explains, clarifies, or qualifies something the data entry user 78 wanted to communicate to the display user 81. Secondly, there may also be some computer-generated information with a format that uses parentheses, such as a date with age calculation 116 field, day of week calculation, etc. In both these situations, the parenthetical comments should not be excluded.

Referring to FIG. 5C, heading text 430 is computed from heading text 402 by applying the user defined heading attributes for font and paragraph. Prompt text 432 is what remains of the original prompt text 404 after excluding the parenthetical comment 406 at the point where the parenthesis began 434. The output string continues with the user defined combining string 436. The converted answer value 438 is the answer field 408 with the user defined answer attributes. Notably, the total height 440 of the converted version is at least one text line less than either the height 410 of the field presented to the data entry user or the height of a printout 428 because it made use of the previously unused space 426.

FIG. 6A depicts an example of what a data entry user 78 or display user 81 would normally see when viewing an answered multi-select text box using existing systems (e.g., currently employed EMR systems). FIG. 6B shows an alternate view of the same for a display user when previewing a printout. The current example includes a prompt text 452 and three selected answers (option 454, option 456 and option 458). The field has a total height 460 and a total width 462, and includes three horizontal lines. The first horizontal line 464 separates the current prompt text 452 from the previous question, the second horizontal line 466 separates the prompt text 452 from the potential answer options, and the third horizontal line 468 marks the end of the options.

FIG. 6B shows a typical printout from an EMR, as a display user 81 might see it. On the successive text lines following the prompt text 452 are the texts of the various answers selected (option 454, option 456 and option 458) each prepended with a tick mark to indicate a separate answer value to the current prompt text 452. While the vertical alignment of the answer values helps the display user determine where each answer begins and ends, it wastes a lot of space. This unused space 470 is caused by the format of the display, and may be representative of other unused spaces common to most documents, including EMR documents.

FIG. 6C shows an embodiment of a conversion, generated in accordance with the present invention, of the data shown in FIG. 6A. The prompt text 478 shows the prompt text 452 after applying the user defined prompt attributes. More specifically, the prompt text 478 is appended by the user defined combining string 480 (e.g., a colon followed by a space) and the first option selected 482 is formatted using the user defined answer attributes. Note that the selected answer option 454 ended with a parenthetical comment. The place 484 where the parenthetical comment "(platea)" was excluded, is shown. The other two selected answers (option 488 and option 492) are appended by user defined concatenation strings 486 and 490 between each. Both of these are also displayed using the user defined answer attributes. The total width 496 (which is the same size as the original width 462), and total height 494 are also shown.

The horizontal lines of the data form design 49 fit into the subcategory of non-textual design of the other entity 40 and since they are neither a title text, a heading entity, a prompt entity, nor an answer entity are excluded from being incorporated.

Note that the prompt-answer pair of FIG. 6A has a total height 460 of approximately 6 text lines, prompt-answer pair of FIG. 6B has a total height 472 of 4 text lines, and the prompt-answer pair of FIGS. 6C-6D has a total height 494 (or 510 for FIG. 6D) of only 2 text lines to display the same content. Both the total width 462 of the prompt-answer pair and the total width 496 of the prompt-answer pair are identical. The amount of space used up by the selected fonts in this example is larger in FIGS. 6C-6D than in FIG. 6B because bold proportional fonts occupy more space than non-bolded versions of the same font. Even with the wider, more readable font of the answer value in FIGS. 6C-6D, the invention of the present disclosure takes fewer text lines to display the same text than would have otherwise been required (e.g., using existing systems). The result is that more information is now able to fit on the screen because there may be more space available for additional rows that were previously lower than the bottom of the display screen.

Whenever the height of a prompt-answer pair is greater than 1 and the converted answer value is composed of multiple selected answers combined together with concatenation strings, there is the chance that the converted answer value can be split in such a way that the prompt-answer pair is no taller than otherwise required, but at least one individual selected answer is displayed on one fewer line(s).

Without being bound by any particular theory, it is believed that if the vertical height is not increased by displaying one option on one fewer line(s) (and if possible, then vertically aligned), the human eye will more quickly discern each option. FIG. 6D shows an optimization of FIG. 6C where the horizontal position 506 of the start of the first character 504 after the combining string 502 is noted. If the vertical height 494 of FIG. 6C was greater than 1 line then, an alternate concatenation string may be tried which appends a carriage return to the global concatenation string. Starting at the last concatenation string 490, the alternate concatenation string is substituted for each concatenation string, one concatenation string instance at a time, until one is found that results in the same total height 510. If that substitute causes one answer option in the converted answer value to appear on one fewer line(s) without increasing the total height 510, that becomes the new concatenation string for that specific instance. Then, if the total height 510 is two, a check is made to see if the second line can fit between horizontal position 506 and right boundary 514 (e.g., fit into space 512 without adding an additional line); and if so, the second line may be adjusted to start at horizontal position 506; otherwise, the second line remains at left boundary 508.

Figure 7A:
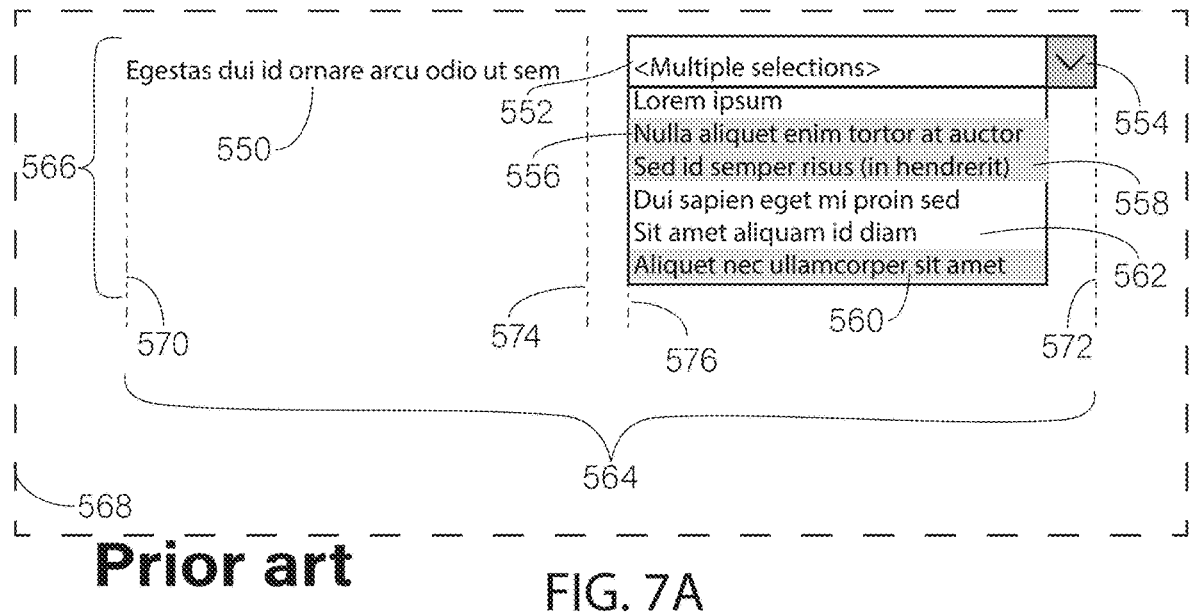
FIG. 7A is an example of a typical multi-select dropdown list.

FIG. 7A depicts an example of what a data entry user or display user would typically see in an answered multi-select dropdown list, using existing systems (e.g., currently employed EMR systems). The prompt text 550 is shown. The answer field 552 includes the available options that may be selected and viewed. The answer field 552 has a hotspot 554 to toggle dropdown viewing. In this example, the three selected answers (option 556, option 558 and option 560) and a sample unselected option 562 is demonstrated. Shown is the left boundary 570 and right boundary 574 for the prompt text area, and the left boundary 576 and the right boundary 572 for the answer value area. The total height 566 and total width 564 of the multi-select dropdown are also shown.

Figure 7B:
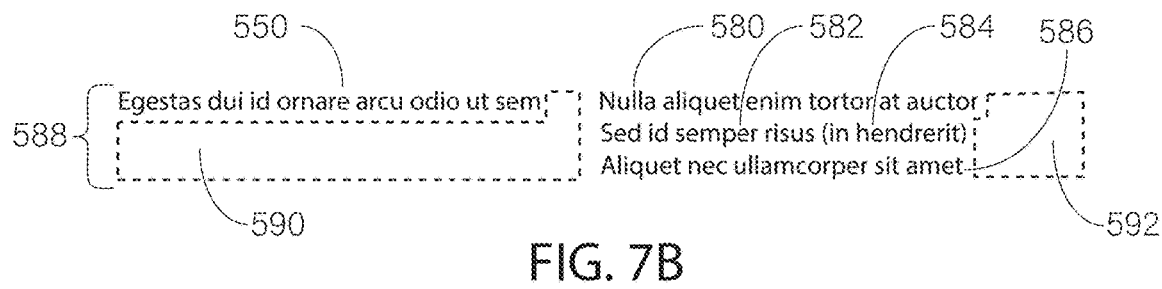
FIG. 7B is an example of what a display user may see in a printout on paper after completing the multi-select dropdown list of FIG. 7A.

FIG. 7B shows a hypothetical printout from an EMR, as a display user 81 might see it. The three selected answers (options 580, 582 and 586) corresponding to the three selected answers (options 556, 558 and 560) of FIG. 7A are shown with one parenthetical comment 584 within these selected options. Also shown is prompt layout cell 594 with its layout cell width 595 and answer layout cell 596 with its layout cell width 597. The total height 588 is shown, as are the prompt and answer text areas which cannot be used for displaying text (unused space 590 and unused space 592).

Figure 7C:
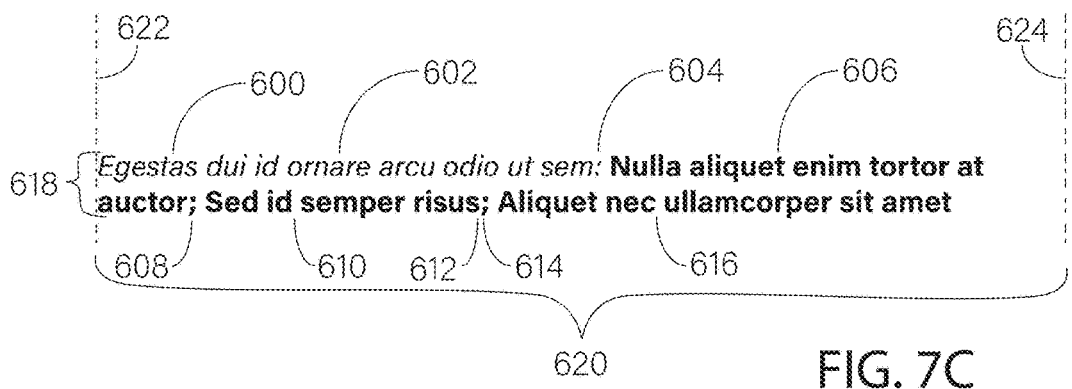
FIG. 7C is an example of an optimized conversion of the multi-select dropdown list of FIG. 7A.

FIG. 7C shows a line of converted text generated using the process of the present disclosure for the data shown in FIG. 7A. The converted field 600 is a concatenation of: (1) the prompt text 602 using user defined prompt attributes and has the user defined combining string 604 appended; (2) the first converted answer value 606 formatted using the user defined answer attributes; (3) the user defined concatenation string 608; (4) the second converted answer value 610 in the same format; (5) the second user defined concatenation string 614; and finally (6) the third converted answer value 616 in the same format. The second converted answer value originally included a parenthetical comment 584 that was excluded at point 612 since it was not typed by a data entry user 78 and is not part of a computed field format. The height 618 of this answered prompt field easily fits into just 2 text lines, even with a larger, more readable, font.

Another issue that is illustrated in FIGS. 7A-7C is the calculation of absolute horizontal boundaries. Comparing left boundary 570 and left boundary 576, it turns out the furthest-left boundary is left boundary 570. Comparing right boundary 574 and right boundary 572, it turns out the furthest-right boundary is right boundary 572. The furthest-left boundary and the furthest-right boundary collectively define a pair of absolute horizontal boundaries. Thus, the absolute horizontal boundaries, in this case, run from left boundary 570 (i.e., left boundary 622) to right boundary 572 (i.e., right boundary 624). The total horizontal space allowed when the prompt with related answer field is laid out is the total width 564, which is the same as total width 620.

Alternatively, the absolute horizontal boundaries can be obtained from the width of the set theory union of the prompt layout cell 594 and its related answer layout cell 596. Note that once the two cells are combined between the absolute horizontal boundaries, the height the cell combination is adjusted to the minimum height required for the text to be displayed (including any padding the layout cell requires below the text).

Figure 8A:
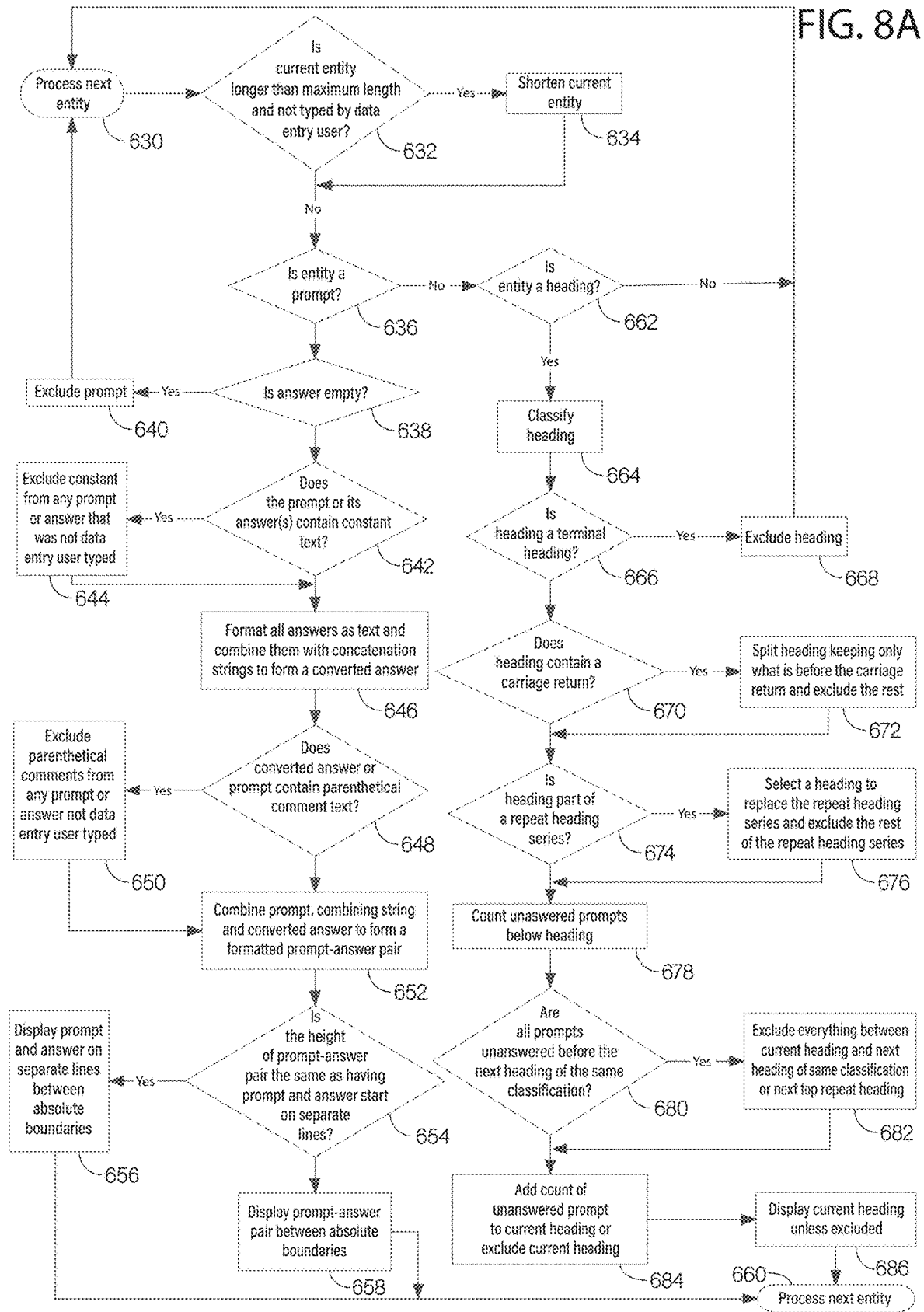
FIG. 8A is a high-level flow diagram illustrating how to process each individual entity in a document.

Referring to FIG. 8A, depicted is a flow diagram showing a possible ordering of the various processing of prompt entities and heading entities that may be performed within each document. This is an overview of FIGS. 2-23. For a higher-level view that includes whole document processing, see FIG. 25A and its accompanying text.

The process for each entity starts with step 632, where two checks are made. First, a check is made if the text of the current entity is longer than a pre-specified maximum length. If so, a second check is made to determine if the data entry user typed this text. Whenever a determination is made that the text of the current entity is too long and the text was not typed by the data entry user, step 634 shortens the text. FIGS. 12-18 and their accompanying text and steps 790, 792, 924, 3905, 4055 and 8409 further describe and illustrate steps 632 and 634.

Steps 636 checks if the current entity is a prompt entity and, if so, control passes to step 638. Step 638 checks if the current prompt entity is an unanswered prompt entity or the prompt entity is otherwise previously excluded (e.g., from processing of steps 672, 676 or 682), and if so, it is excluded from being displayed in step 640. Steps 1271, 1295, 1413, 3971, 3973, 4017, 4021 and 8411 further describe steps 638 and 640.

Step 642 checks if the current prompt entity or an answer to the current prompt entity contains certain pre-defined characters, possibly at a location (e.g., at the beginning, at the end, in the middle, or anywhere). If the predefined text is found, then a secondary check is made to verify that the data entry user did not type the text. If both conditions are met, the pre-defined characters are removed from the prompt or answer text in step 644. Steps 786, 788, 904 and 8409 further describe steps 642 and 644.

Step 646 combines all the answer entities to the current prompt entity into a single converted answer value by converting each into text (if they are not already so formatted) and combining all the individual texts together with concatenation strings between them. FIGS. 2, 3B, 4B, 6C, 6D, 7C, 31D and their accompanying text, steps 702, 3975, 3979, 3981, 8403 and process 750 further describes and illustrates step 646.

Step 648 checks if the current prompt text or the converted answer value contains a parenthetical comment that was not typed by the data entry user, and is not a computed answer. If so, step 650 excludes the parenthetical comment from being displayed. Steps 268, 782, 784, 902, 906-922, 4067 and 8405 further describe steps 648 and 650.

Step 652 combines the current prompt text and converted answer value together with a combining string between the two into a prompt-answer pair by applying the user defined prompt and answer attributes. This process may also add encoding strings to the final underlying string required to format the prompt text differently than the converted answer value. This may result in the underlying string having more characters than the string length for the visible characters plus spaces, tabs, carriage returns and line feeds would compute. FIGS. 2, 3B, 4B, 50, 6C, 6D, 7C, 31A, 31G and their accompanying text and process 700 further describes and illustrates step 652.

Step 654 is an optimization of the normal process of displaying the prompt-answer pair. If it takes the same amount of vertical space to display the prompt-answer pair as it would to display the prompt text (with the combining string) on one line and the answer on the next line, then secondary considerations could be taken into account such as a rule to display each entity or individual answer on as few of lines as possible. If the optimization works for this specific case, then step 656 displays the prompt text on one line and the answer text on the next line. If the optimization does not work, then step 658 displays the prompt-answer pair calculated in step 652. Steps 704-738 and FIGS. 6D, 31G-31H and their accompanying text further describe and illustrate steps 654-658.

Step 660 processes the next entity in the current document beginning at step 630. If there is no next entity in the current document, the next document may be processed (not shown in FIG. 8A). If there is no next document, the process is complete (not shown in FIG. 8A).

If step 636 determines that the current entity is not a prompt entity, step 662 checks if the current entity is a heading entity. If step 662 recognizes a heading entity, the heading is termed the heading entity of interest and step 664 classifies the classification of heading. Step 1269, process 1325, and FIGS. 19C-19H and its accompanying text describe and illustrate a few approaches to classifying headings.

Step 666 checks if the heading entity of interest is a terminal heading or if the heading is marked as excluded (e.g., as one possible implementation of steps 672, 676 or 682), and if so, step 668 excludes the heading entity of interest. Processing then resumes with the next entity. Steps 666 and 668 is further described in steps 1273, and 1297.

Step 670 is an optimization that checks if there is a carriage return in the heading entity of interest after a predetermined minimum quantity of characters (e.g., a user settable variable), and if so, step 672 splits the heading entity of interest into two headings, keeping only the first portion as the heading entity of interest. The remaining heading entities may be marked excluded or otherwise suppressed from being displayed. Step 1279 further describes steps 670-672.

Step 674 checks if the heading entity of interest is part of a repeat heading series (e.g., a top repeat heading, a repeat heading or a lowest repeat heading). If so, step 676 chooses text to replace all the elements in the series and the remaining elements in the series are marked as excluded or otherwise suppressed from being displayed. Steps 4053 and 4059 further describe these steps 674-676.

Step 678 is an optimization that counts the quantity of prompt entities under the heading entity of interest to determine if any answered prompt entities exist within the heading entity of interest's scope. This step is further illustrated or described in steps 1293 and 1297, and FIG. 19D-19G and its accompanying text.

Step 680 checks if all the prompt entities under the heading entity of interest are unanswered prompt entities. If so, step 682 excludes everything between the heading entity of interest and the next such identified heading entity. The heading entity of interest may be flagged that it is subject to flagged special processing (described elsewhere and illustrated here by the addition of text to the heading text indicating that a complete section was skipped by the data entry user, as in step 684). This step is further described and illustrated in steps 1271-1273, 1293, 1297, 1669 and FIGS. 19D-19H, 20-23.

Step 684 is an optimization that adds a count of the quantity of unanswered prompts under the heading entity of interest. This step is further described in steps 1293 and 1297.

Step 686 displays the heading entity of interest provided it has not been excluded in steps 672, 676, 682, or 684.

Figure 8B:
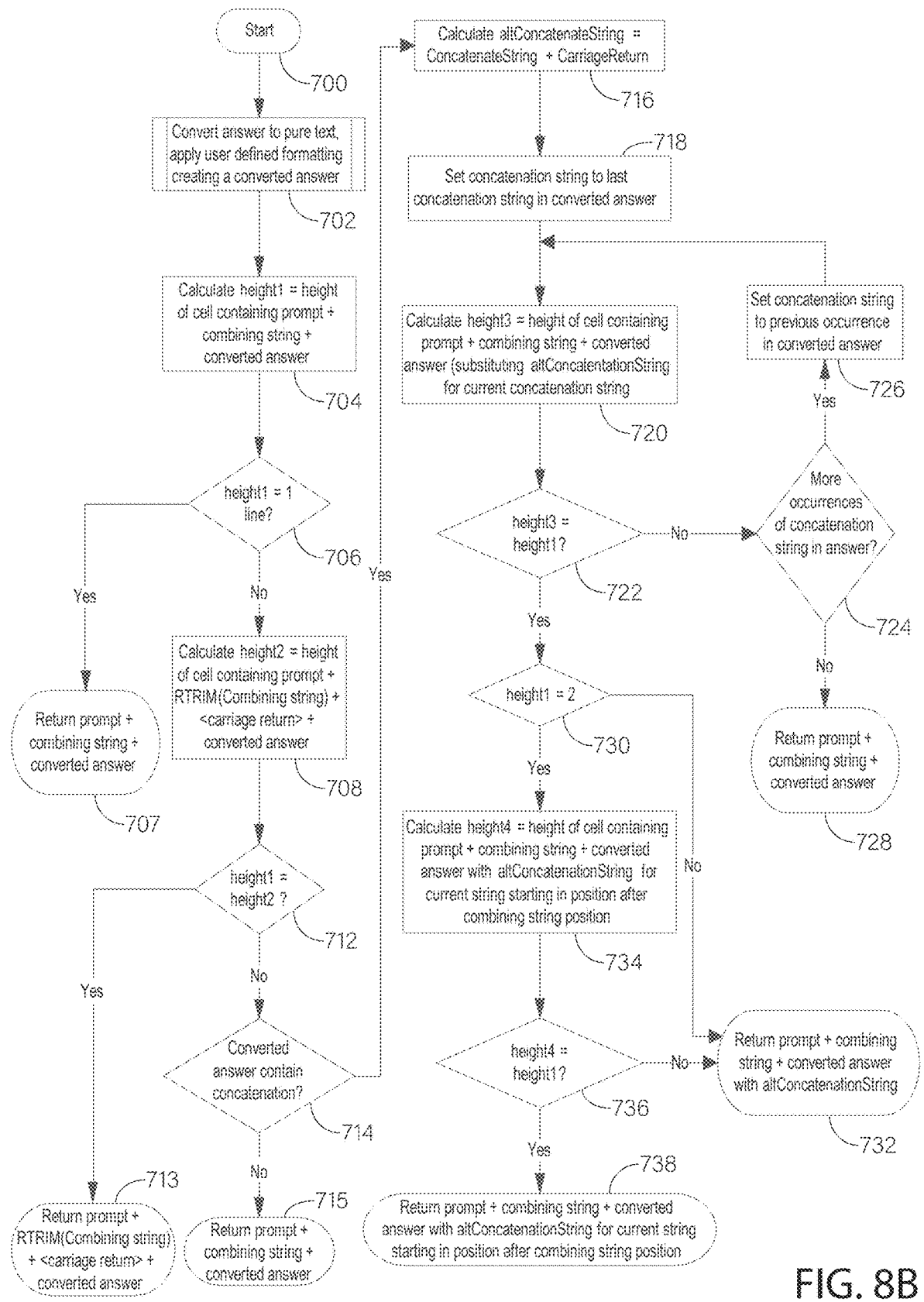
FIG. 8B is a flow diagram depicting how to convert an answer entity into converted text while optimizing keeping text together.

Referring to FIG. 8B, depicted is a flow diagram illustrating one example method of converting the prompt and a related answer (i.e., the answer to the prompt) into a prompt-answer pair. Step 700 is the start. This function is passed a prompt, a list of answers, and the width of the prompt and answer field (i.e., the width of the absolute horizontal boundaries).

Figure 8C:
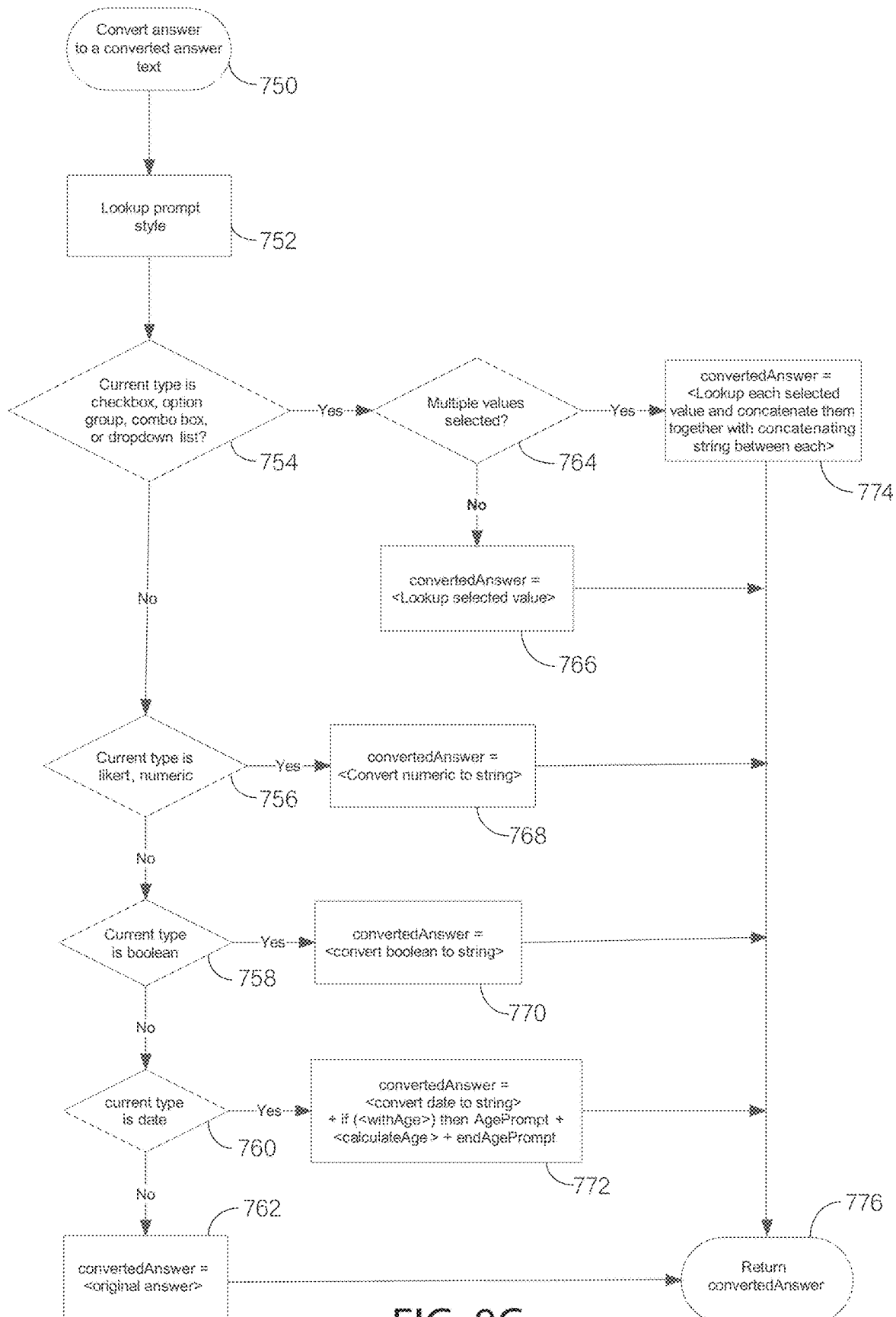
FIG. 8C is a flow diagram depicting how to convert an answer entity into a text string.

Step 702 converts the list of answers into a converted answer value by calling the function in FIG. 8C. It then applies the user defined answer attributes to the value return from FIG. 8C, creating the converted answer value. Steps 704, 708, 720, and 734 represent various optional optimizations of the return string.

Step 704 calculates the height of the prompt text with the converted answer value. This step starts by computing the full string, by adding together: the prompt text (in the user defined prompt attributes), the combining string, and the converted answer value (in the user defined answer attributes). The full string can then be passed to a system provided function that takes a formatted string and a width and returns the height. If such a function is not provided by the system, the following procedure may be performed: dynamically create a system generated rich text box; set the display width of the box to the width that was passed to Step 700; insert the full text of the prompt text (in the user defined prompt attributes) and the combining string with the converted answer value (in the user defined answer attributes); and then check the height of the box to obtain the height to report.

Step 706 compares the value calculated in step 704 to the height of one text line. If the calculated value is not greater than one text line, then there is nothing further to be done by this function. Step 707 returns the prompt-answer pair calculated in step 704.

If Step 706 determines that the text takes at least two text lines to display, then an alternate combining string is tried in Step 708. A recommended alternate combining string may be the current combining string, trimmed of all white space at the right end with a carriage return appended. The effect of this string is that the prompt text (with its combining string) looks identical to what it did previously. The converted answer value, however, starts at the beginning of the next text line. This secondary test string is calculated by concatenating the prompt text (in its user defined prompt attributes), the alternate combining string and the converted answer value together. Then, use the same method as Step 704 did to calculate the height. In Step 712, if the total height remains the same between what was calculated in Step 704 and 708, then there is no harm to vertical height caused by splitting the first text line of the converted answer value between two different text lines. Without being bound by any particular theory, it is believed that the human eye more quickly discerns information if the answer text (or an individual answer, if there are multiple answers to the same prompt) is on fewer text lines and the format used in step 708 may have the answer text displayed on one fewer text lines than the format used in step 704.

If Step 712 determines that the two heights are the same, then step 713 returns the prompt-answer pair calculated in step 708.

If Step 712 determines that the string calculated in step 708 causes the height to increase, then step 714 checks if the converted answer value contains a concatenation string. If there is no concatenation string, step 715 returns the prompt-answer pair calculated in step 704. If the converted answer value includes a concatenation string, attempts are made to split the prompt-answer pair at the point of each concatenation strings in steps 716-726, while also trying to find a place to split the prompt-answer pair at a point where the split does not increase the overall vertical height using similar methods as was used in steps 704, 708 and 712.

The process continues at step 716 where an alternate concatenation string is calculated similar to the alternate combining string of step 708. A recommended alternate concatenation string may be the user defined concatenation string, trimmed of all white space at the right end with a carriage return appended.

Steps 718-726 create a loop trying to substitute the alternate concatenation string for each concatenation string in the converted answer value, one at a time, starting from the right end of the converted answer value until one position is found that does not increase the height of the prompt-answer pair when substituted. Each pass through the loop, only one concatenation string position uses the alternate concatenation string calculated in step 716.

More specifically, step 718 may create a pointer to the last concatenation string in the converted answer and the following loop may use that pointer to find a location to insert a carriage return in the string.

Step 720 may copy the original prompt, combining string and converted answer, replacing the concatenation string pointed to by the pointer with the alternate concatenation string. Without being bound by any particular theory, it is believed that the human eye more quickly discerns information if the text of one of the answers is on fewer text lines and the format used in step 720 may have one of the answer texts displayed on one fewer text lines than the format used in step 704. Step 720 then measures the height of the resulting text using the method used in step 704.

Step 722 checks if the height measured in step 720 is the same as the height measured in step 704, and if not, flow passes to step 724. In step 724, a check is made if there are any more concatenation strings that have not been tried yet. If there are additional concatenation strings, in step 726 the current pointer is set to the next concatenation string closer to the start of the converted answer in preparation for another pass through the loop. If there no additional concatenation strings, step 728 returns the prompt-answer pair calculated in step 704.

If step 722 indicates that a position was found in step 720 to place the alternate concatenation string without increasing the height, step 730 checks if the height of the prompt-answer pair is two text lines. If the height calculated in step 704 is not the height of two text lines, step 732 returns the last string calculated in step 720.

If step 730 finds that the height is two lines, an attempt is made to left align the answer(s) on the second line with the answer(s) on the first line by using the horizontal position of the first character on the first line after the combining string and making that the left margin of the text on the second line.

Step 734 calculates the height of the prompt-answer pair using the indented left margin. Without being bound by any particular theory, it is believed that the human eye more quickly discerns information if the text of the answers have the left margin vertically aligned and the format used in step 734 has the opportunity to display the two text lines vertically aligned.

Step 736 checks if the heights calculated in step 734 and 704 match, and, if so, step 738 returns prompt-answer pair calculated in step 734; otherwise, step 732 returns the prompt-answer pair calculated in step 720.

Referring to FIG. 8C, depicted is a flow diagram illustrating one example method for converting the answer field into converted text. Step 750 is the start. This function should be passed the identity of the answer style (e.g., obtained from style 3912), and a list of answer entities. Alternatively, a pointer could be passed to a structure that contains this information.

If the current function is passed a prompt entity 52, Step 752 looks up the current answer style from the prompt entity (e.g., a checkbox, an option group, a combo box, a drop-down list, a Likert group, a numeric value, a Boolean, a date, etc.). In general, however, this may be performed by a lookup in a database (e.g., "SELECT Style FROM DataFormDesign WHERE [Primary key]=: PromptKey").

Step 754 checks if the converted answer value is going to be text that merely needs to be looked up from the numeric value 3965 of the answer entity. If so, Step 764 checks whether there are multiple values to look up. If there are not multiple values, then Step 766 converts the single value to a [Text of answer] and applies the user defined answer attributes (e.g., a "converted answer value"). Again, this may be done by a database lookup, such as "SELECT [Text of answer] FROM Lookup WHERE [Primary key]=AnswerKey". If there are multiple values, then Step 774 does such a lookup for each answer entity and concatenates the text of each together with the user defined combining string between each answer value to create a single [Text of answer] and applies the user defined answer attributes (e.g., a "converted answer value"). Either way, the data is ready to return from the function afterwards in Step 776.

Step 756 checks if the prompt entity indicates the answer style is a numeric value. If so, the process converts the numeric value to text and applies the user defined answer attributes in Step 768 (e.g., a "converted answer value"). The conversion of a numeric to a text is done using processes well known to those skilled in the art. The process then returns the converted answer value in Step 776.

Step 758 checks if the prompt entity indicates the answer style is a Boolean value. If so, the process converts the Boolean value to text and applies the user defined answer attributes in Step 770 (e.g., a "converted answer value"). This conversion is done using processes well known to those skilled in the art. The process then returns the converted answer value in Step 776.

Step 760 checks if the prompt entity indicates the answer style is a date value. If so, the date is converted to text and the user defined answer attributes are applied (e.g., a "converted answer value"). The conversion of a date to a wide variety of text formats are well known processes to those skilled in the art. The process at Step 772 checks if the format of this date includes an age calculation. If an age calculation is included, an additional calculation of age is done by processes well known to those skilled in the art (e.g., the SQL function DATEDIFF (Years, DateOfBirth, Date Today)). The age is then appended to the converted answer value in a pre-determined format and the user defined answer attributes are applied (e.g., a "converted answer value"). For example, the format could be "Jul. 1, 1990 (Age 28)".

If the format includes parenthesis, as in this example, it is generally contemplated that something should be done to prohibit other portions of the current embodiment of the invention from excluding parenthetical comments. This may include, for example, using square parenthesis instead of rounded parenthesis, inserting a placeholder in place of the parenthesis at this stage and replacing the placeholder with parenthesis after automatic excluding of parenthetical comments is complete, and/or inserting a flag in the converted answer value or its associated answer entity that tells the automatic exclusion of parenthetical comments process to skip this string, then, optionally, removing that flag from the string after excluding parenthetical comments is complete. The process then returns the converted answer value in Step 776.

If none of the above is applicable, Step 762 simply applies the user defined answer attributes to the text of the answer passed to procedure 750 (e.g., the "converted answer value") and then returns the converted answer value in Step 776.

Figure 8D:
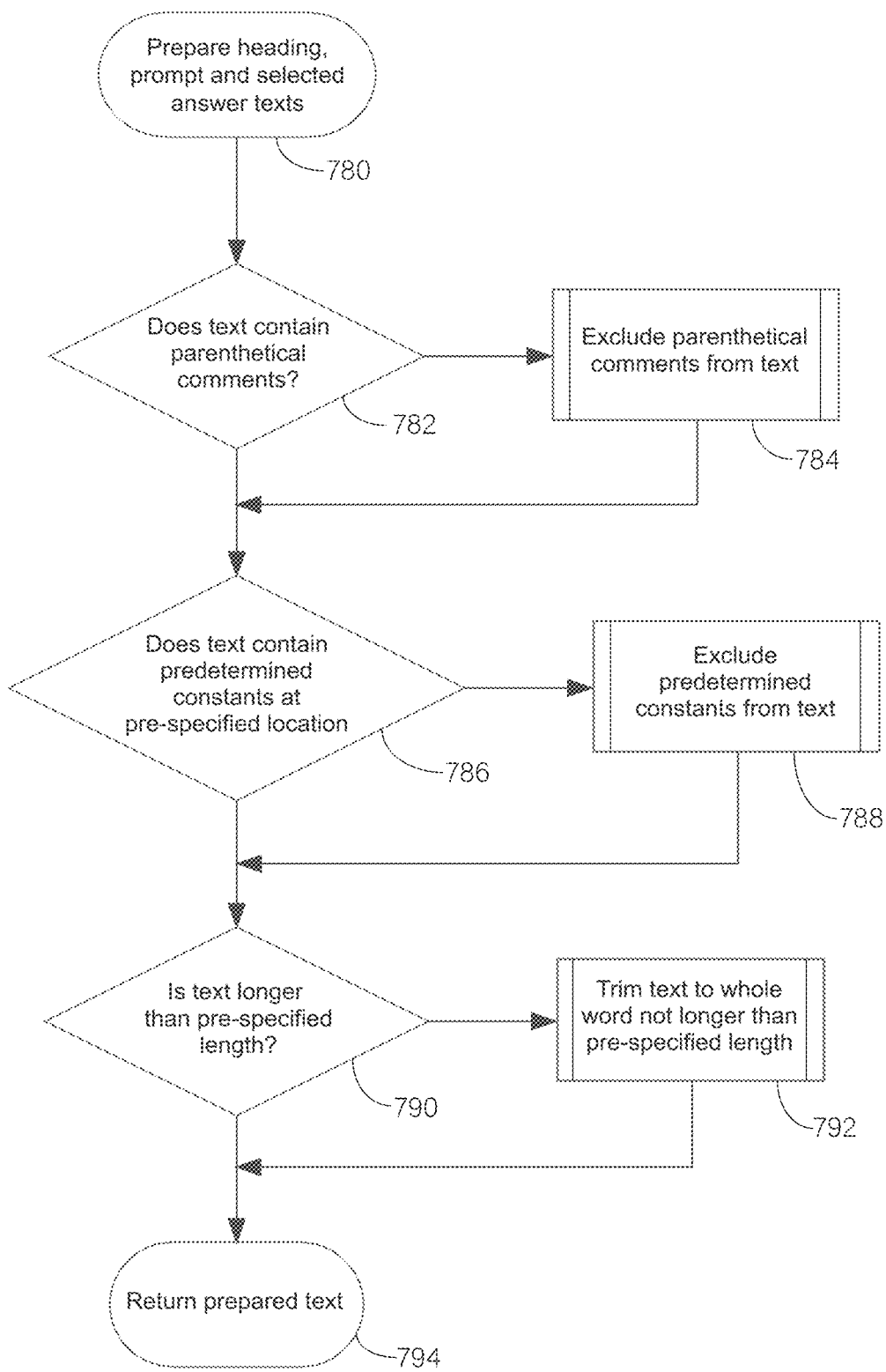
FIG. 8D is a flow diagram illustrating an example method for converting the text of heading, prompt and answer entities into prepared text.

Referring to FIG. 8D, depicted is a flow diagram illustrating one example method for converting the heading and prompt text into prepared text. This also handles any answer text that was not (1) typed by a data entry user, and not (2) a system generated answer text that includes a parenthetical comment. Process 780 prepares the text by checking if it has any of three specific conditions, and if so, it handles each specific condition. First, step 782 checks if the text contains parenthesis, and if so, step 784 calls the process 830 or process 860. Next, step 786 checks if any pre-specified text occurs at the beginning, end or middle of the text, and if so, step 788 calls step 904. Finally, step 790 checks if the text is longer than a pre-specified maximum length for the element type, and if so, step 792 calls procedure 900. The prepared text is return in step 794.

Figure 9:
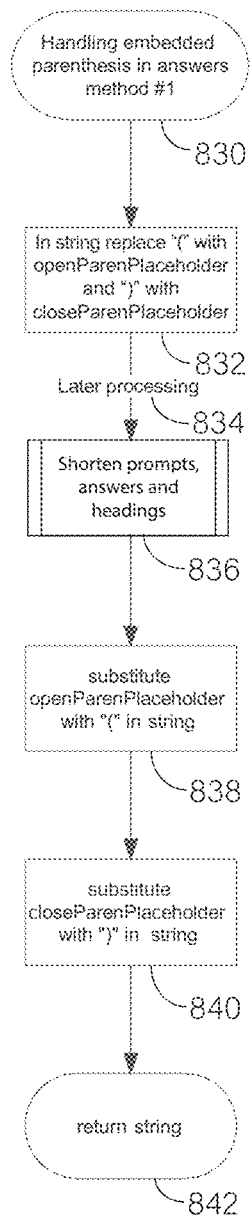
FIG. 9 is a flow diagram depicting a first example method of suppressing automatic exclusion of parenthetical comments.
Figure 10:
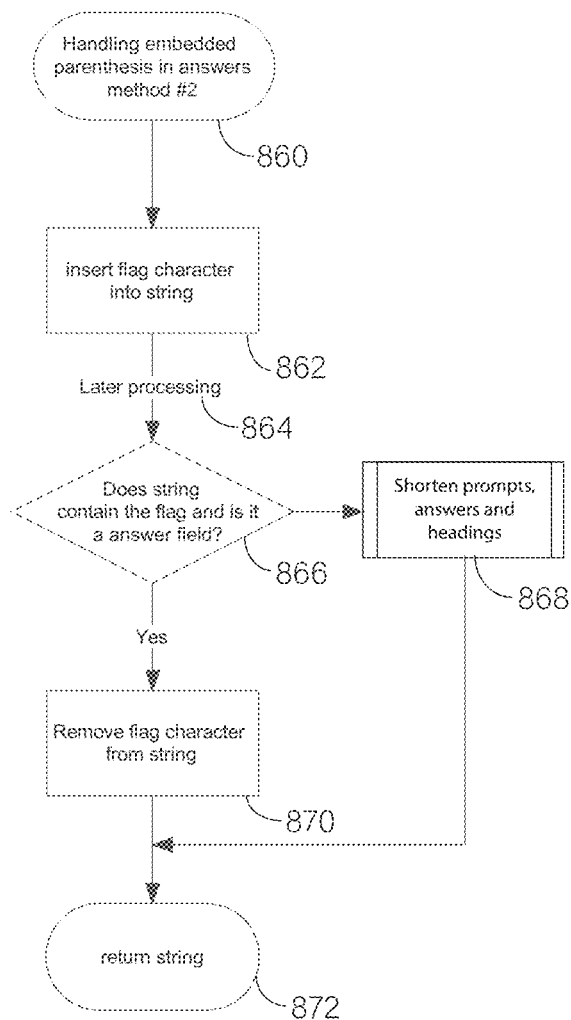
FIG. 10 is a flow diagram depicting a second example method of suppressing automatic exclusion of parenthetical comments.

FIGS. 9 and 10 show two alternate functions that restrict shortening by excluding parenthetical comments in answer values that were either manually typed by the data entry user 78 or are computed fields that include a parenthesis in the format. If the format of a converted answer value includes parenthesis, the functions prohibit shortening the answer value using excluding parenthetical comments. Some of the various methods of doing this may include, for example, (1) using square parenthesis instead of rounded parenthesis, (2) the method starting in Step 830 (e.g., inserting a placeholder in place of the parenthesis at this stage and replacing the placeholder with parenthesis after automatic excluding of parenthetical comments is complete), and (3) the method starting in Step 860 (e.g., inserting a flag in the answer value that tells the automatic exclusion of parenthetical comments to skip this string when processing, then removing that flag from the string after automatic exclusion of parenthetical comments is complete). Note that these two functions are shown as two continuous streams, but each stream actually occurs at two different places. Steps 832 and 862 actually occur earlier in processing but is shown connected here because the only reason to perform these Steps is what follows here.

In Step 830, a string is passed into the function.

In Step 832, the string optionally (e.g., right after performing Step 772 of FIG. 8C) has all the parenthesis replaced by openParenPlaceholder or closeParenPlaceholder, depending on whether it is an open parenthesis or a close parenthesis.

In Step 834, a period of time is provided during which other processing operations may occur. Then, in Step 836, procedure 900 is executed, the temporary openParenPlaceholder and closeParenPlaceholder with "(" in Step 838 and ")" in Step 840, respectively. Finally, return the computed string in Step 842.

In Step 860, a string is passed.

In Step 862, a flag is optionally (e.g., right after performing Step 772 of FIG. 8C) set to indicate that this string does not get processed by procedure 900. This may be as simple as placing a tilde character as the first character of the string or as complex as having a structure that accompanies the string through processing.

In Step 864, another period of time is provided during which other processing operations may occur. A check is made to see if the flag is associated with the string, and whether it is an answer field in Step 866. (Obviously, a check could have been made before executing Step 862 to see if it is an answer field and move that test to there and that would accomplish the same thing.) If the flag is not present, the call is made to procedure 900 in Step 868.

If the flag is present, then it may optionally be removed after it has served its purpose in Step 870. Finally, the computed string is returned in Step 872.

Figure 11:
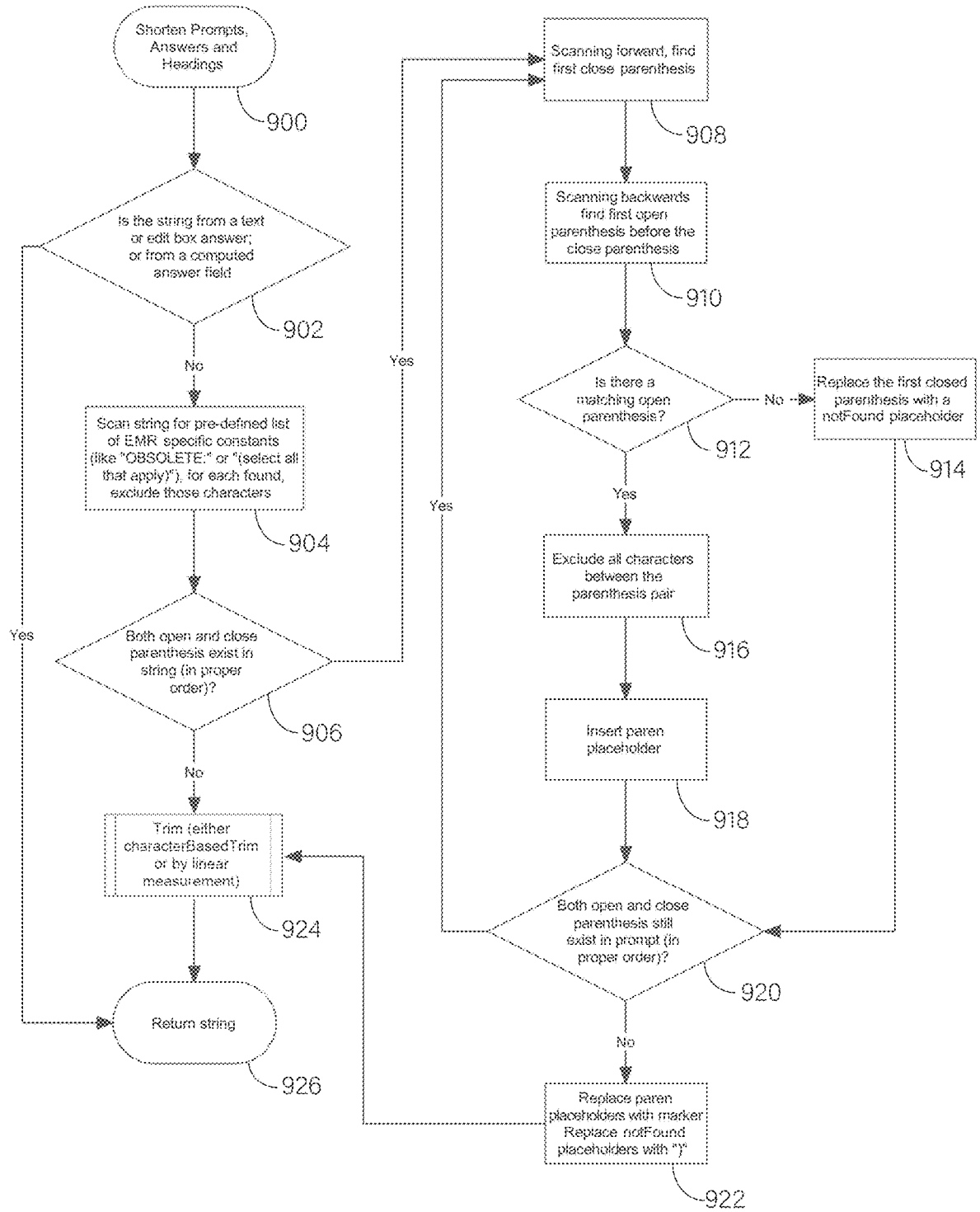
FIG. 11 is a flow diagram depicting an example method of shortening texts of prompt, answer and heading entities by excluding characters.

Referring to FIG. 11, depicted is a flow diagram that shows an example process of how to shorten prompt texts, answer values and heading texts by excluding characters. It starts at step 900 by passing in the string to shorten.

In step 902, a check is made to prevent character exclusion when either the data entry user 78 types the text of the current field or the current field is a system generated field that includes a parenthesis. If so, the process skips to step 926.

In step 904, the program is presented with a list of phrases that may be automatically excluded when they are encountered, and possibly also a location indicator indicating where each phrase has a desired meaning (e.g., this may be in the form of a RegEx expression or start/middle/end/anywhere flags). For example, one phrase on the list in an embodiment is "OBSOLETE:" (which has been previously employed to mark no longer used fields in standardized data forms with this as a prefix). Then, if an obsolete prompt text is accidentally included in the data form design, that prompt text will start with the characters "OBSOLETE:", thereby making it easier for a form designer to catch the error. This practice, however, unfortunately produces an exorbitant number of "OBSOLETE:" strings when older data forms are viewed. Excluding these "OBSOLETE:" strings not only potentially decreases the quantity of text lines required to display the data form, but also makes the resulting data forms more readable because they do not contain random "OBSOLETE:" strings scattered around the data form.

To complete this example of excluding this specific visual prompt text queue, a command may be issued to exclude the first 10 characters from any string starting with a capital "OBSOLETE:", such as "UPDATE #Elements SET Prompt=LTRIM (SUBSTRING (Prompt, 10, LEN (Prompt))) WHERE Prompt LIKE 'OBSOLETE: % %' COLLATE Latin1_General_BIN".

A similar example would be to eliminate the characters "(select all that apply)" from the end of a prompt text where it is case insensitive. A sample SQL command for this may be: "UPDATE #Elements SET Prompt=RTRIM (SUB- STRING (Prompt, 1, LEN (Prompt)-23)) WHERE Prompt LIKE '% % (select all that apply)';".

A third example shows an example of eliminating the characters "(include all that apply)" from anywhere in a prompt: "UPDATE #Elements SET Prompt=REPLACE (REPLACE (Prompt, "+'(include all that apply)',"), '(include all that apply)', "");". In the innermost replace, the single space inserted before the phrase to be removed prevents from leaving a double space where the phrase was removed. The outermost replace catches any case where there was some punctuation immediately before the characters being eliminated or it occurred at the beginning of the prompt. The case sensitive version of the same replace might appear as "UPDATE #Elements SET Prompt=REPLACE (REPLACE (Prompt COLLATE SQL_Latin1_General_CP1_CS_AS,"+'(include all that apply)',") COLLATE SQL_Latin1_General_CP1_CS_AS, '(include all that apply)',"");"

With these examples, it should be apparent to those skilled in the art how to develop a robust system to allow excluding pre-specified strings from the beginning, end, or anywhere in a heading, prompt and any answers the data entry user did not type.

In step 906, a scan may be performed in search of an open parenthesis followed by, after some minimum predetermined quantity of characters, a close parenthesis. If found, at step 908, a scan may be performed to find the first closed parenthesis. Once found, a scan may be performed for the matching open parenthesis by scanning backwards from that point in step 910. If, in step 912, no open parenthesis is found in this backward scan, then the closed parenthesis that was found may be hidden by changing it to a notFound placeholder in step 914.

If, in step 912, an open parenthesis was found, then all the characters between the parenthesis pair may be excluded, including the parenthesis in step 916. In optional step 918, a paren placeholder can optionally be added to mark where the parenthesis pair was excluded.

In step 920, the same check that was performed in step 906 may be performed again to determine whether any further open and close parentheses pairs still exist in the string.

In step 922, if there were any paren placeholders placed in the string, they may be replaced with appropriate character strings. This character string can be any suitable value, such as NULL, "( )" or any other suitable character or combination of characters. The character string may also be user definable. Also, the notFound placeholder may be changed back to the character it replaced (e.g. ")").

In step 924, an optional call may be made to a procedure for trimming the string such that the string does not exceed a maximum length. This can be accomplished with a call to procedure 1031 or a call to procedure 1111.

Finally, in step 926, the string is returned from the function.

Figure 12:
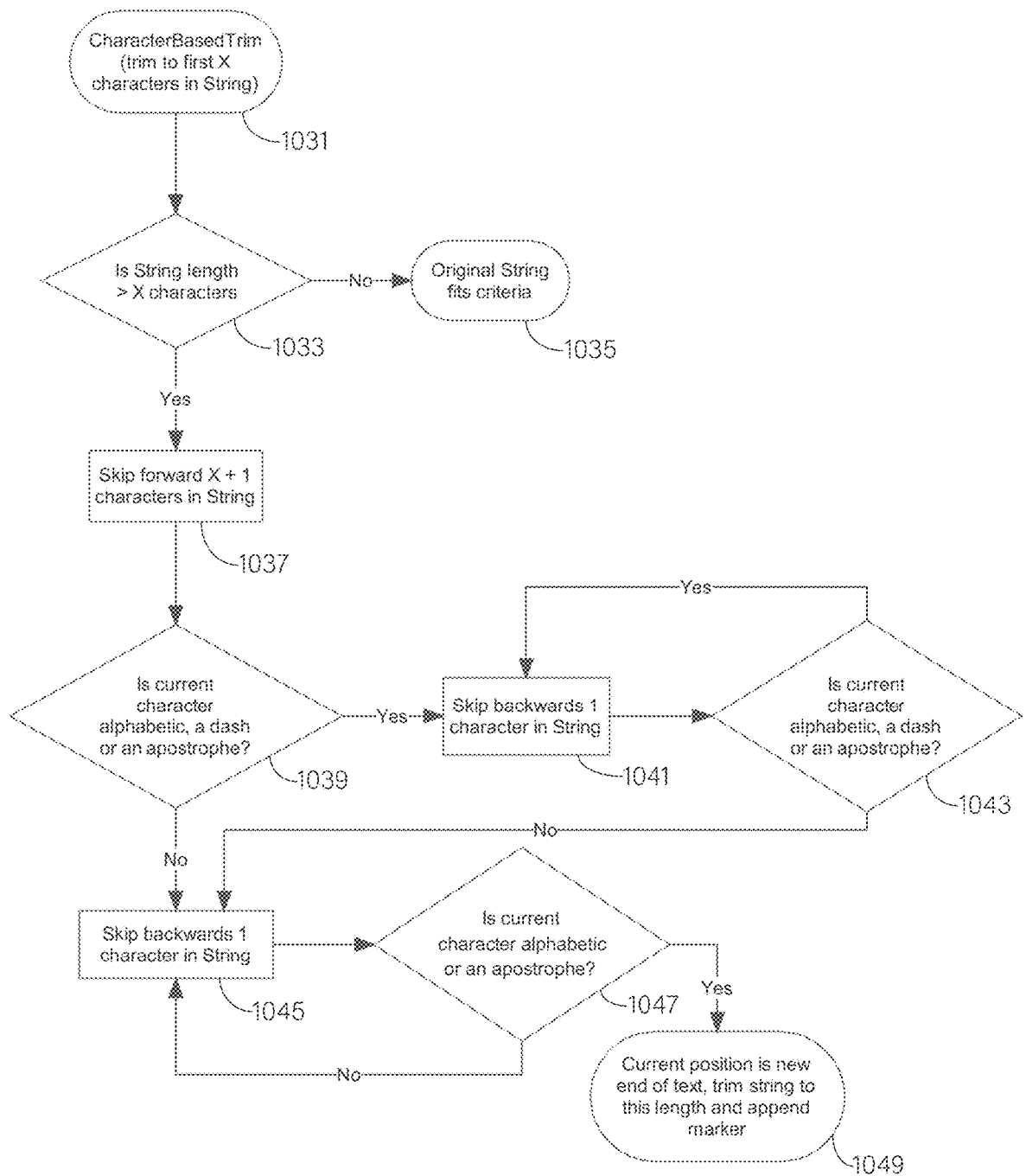
FIG. 12 is a flow diagram depicting an example method of trimming a string to the maximum number of whole words less than a pre-specified maximum quantity of characters.

Referring to FIG. 12, depicted is a flow diagram of one example of a method for trimming a string based on a pre-specified maximum quantity of characters and returning the quantity of said characters that make up the maximum number of words (i.e., whole words) that can be formed with said characters. Procedure 1031 starts with step 1033, checking if the string is larger than the pre-specified maximum quantity of characters. If not, step 1035 may exit the function by returning the whole string. In step 1037, the function skips to one character beyond the pre-specified quantity of characters (e.g., the "current character").

Step 1039 checks if the current character could be a character within a word (e.g., alphabetic, a dash for hyphenated words or a character that can end a word). If so, step 1041 scans backwards looking for the first character that is not a character within a word in step 1043. Once that first character is encountered, processing resumes at step 1045, as if step 1039 had not detected a character in the middle of a word.

If the current character at step 1039 is not a character within a word, then step 1045 backs up one character, and loops through by backing up a single character at a time until a character is encountered that could be the last character in a word in step 1047. Finally, the end of the last word is located in step 1049. The function may then return the characters between the start of the string passed to Step 1031 and the end of that last word.

Figures 13, 14:
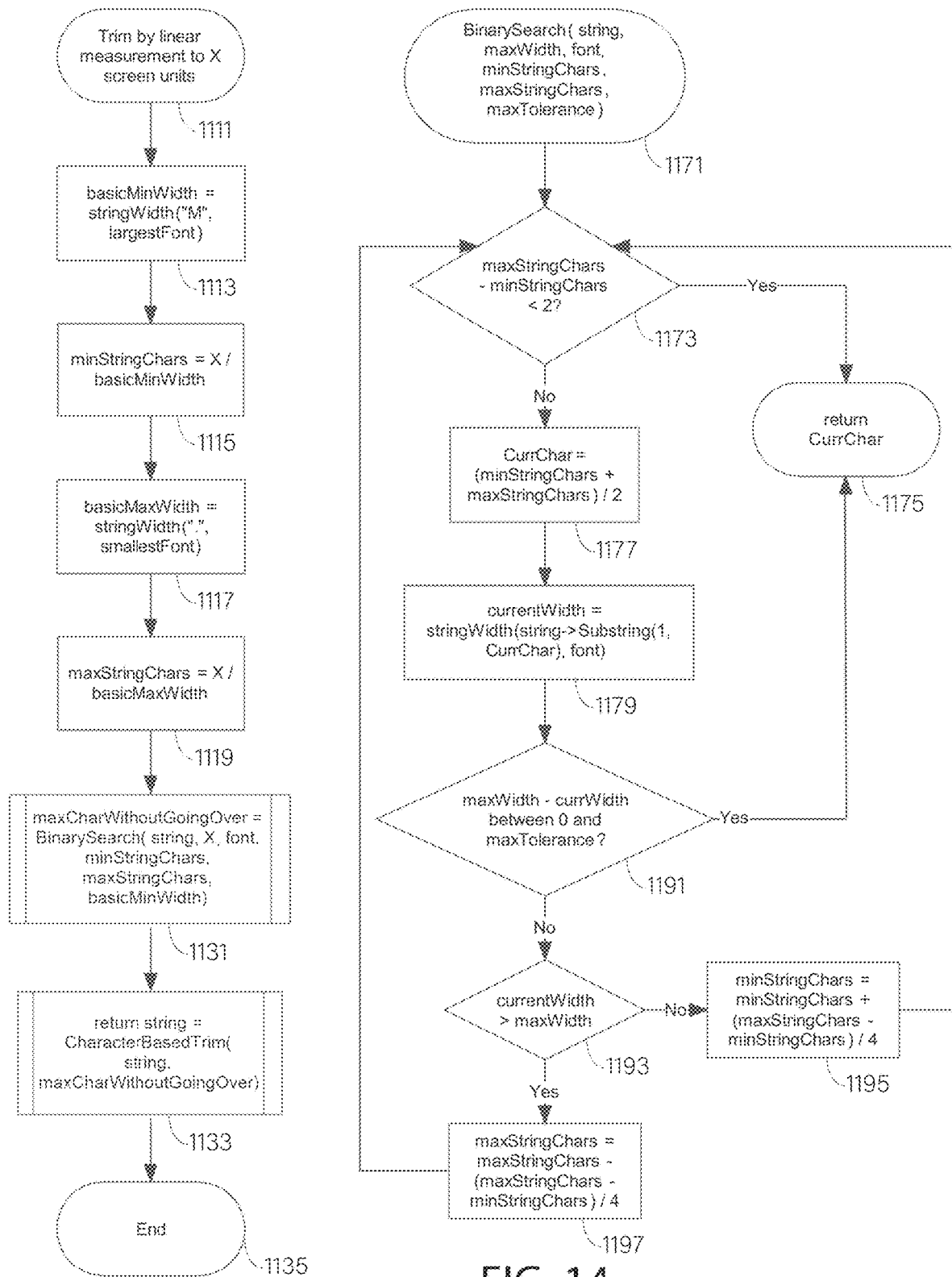
FIG. 13 is a flow diagram depicting an example method of trimming a string to an output linear length only showing whole words.
FIG. 14 is a flow diagram depicting an example method of performing a binary search to find a string with an output linear length not exceeding a pre-determined length.

Referring to FIG. 13, depicted is a flow diagram illustrating one example of a method for trimming a string to a linear length without breaking in the middle of a word. The linear length may be measured in various units of measurement such as, for example, points, quantity of characters, quantity of twips, and/or traditional measurement units (e.g., Imperial system and/or Metric system). The shortened string may then be returned, and then shown to the display user.

This function assumes the availability of a measurement function that can be provided with a converted text and is able to return the converted text's linear length. Recall that a converted text includes the font definitions (font name, size and other font attributes such as weight) and possibly paragraph definitions. The measurement function can be a system provided function or it can be constructed "on the fly" using a text or RTF box of a specified width by measuring the height of the text/box after inserting the string to see if it is one line tall or not. If it is more than one line tall, then the string is too long to fit on one line. If an RTF box is used in the calculation, then step 1133 becomes optional since the RTF box may automatically split the string on whole word boundaries. Furthermore, if an RTF box is used, process 1111 could be easily modified to allow the process to work on vertical measurements, thereby allowing for additional units of measure such as vertical height or vertical lines (e.g., the text area is to be no more than 2 lines tall instead of one line tall).

The widest standard character in most proportionally spaced fonts is a capital "M". The smallest character in most proportionally spaced fonts is a period ("."). The space occupied by a capital "M" (e.g., the width) is approximately equal to the space occupied by four periods. For most fonts, the space occupied by four periods is very slightly wider than the space occupied by a capital "M", but the two are very close.

Procedure 1111 starts with steps 1113 and 1115, calculating the minimum quantity of characters that could fit in a space that is requested. This is accomplished by dividing the total width passed to procedure 1111 by the width of the widest character in the largest font used in the string (e.g., the letter "M"). In other words, if the string only contained the letter "M" repeatedly in the largest size font used, that would be the minimum quantity of characters possible in a string of the desired size.

Similarly, in steps 1117 and 1119, a calculation is made of the maximum quantity of characters that could fit in the space requested. This is accomplished by dividing the total width passed to procedure 1111 by the width of the narrowest character (e.g., a period) in the smallest font used in the string. If the font was limited to only one size, weight and font name in the string, calculation of this second value can be shortcut by just multiplying the value from step 1115 by 4 (because of the generalization that there is slightly more space occupied by 4 periods than in the space that a letter "M" occupies).

In step 1131, a call is made to procedure 1171 to determine the maximum quantity of characters that may fit in the pre-specified output linear length. In step 1133, a call is made to procedure 1031 to force the trimming to end with a whole word. The function ends in step 1135.

For mixed font text, such as in a prompt-answer pair, the text of each font may be handled separately and in the order in which they appear (in the string) until the desired total length is reached. Alternatively, an RTF box-based function (such as the TRichView product available from TRichView-.com) may be used to handle the whole string at once.

Referring to FIG. 14, depicted is a flow diagram illustrating how to perform a binary search in order to find the quantity of characters in a string whose output linear length does not exceed a pre-determined length. The function begins in step 1171. Note that the parameters start with an estimate of both the minimum quantity of characters and a maximum quantity of characters, and a tolerance of how close one has to be before exiting the loop early. This degree of tolerance may be applied later in step 1191 and is an optional optimization.

In step 1173, the loop should exit if the difference between the minimum and maximum character position is less than a predetermined quantity of characters. In the embodiment shown, two is the predetermined quantity.

In step 1177, the current character position may be calculated. Because the current character is positioned between the minimum and maximum character, in one example, the calculation may include averaging the two extremes (e.g., the minimum and the maximum character). If this averaging step results in a number with a fractional value, the fractional value is dropped to get the current character position with a bias toward the lower value. Since this step is averaging (i.e., the only fraction from averaging two whole numbers can be a half), this amounts to rounding down.

In step 1179, a system call may be made to determine how wide the string up to the current character position would be, if printed to the screen using the current font.

In step 1191, a check may be made to determine if the current character position would yield a string that is not larger than the maximum width, but within the pre-specified tolerance for being acceptably close. Those skilled in the art will appreciate that it may be expensive in terms of computer cycles to perform step 1179, but once that value has been calculated for the loop, it is relatively quick to do this check and possibly shortcut several cycles of the loop. Further, if it is within the pre-specified tolerance, the character position has been found and is returned at step 1175.

In step 1193, a check may be performed to determine which value to adjust for the next pass through this function. This may entail raising the minimum quantity of characters and/or decreasing the maximum quantity of characters.

In step 1195, the minimum quantity of characters may be increased if the current width is less than the pre-determined length. In the example shown, the amount of increase is-° of the difference between the minimum quantity of characters and the maximum quantity of characters. If the result of calculating the increase results in a fractional amount, the fractional amount may be dropped to get a minimum quantity with a bias toward the lower amount.

In step 1197, the maximum quantity of characters may be decreased if the current width is more than the pre-determined length. In the example shown, the amount of decrease is-° of the difference between the minimum quantity of characters and the maximum quantity of characters. If the result of calculating the decrease results in a fractional amount, the fractional amount may be dropped and the maximum quantity increased by 1 to get a maximum quantity with a bias toward the higher amount.

In FIG. 15, the string "this is a test to see how much will fit" 1215 is being processed starting at step 1111. Character count positions are shown for the $10^{th}$, $20^{th}$, $30^{th}$, and $40^{th}$ character positions 1211. An inch ruler 1219 and a point ruler 1217 is shown to measure the width of the string. Further, string width 1213 also shows a graphical representation of the values for the $1^{st}$, $2^{nd}$, $3^{rd}$, $4^{th}$ and $5^{th}$ cycles of step 1179 through the loop.

FIG. 16 shows a number of different values calculated at various steps of FIG. 13 while processing the string of FIG. 15. The first column 1231 shows the step number. The second column 1233 shows the computed values resulting from executing that step.

FIG. 17 shows the calculated values at five different passes through the loop of FIG. 14 while processing the string of FIG. 15. First column 1235 shows the various pass numbers where 1 corresponds to the first pass, 2 corresponds to the second pass, and so on. The cycle numbers 1213 correspond to the pass numbers 1235. The second column 1237 and third column 1239 show the values for the minimum quantity of characters and maximum quantity of characters respectively at the start of the loop, step 1173. The fourth column 1241, shows the value of CurrChar at the end of step 1177. The fifth column 1243, shows the value of CurrWidth at the end of step 1179. The sixth column 1245, shows the choice of whether the calculated value was too long in step 1193. The seventh column 1247, shows the calculated values calculated during the loop at the end of step 1195. The eighth column 1249 shows the values calculated during the loop at the end of step 1197. On the fifth pass, the loop exits early in step 1191.

FIG. 18 shows the processing of the text of FIG. 15 through the loops of FIG. 12. The value passed in step 1133 to the function 1031 is 29 (i.e., the "c" in "much"). After step 1037, the string pointer points to the "h" in "much" 1251. Since "h" 1251 is alphabetic, step 1041 changes the string pointer to the "c" in "much" 1253. Since "c" 1253 is alphabetic, step 1041 changes the string pointer to the "u" in "much" 1255. Since "u" 1255 is alphabetic, step 1041 changes the string pointer to the "m" in "much" 1257. Since "m" 1257 is alphabetic, step 1041 changes the string pointer to the space before "much" 1259. Since the space 1259 is not alphabetic, step 1045 changes the string pointer to the "w" in "how" 1261. Since "w" 1261 is alphabetic, the function has found the end of the last whole word that can be displayed with the string.

Figure 19A:
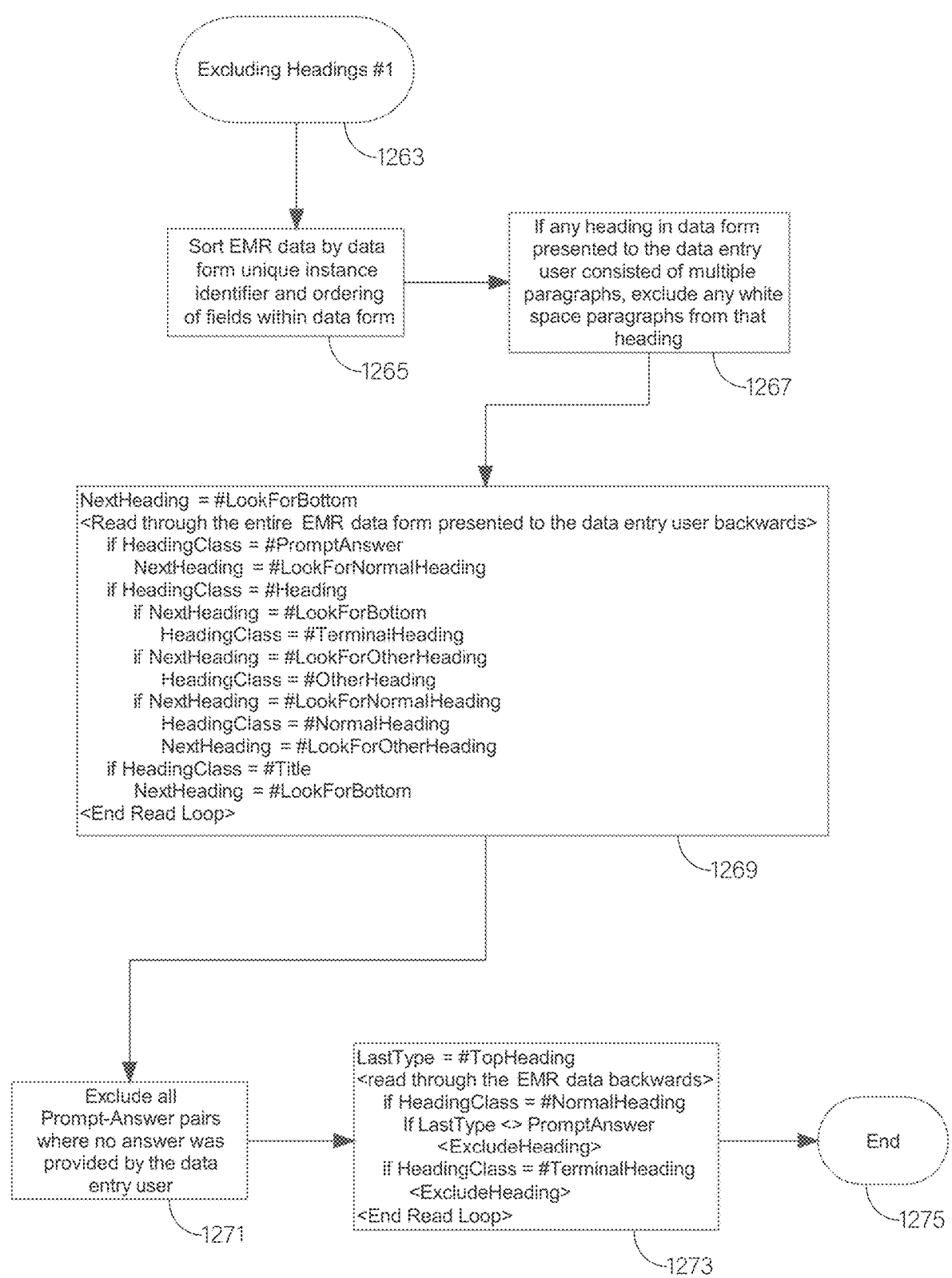
FIG. 19A is a flow diagram depicting a first example method of calculating heading entities to exclude.

Referring to FIG. 19A, depicted is an example of a method for excluding heading entities (and the associated heading text) from an electronic medical record data form. Heading entities are classified based on data form design (e.g., where each heading entity occurs relative to other heading entities and/or the next prompt entity closest to the heading entity, and whether the heading entity occurs after the final prompt entity in the data form). Excluding heading entities may be performed by determining, for each heading entity in the data form, what classification of heading the heading entity is, and then preventing certain classifications of heading entities from being displayed. Excluding heading entities may also include preventing heading texts from being displayed if those heading entities are not followed by an answered prompt entity before the next heading entity of the same classification (and, as will be shown in FIG. 19C, same style).

Procedure 19A starts with step 1263. Step 1265 sorts data from the EMR by the view order. This may be performed by using a unique instance identifier that identifies the unique data form document instance being used and the order that the heading and prompt entities in that data form appear. For example, this might include the date or appointment identifier, an attachment counter, and an ordering of the fields within the data form. Typically, the ordering includes either a row plus a column number (and optionally, a panel identifier) or a ViewByOrder column associated with the data form layout in the EMR).

In step 1267, blank text lines (preferably all of them) may be excluded in the heading entities. These blank text lines may have been added to the data form design for emphasis but generally are not required for the display user 81.

In step 1269, a loop may be set up to classify the different classifications of headings. In step 1269, the data form fields being referred to are the data form design, regardless of whether any answers to prompts have been provided by a data entry user. A heading entity after the last prompt entity in a data form is classified a "terminal heading." A heading entity immediately proceeded by something other than a heading entity of the same style, and followed by a prompt entity, is classified as a "normal heading." All other heading entities are classified as "other headings." Since each heading entity classified using this system of classification (e.g., all heading entities are either normal headings, terminal headings or other headings) are based on what follows it, the method (for excluding heading entities from an electronic medical record data form) may be performed more efficiently by scanning the data form from the bottom to the top. In this way, processing may be performed in a single pass without any backtracking. The analysis of step 1269 may be performed before any analysis of any specific answered prompt entities and stored as the classification of the heading entities somewhere for future use. These classifications of heading classification would only need to be updated after changing the data form design.

In step 1271, every unanswered prompt may be excluded since there is no user input by the data entry user 78. The remaining entities may then be processed in step 1273, wherein any normal heading entity that is followed by anything other than an answered prompt entity may be excluded. Further, still in step 1273, each heading entity classified as a terminal heading may also be excluded. As in step 1269, it may be more efficient to read the EMR data backwards (i.e., from bottom to top). The difference between the current step and step 1269 is that the current step can only be performed after a data entry user has completed the data form, and only includes heading and answered prompt entities. In step 1269, all heading and prompt entities (both answered and non-answered) were included. In step 1275, the process is complete.

Figure 19B:
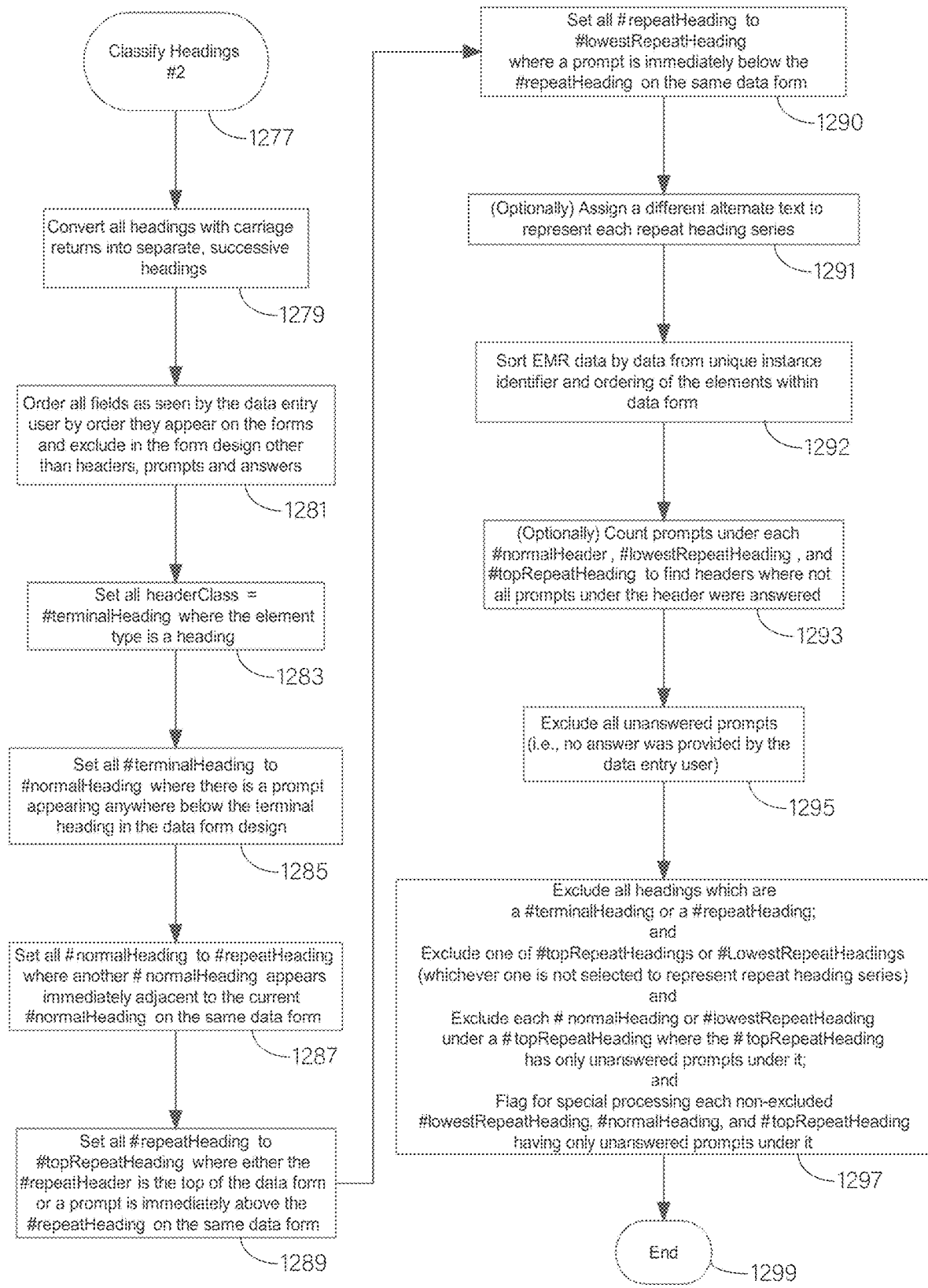
FIG. 19B is an alternate flow diagram depicting a second example method of calculating heading entities to either exclude or augment with information about unanswered prompts.

Referring to FIG. 19B, depicted is a second example of a method for excluding heading entities (and the associated heading text) from an electronic medical record data form with only one style of heading entity. The method of this example is intended to be optimized for implementation by SQL beginning in step 1277. Step 1279 is an optional step which involves searching for carriage returns within the text of each heading entity. Step 1279 further includes splitting these heading entities at the carriage return such that the text of the heading entity yields two new heading entities. Different embodiments may handle the split pieces differently. In one embodiment, only the first entity is kept, but there is a minimum size of the first segment. In another embodiment, all the sections are kept as separate entities. Finally, in step 1279, any blank heading entities are excluded.

In Step 1281, each heading 51 and prompt 52 entities from the design 49 of the data form 48 may be selected. The elements in the design 49 of the data form 48 is what the data entry user 78 would see as they are entering data on the user interface display 76. Depending on the programming of the EMR, the display user 81 may not see every heading 51 and prompt 52 entities designed into the data form 48. One way to accomplish step 1281 in SQL would be to create a temporary table, then import just the heading and prompt entities into that table.

In Step 1283, each heading entity may be initialized (e.g., set) by default to a terminal heading. In Step 1285, any of these heading entities (i.e., the terminal headings) may then be set to a normal heading if a prompt entity occurs anywhere after the heading entity in the same data form.

In Step 1287, all of the heading entities currently classified as normal headings may be set as a member of a repeat heading series if there is another heading entity of the same style immediately above or below each heading entity on the same data form, thereby creating a repeat heading series. In Step 1289, the first heading entity in each repeat heading series may then be found and marked as being a top repeat heading. In Step 1290, the last heading entity in each repeat heading series may be found and marked as being a lowest repeat heading.

In Step 1291, a different single heading text may be substituted to represent each repeat heading series (e.g., use the text of the highest repeat heading entity or use the text of the lowest repeat heading entity or use an alternate text 3911 from the EMR design). The repeat heading series consists of a top repeat heading entity, a lowest repeat heading entity, and possibly one or more repeat heading entities between the two. If each entity in the series takes at least one line to display its text, the vertical height of the series can usually be decreased by at least one line by making this substitution and excluding the other entities in the repeat heading series.

In Step 1292, filled out data forms (e.g., data forms with answered entities) may be returned to processing, instead of data form design. Data forms are sorted by (1) an identifier that distinguishes between different instances of the same data form, and (2) the order entities occur within the data form.

Step 1293, in combination with one version of the flagged special processing of step 1297, shows how to implement an option of selectively deleting certain heading entities and augmenting the text of remaining heading entities with a count of the quantity of prompt entities under each heading entity.

If there is only one heading style, as each heading entity is individually inspected, the scope of a heading entity of interest is determined by searching for the first occurrence of (1) a heading entity of the same classification as the heading entity of interest, (2) a heading entity of a substitute classification for the heading entity of interest, (3) a top repeat heading entity after the heading entity of interest, or (4) the end of data form marker. Once the scope of each heading entity is identified, a count can be made of the quantity of prompt entities under the heading entity of interest. Furthermore, both normal and lowest repeat heading entities under a top repeat heading entity of interest with 100% unanswered prompt entities under the top repeat heading entity of interest may be excluded without losing significant information. So, if the heading entity of interest is a top repeat heading, the end of its scope may be either the next top repeat heading entity in the document or the end of the document. If the heading entity of interest is a lowest repeat heading entity, the end of its scope may be the next normal heading entity (e.g., because a normal heading entity is a suitable substitute for a lowest repeat heading), the next top repeat heading entity or the end of document marker. If the heading entity of interest is a normal heading entity, the end of its scope may be either the next normal heading entity, the next top repeat heading entity or the end of document marker.

Figure 19C:
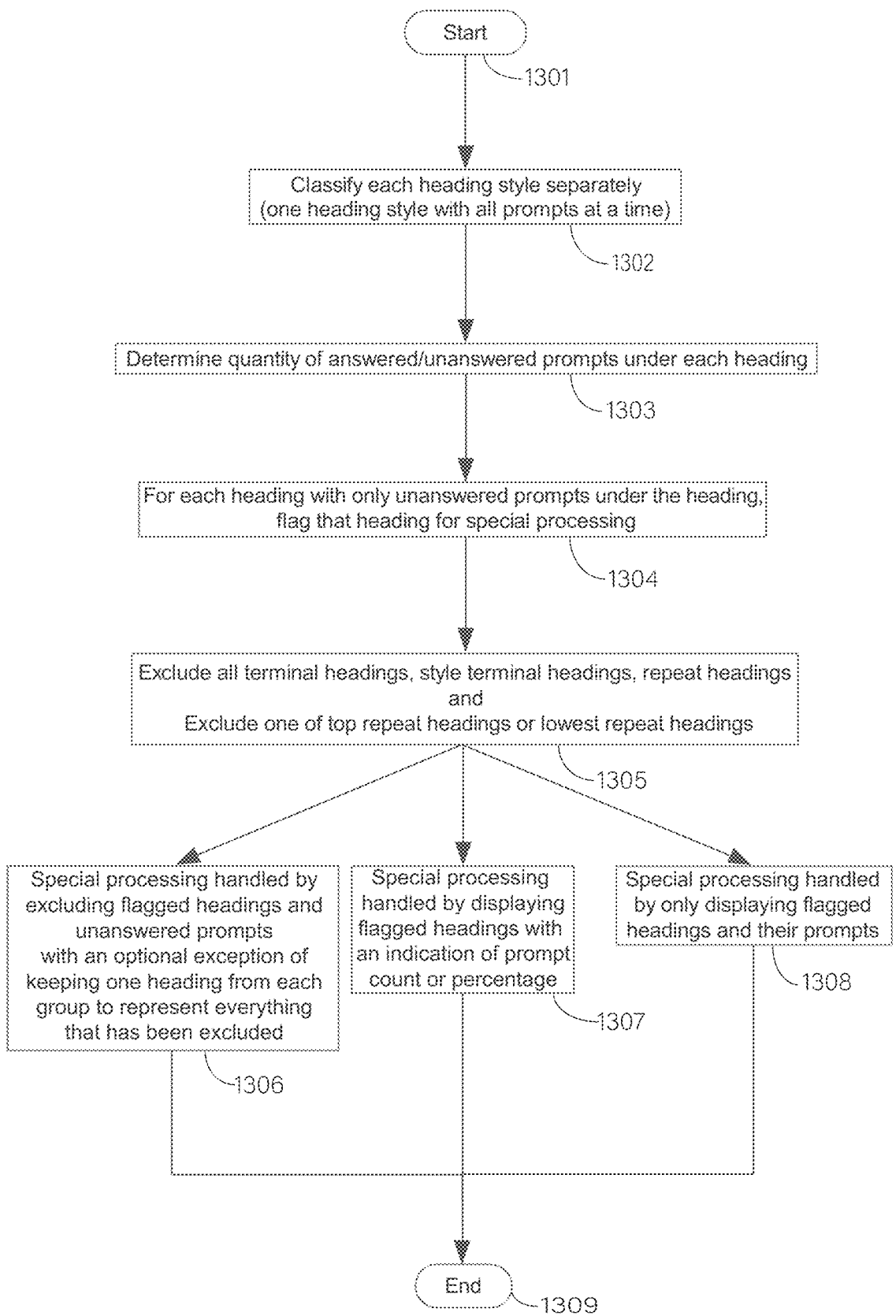
FIG. 19C is a flow diagram depicting a method of calculating heading entities to exclude or augment with information about unanswered prompts when a document contains different styles of heading entities.
Figure 19D:
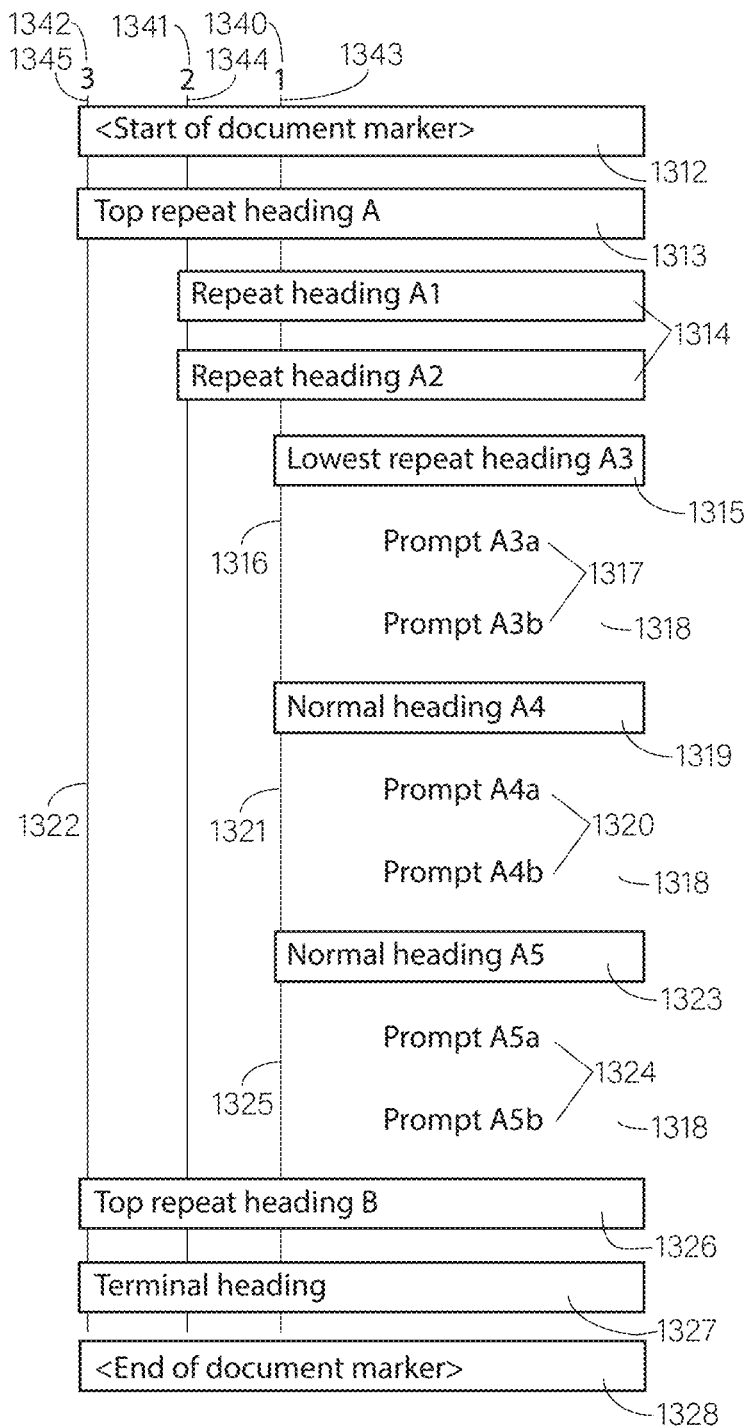
FIG. 19D is an illustration showing the general structure and relationships of the heading and prompt entities handled by FIGS. 19B-19C.
Figure 19E:
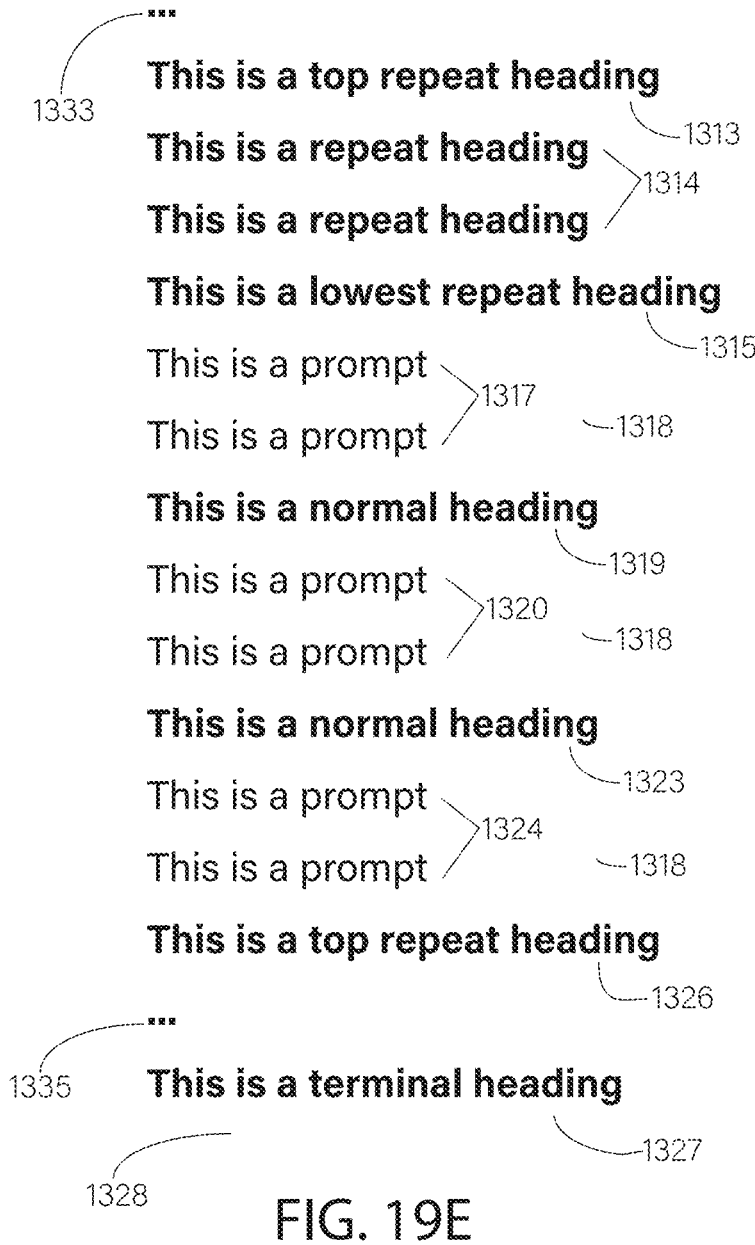
FIG. 19E is an illustration showing sample text that may be used to create the example of FIG. 19D.
Figure 19F:
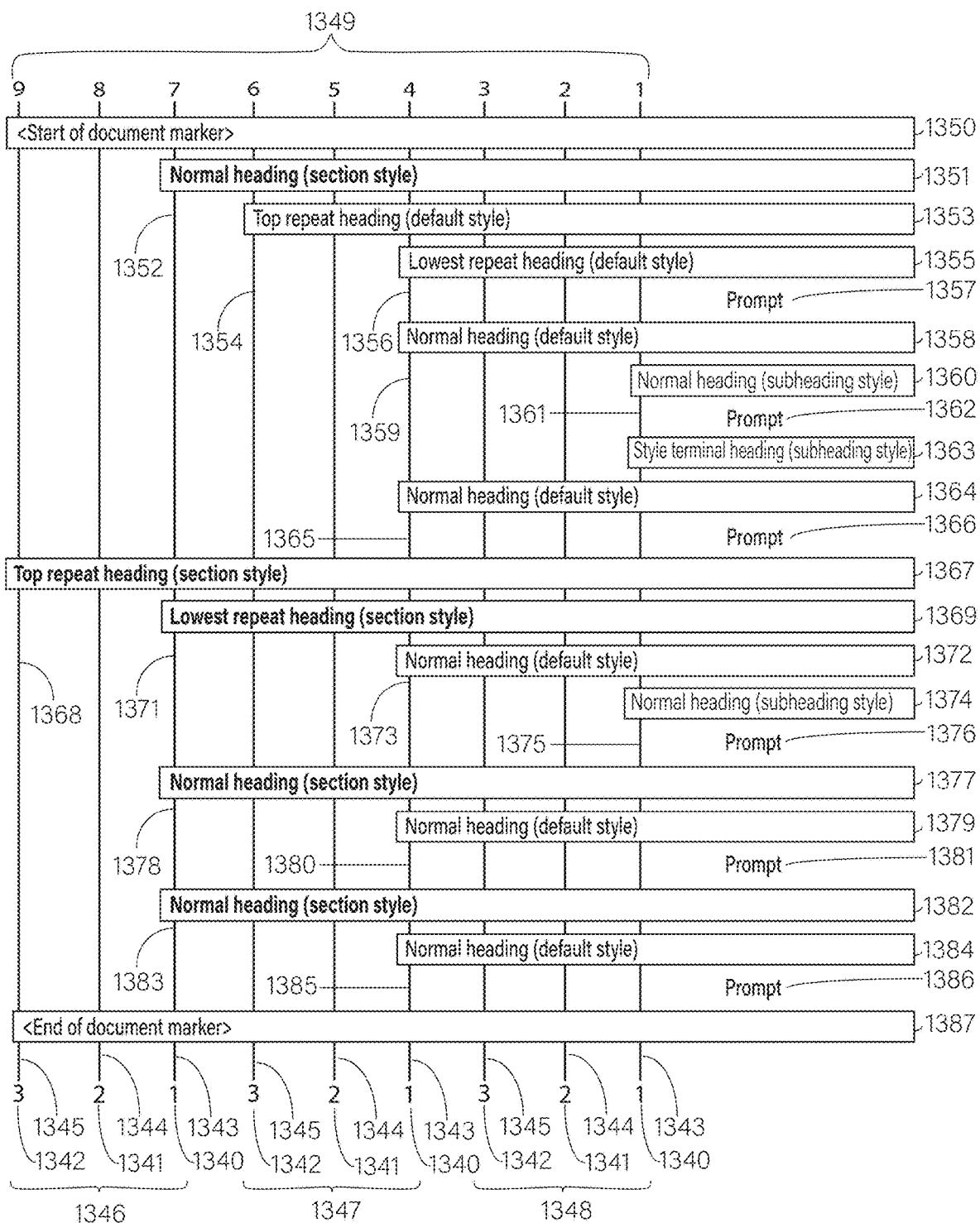
FIG. 19F is an illustration showing an example of structure and relationships of multiple styles of heading and prompt entities handled by FIGS. 19B-19C.

If there are multiple heading styles in the data form, FIG. 19F-19G shows how to compute which prompt entities are in the scope of each heading entity of interest.

It may be desirable to present to the display user how much information from a particular section of the data form is skipped (i.e., excluded). In this way, the display user may be enabled to realize what information is excluded, and may investigate further if desired. Thus, a count of how many unanswered prompt entities exist under each heading entity can be significant information. The flagged special processing of step 1297 may then further offer the option to include this count in the text of each remaining repeat heading series member, and exclude certain heading entities under top repeat heading entities of interest that only have unanswered prompt entities under the repeat heading entities of interest.

In Step 1295, all unanswered prompt entities may then be excluded from each data form.

In Step 1297, heading entities which fall into either of the following categories may be excluded: terminal headings and repeat headings. Also, only one heading entity should be kept to represent each repeat heading series, so the other heading entity (e.g., lowest repeat heading entity or top repeat heading entity) may be excluded.

Also, any normal heading entity or lowest repeat heading entity under a top repeat heading entity of interest (e.g., between the top repeat heading entity of interest and the first occurrence of another top repeat heading entity or the end of document) may be optionally excluded where only unanswered prompts are under the top repeat heading entity of interest. The reason this is optional is the situation where one wants to create a display of only unanswered prompts and headings.

In addition, any heading entity of interest other than a repeat heading entity (e.g., lowest repeat, normal and top repeat heading entities) with only unanswered prompts under the heading entity of interest may be flagged for special processing (e.g., headings 1409 and 4013).

Typical examples of flagged special processing may include, but is not limited to, (1) excluding the flagged heading entity itself, as in step 1306, (2) displaying the flagged heading entity with an indication that there were no answered prompts under the entity, as in step 1307, and (3) creating a view that only shows the sections of the document that were completely skipped by (a) optionally flagging each entity below the flagged heading entity, (b) flagging each ancestor (e.g., any heading entity which includes the flagged heading entity within its scope) of a flagged heading entity, then, (c) excluding all non-flagged entities, as in step 1308.

Referring to FIG. 19C, shown is a flow diagram of handling entities within the scope of a heading entity of interest from documents (e.g., data forms) where the scope may include unanswered prompt entities or the documents have multiple style headings. The handling may include excluding all entities under the heading entity of interest when all prompts within the scope are unanswered (or answered, in some embodiments), augmenting the text of the heading entity of interest, and creating a view highlighting unanswered prompts under the heading entity of interest.

Procedure 1301 starts with step 1302 where a heading classification is calculated for each heading entity. If the document (e.g., data form) has only a single style of heading on the document, the calculation may be performed as outlined in FIG. 19B. If the document has multiple styles of heading on the document, each style of heading may be classified separately from the other styles of heading (e.g., as if the document only contained current style of interest heading entities and all those other styles of heading entities are not heading entities at all) as shown in FIGS. 19B, 19F, and 19G.

Step 1303 checks each individual heading entity to determine if there are any answered prompt entities within the scope (e.g., under) of that individual heading entity. Determining the scope of heading entities and enumerating the prompt entities within that scope is further discussed in FIGS. 19D-19G. An equivalent to counting is to first exclude all unanswered prompt entities, then check for any normal heading, lowest repeat heading or top repeat heading entity not followed by a prompt entity (when only considering heading and prompt entities).

Step 1304 searches for each heading entity of interest (e.g., every heading entity where all prompt entities within the scope of the heading entity are unanswered). For each such heading entity of interest, that heading entity is flagged for special processing.

Step 1305 may exclude all terminal heading, style terminal heading, and repeat heading entities. Also, if each repeat heading series is scheduled to be shortened by allowing the repeat heading series to be represented by just one of the heading entities within the series, the other heading entities of the heading series may be excluded (e.g., if the representative heading entity is of classification top repeat heading, the heading entity of the series that can be excluded is the lowest repeat heading entity).

The three lines coming from the bottom of step 1305 are intended to show there are different flagged special processing options available. Three representative options are illustrated, but the options for handling flagged special processing are not limited to those shown.

Step 1306 handles the flagged special processing by excluding the flagged heading entities and each unanswered prompt. There may possibly be optional exceptions such as keeping a class of headings (such as keeping each top repeat heading) and augmenting that kept heading with an indication that all the prompts under that heading were unanswered. The indication might be, for example, but not limited to, a change in color for that heading or additional text appended to that heading (such as "(unanswered)"). If this results in multiple headings with indications being adjacent to each other with no prompts between them, then just one of the adjacent headings can be selected to represent all of them (e.g., keep the first one of all the adjacent headings with indications).

Step 1307 handles the flagged special processing by augmenting the text displayed for the flagged heading entity with an indication that the prompts under the flagged heading entity were all skipped by the data entry user.

Step 1308 handles the flagged special processing by excluding heading entities which are not flagged and are not the ancestors (e.g., any heading entity which includes the flagged heading entity within its scope) of the flagged heading entity. This effectively creates a pruned tree of heading entities that can be used as a guide to sections that were skipped by the data entry user.

Step 1309 ends process 1301.

FIG. 19D shows the general structure and relationships of heading and prompt entities handled by FIGS. 19B-19C. This diagram is designed to teach how to determine the scope of each heading entity. After reading this disclosure, a person skilled in the art should be able to implement a version of performing the information in FIG. 19D-19E without undo experimentation, but these two diagrams may provide an understanding of what a program may do to properly handle the scope of each heading entity. This diagram excludes all document entities except start and end of document markers, heading entities and prompt entities (e.g., there is no need to list entities such as horizontal lines for an understanding). The sequence for each document begins at the start of document marker 1312 and terminates at the end of document marker 1328. The two markers may be explicit or implied. Examples of a typical start of document marker may include a title entity (as an example of an explicit marker) or it may be a pointer (as an example of an implicit marker) from some document entity to the first entity for displaying a document. Similar examples of a typical end of document marker may include an end of document entity (as an example of an explicit marker) or it may be a null pointer for the next entity in the sequential list of entities that make up a document entity (as an example of an implied marker). Each element is sequentially ordered as presented on the drawing (e.g., heading 1313 precedes heading(s) 1314, if present, which, in turn precedes heading 1315, etc.). In this figure, when a reference number points to two entities, it represents either one or more entities (for reference numbers 1317, 1320 and 1324) or zero or more entities (for reference number 1314). The reference line to terminal heading 1327 actually refers to zero or more entities, each a terminal heading entity. There are additional headings and prompts following and under top repeat heading 1326 that are not shown in FIG. 19D, making reference number 1326 a top repeat heading rather than a terminal heading. The figure shows three vertical lines 1343, 1344 and 1345 extending from start of document marker 1312 to end of document marker 1328 representing three heading levels. As the entities that make up the data form are sequentially read, each heading entity is placed on a new text line and either on vertical lines 1343, 1344, or 1345 or in the prompt area 1318, in sequential order. On vertical line 1345 is placed all the following entities: start and end of document markers, all terminal heading entities and all top repeat heading entities. On vertical line 1344 is placed all repeat heading entities. On vertical line 1343 is placed all lowest repeat heading entities and all normal heading entities. Vertical line segments 1322, 1316, 1321 and 1325 start below each heading 1313, 1315, 1319 and 1323, respectively. Each vertical line segment continues unbroken through text lines containing the prompt and heading entity identifiers that are under the heading entity identifier at the top of the vertical line segment. For example, unbroken line segment 1322 begins under heading 1313 and continues unbroken until just before heading 1326, so the entities in scope (e.g., under) heading 1313 are headings 1314, 1315, 1319, and 1323; and prompts 1317, 1320 and 1324. Line segment 1316 begins under lowest repeat heading 1315 and ends just before normal heading 1319, so the entities under heading 1315 are prompts 1317. Line segment 1321 begins under normal heading 1319 and continues until just above normal heading 1323, so the entities under normal heading 1319 are prompts 1320. Line segment 1325 begins under normal heading 1323 and ends just before top repeat heading 1326, so the entities under normal heading 1323 are prompts 1324.

If, in FIG. 19D, neither top repeat heading 1326, nor terminal heading 1327 existed, then the results of the sequences which vary would be as follows. Line segment 1322 would begin under heading 1313 and would continue unbroken until just before end of document marker 1328, so the entities in scope (e.g., under) heading 1313 would be headings 1314, 1315, 1319, and 1323; and prompts 1317, 1320, and 1324. Similarly, line segment 1325 would begin under normal heading 1323 and would end just before end of document marker 1328, so the entities under normal heading 1323 would be prompts 1324. This is the exact same results as above for which entities are in scope of each heading entity identifier.

Note that since terminal headings 1327 are optional, and have no prompt entities after them and may be excluded by other methods in this disclosure, scope actions that may have been performed on terminal heading entities (e.g., counts of prompt entities and excluding heading entities) would not change by using the end of document marker and ignoring the terminal heading entities for the purpose of determining scope under each top repeat heading, lowest repeat heading and normal heading entities. Also note that repeat heading and lowest repeat heading entities only occur after a top repeat heading entity (because a single heading entity by itself is a normal heading classification; and a sequence of two or more heading entities starts with a new top repeat heading entity), so, when looking for scope endings, one would always encounter the top repeat heading entity of the repeat heading series first, so there is not a need to look for either a repeat heading or a lowest repeat heading entity as the end of the scope for any heading entity.

As shown, there are six prompt entities 1317, 1320, 1324 under the top repeat heading 1313 before the next heading entity of the same classification 1326 or the end of document marker 1328. As shown, there are also five headings 1314, 1315, 1319 and 1323 under the top repeat heading 1313 before the next heading entity of the same classification 1326 or the end of document marker 1328. The repeat heading series members entities make up a sequence that includes a top repeat heading 1313 and a lowest repeat heading 1315, and any repeat headings (e.g., 1314) between the two.

Lowest repeat heading 1315 may be classified as a suitable substitute for normal headings 1319 and 1323. Similarly, normal headings 1319 and 1323 may be suitable substitutes for lowest repeat heading 1315. The only difference between these heading entities is that lowest repeat heading 1315 is immediately preceded either by repeat heading 1314 or top repeat heading 1313, whereas normal headings 1319 and 1323 are never proceeded by a heading entity.

Lowest repeat heading 1315 may have one or more prompt entities 1317 (two being shown) under lowest repeat heading 1315, before the next heading entity (e.g., normal heading 1319). If optional step 1293 is exercised, the count would be a measurement of the prompt entities in the sequence (e.g., quantity, percentage, and the like that gives the display user an idea how many prompts were left unanswered) before the next heading entity, which may be the next heading entity that is identical or almost identical to lowest repeat heading 1315 (e.g., normal heading 1319), the next top repeat heading entity 1326 (e.g., if headings 1319 and 1323 and prompts 1320 and 1324 did not exist), the terminal heading entity 1327 (e.g., if headings 1319, 1323 and 1326 and prompts 1320 and 1324 did not exist), or the end of document marker 1328 (e.g., if headings 1319, 1323, 1326 and 1327 and prompts 1320 and 1324 did not exist).

The sequence starting at normal heading 1319 may include one or more prompt entities 1320 (two being shown) before the next heading entity of the same classification (e.g., normal heading 1323). If optional step 1293 is exercised, the count would be a measurement of the prompt entities in the sequence (e.g., quantity, percentage, and the like that gives the user an idea how many prompt entities were left unanswered) before the next heading entity of the same classification (e.g., normal heading 1323).

The sequence starting at normal heading 1323 may include one or more prompt entities 1324 (two being shown) before the next heading entity (e.g., top repeat heading 1326). If optional step 1293 is exercised, the count would be a measurement of the prompt entities in the sequence (e.g., quantity, percentage, and the like that gives the display user an idea how many prompts were left unanswered) before the next heading entity, which may be the next heading entity that is identical to normal heading 1323 (e.g., see previous paragraph for a discussion of the scope of a normal heading followed by another normal heading), the next top repeat heading entity 1326, the terminal heading entity 1327 (e.g., if heading 1326 did not exist), or the end of document marker 1328 (e.g., if headings 1326 and 1327 did not exist).

FIG. 19E shows a document that could have created the structure shown in FIG. 19D. Ellipses 1333 and 1335 indicate that there could have been additional entities earlier or later in the same document.

Note that the indentations of FIG. 19D (e.g., heading 1314 may appear to be indented in FIG. 19D from heading 1313), but any indentation in FIG. 19D is only to show that the two heading entities are on different vertical lines in the drawing. Heading 1313 is on vertical line 1345 and heading 1314 is on vertical line 1344 in FIG. 19D.

As shown in FIG. 19E, headings 1313 and 1314 may both be completely left aligned in an actual document.

FIG. 19F expands on the concepts introduced in FIGS. 19D-19E to teach how to interpret the scope of each heading entity in an EMR document (e.g., data form) with multiple heading styles. In an EMR document with multiple heading styles, the initial categorization of each heading classification may be handled exactly as shown elsewhere in this disclosure (e.g., heading entities are classified as top repeat headings, repeat headings, lowest repeat headings, normal headings and terminal headings) by ignoring the existence of heading entities of any other style. So, if a document has two styles of headings: (1) a default style of heading and (2) a subheading style of heading; firstly, all the default style heading and prompt entities are analyzed together to classify the default style heading entities; then secondly, all the subheading style heading and prompt entities are analyzed together to classify the subheading style heading entities.

FIG. 19F shows an EMR with three instances of heading styles 1346, 1347 and 1348. Heading style 1346 is the section heading style. Heading style 1347 is the default heading style. Heading style 1348 is the subheading style. The left side of FIG. 19F represents heading entities that are higher level heading entities. Note that there is a specific arrangement of the heading styles that may be selected by either the user, the programmer or implied from the font characteristics (e.g., the more prominent font styles are higher level heading entities and more subtle font styles are lower level heading entities) to determine the order on FIG. 19F (e.g., where being located further to the left represents a higher level style, determining if heading style 1346 is further to the left or heading style 1347 is further to the left, and so on). Each of the heading style layouts resemble the layout of FIG. 19D with three vertical lines 1343, 1344, 1345, each numbered 1 through 3 (reference numbers 1340, 1341 and 1342, respectively).

After placing the heading styles in the proper order, use the same process of placing each heading entity identifier on the proper vertical line as was done in FIG. 19D. In FIG. 19F, use both the heading style and heading classification to determine the proper vertical line (in FIG. 19D, only heading classifications determined which vertical line to place each heading entity identifier on). For example, normal heading 1351 is a section style heading, as a normal heading classification, its entity identifier is placed on vertical line 1343 of section style 1346 and starts line segment 1352. Each heading entity identifier is then extended all the way to the right from the vertical line where the heading entity identifier is placed on.

After all the heading and prompt entities are recorded on FIG. 19F by sequentially reading through the entities that make up a document and before excluding any unanswered prompt entities, it may be noted that some heading entities cannot have a prompt entity below them because of the form design, as in reference number 1363. This would have originally been classified as a normal heading because prompt entity 1362 is before it and prompt entity 1366 is after it (normal heading entity 1364 is of the default style 1347, so it is a different style, therefore normal heading 1364 is ignored when classifying heading classifications of the subheading style 1348). So, reference number 1363 is reclassified as a style terminal heading and left on the same vertical line it was originally classified on (e.g., since it was a normal heading before being reclassified, vertical line 1343 of subheading style 1348). As a type of terminal heading, style terminal heading 1363 may be excluded when the other terminal headings are excluded. An example of a style terminal heading is instructions, such as "if you checked any of the above boxes, you must also complete forms X1 and Y2".

Also, after all the heading and prompt entities are recorded on FIG. 19F, as in FIG. 19D, unbroken vertical line segments identify which prompt and heading entities are under the current heading entity of interest. For example, all the following are under (e.g., in the scope of) heading entity 1351: heading entities 1353, 1355, 1358, 1360, 1363 and 1364, and prompt entities 1357, 1362 and 1366, as shown by vertical line segment 1352.

The entities under heading entity 1353 are heading entities 1355, 1358, 1360, 1363 and 1364, and prompt entities 1357, 1362 and 1366, as shown by vertical line segment 1354. The entity under heading entity 1355 is prompt entity 1357, as shown by vertical line segment 1356. The entities under heading entity 1358 are heading entities 1360 and 1363 and prompt entity 1362, as shown by vertical line segment 1359. The entity under heading entity 1360 is prompt entity 1362, as shown by vertical line segment 1361. The entity under heading entity 1364 is prompt entity 1366, as shown by vertical line segment 1365. The entities under heading entity 1367 are heading entities 1369, 1372, 1374, 1377, 1379, 1382, and 1384 and prompt entities 1376, 1381, and 1386, as shown by vertical line segment 1368. The entities under heading entity 1369 are heading entities 1372, and 1374, and prompt entity 1376, as shown by vertical line segment 1371. The entities under heading entity 1372 are heading entity 1374 and prompt entity 1376, as shown by vertical line segment 1373. The entity under heading entity 1374 is prompt entity 1376, as shown by vertical line segment 1375. The entities under heading entity 1377 are heading entity 1379 and prompt entity 1381, as shown by vertical line segment 1378. The entity under heading entity 1379 is prompt entity 1381, as shown by vertical line segment 1380. The entities under heading entity 1382 are heading entity 1384 and prompt entity 1386, as shown by vertical line segment 1383. The entity under heading entity 1384 is prompt entity 1386, as shown by vertical line segment 1385.

FIG. 19G shows sample text from a series of entities that could have created the structure shown in FIG. 19F. Each line of this sample text identifies both the heading style and heading classification. To further help visually distinguish the different heading styles, each section heading style 1346 is shown in 16 pt bold font, each default heading style 1347 is shown in 14 pt regular font, each subheading heading style 1348 is shown in 12 pt light font and each prompt text is shown in 9 pt regular font.

FIG. 19H shows an overview table of how to determine the initial (e.g., before finding any style terminal heading) classification of a heading entity based on the closest entities of interest before and after the heading entity. For this purpose, the entities of interest are: a heading entity (of the same style 3912, if heading styles are available), a prompt entity, a start of document marker and an end of document marker. For example, if the closest entity of interest before a heading entity is another heading entity and the closest entity of interest after the heading entity is a prompt entity, the classification of the heading entity is a lowest repeat heading entity.

Figures 20, 21:
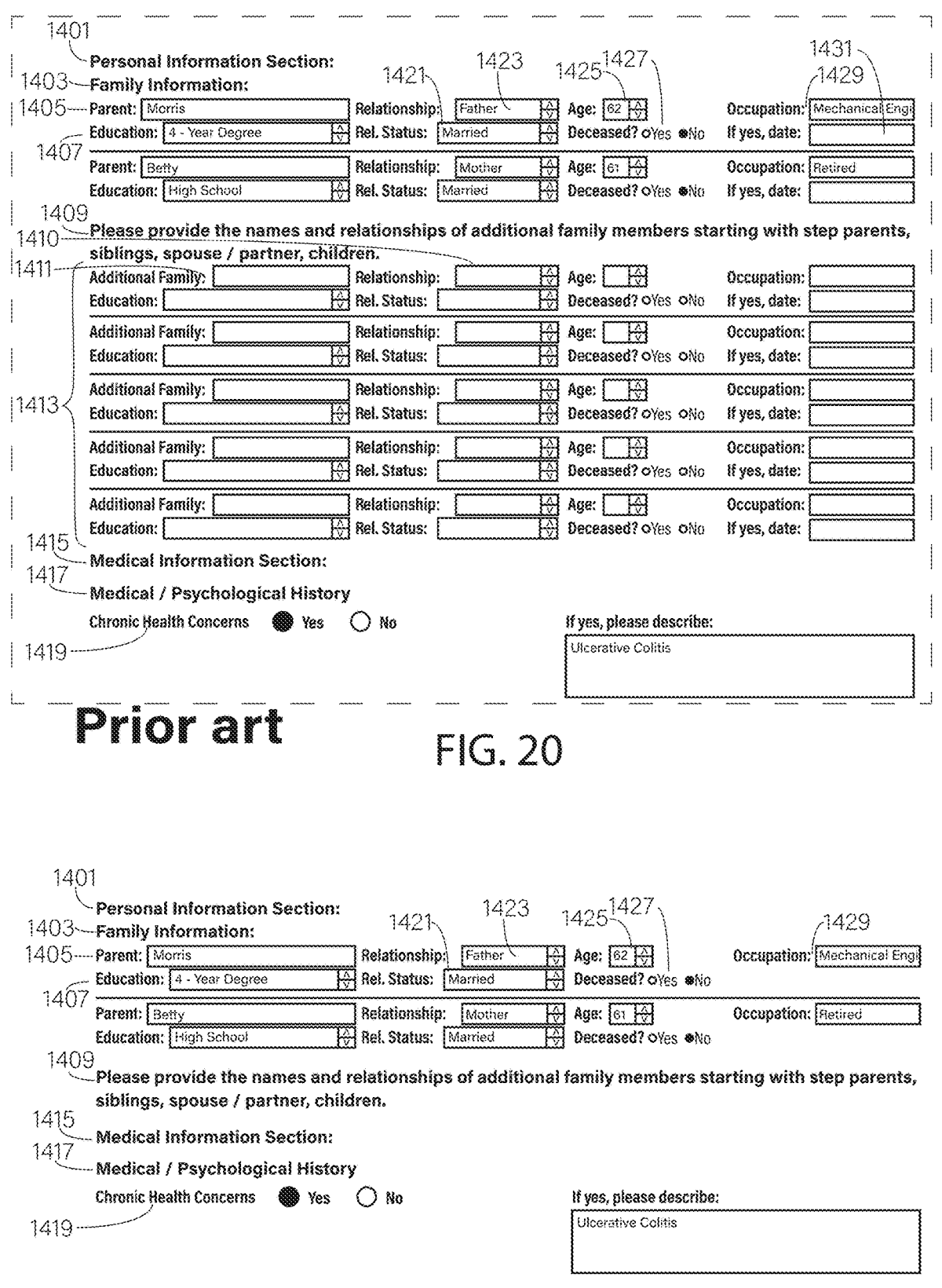

FIG. 20 shows a small portion of a sample data entry form that may demonstrate an example of the method of FIGS. 19A-19B for excluding an unused normal heading. There are five headings shown: 1401, 1403, 1409, 1415 and 1417. Upon initial review, each of these five headings appear to be identical in structure, but with different wording. This data entry form includes seven repetitions of the structure between the parent free text box 1405 and the date box 1431, some headings and an option group 1419. Each repetition includes three free text boxes (1405, 1411 and 1429), three combo boxes (1407, 1421, and either 1410 or 1423), one numeric field (1425), one yes/no prompt field (1427), and one date field (1431) in the structure.

Combo box 1407 has the possible answers: "Grade School", "Less than High School", "Completed High School", "Some College", "4-YearDegree", and "Graduate/ProfessionalDegree". In document area 1413, Combo box 1410 (with the possible answers: "Stepfather", "Stepmother", "Brother", "Sister", "Spouse/Partner", and "Child") may replace combo box 1423 (with the possible answers: "Father", "Mother", "Guardian", and "Spouse/Partner"). Otherwise, document area 1413 has an identical structure to the two similar structures shown under the heading 1403. Combo box 1421 has the possible answers: "Single", "Serious dating or committed relationship", "Civil union, domestic partnership, or equivalent", "Married", "Separated", "Divorced", and "Widowed".

FIG. 21 shows an example of how FIG. 20 may appear if displayed after steps 1271 and 1295. Each unanswered prompt text has been excluded, with everything else remaining.

FIG. 22A shows selected calculated values from the loop in Step 1269 as it processes the data entry form of FIG. 20 using the method of FIG. 19A. The first column (from the left) lists the various pass numbers (3 corresponds to the third pass, 4 corresponds to the fourth pass, etc.). Rows that do not set a new classification of heading have been omitted. The second column lists the reference numbers used in FIG. 20. The third column lists the value of the NextHeading variable in step 1269 before executing the loop. The fourth column lists the value of the HeadingClassification variable (i.e., the classification of the heading entity of interest) after the current execution of the loop. The fifth column lists the value of the NextHeading variable in step 1269 after executing the loop. By way of example, the second pass through the loop (not shown since this is not a heading entity) looks at Yes/No prompt text 1419, and is in the category of a #PromptAnswer. As a #PromptAnswer, NextHeading is set to #LookForNormalHeading. Then, at the third pass 1501 through the loop, the loop processes heading 1417. Since heading 1417 is, in fact, the text of a heading entity, the method categorizes the HeadingClassification as #NormalHeading and sets the NextHeading to #LookForOtherHeading. Then, in the fourth pass, it finds heading 1415. Since heading 1415 is, in fact, the text of a heading entity, the method categorizes the HeadingClassification as #OtherHeading.

FIG. 22B shows the calculated classification of heading entity as it processes the data entry form of FIG. 20 after selected steps of FIG. 19B. Column 1521 shows reference numbers in FIG. 20.

Columns 1523, 1525, 1527, 1529, and 1531 show the current calculated classification of heading entities after steps 1283, 1285, 1287, 1289, and 1290 respectively. For example, heading 1401 initially is assigned a classification of #TerminalHeading after step 1283, which is changed to #NormalHeading after step 1285, which is changed again to #RepeatHeading after step 1287, and finally changed to #TopRepeatHeading after step 1289.

Referring to FIG. 23, shown is an example of how FIG. 20 may appear after using the method of FIG. 19A or 19B, with everything not excluded turned into text. At reference number 1575 (where normal heading 1409 was in FIG. 21), normal heading 1409 is excluded. In Step 1273, normal heading 1409 may be excluded from the display of FIG. 21 because normal heading 1409 is followed by other heading 1415, (which is the text of another heading entity, and not the text of a prompt entity). Alternatively, using the method of FIG. 19B step 1297, normal text heading 1409 may be excluded from the display of FIG. 21 because after normal text heading 1409, all prompt entities under heading 1409 are unanswered prompt entities.

Figure 24:
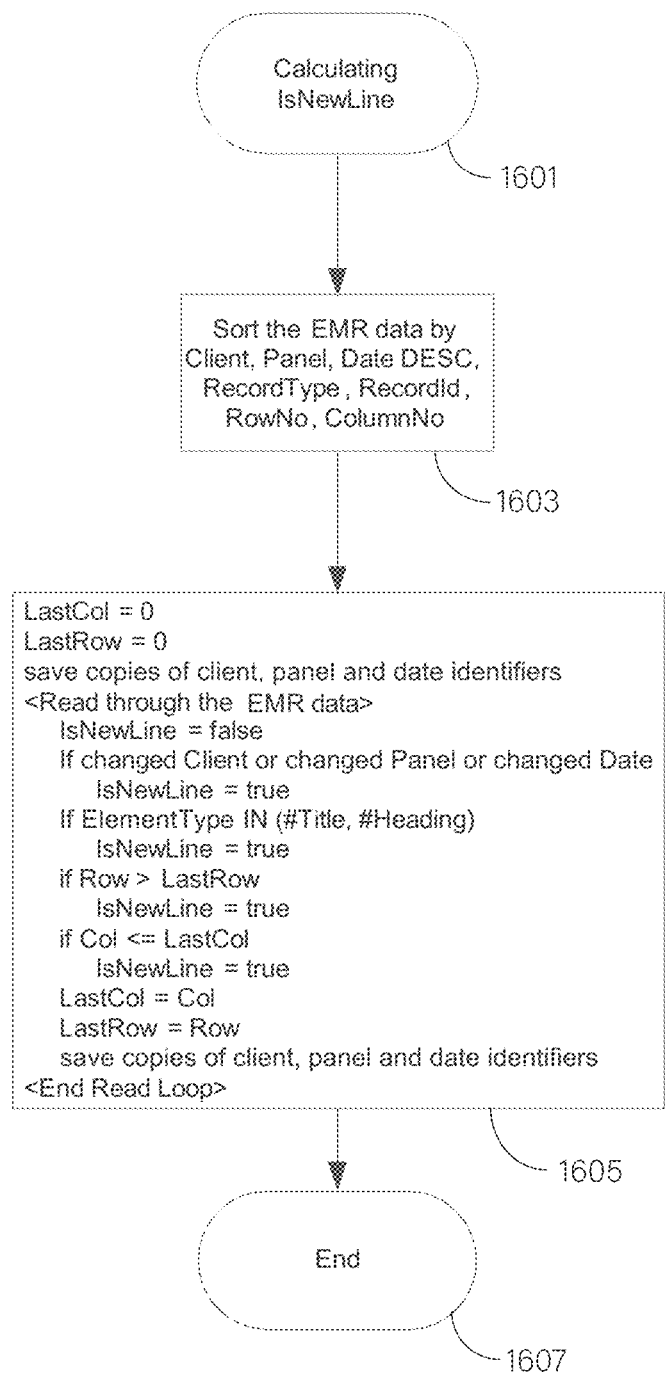
FIG. 24 is a flow diagram depicting an example method of computing a flag indicating whether the current record starts on a new output line.

FIG. 24 shows an example of how to compute a flag indicating whether the current record starts on a new output line (e.g., element on new line indicator 3938). This may be necessary if the EMR uses row and column numbers to lay out data forms rather than a flag that indicates the current record starts a new output line.

Process 1601 may start with step 1603 sorting EMR data by a document identifier (e.g., clientId, relevant date of the document, document record type, and document record Id), and a location within the document (e.g., the panel on the page on which the data may appear, row number, and column number). The "panel" here is being used in the sense of the TPanel control in Embarcadero products where one can have multiple layout panels on a single page and is optional.

In step 1605, all the records may be looped through reading one field at a time. Every row in the EMR for a client may be sequentially read through in order marking the row whether or not the row represents a new output line on the screen. A new output line on the screen occurs every time the document identifier changes (e.g., the clientId changes, the relevant date changes, the document record type changes, or the document record Id changes), whenever the panel or row number changes, whenever the element type is a title or (optionally) a heading entity, and whenever the column number is not larger than the last column number. The process ends at step 1607.

Figure 25A:
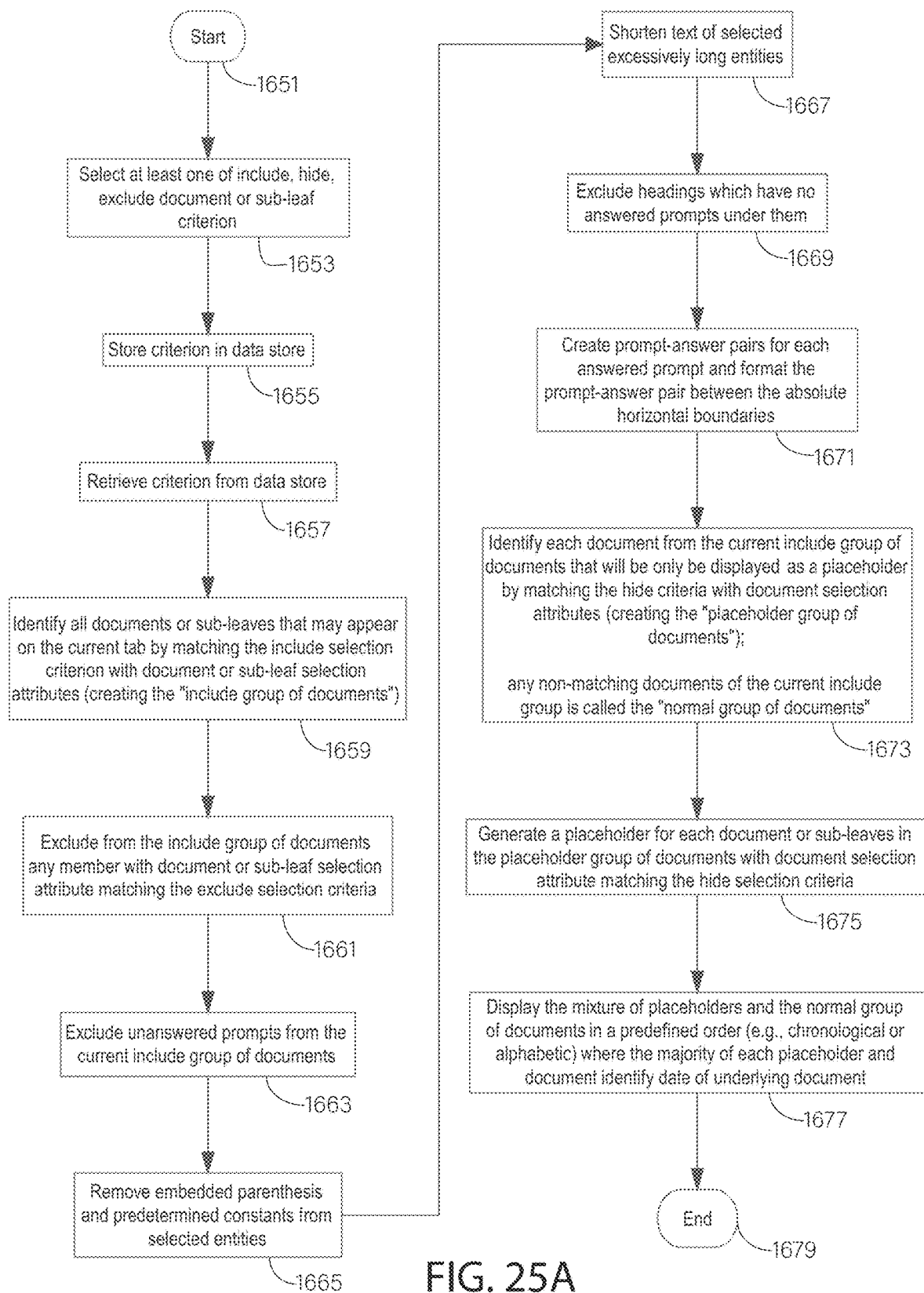
FIG. 25A is a flow diagram depicting an overview of an example of a display user configurable method of displaying multiple documents on a tabbed screen in order to decrease the quantity of, and increase the relevancy of, documents appearing on any particular tab.

Depicted in FIG. 25A is a flow diagram illustrating an overview of an example of a user configurable method of displaying multiple documents on a tabbed screen in order to decrease the quantity of, and increase the relevancy of, documents appearing on any particular tab. It represents one more way of decreasing the vertical height of relevant documents displayed on a screen, resulting in less navigation operations to review significant elements of a client's chart. The particular advantages here are: (1) the display user can configure tabs that represent what is significant to the display user's specialization and the same set of pre-configured tabs can pop up for each client the display user sees, (2) if a document may be important, but not usually, there is a mechanism to include the document without using much vertical space by replacing it with a placeholder automatically on the tab, (3) the tree mechanism of selecting documents to include, hide and exclude allows configuration of tabs to be very quick, even configuring a one-time use tab on the fly, (4) the example is ideally suited to allowing offline work with a client's chart and decrease network traffic since it does not require a live connection to the EMR when the chart is being reviewed (this can, for example, allow downloading a day's worth of appointments each night, download any updates at the appointment time, merge those updates into the downloaded copy and have near instantaneous access to on the fly different selections of EMR documents, all without requiring any changes to the rest of the EMR, e.g., no new indexes required to support this program in a third party EMR environment that cannot be modified), (5) as new document formats are added to the EMR, they can be automatically included in preconfigured tabs without requiring manual reconfiguring of tabs based on selection attributes of the new format, (6) the display method is an ideal way to further benefit from the other techniques described in this specification to decrease vertical space, and (7) this same program can be added to any EMR without requiring changes to the EMR by downloading the EMR data into a standardized format allowing the unaltered program to function with a totally different environment.

Procedure 1651 starts in step 1653 where the display user selects which document criterion is used to place documents on the tab. Up to three document criterion categories are generally included. In one embodiment, at least one of the document criteria must be an include document criterion or an include sub-leaf criterion. The other two document criterion for that embodiment is a hide document criterion and an explicitly exclude document criterion. Step 1653 is further described in procedure 1701, FIGS. 29A-E.

Step 1655 is an optional step to save the configuration of a tab. Document criterions may be stored to the data store. By way of example, these criteria may include criterion of which documents to show fully expanded, which documents to hide behind a placeholder and which documents to explicitly exclude. If the tab is a one-time use (e.g., on the fly) tab there is no reason to save its document criterion. This step is further described in steps 1811 and 1869.

Step 1657 generally occurs after some time has passed since executing step 1655 and is also optional. Document criterions are retrieved to start the process of selecting which documents may appear on the current tab. Step 1657 is further described in step 2703.

Step 1659 identifies all documents that may appear on the current tab by matching one or more include document criterion selected in step 1653 with selection attributes stored in the data store 48. These selection attributes may include attributes 54 such as a date the document was created or signed and by whom, the title 50 of the document design, and other external entities 38 such as a viewing verification data set indicating when the current display or data entry user last viewed the document. The end result of this step is creation of an "include group of documents". Step 1659 is further described in steps 1803, 2803, 2805, 2813 and 2903-2921 and FIGS. 29A, 29E, 30A-30C.

In step 1661, optionally, each document in the include group of documents is further processed by applying the explicitly exclude document criterion selected in step 1653. This is accomplished by matching the explicitly exclude criterion with the selection attribute of each document in the include group of documents. For partial documents, match the exclude sub-leaf criterion with the entity identifier (e.g., primary key of the heading or prompt entity). For each match, that document or entity is excluded from the include group of documents. Having the process of including documents/entities on one axis and explicitly excluding from those included on a different axis creates a very powerful, flexible, but simple method of selecting exactly the documents to include in just a couple of steps. Step 1661 is further described in steps 1807, 2811, 2815 and 2943-2959 and FIGS. 29C, 29E, 30A-30C.

Step 1663 is an optional step in which unanswered prompt entities are removed to shorten the vertical height of data forms. Step 1663 is further described in steps 1271, 1295, 1413, 3971, 3973, 4017, 4021 and 8411.

Step 1665 is an optional step in which embedded parentheses and predetermined constants are removed from heading entities, prompt and selected answer entities (e.g., prompt-answer pairs that were not manually typed by the data entry user). Embedded parentheses processing is further described in procedures 830 and 860 and steps 782, 784, 906-922 and 8409. Predetermined constants are further described in steps 786, 788, 904 and 8409.

Step 1667 is an optional step in which excessively long text is shortened from heading, prompt and selected answer entities (e.g., prompt-answer pairs). FIGS. 12-18 and steps 790, 792, 924, 3905, 4055 and 8409 further describe step 1667.

Step 1669 excludes heading-prompt series that have no answered prompt entities under (e.g., in the scope of) a higher-level heading entity of interest. This step may also optionally exclude any heading entity of interest if all prompt entities under the heading entity of interest are unanswered. This step may also replace each series of a top repeat heading entity, possibly one or more repeat heading entities and a lowest repeat heading entity with a single heading entity. This step is further described in FIGS. 19A-23 and steps 4053, 4057 and 8411.

Step 1671 optionally creates prompt-answer pairs and displays the pairs between absolute boundaries as described in FIGS. 2-8B and steps 4069, 4071 and 8403.

Step 1673 splits the first group of documents of step 1659 (possibly minus any documents excluded by step 1661) into two groups using a hide document criterion that was selected in step 1653. Those documents whose selection attribute does not match the hide document criterion may be displayed fully expanded in step 1677. Each document whose selection attribute matches the hide document criterion may be converted to a placeholder by step 1675 and displayed as a placeholder in step 1677. Step 1673 is further discussed in steps 2809, 2817, 2923-2941, 8413 and FIGS. 29B, 30A-30C.

After reading this disclosure, it should be obvious to those skilled in the art, that there are various ways of arranging steps 1659, 1661 and 1673. For example, it is possible to identify the documents whose selection attributes matches the include document criterion of step 1653 creating an include group of documents. Then, split the include group of documents into a group of documents whose selection attributes matches the hide document criterion of step 1653 (creating a placeholder group of documents) and another group of documents whose selection attributes doesn't match the hide document criterion (creating a normal group of documents). Finally, exclude all documents from the placeholder group whose selection attributes match the explicitly exclude document criterion of step 1653 and exclude all documents from the normal group whose selection attributes match the explicitly exclude document criterion.

A third example of arranging steps 1659, 1661 and 1673 is to build a SQL statement that does all three operations in one or two steps. Even in a SQL statement, it may be possible to separate out clauses that function to identify documents to include, identify documents to explicitly exclude and identify documents to hide behind placeholders. This option is further discussed in steps 2709, 2817, FIGS. 30A-30C and with the discussion of button 3901.

Step 1677 intermixes the two groups of entities (i.e., fully expanded documents and placeholders) that came out of step 1673 and displays them in a pre-determined order on the tab. The pre-determined order may be based on chronological or alphabetical highest-level ordering. A reason to use alphabetical order is to display a medication history. The chronological order in one embodiment has the newest document nearest the cursor when the tab is initially opened. In that embodiment, the date field is also used with each placeholder and document. For example, placeholder button 3901 shows the date on the button itself and title 3902 shows the date on the title line. It is in the same spirit of this disclosure for the date to be displayed outside the text of the placeholder button or document but elsewhere on the screen, but the displayed date gets updated to reflect the date field when the visible portions of the document and placeholders are scrolled off and on the screen, as would be possible using actions of the TRichView.com's TRichView product. In that embodiment, such use of the date is possible because the date is stored as separate fields of both the document and placeholder entities. Alternatively, the date field may be stored only as an attribute of the document entity, and the placeholder entity contains a pointer link to the document entity where the pointer link is used to look up the date field whenever the placeholder or document scrolls onto the screen. Step 1677 is further discussed in steps 3109 and 3111 and illustrated in FIG. 31A.

Figure 25B:
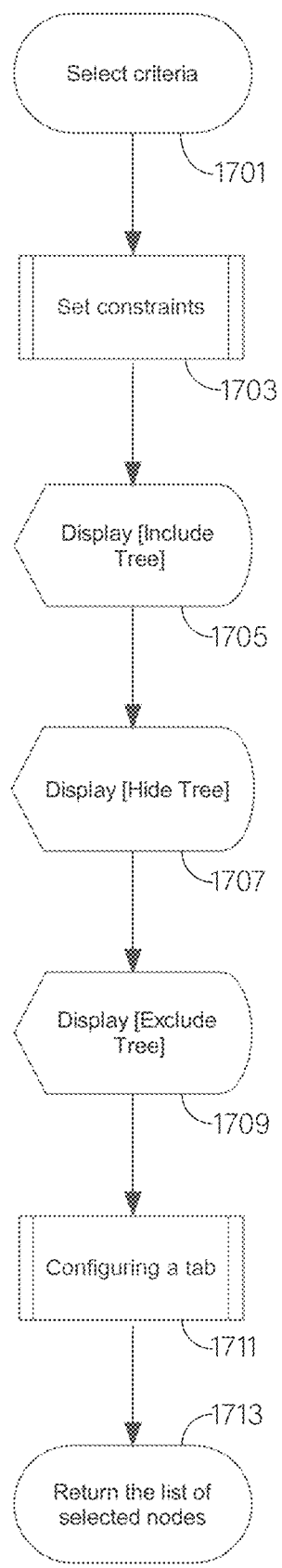
FIG. 25B is a flow diagram depicting an example method of selecting and storing document criterion.

Depicted in FIG. 25B is a flow diagram illustrating an example of a method for selecting and storing one or more document criterion (e.g., a first document criterion, a second document criterion, a third document criterion, etc.) that is used to configure which selection attributes may be included and hidden on a tab. The document criterion may later be used to select individual documents to appear on the tab and what state they may be in when initially displayed on the tab (e.g., expanded or hidden).

Figures 25C, 25D, 25E:
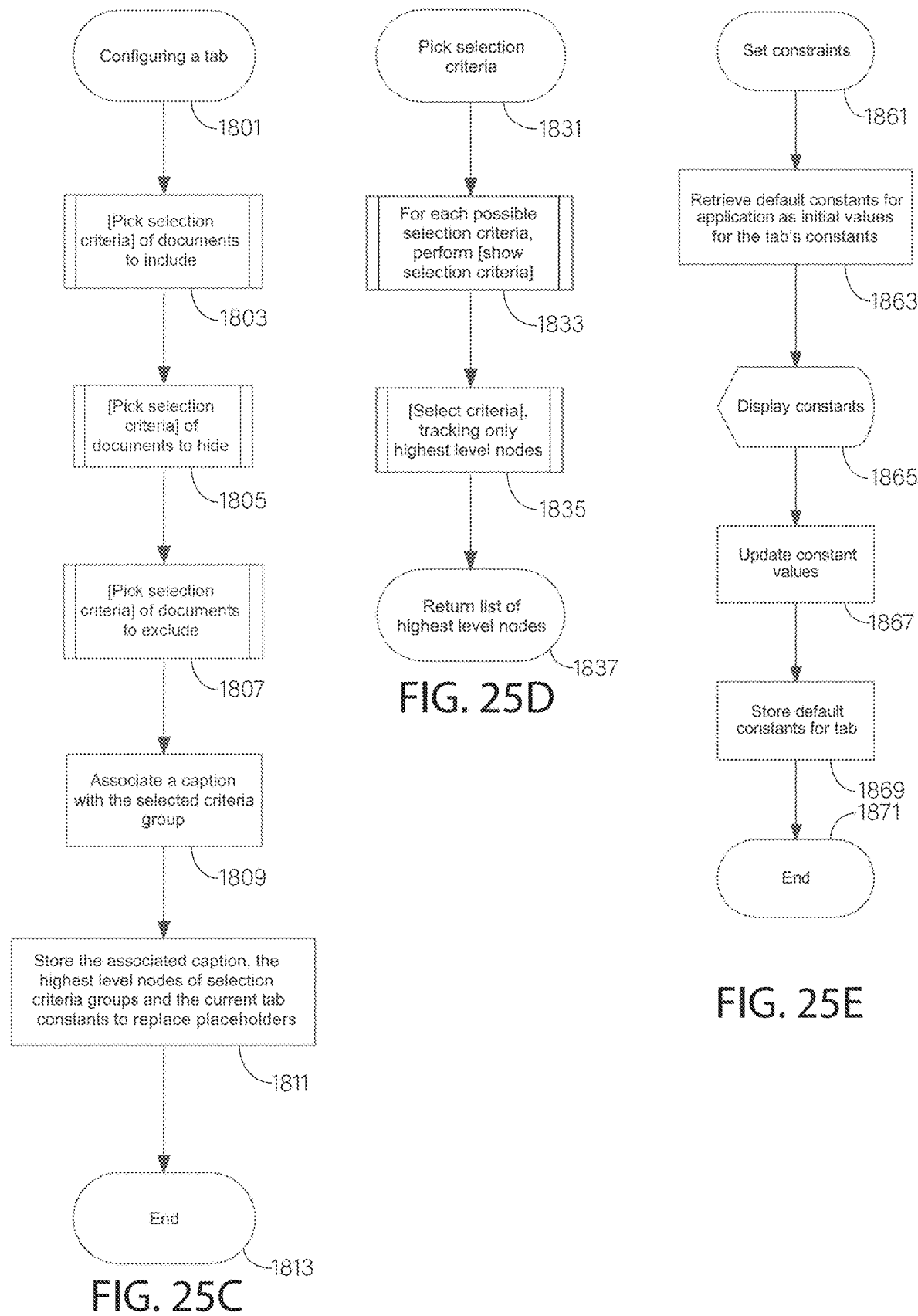
FIG. 25C is a flow diagram depicting an example method of choosing captions, laying out which nodes are selected by subtrees, picking which nodes are going to be selected and storing the captions and subtree roots on one tab.
FIG. 25D is a flow diagram depicting an example method of providing a caption and selecting nodes for one layout subtree.
FIG. 25E is a flow diagram depicting an example method of displaying, updating and storing the constraints.

Procedure 1701 starts in step 1703 by setting the defaults for how the trees may interpret various variables that may replace placeholders in the text displayed to the display user. The function called to accomplish this is procedure 1861 (FIG. 25E).

In one example, three different trees may be shown to the display user during the configuration state. The first tree has the display user picking all the document categories to include on the current page in step 1705. The second tree has the display user picking all the document categories to hide on the current page in step 1707. If a document is both included and hidden, the net result may be that the document is hidden. If a document is selected to hide, but never selected to include, the document may not appear at all.

The third tree is the list of document categories to exclude from the current page in step 1709. It may have priority over the other two trees, meaning that if a document is both selected to include or hide and also selected to exclude, the net effect may be that the document may be excluded.

Without being bound by any particular theory, it is generally contemplated that the idea of a tree may be novel for choosing document categories to include. By way of comparison, when one selects to print a report in an EMR, they are provided with a list of specific documents to include in the report. Effectively, the display user has to either take a predefined list of documents or check or uncheck each individual document type, where the leaves of the tree is the level display users have had to work in the past. In contrast, using a tree to pick from provides different levels of granularity. The individual document types are all at the leaf level of the tree. Being able to pick at the level of branches of the tree allows quick selection of which document types to include rather than having to do it at the leaf level. In addition, as new document types are added to the EMR, if the selections have been made at the branch level rather than at the leaf level, the new document types may automatically be included whenever they fit below a previously selected branch.

In one or more examples, there are some documents that contain raw data that a display user may generally not want to see, preferring instead to only see the computer-generated reports that come from that raw data. For example, if the client took a standardized test to evaluate their mental state, it is generally contemplated that the display user would typically want to see the computer-generated scores that indicate the client's mental status, and would only rarely want to see how a client answered all the individual questions. In addition, if there were a few questions that a display user wants to see with the standardized report, the individual questions could be included on the tree as sub-leaves allowing each display user to have their own custom list of questions displayed with the standard computer score (but still allowing the leaf level to control document selection) by having a setting that associates the standardized report type with the data form type that the data entry user completed.

In the process of selecting and unselecting various branches or leaves of the tree, the corresponding parents or children of the current node may also be selected or unselected. The net effect of doing so would be that only the root of each subtree would need be saved and the tree can quickly be reconstructed with just a list of subtree root nodes (and any individual sub-leaf node that needs to be changed from the default for standardized reports).

After the trees are displayed, the trees may be used to select which leaf nodes may be included, hidden, and excluded from the tab. This may be performed in step 1711, and the function called here is the procedure beginning at step 1801. The process ends at step 1713.

FIG. 25C is a flow diagram depicting an example of a method for laying out which nodes may be selected by subtrees, and picking which nodes may be selected on one tab and what else needs to be stored with the document criterion (e.g., subtree root nodes). Process 1801 starts by calling process 1831 in steps 1803, 1805 and 1807. This generally represents the steps a display user would take to select which document categories may appear on a tab.

In step 1809, a caption may be chosen for the tab. In one example, the caption may be stored with the constraints and list of subtree nodes selected in step 1811. The constants stored in this example are: quantity of days, absolute date, use absolute dates flag, quantity of appointments, quantity of characters, and length of measurement. In addition, each tab may have settings for separate formatting (e.g., font and paragraph settings) and which options (e.g., parenthetical comment exclusion; predetermined constant text exclusion; the maximum lengths, if any, for shortening the text of heading, prompt and selected answer entities; and excluding unanswered prompt entities and selected heading entities) are handled on the tab. Depending on how the software functions, these tab constants may be stored either in program data 8329, in the data store 43, or in some other location the computer has access to. The use of this example of specific constants is not intended to be interpreted as these are the only constants, or any of these specific constants must be present, or all these constants must be present. This is just one non-limiting embodiment of the invention functions. Step 1813 is the end of the process.

FIG. 25D is a flow diagram depicting an example of a method for providing captions for the layout subtrees, picking subtree roots and having those translate into leaf nodes, and picking combinations of leaf nodes and having that turn into subtree roots. The method starts at procedure 1831.

Step 1833 calls procedure 1901 which lays out a single caption of the tree. Procedure 1901 is called one time for each node in the three trees.

Step 1835 calls both procedure 2501 and its corresponding undo procedure 2201. Step 1835 is the display user interactions of selecting and unselecting nodes and calculating which other nodes are selected or unselected when one node in the tree has its selection status changed.

Step 1837 returns a list of the highest-level nodes for each subtree, one set of subtree root nodes for each of the three trees (include, hide and exclude).

FIG. 25E is a flow diagram depicting an example method of displaying, updating and storing the constraints (e.g., procedure 1861). The process starts out retrieving either the application wide current defaults for each of the constraints or the last saved defaults for the current tab in step 1863, depending on whether the defaults have already been saved for this tab. Depending on how the software functions, retrieving the application wide defaults may be performed either from program data 8329, or from the data store 43, or some other location the computer has access to. It then displays those values in step 1865, allows updating the values in step 1867, then stores the constraints for the single tab in step 1869. In 1865, the constraints listed are the tree constraints that may be applied to all three trees for the single tab. Examples of these constraints are shown in FIG. 29A-D. The process ends at step 1871.

Figure 25F:
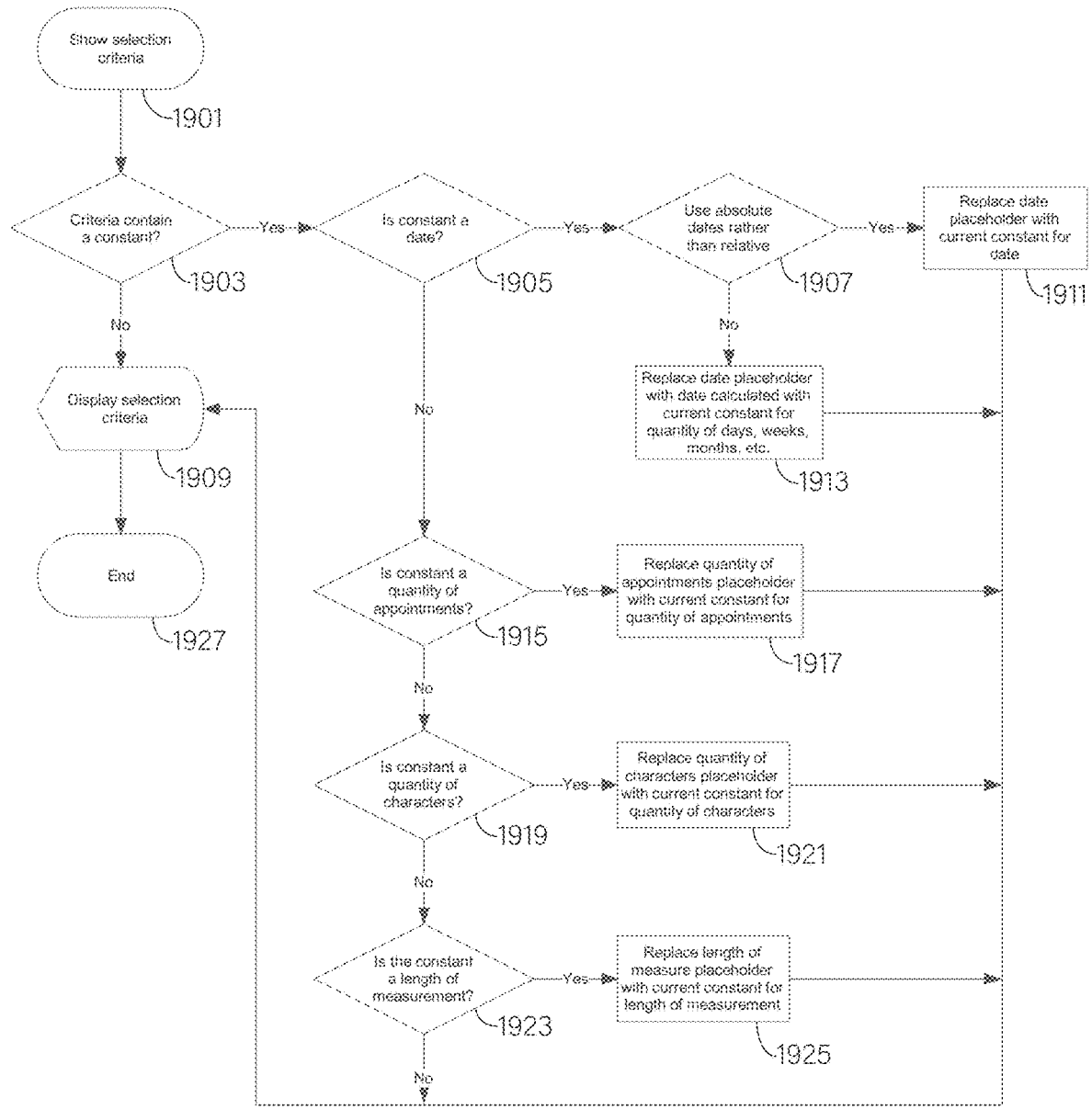
FIG. 25F is a flow diagram depicting an example method of displaying a single node caption of a tree.

FIG. 25F is a flow diagram depicting an example method of displaying of a single node caption of a tree (e.g., procedure 1901). In one embodiment, the tilde character marks the presence of a constant in the current output line. A check is made to determine if the current output line contains a placeholder for a constant in step 1903. If it does, a check is made for the type of constant to insert into the text.

Step 1905 checks if the placeholder is a date. If so, step 1907 checks if the use absolute dates flag is set true, if so, then step 1911 replaces the placeholder with the current absolute date constant. For example, if the prompt text is "Only include appointments since ~Date~", the display user would see "Only include appointments since Sep. 1, 2019", if the absolute date constant for the tab was Sep. 1, 2019 and the use absolute dates flag was true.

Similarly, if the current date is Jan. 24, 2020 and relative date is set to 365 days and use absolute dates flag is false and prompt text is "Only include appointments since ~Date~" then step 1913 calculates the Jan. 24, 2020 minus 365 days is Jan. 24, 2019 and the text the display user would see is "Only include appointments since Jan. 24, 2019".

If the constant is of type "quantity of appointments" in step 1915, then that quantity would be substituted in the text in step 1917. If the constant is of type "quantity of characters" in step 1919, then that quantity would be substituted in the text in step 1921. If the constant is of type "length of measurement" in step 1923, then that length would be substituted in the text in step 1925.

The use of this example of specific constants is not intended to be interpreted as these are the only constants, or any of these specific constants must be present, or all these constants must be present, or this is the only way to mark the presence of a constant. This is just one non-limiting embodiment of the invention functions.

The display is then updated in step 1909 and the process ends in step 1927.

Figure 25G:
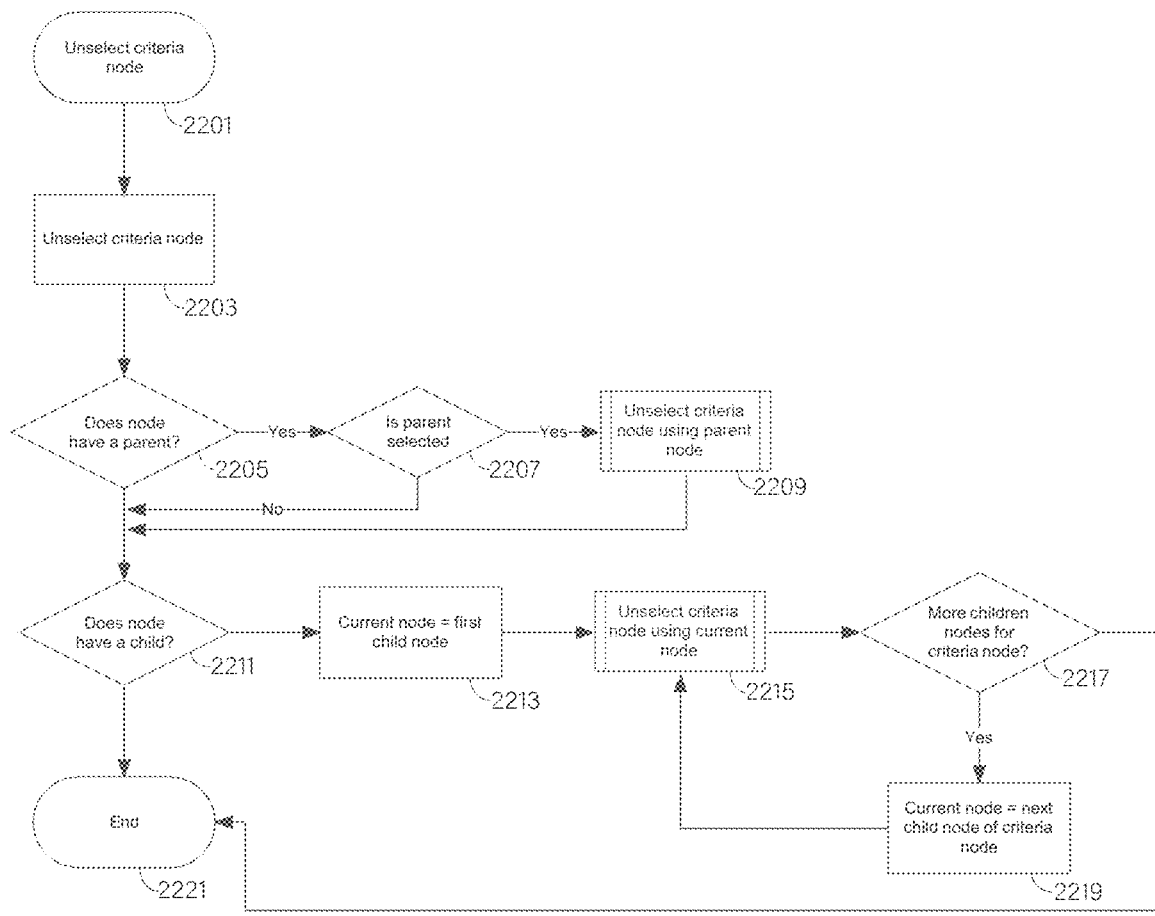
FIG. 25G is a flow diagram depicting an example method of propagating unselecting a tree node to the children and parents of the tree node.

FIG. 25G is a flow diagram depicting an example method of propagating unselecting a tree node to its children and parents (e.g., procedure 2201). Since this function can be recursively called, it starts with the display user action to unselect the current node in step 2203. A check is made to see if the current node has a parent in step 2205. If so, check if the parent is selected in step 2207. If the parent node is selected, then a recursive call is made to procedure 2201 in step 2209.

Next, the function checks if the current node has children in step 2211. If so, step 2213 sets the current node to the first child node. It then loops through each of the children recursively until there are no more children in steps 2215 through 2219. The loop recursively calls procedure 2201 in step 2215. Step 2217 checks if more children are present, and if so, step 2219 sets the current node to the next child and the loop goes back to step 2215.

The function ends in step 2221.

Figure 25H:
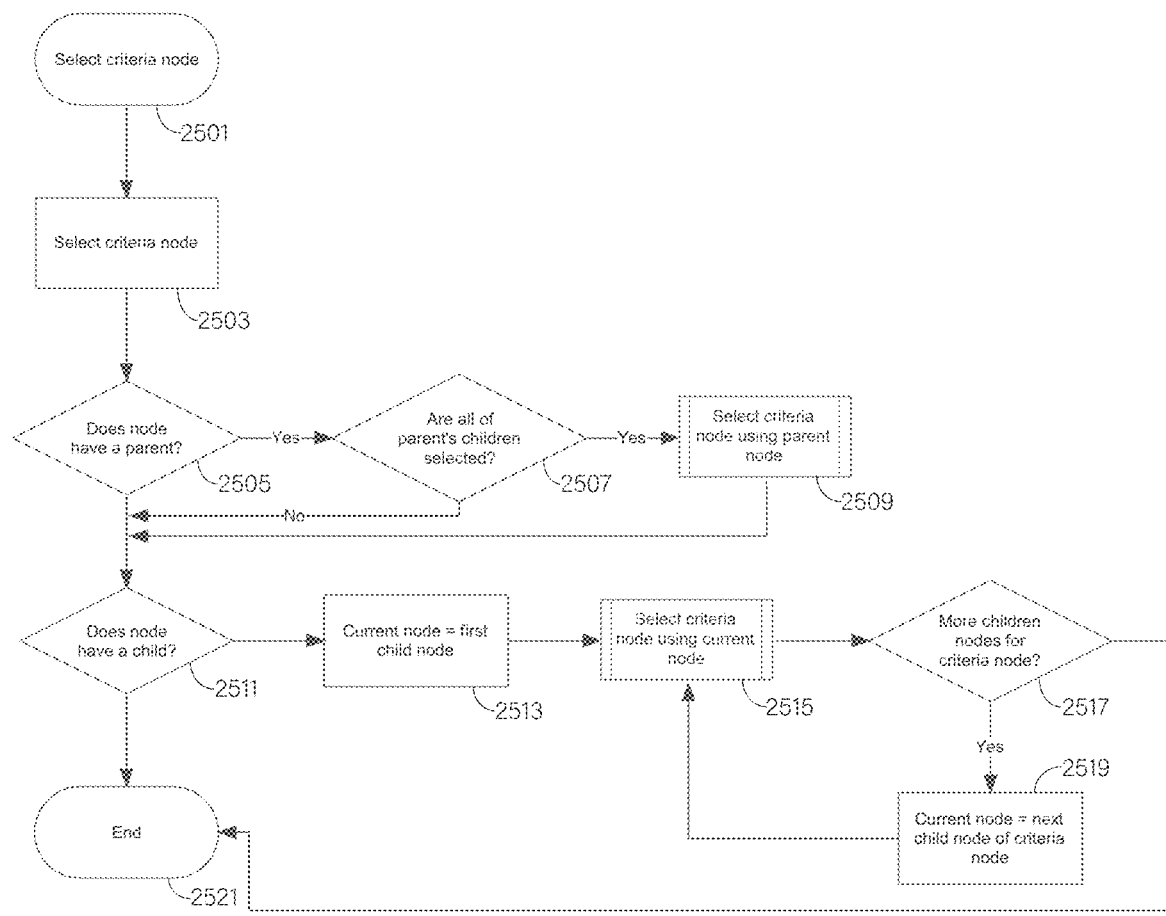
FIG. 25H is a flow diagram depicting an example method of propagating selecting a tree node to the children and parents of the tree node.

FIG. 25H is a flow diagram depicting an example method of propagating selecting a tree node to its children and parents (e.g., procedure 2501). Since this function can be recursively called, it starts with the display user action to select the current node in step 2503. A check is made to see if the current node has a parent in step 2505. If so, a check is made if all the parent's children are selected in step 2507. If all the parent's children are selected, then a recursive call is made to this same function to select the parent node in step 2509.

Next, the function checks if the current node has children in step 2511. If so, step 2513 sets the current node to the first child node. It loops through each of the children recursively until there are no more children in steps 2515 through 2519. The loop recursively calls procedure 2501 in step 2515. Step 2517 checks if more children are present, and if so, step 2519 sets the current node to the next child and the loop goes back to step 2515. The function ends in step 2521.

Figure 26:
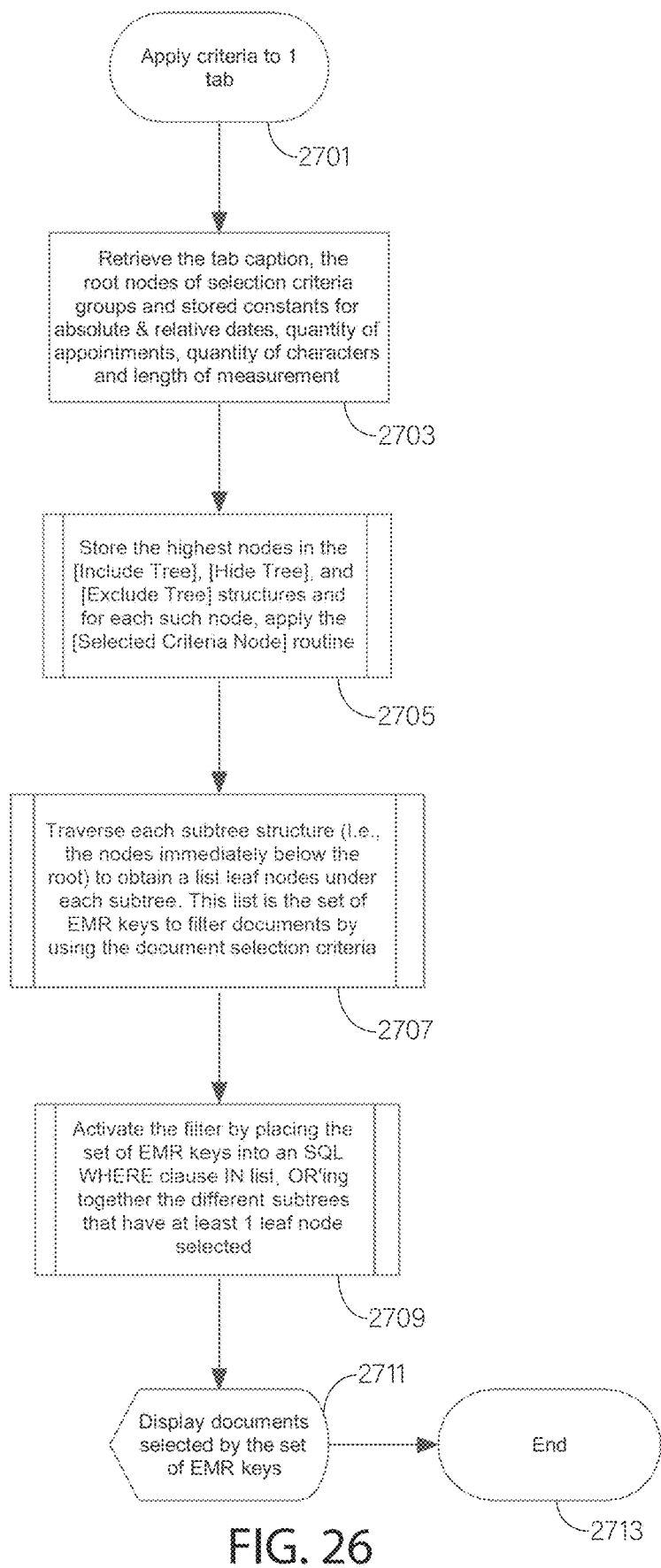
FIG. 26 is a flow diagram depicting an example method of retrieving the document criterion and activating the document criterion for each tab to choose the documents to display on a tab.

FIG. 26 shows an overview of how to retrieve the document criterion and activate the document criterion for each tab to choose the documents to display on the tab. It starts in step 2701.

There are number of items that should be stored with the tab information describing the appearance of a tab in step 2703. Depending on how the software functions, this information may be retrieved either from program data 8329, or from the data store 43, or some other location the computer has access to, but it may match where step 1811 stored it. This includes the caption of the tab, a list of the root nodes for each subtree selected and the stored constants that apply to that page. The stored contents in one embodiment may include, for example, an absolute date, a quantity of days to calculate a relative date, a quantity of appointments, a quantity of characters, a length of measurement, a flag indicating whether or not parenthetical comments are excluded, and a text of the marker to be left when parenthetical comments are excluded. Certain special case nodes substitute the constant for the placeholder in the caption before displaying the caption, such as a node which states "Hide items more than ~Qty~ appointments old" where the current tab's quantity of appointments is substituted in the caption for the placeholder ~Qty~ before displaying the caption. Similarly, prior to filtering by this criteria, the current value for quantity of appointments on the current tab may be substituted into the filtering statement. Another tab may use a totally different value for quantity of appointments. This is at least one reason why some constant values should be stored and retrieved for each tab rather than just once for all tabs. Other constant values (e.g., the fonts used for prompt and answer texts) may be application wide and stored once for all tabs. The tabs are navigated to by pointing devices 8375 such as a mouse on a screen, pen, trackball, or even a finger or stylus on a touch screen 8377. The use of this example of specific constants is not intended to be interpreted as these are the only constants, or any of these specific constants must be present, or all these constants must be present. This is just one non-limiting embodiment of the invention functions.

The very first time that the program is run, there are two possible options. The first option is that no document criterion is active by default. The second option is that there is some default list of what is initially selected and certain items are selected by default. One item that an embodiment considers hidden by default is to hide detailed test results, such as a mental status inventory with questions that a client responded to.

Step 2705 calls procedure 2501 to activate each individual root node for subtrees retrieved in step 2703. The end result of this process is that all the leaf nodes below each subtree root node are also activated. The list of leaf nodes is the list that may be fed to the filter that chooses documents to display in step 2707.

Step 2707 calls procedure 2851 which builds a list of each selected leaf node's tag property; more specifically, in one embodiment, a primary key such as in 3105. These primary keys are concatenated together with commas between them to create a list that can be used by an SQL WHEN. . . . IN ( . . . ) type clause.

Step 2709 calls procedure 2801 to build the full SQL WHERE clause.

Finally, the documents which have selection attributes that match the selected leaf nodes are displayed in step 2711. More specifically, the documents that are selected by the set of EMR keys may be displayed in an order based on date (e.g., reverse chronological order such that newer documents are on top and older documents are on the bottom and the initial cursor position on the tab is at the top; or chronological order and the initial cursor position on the tab is at the bottom). Documents selected to be hidden may be hid behind appropriate placeholders (e.g., links). Once the tab is displayed, there is nothing further to be done in step 2713.

Figure 27A:
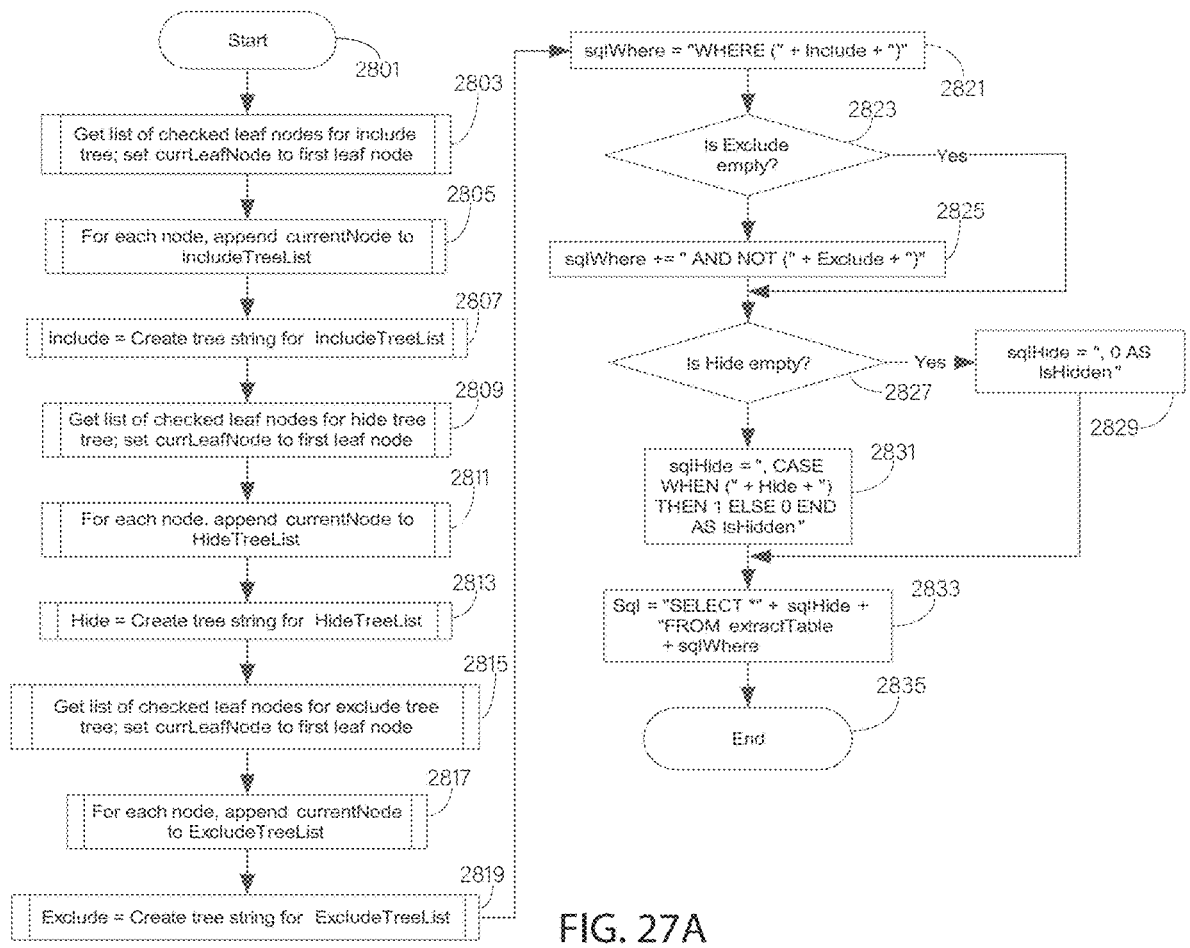
FIG. 27A is a flow diagram depicting an example method of generating a SQL statement from leaf nodes of configuration trees.

FIG. 27A shows a flow diagram of an example method to generate SQL statements from leaf nodes of the configuration trees.

The nodes may be used for the values in a WHEN. . . . IN ( . . . ) clause. In the case of the example of FIG. 29A, the root node leads to two subtrees which are checked for the tables "Appointments" and "Authors" and the manifest constants found in the current node that represent these two are APPT_TYPE and STAFF, respectively. Each table may be identified using a simple function (e.g., "EmrName (tableId)") that, given the table identifier parameter, returns the name of the field that must be checked for the corresponding values, typically, a foreign key to some table that is a lookup table for appointments, authors, etc. The EmrName ( ) function is commonly written for a specific EMR, but is not included here because that is dependent on the specific EMR to just list foreign key names. The EmrName ( ) function would be very much like:

function EmrName (tableId)
        switch (tableId) {case
        APPT_TYPE: return "ApptType"; break;
        case STAFF: return "StaffId"; break;
        case NOTE_TYPE: return "NoteType"; break;}

Procedure 2801 starts in step 2803 where a list of checked nodes is obtained for the include tree by passing the root node of the include tree to procedure 2841 and obtaining back a list of checked leaf (and possibly, sub-leaf) level nodes.

Step 2805 passes each checked leaf level node to procedure 2861 and after all checked leaf level nodes have been processed by procedure 2861, obtains back up to two types of SQL clauses. First, SQL clauses of special cases built by procedure 2901. Second, SQL clauses in the format "(<variableName>) IN (<identifier>, <identifier>, . . . )" format where the <variableName> may be a column name either in the EMR, a view of the EMR, or an extract table originating from the EMR and each <identifier> may be a possible value in that named column. This second clause may be modified as processing of the leaf nodes continues and the same <variableName> is encountered rather than add another new clause. For example, rather than creating two separate clauses (e.g., both the SQL clause "(appType) IN (131)" and the SQL clause "(appType) IN (140)") for the nodes within circle 3105, just one clause can be used by modifying the existing clause when the second include node is encountered that references the same <variableName> (e.g., "(appType) IN (131,140)").

When dealing with sub-leaf level nodes, the format of this second SQL clause type changes for documents specified as using sub-leaf level nodes. A general format may be "CASE WHEN (<variableName>)=<identifier> THEN CASE WHEN (<fieldName>) IN (<fieldIdentifier>, <fieldIdentifier>, . . . ) THEN 1 ELSE 0 END ELSE 0 END=1" where <fieldname> may be the primary key of each prompt or heading entity (e.g., primary key 3908) and <fieldIdentifier> is a primary key of an individual row. A simplified version of the same SQL clause might be to just eliminate the reference to <variableName> and <identifier> and use the clause "WHEN (<fieldName>) IN (<fieldIdentifier>, <fieldIdentifier>, . . . )". Either way, any corresponding <identifier> for the whole document from "(<variableName>) IN (<identifier>, <identifier>, . . . )" format should be removed or otherwise inactivated for any document with sub-leaf nodes.

The format of these SQL clauses are non-limiting examples of the present invention, regardless of whether the current invention is performed using SQL clauses rather than some other language.

Step 2807 combines each of the SQL clauses together created in step 2805 with an "OR" between each to create one combined include clause by calling procedure 2889.

Similar to steps 2803-2807 creating a single combined include clause from the include tree root node, steps 2809-2813 creates a single combined hide clause from the hide tree root node, and steps 2815-2819 creates a single combined exclude clause from the exclude root tree node.

In steps 2821-2833, a SQL statement is built up from the individual pieces. Steps 2821-2825, creates a WHERE clause. Steps 2827-2831 creates a hide clause. Step 2833, then assembles the hide clause and WHERE clause into a complete SQL statement.

Step 2821 places the combined include clause inside of parenthesis and after the reserved word "WHERE<space>". Step 2823 checks if the combined exclude clause is empty, and if not step 2825 appends the following to the WHERE clause: "<space>AND<space>NOT<space> (<excludeClause>)", where <space> represents the space character (e.g., ASCII 32) and <excludeClause> represents the combined exclude clause.

Step 2827 checks if the combined hide clause is empty. If the clause is empty, then step 2829 may set the hide clause to the characters ",<space>0<space>AS<space>IsHidden". If the clause is not empty, the step 2831 may set the hide clause to the characters ", <space> CASE <space> WHEN <space> (<hideClause>)<space> THEN <space>1<space> ELSE <space>0<space> END", where <hideClause> is the combined hide clause.

Step 2833 creates a SQL statement by combining the various clauses that have been created to this point. For example, "SELECT <space>*, <sqlHide><space>FROM <space> extractable <space><sqlWhere>", where <sqlHide> is the clause calculated in either step 2829 or 2831 and <sqlWhere> is the final clause calculated in step 2821 or 2825.

The process ends in step 2835.

Figure 27B:
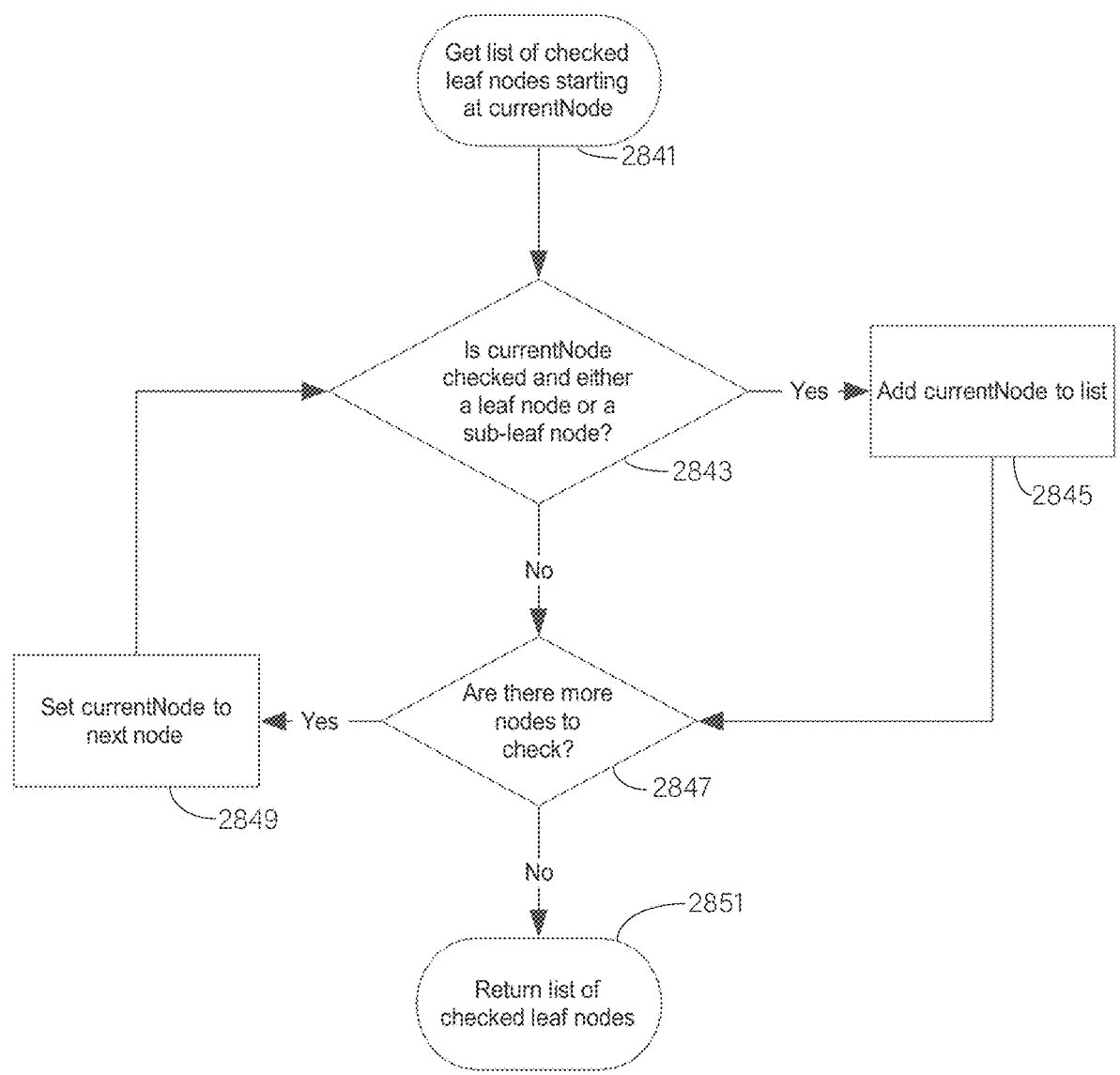
FIG. 27B is a flow diagram depicting an example method of obtaining a list of checked nodes from a subtree.

Referring to FIG. 27B, depicted is a flow diagram showing how to convert a tree root into a list of checked leaf or sub-leaf level nodes. Process 2841 is provided a root node of a configuration tree and returns a list of checked leaf or sub-leaf nodes. Leaf nodes are document criterion that matches up to selection attributes of each document used to determine if the document will be displayed. Sub-leaf nodes are each individual entity (e.g., heading entities and prompt entities) that make up the structure of the document they are a part of. Sub-leaf nodes may be allowed to be chosen because some documents in the EMR might not normally be accessed as the information originally provided, but as computer generated graphs and numerical computed values (e.g., a mental status inventory), but a specific user might want to see certain specific (e.g., critical) answers the client provided when viewing the computer scored results. Sub-leaf nodes allow that customization without using the entire vertical space of a full document.

Step 2843 checks if the current node is both checked and either a leaf or sub-leaf node. If the current node is both checked and at the leaf level or lower in the configuration tree, step 2845 adds the current node to a found list.

Step 2847 checks if there are any additional nodes in the subtree that have not yet been asked the questions of step 2843, and if so, step 2849 sets the current node to the next node available and control passes to step 2843.

Step 2851 returns the found list of step 2845.

Figure 27C:
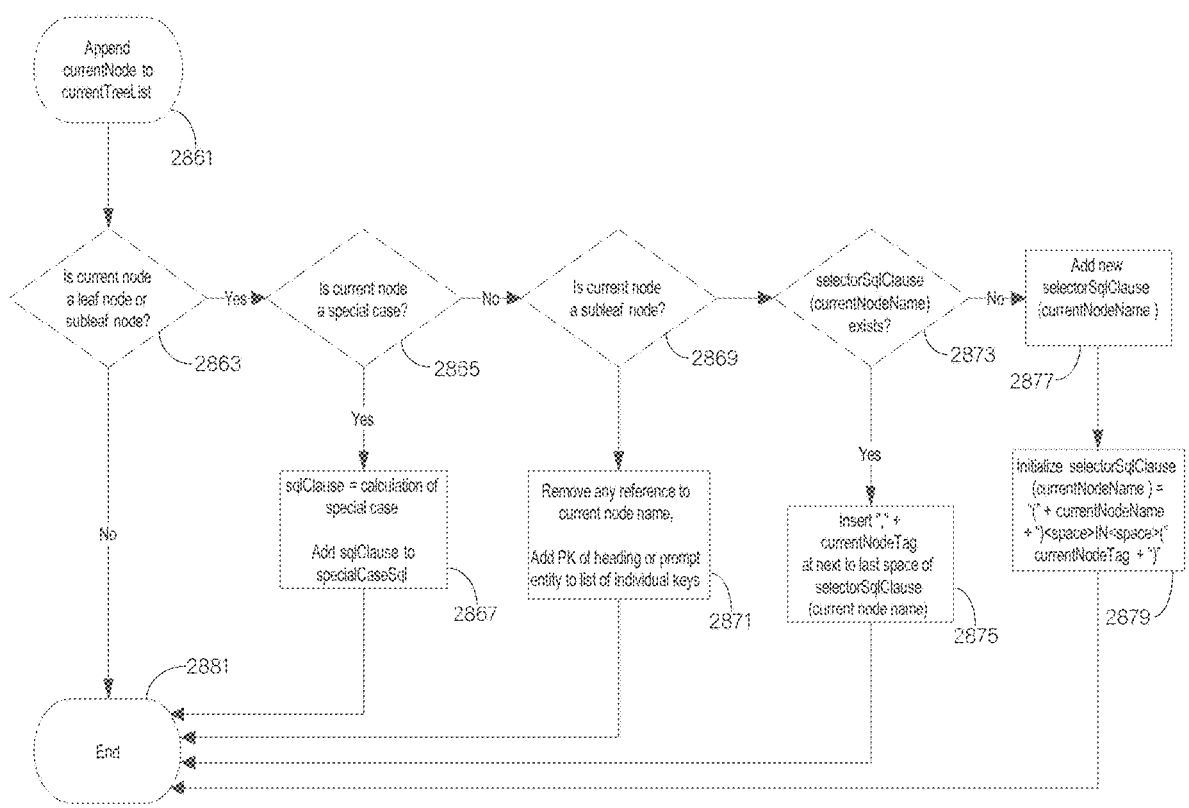
FIG. 27C is a flow diagram depicting an example method of obtaining one clause from a checked node to be used in a generated SQL statement.

FIG. 27C depicts a flow diagram processing each checked node at the leaf or sub-leaf level. Process 2861 begins at step 2863 where it is verified the node is at the leaf or sub-leaf level. Step 2865 checks if the current node is a special case, and if so, step 2867 calls process 2901 to get the text of the special case and may call process 2881 to append the special case text to any special case text that already existed.

If step 2865 determines the current node is not a special case, step 2869 checks if the current node is a sub-leaf node. If it is a sub-leaf node, step 2871 eliminates any reference to the whole node in the selector (e.g., document criterion) SQL clauses and adds a reference to the primary key of the heading or prompt entity pointed to by the tag of the current node to a list of individual entity keys. Individual heading and prompt entities can be selected out of a whole document to display just those desired entities without selecting the whole document for certain special case needs (e.g., a mental status inventory where one wants to view computer scored results with selected critical answers provided by a client, but not use the vertical space of displaying the whole document of answers by the client).

Step 2873 checks if the current node name already exists from the list of previous passes through this block of code as other checked nodes were processed. An easy way to accomplish step 2873 may be to sort the list of checked nodes by (1) the selector (e.g., document criterion) identified in each node, and possibly (2) whether or not sub-leaf nodes are used by the document before any processing. Each time the selector changes, step 2877 can be executed one time and the rest of the time step 2875 can be executed.

If the current node name doesn't exist, step 2877 adds the selector and step 2879 initializes the selector SQL clause. If the current node name already exists, the existing selector SQL clause may be modified to accommodate the new document criterion.

Figure 27D:
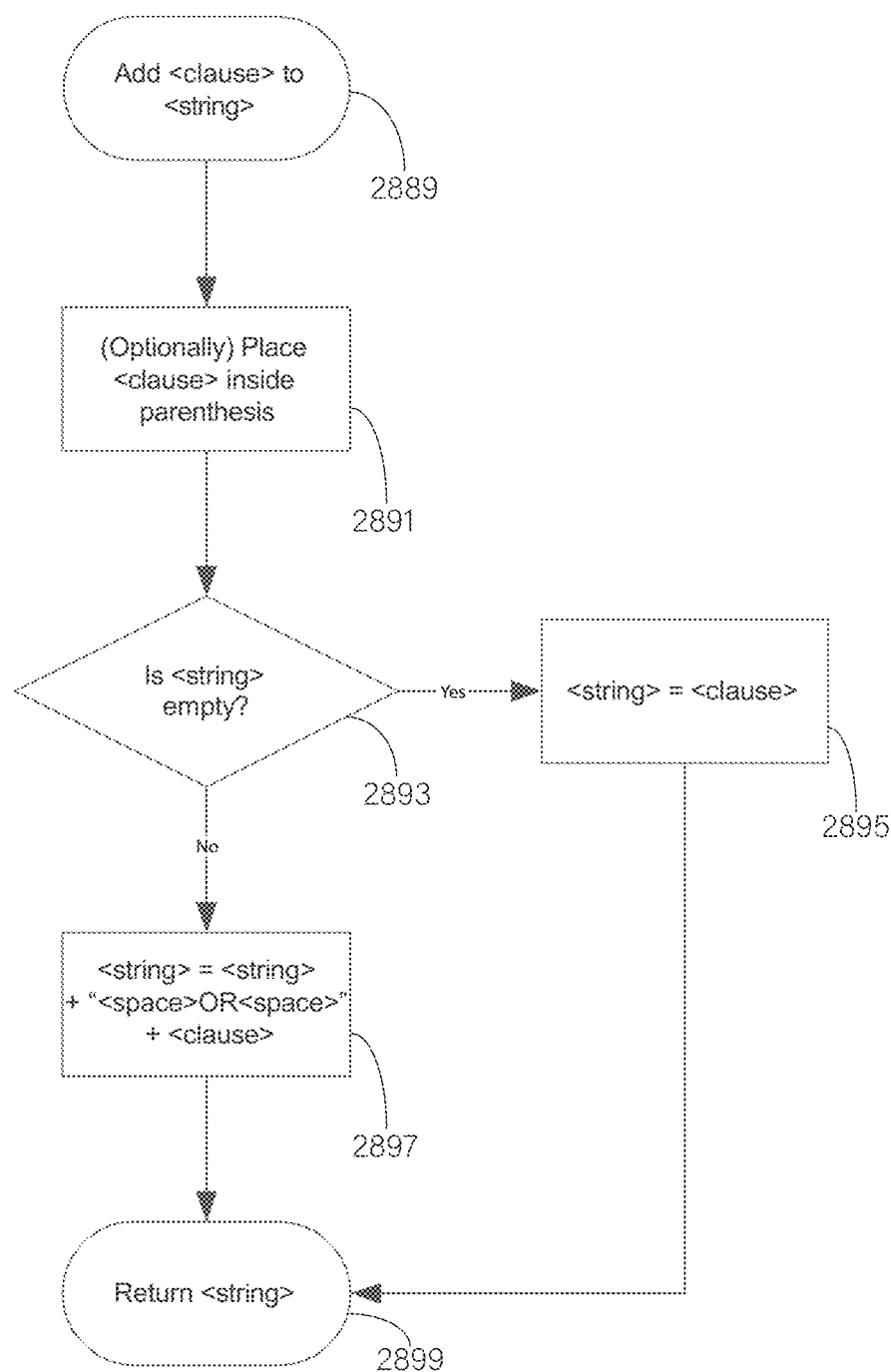
FIG. 27D is a flow diagram depicting an example method of combining SQL clauses together.

FIG. 27D is a flow diagram depicting the process of adding a new clause to a SQL string where each new clause is to be OR'ed together. Process 2889 starts in step 2891 where parenthesis may be placed around the new clause. If it is known that no future clause may contain a logical operator other than "OR", "IN" and "NOT IN" then no parenthesis is necessary around the new clause. However, if some SQL string might include the other logical operators (e.g., "AND"), a parenthesis should be placed around the new clause. Step 2893 checks if the SQL string is empty. If the SQL string is empty, step 2895 copies the new clause to the SQL string. If the SQL string is not empty, step 2897 appends the word "OR" to the SQL string, followed by the new clause. Step 2899 returns the final SQL string.

Figure 28A:
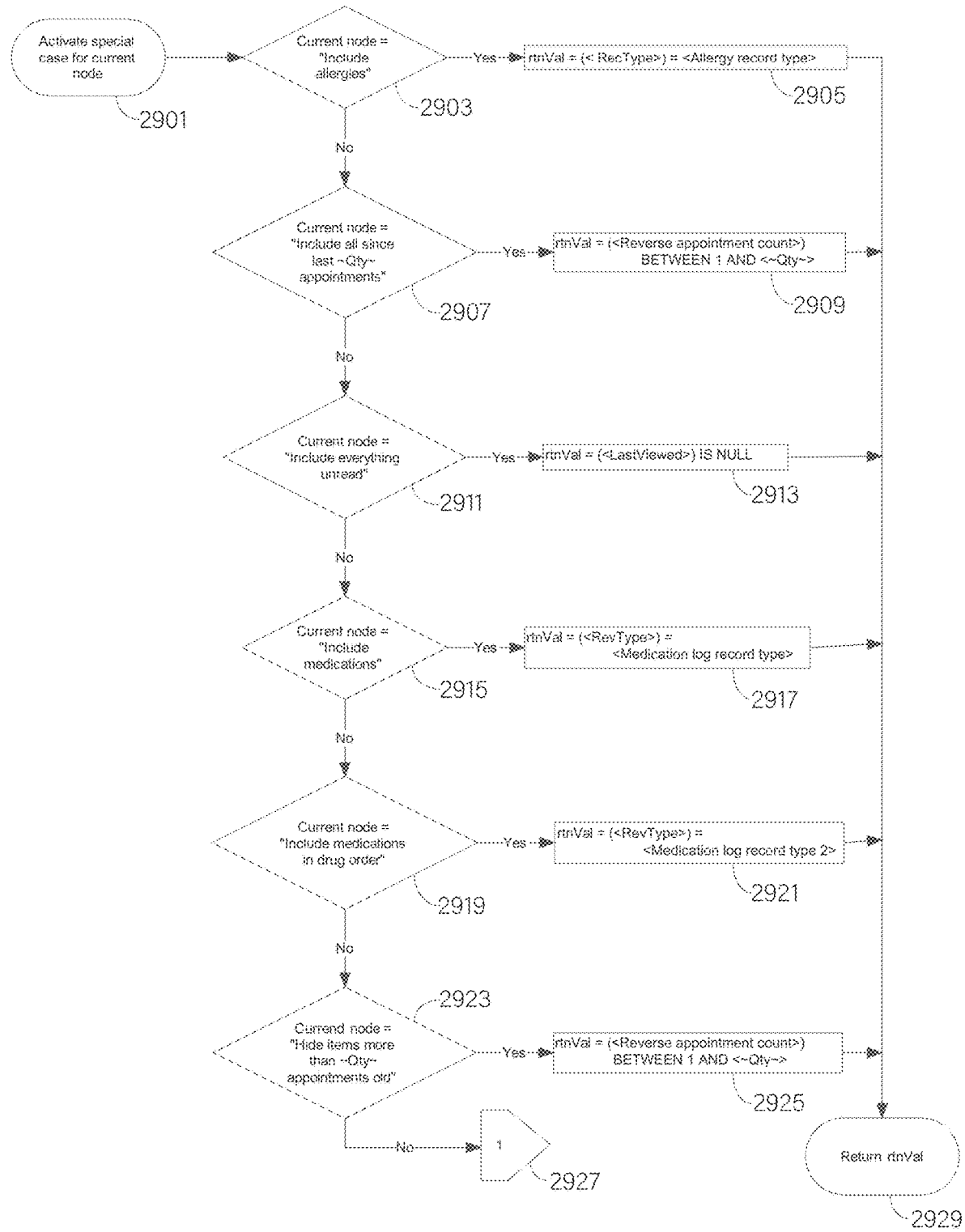
FIG. 28A is a flow diagram depicting the first part of a method of generating SQL clauses from special cases.
Figure 28B:
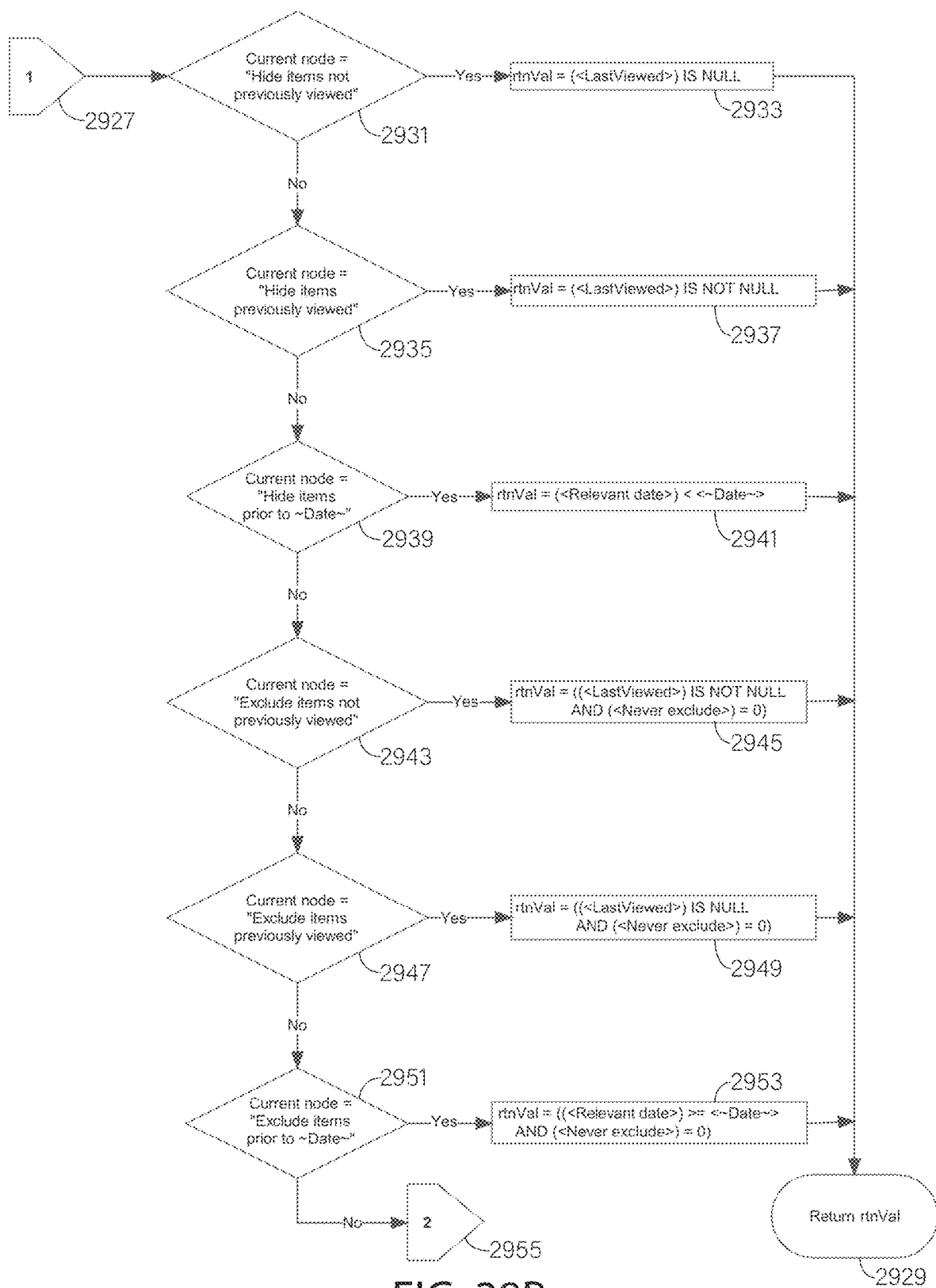
FIG. 28B is a flow diagram depicting the second part of a method of generating SQL clauses from special cases.
Figure 28C:
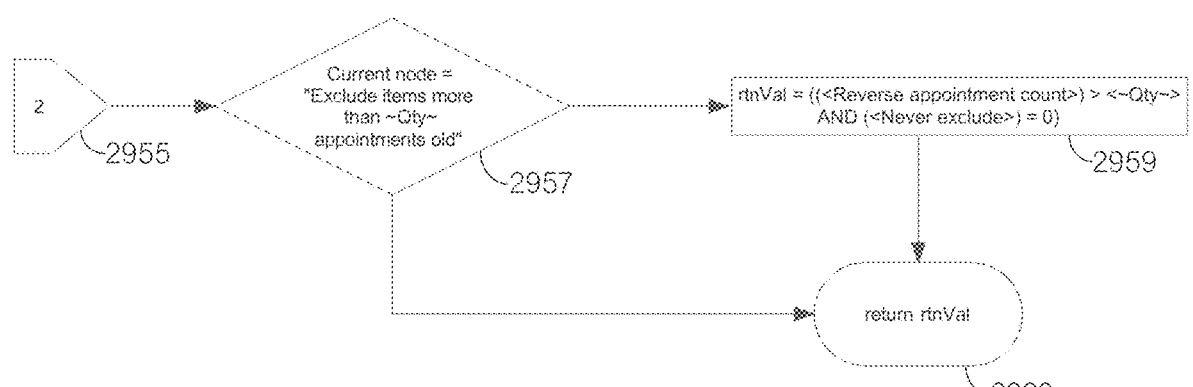
FIG. 28C is a flow diagram depicting the third part of a method of generating SQL clauses from special cases.

FIG. 28A to 28C shows procedure 2901 which generates SQL clauses for one embodiment's special cases. The three pages are one continuous function. The return step 2929 of the procedure is reproduced on each page.

If the current node caption is "Include allergies" in step 2903, then this one may be triggered. Alternatively, the leaf nodes contain a tag property and a negative number 2961 can be used to represent this special case (since that number represents foreign key values and foreign key values for real tables would always be positive) and compare the node's tag property to the constant negative number for this option to trigger it. If triggered, it sets the rtnVal to the RecordType column name (in parenthesis, if necessary), an equals sign, and the RecordType value indicating allergy records in step 2905. Control is then returned to the caller in step 2929.

If the current node caption is "Include all since last ~Qty~ appointments" in step 2907, then this one is triggered. Alternatively, compare the node's tag property to a negative number 2963 representing this special case and if the two match, this option is triggered. If triggered, it sets the rtnVal to the ReverseApptCount field name (in parenthesis, if necessary), plus the text BETWEEN<space>1<space>AND<space>, plus value for the tab's quantity of characters in step 2909. Here, "<space>" represents the ASCII character 32. Note that the comparison is easily performed by taking the string "Include all since last ~Qty~ appointments" and substituting the tab's quantity of characters for the "~Qty~" first, then perform the comparison against the caption that the display user sees on the tab. Control is then returned to the caller in step 2929.

If the current node caption is "Include everything unread" in step 2911, then this one is triggered. Alternatively, compare the node's tag property to a negative number 2965 representing this special case and if the two match, this option is triggered. If triggered, it sets the rtnVal to the LastViewed column name (in parenthesis, if necessary), and the characters "<space>IS<space>NULL" in step 2913. Control is then returned to the caller in step 2929.

If the current node caption is "Include medications" in step 2915, then this one is triggered. Alternatively, compare the node's tag property to a negative number 2967 representing this special case and if the two match, this option is triggered. If triggered, it sets the rtnVal to the RecordType column name (in parenthesis, if necessary), an equals sign, and the RecordType value indicating medication log records in step 2917. Control is then returned to the caller in step 2929.

If the current node caption is "Include medications in drug order" in step 2919, then this one is triggered. Alternatively, compare the node's tag property to a negative number 2969 representing this special case and if the two match, this option is triggered. If triggered, it sets the rtnVal to the RecordType column name (in parenthesis, if necessary), an equals sign, and the RecordType value indicating medication log type 2 records in step 2921. Control is then returned to the caller in step 2929.

If the current node caption is "Hide items more than ~Qty~ appointments old" in step 2923, then this one is triggered. Alternatively, compare the node's tag property to a negative number 2971 representing this special case and if the two match, this option is triggered. If triggered, it sets the rtnVal to the ReverseApptCount field name (in parenthesis, if necessary), plus the text BETWEEN<space>1<space>AND<space>, plus value for the tab's quantity of characters in step 2925. Note that the comparison may easily be performed by taking the string "Hide items more than ~Qty~ appointments old" and substituting the tab's quantity of characters for the "~Qty~" first, then perform the comparison against the caption that the display user sees on the tab. Control is then returned to the caller in step 2929.

Step 2927 is the off-page connector that connects FIG. 28A to FIG. 28B.

Step 2929 is the end of the function. It returns the rtnVal to step 2863, which, in turn, gets the values concatenated together with ORs using prefix recursion in step 2855 and returned in steps 2865 to 2805 (and its equivalent in steps 2809 and 2811). Of course, it would be a trivial change to use postfix recursion.

If the current node caption is "Hide items not previously viewed" in step 2931, then this one is triggered. Alternatively, compare the node's tag property to a negative number 2973 representing this special case and if the two match, this option is triggered. If triggered, it sets the rtnVal to the LastViewed column name (in parenthesis, if necessary), and the characters "<space>IS<space>NULL" in step 2933. Control is then returned to the caller in step 2929.

If the current node caption is "Hide items previously viewed" in step 2935, then this one is triggered. Alternatively, compare the node's tag property to a negative number 2975 representing this special case and if the two match, this option is triggered. If triggered, it sets the rtnVal to the LastViewed column name (in parenthesis, if necessary), and the characters "<space>IS<space>NOT<space>NULL" in step 2937. Control is then returned to the caller in step 2929.

If the current node caption is "Hide items prior to ~Date~" in step 2939, then this one is triggered. Alternatively, compare the node's tag property to a negative number 2977 representing this special case and if the two match, this option is triggered. If triggered, it sets the rtnVal to the RelevantDate field name (in parenthesis, if necessary), plus the less than sign, plus value for the tab's (absolute or relative; the decision of which is determined by flag "use absolute dates") date field in step 2941. Note that the comparison is easily performed by taking the string "Hide items prior to ~Date~" and substituting the tab's date for the "~Date~" first, then perform the comparison against the caption that the display user sees on the tab. Control is then returned to the caller in step 2929.

If the current node caption is "Exclude items not previously viewed" in step 2943, then this one is triggered. Alternatively, compare the node's tag property to a negative number 2979 representing this special case and if the two match, this option is triggered. If triggered, it sets the rtnVal to the LastViewed column name (in parenthesis, if necessary), and the characters "<space>IS<space>NOT<space>NULL<space>AND<space>" plus the NeverExclude column name (in parenthesis, if necessary), and the characters "=0" in step 2945. The NeverExclude variable handles situations for documents (e.g., client allergies) that should never be excluded from being handled by an exclude (e.g., the LastViewed column is a single attribute which is either NULL or NOT NULL, but either way, the client allergies document should not be excluded based on the value of the LastViewed column, if it would otherwise be included). Control is then returned to the caller in step 2929.

If the current node caption is "Exclude items previously viewed" in step 2947, then this one is triggered. Alternatively, compare the node's tag property to a negative number 2981 representing this special case and if the two match, this option is triggered. If triggered, it sets the rtnVal to the LastViewed column name (in parenthesis, if necessary), and the characters "<space>IS<space>NULL<space>AND<space>" plus the NeverExclude column name (in parenthesis, if necessary), and the characters "=0" in step 2949. Control is then returned to the caller in step 2929.

If the current node caption is "Exclude items prior to ~Date~" in step 2951, then this one is triggered. Alternatively, compare the node's tag property to a negative number 2983 representing this special case and if the two match, this option is triggered. If triggered, it sets the rtnVal to the RelevantDate field name (in parenthesis, if necessary), plus the greater than sign, plus the equals sign, plus value for the tab's (absolute or relative; the decision of which is determined by flag "use absolute dates") date field "<space>AND<space>", plus the NeverExclude column name (in parenthesis, if necessary), and the characters "=0)" in step 2953. Note that the comparison is easily performed by taking the string "Exclude items prior to ~Date~" and substituting the tab's date for the "~Date~" first, then perform the comparison against the caption that the display user sees on the tab. Control is then returned to the caller in step 2929.

Step 2955 is the off-page connector that connects FIG. 28B to FIG. 28C.

If the current node caption is "Exclude items more than ~Qty~ appointments old" in step 2957, then this one is triggered. Alternatively, compare the node's tag property to a negative number 2985 representing this special case and, if the two match, this option is triggered. If triggered, set the rtnVal to the open parenthesis, plus the ReverseApptCount field name (in parenthesis, if necessary), plus the greater than sign, plus value for the tab's quantity of characters, plus the characters "<space>AND<space>" plus the NeverExclude column name (in parenthesis, if necessary), and the characters "=0)" in step 2959. Note that the comparison is easily performed by taking the string "Exclude items more than ~Qty~ appointments old" and substituting the tab's quantity of characters for the "~Qty~" first, then perform the comparison against the caption that the display user sees on the tab. Control is then returned to the caller in step 2929.

The use of this example of specific constants and patterns of which special cases are available to display users of is not intended to be interpreted as these are the only constants or patterns, or any of these specific constants or patterns must be present, or all these constants or patterns must be present, or this is the only way to mark the presence of a constant or a pattern. This is just one non-limiting embodiment of the invention functions.

FIG. 28D shows an example of a pseudocode for an alternate method of generating SQL clauses from the single integer value currNodeTagNo for the same non-limiting set of specific constants (steps 2961 through 2985) and patterns of which specific cases are available to display users. The variable currNodeTagNo represents a value from the current node's tag.

FIG. 29A shows an example of a simple Include configuration tree. This tree could have been completed by selecting node 3101 and node 3103. This tree can be completely described by listing the path to the two subtree roots (Include|Appointments|Psychiatry;Include|Authors|Psychiatry). In one embodiment, this is an example of the string stored in 1811 and retrieved in step 2703 for the root nodes. There is no need to store any leaf nodes, in this case.

The box 3105 and 3107 are pointing to is not visible to the display user. This box represents the tag property of the leaf nodes. The leaf nodes are the only items searched for when filtering data. In this case, the all-cap words, "APPT_TYPE" and "STAFF", represent manifest constants and are used to look up the column names that contain foreign keys to a table that contains details of appointments and staff, respectively. The appointments table would contain such items as the appointment name and the default length of the appointment. The staff table would contain such items as the staff member's first and last name and possibly whether that staff member is able to prescribe medications in the EMR.

There is no requirement that the program have access to the table being pointed to, just that there is some unique value (e.g., document criterion) that points to the table. Nothing further needs to be looked up in the EMR data store using that unique value. In one embodiment, the data has all been extracted from the EMR and placed into a data extract table for the current history of appointments for the client and these values (e.g., selection attributes) are just a column of the extract table when the program extracts information from the data store (e.g., a column for the table represented by APPT_TYPE and a separate column for the table represented by STAFF). If the value in the column (e.g., document criterion) matches what is in the extract table (e.g., selection attributes), that row of the table is included. For this specific example, suppose the foreign key to appointment table is ApptType and the foreign key to the staff table is StaffId. Whenever the ApptType column (e.g., selection attribute) has any of the values in the circle 3105 (e.g., 131 or 140), that row of information should be included on the screen display for the tab. Also, whenever the StaffId column (e.g., selection attribute) has any of the values in the circle 3107 (e.g., 225, 218 or 140), that row of information should be included on that tab also. The values selected in FIG. 29A are document criteria. Here, each row of information would be a different document criterion.

Selections 3109 and 3111 show one possible option of how to handle the ordering of documents. Normally, in an EMR, one would expect the documents selected to appear on a tab to be presented in a chronological order (e.g., with the most recent document on top if the initial cursor position is at the top of a tab, or reversed of that if the cursor starts at the bottom of the tab). For example, as with medications, it may be helpful to have the medications grouped together, then organized by dosage or date. Furthermore, for certain categories of documents, there may be documents that should not have a relevant date associated with them, such as allergy information (e.g., once an allergy is identified, for prescribing purposes, a display user may want to be made aware of the existence of the allergy, and to not be required to sort through such information by date the allergy was entered), medication records, client identifying information, and the like would not benefit from the actual date of the document, so a default date may be used. Some possible ways of handling these documents that do not have a date using default dates may include: (1) using null dates, (2) using maximum value dates, and (3) using a list of predefined dates that represents the content of the document (e.g., using Jan. 1, 4999 for allergy information and Dec. 31, 4999 for client information) which may force the undated document to the top or bottom of the tab (perhaps in a pre-determined order with other undated documents).

FIG. 29B shows an embodiment of a hide configuration tree. Note that structure of this tree is nearly identical to FIG. 29A with the only differences being what appears below the "Other" subtree and the top-level nodes ("Include" and "Hide"). Even when some of the texts in the "Other" subtree are similar, they should still be custom worded for the "Other" subtree rather than identical.

In this case of the current embodiment, the leaf node 3301 is checked. The casenote table contains such items as the name of the casenote. For this example, assume the foreign key (e.g., selection attribute) to the casenote table stored in the extract table is NoteTypeId. Because the value (e.g., document criterion) in circle 3303 is 157, whenever NoteTypeId (e.g., selection attribute) is 157, any data that otherwise would have been placed on the screen, needs to be initially hidden, such as behind a placeholder button 3901 or other link for the whole hidden document. As shown in FIG. 31A, the generated placeholder button 3901 includes/retains a date that matches the date of the document for which it was generated.

FIG. 29C shows an embodiment of an exclude configuration tree. In this case, only the leaf node 3801 is checked. Whenever a document would otherwise be included based on FIG. 29A or hidden based on FIG. 29B, but it is more than 4 appointments old, the document may be excluded from being displayed in the final output. One embodiment uses a reverse appointment counter (e.g., 1 represents the most recent appointment, 2 represents the next most recent appointment relevant to the display user, and so forth) to accomplish this, where most documents are assigned an appointment number that is either associated with or based on the closest appointment to the date of the document. Any document (e.g., client allergy information) which should never be excluded based on appointment number (e.g., age of information) may be assigned a value of zero or less for the reverse appointment counter (e.g., selection attribute), so this setting can have no impact on whether that document is displayed or not. This setting can then be implemented by step 2959.

Figure 29D:
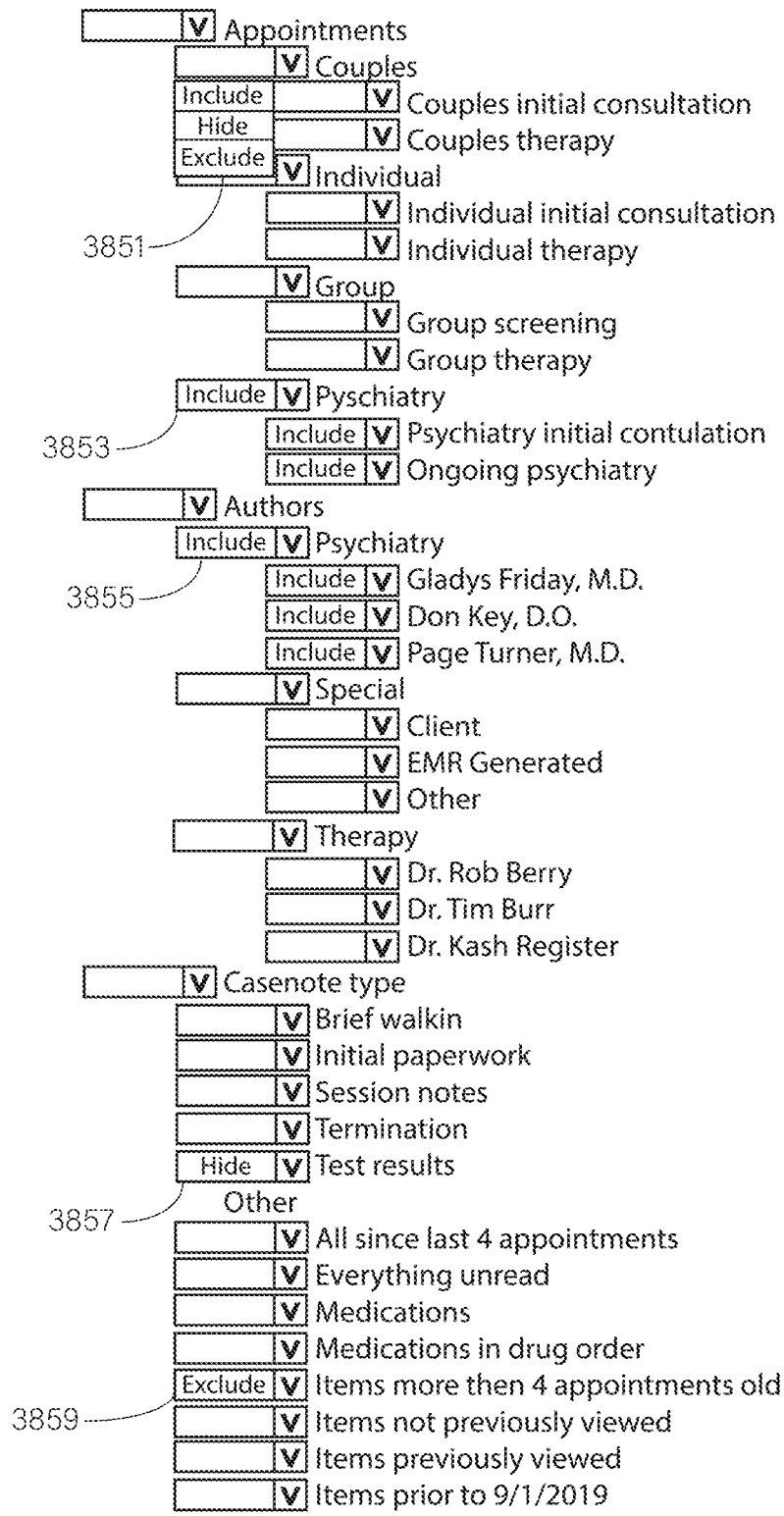
FIG. 29D is an example of a configuration tree that may be an alternative to the configuration trees of FIGS. 29A-29C.

FIG. 29D shows an alternate embodiment to FIG. 29A-29C setting up the identical case. Combo box 3851 is shown expanded to make clear how this tree is filled out. There is a similar combo box with the three options available at every node with the possible exceptions of the root nodes (three shown in this embodiment: Appointments, Authors, and Casenote type) and the "Other" node. The most that would make sense at the root node would be to include the options "Include" and "Hide" (because it may be meaningless to exclude everything—that would just be a blank page associated with a tab). The "Other" option either may not have any dropdown box at all or not all the options (e.g., include, hide and exclude) will be available, if the options under it are mutually exclusive (e.g., "Items not previously viewed" and "Items previously viewed" are opposites, so if both are selected by a single dropdown to exclude, the net effect of each individual button may be that everything viewed and everything not viewed are both excluded, meaning nothing will show on the display page).

Just like FIG. 29A, combo box 3853 and combo box 3855 only need be set to "Include" to set all the leaf nodes that are required for this example. Just like FIG. 29B, only the combo box 3857 needs to be set to "Hide". Like FIG. 29C, only the combo box 3859 needs to be set to "Exclude".

To program this embodiment, there are some obvious differences that would be apparent to anyone skilled in the art after reading this disclosure. These include: (1) a node selected to "hide" has an implied value that the node is also selected to "include", and (2) the propagating of values to the parent and child nodes the old way does not work and has to be changed. Below is a solution to the propagation problem.

Propagation is done not just on parent and child paths, but on a priority system along those paths. The top priority is an Exclude. The middle priority is a Hide. And the lowest priority is an Include. Only higher priority nodes can overwrite lower priority nodes when propagating.

Care has to be taken when a node that was set to a non-blank value (either include, hide or exclude) is changed to a blank value because of two differences. First, the current node has to inherit its parent's value and the parent's value gets propagated to all of the current node's children (using the priority system). Second, if all the siblings of the parent match the parent node, the grandfather node also gets recursively set to the parent's value.

FIG. 29E shows an embodiment of a configuration tree specifically for data forms (e.g., data form 3871) where selecting sub-leaves are enabled. In this tree, toggle hotspot 3870 is enabled to show or hide the heading and prompt entities as sub-leaves. Currently, since the sub-leaves are visible, pressing the toggle hotspot 3870 will hide the sub-leaves. There is a series 3879 of individual sub-leaves (e.g., entities) that are all checked and a sample unchecked leaf 3877. Within the series is checked prior major 3873 and international student 3875. There is a preview 3887 of how the data form will appear when displayed for the current data form including the document title 3881. The preview below the title matches up to a section of FIG. 31A. Note that since prior major 3873 was an unanswered prompt, it is excluded at reference number 3883. The rules for displaying entities are similar to those elsewhere in this disclosure: unanswered prompts may be excluded, prompt and answers may be combined together and displayed in the total area originally allocated for each and in the same order they appear in the design (e.g., even though there is blank area above reference number 3885, the view order it appeared in area 3879 was after the prompts for prior major and current major, so it may be restricted to being displayed no higher than those entities), etc. Also note that the prompt for international student 3885 was configured to appear in the second of two columns, and that follow through when displaying sub-leaves rather than the whole document.

FIGS. 30A-30C show examples of SQL generated for the configuration trees of FIG. 29A-29C using the methods of FIGS. 27 and 28. After viewing these three queries, it should become apparent to those skilled in the art that there may be many different varieties of SQL statement formats that can generate the same results, and that most of the calculations to identify documents can be placed in, for example, and not in way limited to, in WHERE clauses, in JOIN clauses and in SELECT clauses. The exact statement may not be determinative (e.g., SELECT, SELECT INTO, SELECT DISTINCT may all give equivalent results). Perhaps most importantly, what each of these types of clauses have in common is that regardless of whichever clause format is used, the same clauses that identify documents can be placed elsewhere in the SQL statement. The documents are still being identified, even if it is not in three separate steps.

FIG. 30A shows SQL where the calculation of whether the document is included and not explicitly excluded is in the WHERE clause and whether the document is hidden by a placeholder is in the SELECT clause.

FIG. 30B shows SQL where the calculation of whether the document is included is in the WHERE clause, and the calculation of both whether the document is explicitly excluded and whether the document is hidden by a placeholder are in the SELECT clause.

FIG. 30C shows two separate queries. The first query identifies all the placeholders and the second query identifies all the normal documents. In each of the queries, the identification of documents included and documents explicitly excluded happens in the WHERE clause.

FIG. 30D shows a modification of FIG. 30A showing how the SQL statement could appear if a user selected to limit a data form (e.g., assuming the Client Information data form can be identified by the DocumentId attribute with a value of 131) to only display the 9 checked sub-leaves (e.g., that can be identified with PrimaryKey 3908 values of 25, 191, 63, 131, 71, 238, 77, 400, and 501) of FIG. 29E.

Corresponding opening parenthesis 3891 and closing parenthesis 3893 are shown in both FIGS. 30A and 30D. A new grouping parenthesis pair 3892 and 3894 is shown that combines clause 3895 with the same clause as clause 3891 of FIG. 30A. The new clause 3895, restricts the Client Information data form from being selected by the same clause as clause 3891 of FIG. 30A.

FIG. 31A shows an embodiment of the appearance of some elements of the present invention in the context of a tablet computer.

Button 3901 shows an example of a hidden document as a result of the display user configuring a document type to hide, like node 3301. For example, if this button hid the client's answers to a mental status inventory, because, in normal practice, one may only want to refer to the computer-generated graphs and numerical computed values. However, if someone wanted to drill down to specific questions and answers they could by pressing this button.

Title 3902 shows an example of the appearance of a document title in one embodiment where the actual title of the document was "Client Information" and the date of the document was Aug. 20, 2015.

Converted text 3903 shows the results of a multi-select check box, as in FIG. 6C.

Heading 3905, is an example of shortening a heading entity text, as in FIG. 11. As in reference number 1409, the full original heading entity text was "Please provide the names and relationships of additional family members starting with step parents, siblings, spouse/partner, children." The original heading entity text would have taken 2 text lines to display.

Document area 3907 is expanded upon in FIGS. 31B-31H.

Referring to FIG. 31B, an idealized embodiment of heading entity 51 and prompt entity 52 is shown. In this case, the section shown is document area 3907 of FIG. 31A.

There may be various other columns in a full implementation of these entities, but the other columns would have the same values for each of the shown table rows or are not needed to understand the process, so they were omitted. For example, a full implementation may contain an order by column to allow reordering entities, but one does not have to understand how that process would work to understand entities are in a predefined order. Also, a complete prompt entity 52 may contain columns for specifying the alignment of prompt texts and answer values, and a flag indicating whether the prompt text appears first or the answer value appears first. For heading entities, there may be additional columns for such functions as alignment and paragraph spacing. For both entities, there may be additional columns for such items as whether characters word wrap or not.

The table is organized in table rows and columns with the table rows representing separate instances of entities and non-empty columns representing values of attributes of those entities. The information from this table can be used to format the output that may appear on the data entry user interface display 76 or display user interface display 79.

There is a darkened line to the left of element starts at 3917 representing the beginning of calculated values on each row. Everything to the left of that darkened line may be values stored in the element entity. Everything to the right of that darkened line may be calculated based on the values to the left of the darkened line and possibly the screen and padding widths. Note, in an actual EMR, element on new line indicator 3938 would be to the left of that darkened line because there are situations where a data form designer may need to override the calculated value and force a particular prompt text to start on a new line, so this one column will be referred to as a default value. In the calculated values, the assumption has been made that screen width is 400 (with 1 wasted pixel to make all the numbers turn out evenly distributed) and the padding between columns on the display is 2. The actual formulas are discussed below.

Primary key 3908 allows the foreign keys (e.g., design id column) of FIG. 31C to reference table rows. In this embodiment, since there is no order by column, primary key 3908 also controls the order entities appear on the data form.

Element type 3909 identifies whether the table row it appears on is a heading entity or a prompt entity.

Default text 3910 contains the text of the heading or prompt entity. The values in this column are the texts normally displayed by the EMR when displaying and printing data forms.

At least one EMR manufacturer found it helpful to create alternate text column 3911 for prompt entities in order to better fit prompt text horizontally when displaying rows with four or five columns on a data form, such as document area 1413 of FIG. 20. For example, the answered prompt 1411 ("additional family") may have a default text 3910 value of "additional family member name". However, in order to fit the prompt text in a shorter horizontal space, the EMR allows a form designer to shorten (for online data forms only) the prompt to "additional family" by using an alternate text column and adding a flag to indicate whether the online data form displays the default text 3910 or the alternate text 3911. For that EMR manufacturer, when a report is printed, the full default text 3910 can print all four words. When a display user views the data form online, only the two words appear.

It should be noted that, in the prior art, the value of the alternate text column 3911 for a heading entity was undefined. There was no benefit to using the alternate text column for heading entities, so it was always left empty. Texts of heading entities occupy the full width of the row they are assigned to, so there was no benefit to having an alternate text for a heading.

In the current invention, each repeat heading series entity may use a single row of the alternate text column 3911 associated with the rows of the series to hold the text to use to replace that repeat heading series entity. For example, on row 3924, the single alternate text 3911 can replace multiple rows of heading entities (e.g., an initial entity group of heading entities), thereby shortening the vertical space required for the block of heading entities shown on rows 3924, 3925 and 3926, each of which originally used default text 3910. It should be noted that, in the present invention, the initial entity group of heading entities (or the corresponding alternate text) may only remain on the screen display if the subsequent entity group (e.g., the prompt entities following the initial entity group before the next heading entity) contains one or more answered prompt entities.

Style 3912 contains the style of the element on that table row. For heading entity rows, this contains the style of the heading entity. Since this example has multiple styles for heading entities (e.g., there is a "section heading" on row 3923 and a "text heading" on row 3924), other styles of heading entities should be ignored when calculating heading classifications (e.g., repeat heading, top repeat heading, lowest repeat heading, normal heading, and terminal heading). In the case of a prompt table row, style 3912 refers to answer restrictions (e.g., what format a data entry user must use to provide answers for the element, and how to lay out the answer).

Supplemental list id 3913 is a foreign key to FIG. 31D and corresponds to the value in the list id 3989 column there. Supplemental list id 3913 thereby contains the various answer options that would appear in a dropdown list of a combo box. This column need only be filled in for certain answer styles, so a value here is only defined if there is a list required for the answer style 3912, and is undefined for all heading entities.

Answer on new line indicator 3914 determines whether the answer value appears on the same output line as the prompt text or the output line immediately below the prompt text. Since heading entities do not include an answer value, this column is undefined for heading entities.

Column number 3915 and total columns 3916 indicate which column the element fits into and how many columns exists in the output line that the element may be placed.

If element type 3909 indicates "prompt", then the prompt-answer pair has to fit into the column specified by column number 3915. So, in that case for the underlying EMR, if answer on new line indicator 3914 indicates "no", the single column is split into 2 columns horizontally. The data entry user saw two half columns used to display this instance (i.e., the first portion of the column for the prompt text and the last portion for the answer value). If the prompt entity does not contain a column to allow a data form designer to specify what percentage of the column is devoted to prompt text and what percentage is devoted to answer value, a reasonable default is 50% to each, so that is what the rest of this embodiment description will use.

The present invention, on the other hand, may combine the two half columns into one before laying out the prompt-answer pair for this instance.

The final seven columns of FIG. 31B are idealized calculated values assuming that the total window width is 400 column positions. With the possible exception of element on new line indicator 3938, these columns are not stored in a table because they are completely dependent on the width of the current display window and the current setting for padding.

Element starts at 3917 and element ends at 3918 form horizontal boundaries for either the heading entity text or the prompt entity text. Answer starts at 3919 and answer ends at 3920 form horizontal boundaries for displaying the answer value. Note, answer starts at 3919 and answer ends at 3920 are undefined for heading entities since heading entities do not have a related answer field. The units for these four columns is column positions.

Element on new line indicator 3938 determines if the element is displayed on the same output line as the previous element or on the next available completely blank output line. Furthest-left boundary 3921 is calculated by taking the minimum value from element starts at 3917 and answer starts at 3919. Furthest-right boundary 3922 is calculated by taking the maximum value from element ends at 3918 and answer ends at 3920.

If element type 3909 has a value "prompt" and answer on new line indicator 3914 has a value "no", a possible formula for element starts at 3917 is (ColumnNumber−1)×(WindowWidth/TotalColumn)+PaddingWidth, where PaddingWidth is the amount of space from the edge of the text box to a theoretical edge of the grid box containing the text. A possible formula for element ends at 3918 is (ColumnNumber−0.5)×(WindowWidth/TotalColumn)−PaddingWidth. A possible formula for answer starts at 3919 is (ColumnNumber−0.5)×(WindowWidth/TotalColumn)+PaddingWidth. A possible formula for answer ends at 3920 is (ColumnNumber)×(WindowWidth/TotalColumns)−PaddingWidth.

If element type 3909 does not have the value "prompt" or answer on new line indicator 3914 has a value "Yes", a possible formula for both element starts at 3917 and answer starts at 3919 is (ColumnNumber−1)×(WindowWidth/TotalColumn)+PaddingWidth, A possible formula for both element ends at column 3918 and answer ends at 3920 is (ColumnNumber)×(WindowWidth/TotalColumns)−PaddingWidth.

To calculate the default value for element on new line indicator 3938 from the data provided in this embodiment, this column has a "yes" value if total columns 3916 changes from the previous table row or if column number 3915 does not increase from the previous table row. Otherwise, this column has a default value of "no". An alternate calculation is provided in FIG. 24.

Table rows 3923, 3924, 3925, 3926, 3928, 3931, and 3937 are heading entities. Table row 3923 has a different style 3912 than the rest of the heading entities. Each of the heading entities fills its own single column on the output line, so are presented to the display and data entry user using the full width of the display. Therefore, element starts at 3917 is 1 and element ends at 3918 is 399 for each of these heading entities. Each of the heading entities appear on a new output line because each element on new line indicator 3938 is "yes".

Table row 3927 shows a prompt entity with a longer text prompt with an edit box answer style. The prompt "If you agree to participate in our research, please type your initials here" may be shortened to "If you agree to participate in our research" by process 1031 of FIG. 12 and specifying a maximum string length of 45 or 50.

Table row 3929 shows a prompt entity with a numeric answer style. Table row 3930 and 3932 shows a prompt with a yes/no answer style. Table row 3933 and 3936 shows a prompt text with a text box answer style.

Table row 3934 shows a prompt text with a dropdown list answer style. The prompt text "OBSOLETE: Prior counseling" may be modified as specified in step 904 of FIG. 11 to become "Prior counseling" by the current invention.

Table row 3935 shows the prompt text with a combo box answer style. The prompt text "Prior meds (only counts if taken 30 days or longer)" may be modified as specified using the process 830 of FIG. 9 or process 860 of FIG. 10 and skipping optional step 918 in FIG. 11 to become "Prior meds" by the current invention.

Table row 3937 shows a heading entity that turns out to be a terminal heading so is excluded by step 1273 of FIG. 19A or step 1297 of FIG. 19B.

Table rows 3927, 3929, 3932, and 3935 all have the same columnar layout. The prompt text appears on a new output line because element on new line indicator 3938 is "yes". The prompt text appears on the same output line as the answer value because answer on new line indicator 3914 is "no". The prompt text uses the left quarter of the screen's horizontal boundaries (e.g., column positions 1-99), and the answer value uses the second quarter of the screen's horizontal boundaries (e.g., column positions 101-199). The entire prompt text with answer field occupies the left half of the screen (e.g., column 1 of 2 total columns, or furthest left and furthest right boundaries 3921 and 3922 of 1-199).

Table rows 3930, and 3933 both have the same columnar layout. The prompt text appears on the same output line as the previous prompt-answer pair because element on new line indicator 3938 is "no". The prompt text appears on the same output line as the answer value because answer on new line 3914 is "no". The prompt uses the third quarter of the screen's horizontal boundaries (e.g., column positions 201-299), and the answer value uses the fourth quarter of the screen's horizontal boundaries (e.g., column positions 301-399). The entire prompt with related answer field occupies the right half of the screen (e.g., column 2 of 2 total columns, or furthest left and furthest right boundaries 3921 and 3922 of 201-399).

Table row 3934's prompt text appears on the next blank output line after table row 3933's output line because element on new line indicator 3938 is "yes". The prompt text appears on the same output line as the answer value because answer on new line 3914 is "no". The prompt uses the left half of the screen's horizontal boundaries (e.g., column positions 1-199), and the answer value uses the right half of the screen's horizontal boundaries (e.g., column positions 201-399). The entire prompt with related answer field occupies the whole screen width (e.g., column 1 of 1 total columns, or furthest left and furthest right boundaries 3921 and 3922 of 1-399).

Table row 3936's prompt text appears on the same output line as table row 3935's prompt text because element on new line indicator 3938 is "no". The answer value appears on the line after the prompt text because answer on new line indicator 3914 is "yes". Because the prompt text with related answer value is vertically stacked, the full width of the indicated column (e.g., column 2 of 2 total columns) can be used for both the prompt text and answer value, so each occupy furthest left and furthest right boundaries 3921 and 3922 of 201-399.

Referring to FIG. 31C, shown is an idealized embodiment of a table of partial answer entities 55 that corresponds to document area 3907. Columns which would be constant in this small sample are omitted (e.g., a column that either directly or indirectly links back to a specific client is missing). Also, additional columns may be present in a full implementation (e.g., a binary value column for images). Additional rows may also be omitted, as there may be a need to store which texts of heading entities are presented to the data entry user if the EMR allows the form design to change after an instance of the data form exists in the table of FIG. 31C.

Finally, two rows (e.g., table rows 3971 and 3973) are included here for illustration purposes, but may not exist in an actual EMR. These two rows are included here to emphasize how unanswered prompts might appear, but the same effect may be achieved if the rows were missing (e.g., the answer would be empty) when software tries to look up answer values for rows 3929 and 3930.

FIG. 31C has four columns. The first column, primary key 3961, is a primary key for a single table row of the answer entity table (e.g., shown in FIG. 31C is 8 instances of answer entities, each with their own primary key value). The second column, design id 3963, is a foreign key to primary key 3908 of FIG. 31B. The third column, numeric value 3965, can be used for any prompt entity that a numeric field can be used to answer. The fourth column, text value 3967, is used for any manually typed text the data entry user 78 types.

Numeric value 3965 may be used anytime an answer style is a Boolean value (e.g., checkboxes, yes/no prompts of FIG. 2), a numeric value (e.g., numeric and Likert groups of FIG. 2), a value looked up in the data store (e.g., option groups, combo boxes of FIG. 2), possibly a date (e.g., dates of FIG. 2) or perhaps a foreign key to either an image or a very long text value.

Text value 3967 is used for typed answers (e.g., free text boxes and edit boxes), or possibly a date. Note that checking for manually typed text of step 902 of FIG. 11 could merely check if the value is stored in text value 3967, and if it is, step 902 exits at step 926; otherwise, processing may continue with step 904.

Table row 3969 includes a foreign key to table row 3927 and has a text value of "VF". Table row 3971 includes a foreign key to table row 3929 and has an empty value (e.g., does not contain text, dates, numbers, images, etc.) since there is neither a numeric value nor a text value for that table row. Table row 3973 includes a foreign key to table row 3930 and has an empty value since there is neither a numeric value nor a text value for that table row. Table row 3975 includes a foreign key to table row 3932 and has a numeric value of "1" (e.g., meaning "true" since table row 3932 is a "yes/no" answer style). Table row 3977 includes a foreign key to table row 3933 and has a text value of "Ulcerative Colitis".

Table row 3979 includes a foreign key to table row 3934 and had a numeric value which, in turn, is a foreign key to FIG. 31D (because table row 3934 has a style 3912 of "dropdown list"), table row 3995, which has the value "After starting college (i.e., first college attended)". In the current invention, process 900 of FIG. 11 may exclude the parenthetical comments and cut the answer value down to "After starting college".

Table row 3981 includes a foreign key to table row 3935 and had a numeric value which, in turn, is a foreign key to FIG. 31D (because table row 3935 has a style 3912 of "dropdown list"), table row 3997, which has the value "OBSOLETE: Both". In the current invention, this value may be cut down to "Both" by step 904 of FIG. 11.

Table row 3983 includes a foreign key to table row 3937 and has a text value of "Vitamin B-12, Folic Acid, Xeljanz XR (since age 17)". Unlike, the text of table row 3995, the parenthetical comment is not excluded from this cell because it is something that the data entry user 78 typed (because the answer appears in text value 3967 of table row 3983, or table row 3936 has a style 3912 of "text box"), so step 902 of FIG. 11 takes the "Yes" path to the exit step 926.

Referring to FIG. 31D, shown is an idealized table of lookups entities 39 that finds values for a supplemental list. Columns which are not significant to the current discussion have been omitted from the table (e.g., an order by column to specify the order the table rows will appear on the screen). The table consists of three columns and shown are the three table rows used for the two dropdown lists (rows 3934 and 3935). The first column, primary key 3987, allows looking up values from numeric value 3965. The second column, list id 3983, allows looking up groups of values from supplemental list id 3913. The third column, text of answer 3991, is the text value of the table row.

Referring to FIG. 31E, a layout grid is shown laying out the prompt texts with related answer values according to FIGS. 31B-31D. A layout grid is one conceivable way to layout data forms on display or data entry user screens for an EMR (however it is unknown whether any EMR software manufacturer actually uses a layout grid to lay out their data). Layout grids have the advantage that a program only needs to provide a row indication and a column number and the layout grid takes care of which texts have to word wrap and maintains the relative spacing of each cell of the grid on any width screen. This layout grid represents separate adjacent cells for each prompt text and each answer value. Whether the adjacent cells are vertically aligned or horizontally aligned is dependent upon the answer on new line indicator 3914, with the value "No" meaning the adjacent cells are horizontally aligned and the value "Yes" meaning the adjacent cells are vertically aligned.

Heading cells 4001, 4003, 4005, 4007, 4013, 4023, and 4045 each appear on their own output line and obtain their default text 3910 from table rows 3923, 3924, 3925, 3926,

3928, 3931, and 3937, respectively. Each of these heading cells take up the full horizontal space available because column number 2015 is 1 and total columns 2016 is 1.

Heading cell 4001 has a style 3912 of "section heading" and so may be formatted differently than the rest of the texts of the heading entities, which are all styled as a "text heading".

Prompt cell 4009 is horizontally aligned with its adjacent answer cell 4011, using the edit box style 3912 from table row 3927. The prompt text is contained within the horizontal boundaries of 1-199 and the answer value is contained within the horizontal boundaries of 201-399. The text of prompt cell 4009 comes from default text 3910 of table row 3927. The text of answer cell 4011 comes from text value 3967 of table row 3969.

Prompt cell 4015 is horizontally aligned with its adjacent answer cell 4017, using the numeric style 3912 of table row 3929. The prompt text is contained within the horizontal boundaries of 1-99 and the answer value is contained within the horizontal boundaries of 101-199. The text of prompt cell 4015 comes from default text 3910 of table row 3929. The numeric value of answer cell 4017 comes from numeric value 3965 of table row 3971. In this case, that attribute has an empty value, so an empty numeric value is displayed rather than a numeric.

Prompt cell 4019 is horizontally aligned with its adjacent answer cell 4021, using the yes/no style 3912 of table row 3930. The prompt text is contained within the horizontal boundaries of 201-299 and the answer value is contained within the horizontal boundaries of 301-399. The text of the prompt cell 4019 comes from default text 3910 of table row 3930. The answer value in cell 4021 comes from looking up numeric value 3965 of table row 3973, and if that numeric value is 0 then use the option "No" or if the value is 1 then use the option "Yes". In this case, that attribute has an empty value, so neither option is selected.

Prompt cell 4025 is horizontally aligned with its adjacent answer cell 4027, using the yes/no style 3912 of table row 3932. The prompt text is contained within the horizontal boundaries of 1-99 and the related answer value in cell 4027 is contained within the horizontal boundaries of 101-199. The text of prompt cell comes from default text 3910 of table row 3932. The answer value in cell 4027 comes from numeric value 3965 of table row 3975, and if that numeric value is 0 then use the option "No" or if the value is 1 then use the option "Yes".

Prompt cell 4029 is horizontally aligned with its adjacent answer cell 4031, using the text box style 3912 of table row 3933. The prompt text is contained within the horizontal boundaries of 201-299 and the answer value is contained within the horizontal boundaries of 301-399. The text of the prompt cell 4029 comes from default text 3910 of table row 3933. The text of answer cell 4031 comes from text value 3967 of table row 3977.

Prompt cell 4033 is horizontally aligned with its adjacent answer cell 4035, using the dropdown list style 3912 of table row 3934. The prompt text is contained within the horizontal boundaries of 1-199 and the answer value is contained within the horizontal boundaries of 201-399. The text of prompt cell 4033 comes from default text 3910 of table row 3934. The text of answer cell 4035 comes from taking numeric value 3965 of table row 3979, then using that value (e.g., 401) as a foreign key to FIG. 31D and using the text of answer 3991 of table row 3995.

Prompt cell 4037 is horizontally aligned with its adjacent answer cell 4039, using the dropdown list style 3912 of table row 3935. The prompt cell is contained within the horizontal boundaries of 1-99 and the answer value is contained within the horizontal boundaries of 101-199. The text of the prompt cell 4037 comes from default text 3910 of table row 3935. The text of answer cell 4039 comes from numeric value 3965 of table row 3981, then using that value (e.g., 402) as a foreign key to FIG. 31D and using the text of answer 3991 of table row 3997.

Prompt cell 4041 is vertically aligned with the adjacent answer cell 4043, using the text box style 3912 of table row 3936. Both the prompt text with related answer value is contained within the horizontal boundaries of 201-399, but with the answer value on the output line below the prompt text. The text of the prompt cell 4041 comes from default text 3910 of table row 3936. The text of answer cell 4043 comes from text value 3967 of table row 3983. Note that the answer value seems to contain more information than appeared in document area 3907 in FIG. 31A, because that cell was at the very bottom of the viewable portion and there was additional text below the viewable portion of the cell.

Note that the output line cell 4045 appears on is actually two output lines (e.g., two layout grid rows) below the output line where cell 4037 appeared (ignoring the fact that cell 4037 happened to word wrap for the current width screen) because cells 4041 and 4043 were an answered prompt field that was vertically aligned. So, there was already text on the output line immediately below the output line where cell 4037 appeared.

Column position markers 4047 shows a scale of column positions and is not visible on the screen.

FIG. 31F is exactly the same image as FIG. 31E without the layout grid visible and represents the image the data entry user 78 saw after entering this portion of the data form on his data entry user interface display 76. It is likely the image a display user 81 would also see viewing this portion of the data form.

It should be apparent to those skilled in the art that FIGS. 31B-31F represent one particular idealized way an EMR system may be laid out. FIGS. 31B-31F are presented only as an example of how the current invention might be applied to a specific EMR database, and is not meant to be limiting. Five new concepts are presented by the present disclosure: (1) the use of alternate text for heading entities in alternate text 3911, (2) the use of different styles of heading entities in style 3912, (3) the calculation, use and existence of the column furthest-left boundary 3921 and the column furthest-right boundary 3922 as a boundary for a single combined prompt-answer pair, (4) the particular formulas used to calculate each of the computed values, and (5) possibly, the use of a layout grid to format EMR data in FIG. 31E. Language in this disclosure assuming that the prompt entity contains the specifications for the answer style and layout, even that prompt entity information does not actually appear in the lookups entity 39 are referring to this particular example, and are not meant to be limiting. It should be apparent to those skilled in the art that the processes and methods of the current invention are not limited to any particular layout of the underlying EMR system.

FIG. 31G is the text as it appeared in document area 3907 of FIG. 31A and showing the layout grid. Note that the cells of this layout grid match the cells of the combined prompt and answer cells of the layout grid in FIG. 31E. Cell 4051 contains the horizontal space of cell 4001. Cell 4053 contains the horizontal space of cell 4003. Cell 4055 contains the horizontal space of cells 4009 and 4011 combined. Cell 4059 contains the horizontal space of cell 4023. Cell 4061 contains the horizontal space of cells 4025 and 4027 combined. Cell 4063 contains the horizontal space of cells 4029 and 4031 combined. Cell 4065 contains the horizontal space of cells 4033 and 4035 combined. Cell 4067 contains the horizontal space of cells 4037 and 4039 combined. Cell 4069 contains the horizontal space of either cell 4041 or cell 4043.

The sources of information and formats for most cells have already been covered in the discussion of FIG. 31E, so the rest of the description of FIG. 31G will concentrate on the differences of what happened when processing between FIG. 31E and FIG. 31G. For this example, the process is set to trim characters beyond 40 characters in either a prompt text or an answer value and add an ellipse as the paren placeholder in step 918 of FIG. 11. Also, the combining string for this example will be a colon, followed by a space. Also, the top repeat heading entity will be selected as the entity to represent each repeat heading series (meaning that each lowest repeat heading entity may be excluded in steps 1297 or 1305).

Table row 3923 is classified as a normal heading entity since it is the only section style heading (e.g., style 3912 of table row 3923) and each style is classified separately, so when classifying section style heading entities, the present disclosure may ignore the existence of text style heading entities (e.g., step 1302 of FIG. 19C). Further, judging from the font characteristics, comparing heading cell 4051 with heading cell 4053, it becomes apparent that cell 4051 is a higher-level heading entity (e.g., since the font is larger or bolder than cell 4053, the section style heading entities would be further to the left than the text style heading entities, if graphed out in a diagram like FIG. 19F). As a normal heading entity with a non-null answer under it (e.g., an answered prompt entity in cell 4055 or table row 3969) it is not excluded in step 1297 of FIG. 19B or step 1305 of FIG. 19C and appears as cell 4051.

Table row 3924 is classified as a top repeat heading entity since the style 3912 of the table row is different than the style of the previous table row 3923 and there is another heading entity row immediately below it. As a top repeat heading entity with a non-null answer under it (e.g., an answered prompt entity in cell 4055 or table row 3969 of the answer table and 3927 of the prompt table) which is before the next top repeat heading entity of the same style), it is not excluded in step 1297 of FIG. 19B. It appears as cell 4053.

Table row 3925 is a heading entity classified as a repeat heading, so it is excluded by steps 1297 or 1305.

Table row 3926 is a heading entity classified as a lowest repeat heading since it is proceeded by another heading entity and followed by a prompt entity. By step 1297 or 1305, it is the repeat heading series element that is not selected to represent the repeat heading series, so is excluded.

Because there is an alternate text 3911 in row 3924, which appears in any row for the current repeat heading series (e.g., table rows 3924-3926), and the top repeat heading entity is selected as the entity that represents each repeat heading series, that alternate text replaces the text of heading 3924 for this repeat heading series. Note that the alternate text could have appeared in any of the current repeat heading series rows, there is nothing that says it has to appear in the first row of each repeat heading series. So, cell 4053 becomes "Inclusion application for XYZ research.". Because the final text of cell 4053 is not longer than 40 characters, it does not get trimmed.

Table row 3927 is an answered prompt entity (e.g., table row 3969), so it is not excluded. However, the prompt text is over the length limit, so it is trimmed to be no more than 40 characters by the process of FIG. 11. Even if the answer text were long enough to be trimmed, since it is stored in text value 3967, it was typed by the data entry user, therefor would avoid trimming by taking the "yes" branch at step 902. The trimmed prompt text has the combining string and the converted answer value concatenated with it using the process of FIG. 8B (during which, the user defined attributes are applied to the prompt text with related answer value). The horizontal boundaries of the cell are calculated by furthest-left boundary 3921 and furthest-right boundary 3922 of table row 3927. The results appear in cell 4055.

Table row 3928 is a heading entity classified as a normal heading. However, no prompt entities prior to the next entity classified as a heading of the same style were responded to by the data entry user 78, so the prompt entities between these heading entities may be all excluded by step 1295. Step 1297 may exclude table row 3928 as a normal heading entity not followed by a prompt entity. Step 1305 may exclude table row 3928 as a heading entity with only unanswered prompt entities under it. If it hadn't been excluded, this would have appeared on output line 4057.

Table row 3929 is an unanswered prompt entity where the answer should be stored in table row 3971 in either the numeric value 3965 or text value 3967. It is excluded by step 1295 or 1305.

Table row 3930 is an unanswered prompt entity where the answer should be stored in table row 3973 in either the numeric value 3965 or text value 3967. It is excluded by step 1295 or 1305.

Table row 3931 is a heading entity classified as a normal heading. This heading entity may be displayed and not excluded because an answered entity (e.g., cell 4061 or table row 3975) is present between this normal heading entity and the next normal heading entity, top repeat heading entity or end of document marker. Note that there is an alternate text column 3911 that is not empty for this row, so, in this embodiment, the alternate text is used for the heading entity when the text is being formatted for the screen. In this embodiment, if the heading entity is being formatted for a printout, the default text column 3910 would be used. The output appears in cell 4059.

Table row 3932 is an answered prompt entity (e.g., table row 3975), so it is not excluded. The prompt text with the converted answer value is combined using a colon and space as the combining string using the process of FIG. 8B (during which, the user defined attributes are applied to the prompt text with related answer value). The horizontal boundaries of the cell are calculated by furthest-left boundary 3921 and furthest-right boundary 3922 of table row 3932. The results appear in cell 4061.

Table row 3933 is an answered prompt entity (e.g., table row 3977), so it is not excluded. The prompt text with the converted answer value is combined using a colon and space as the combining string using the process of FIG. 8B (during which, the user defined attributes are applied to the prompt text with related answer value). The horizontal boundaries of the cell are calculated by furthest-left boundary 3921 and furthest-right boundary 3922 of table row 3933. The results appear in cell 4063.

Table row 3934 is an answered prompt entity (e.g., table row 3979), so it is not excluded. The prompt text is shortened using step 904 to exclude the characters "OBSOLETE:" found in default text 3910, table row 3934. The shortened prompt text and the converted answer value are combined using a colon and space as the combining string using the process of FIG. 8B (during which, the user defined attributes are applied to the prompt text with related answer value). The horizontal boundaries of the cell are calculated by furthest-left boundary 3921 and furthest-right boundary 3922 of table row 3934. The results appear in cell 4065.

Table row 3935 is an answered prompt entity (e.g., table row 3981), so it is not excluded. The prompt is shortened using the process of FIG. 9 or FIG. 10 to exclude the parenthetical comment found in default text 3910, table row 3935. The answer value is shortened using step 904 to exclude the characters "OBSOLETE:" found in text of answer 3991, table row 3997. The shortened prompt text and shortened converted answer value are combined using a colon and space as the combining string using the process of FIG. 8B (during which, the user defined attributes are applied to the prompt text with related answer value). The horizontal boundaries of the cell are calculated by furthest-left boundary 3921 and furthest-right boundary 3922 of table row 3935. The results appear in cell 4067.

Table row 3936 is an answered prompt entity (e.g., table row 3983), so it is not excluded. The prompt text with the converted answer value is combined using a colon and space as the combining string using the process of FIG. 8B (during which, the user defined attributes are applied to the prompt text with related answer value). Even though the answer value contains embedded parenthesis, that embedded parenthesis is not excluded because the answer appears in text value 3967 (so was typed by the data entry user). The horizontal boundaries of the cell are calculated by furthest-left boundary 3921 and furthest-right boundary 3922 of table row 3936. The results appear in cell 4069.

Table row 3937 is a heading entity classified as a terminal heading, so it is excluded in step 1273 or 1297.

Note also that FIG. 31G is nine text lines high and FIG. 31F is much taller.

FIG. 31H is identical to FIG. 31G, except for cell 4071. Cell 4071 is the optimization shown in step 706-712 of FIG. 8B based on an analysis of cell 4069. According to step 706, cell 4069 has three lines and the answer is also displayed on 3 lines, so a test is made of starting the answer text on a new line. According to step 712, cell 4071 also has three lines and now the answer text is displayed on two lines. Since there is no vertical spacing benefit to using the layout of cell 4069 and cell 4071 displays the same information with the answer text on one fewer line(s), the final display of this information may be done using cell 4071.

The use of a grid to lay out prompt-answer texts in FIGS. 31E, 31G and 31H is shown by way of illustration, and not as a limitation. While grids make the explanation easier to understand, it may be noted by those skilled in the art that a grid may be too inflexible of structure for some situations in an actual EMR where percentages of the screen width allowed for the various columns may need to be altered. A few alternatives to grids might include using (1) independent text boxes which have a calculated origin position and width on the screen, (2) html and its formatting capabilities, and (3) RTF tables.

Typically, audit logs track whether a specific user opened a specific document in its entirety. From there, it can be inferred, but not actually verified, that the user viewed the whole document. Those skilled in the art will appreciate, however, that this may not always be true. It may be the case, for example, that a user opens a specific document but only looked at a small portion of it. It may also be the case that the user quickly opened and closed a document without spending enough time looking at the document to have reasonably read it.

It is one aspect of the present invention to create viewing verification data sets of a finer detail than traditional audit logs. More specifically, the present invention aims to determine what a specific user viewed all the way down to specific document areas, and whether a specific user viewed the entire document contents.

It is contemplated that an access history data set of the present disclosure may be utilized to enable a variety of useful functions. For example, using the higher level of specificity a user may determine which document areas of an input have not yet been viewed. The display user may also issue commands such as "show me all the document areas that I have not yet viewed" to ensure that the display user has reviewed everything on a specific document or collection of documents. In another example, the display user could set up a list of important document types (or specific document areas of certain document types) to review and the selection could be limited to that list rather than all documents. In yet another example, the user could issue a command to "create a compound document including all documents for a specific client containing unviewed content and highlight sections in each document that I have not yet (or have already) viewed". In yet another example, the user could issue a command to "show me all documents from the past week written by anyone I supervise that I have not viewed in their entirety". In yet another example, "show me everything I haven't reviewed from the past month for clients assigned to me (putting each client on a separate tab)". In yet another example, verify an area of a contract was shown on the screen long enough for a user to have reasonably read it. Highlighting here is not limited to changing background colors of text areas, but also making any other changes to fonts (e.g., boldness, colors, underlining, etc.) and other ways of marking differences (e.g., encircling text sections not yet viewed).

In light of the functions described above, it is further contemplated that the information contained in an audit log and/or an access history data set (including browser-viewing log, viewing history logs and viewing verification data sets, which are described in greater detail below) can be used to determine which documents and/or document areas of an input should be included in an output to be shown on a user device (e.g., a peripheral output device).

In the discussion below, any scrolling that is not either in a purely horizontal nor purely vertical direction is to be taken as two separate scrolls. One of the scrolls is in the horizontal direction and having a distance in the amount of the horizontal component of the scroll. The second scroll is in the vertical direction and having a distance in the amount of the vertical component of the scroll.

In the discussion below, all scrolling is discussed in the vertical direction. Those skilled in the art will appreciate that the same discussion could be repeated in the horizontal direction and therefor systems, devices, and methods of the present disclosure, both horizontal scrolling and diagonal scrolling are within the scope of the current disclosure.

Furthermore, it is within the scope of the current disclosure to have an input having multiple documents scrolled horizontally, but the individual documents of the input are scrolled vertically.

Furthermore, it is within the scope of the current disclosure if the browser window also returns horizontal positions in addition to the vertical positions and the horizontal areas or ranges on the screen are tracked similar to the way vertical areas or ranges on the screen are tracked in the discussion below.

Furthermore, it is within the scope of the current disclosure if areas or ranges which have not been displayed are tracked instead of areas or ranges which have been displayed by the same means discussed below.

There are at least three ways to track specific individual documents viewed in an access history data set. The first option is based on the idea that whatever data was installed in the application is assumed to have been viewed if the application is accessed by a user. For example, an entire input or a tab can be marked as having been viewed so long as it was accessed (i.e., opened) by a user, regardless of how much time was spent viewing the individual document/tab or the amount of the document/tab actually shown on a screen. Those skilled in the art will appreciate that tracking documents in this way is rather indiscriminate because it does not truly indicate that a user has actually read the document.

The second way to track user view of individual documents is to link whatever onscreen controls the user activates, and assume that anything viewable on that page has been viewed. With regard to tabbed applications, this is slightly different than the first option because only those individual documents that are already expanded are counted. In the first option, even hidden documents are counted. With the second option, documents which are hidden or not expanded are not counted as viewed until they are expanded (i.e., un-hidden).

The third way is to use feedback from the browser window as to what has been shown on the screen. There are a couple of options here also. One option is that if any individual document area has been viewed, then the whole individual document is considered viewed. A second option is to track each individual document area that has been viewed. Of course, it would be within the scope of this disclosure if the source of feedback as to what is displayed on the screen is something other than directly from the browser window. For example, if someone did optical character recognition ("OCR") on the screen to determine what was displayed on the screen at the position of the browser window, that would be just another way to obtain the information from the browser window. Another example would be if the browser window only provided relative movement ranges each time, so that the program had to add positive or negative numbers to a running sum to calculate the document area displayed on the screen. Another example is if the ranges come from some underlying control that is actually driving what is displayed and responding to user interactions, that also would be in the scope of what is coming from the browser window.

Figure 32A:
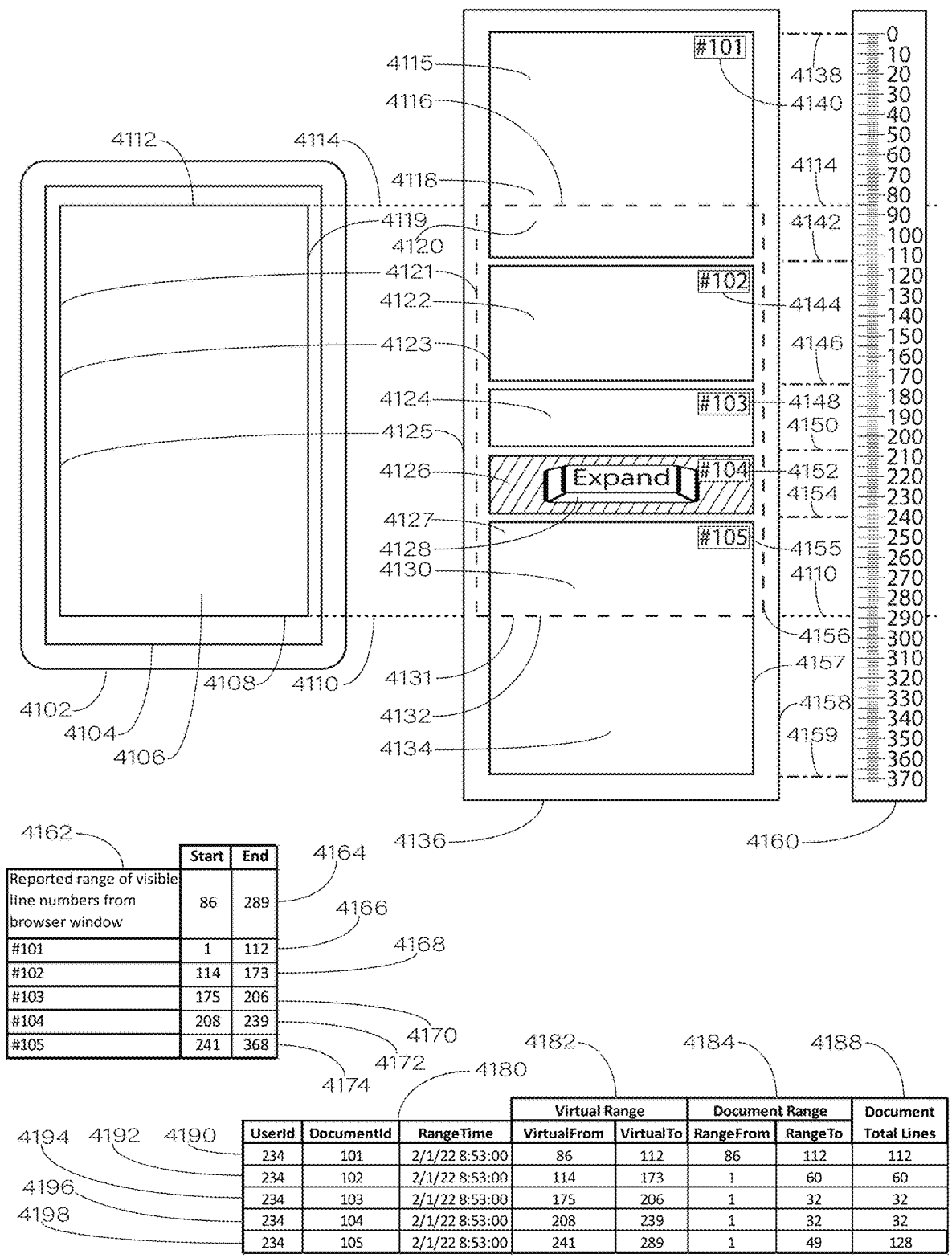
FIG. 32A is an example of calculating a viewing history log when the screen shows five individual document areas.

Turning to FIG. 32A, shown is a display monitor 4102. A portion of the display monitor 4102 includes a viewable screen 4104. A portion of the viewable screen 4104 includes a browser window 4106 in which some of the methods of this disclosure are applied. The browser window 4106 defines a top edge 4112, a bottom edge 4108, and a viewable area therebetween. Also shown in FIG. 32A is input 4136 which includes a plurality of documents 4115, 4122, 4124, 4126, and 4127 that are arranged vertically. Input 4136 can be displayed to a display user through the viewable area of the browser window (though, for the purposes of describing the methods of the present disclosure the input is shown as being off to the side. Furthermore, the three vertical lines 4121, 4123 and 4125 that fall at exactly the same place, are shown slightly offset from each other. Similarly, vertical line 4119 shows its component vertical lines 4156, 4157 and 4158 slightly offset from each other.) Notably, here, the dimensions of the input exceed the dimensions of the browser window vertically. And owing to this, the browser window is generally incapable of displaying the entirety of the input at any single instant of time. The computer application response for the browser window may compensate by enabling user scroll through the input by adjusting the position of the input relative to the browser window.

Narrow-dashed lines 4114 and 4110 extend from the top edge 4112 and bottom edge 4108 of the browser window, respectively, to indicate what part(s) of the input can be displayed on the viewable area at any given time. The wide-dashed rectangle 4131 represents the exact size and position of the browser window over the input.

As shown, individual document 4115 extends above the top edge 4112 of the browser window, and the viewable area of the browser window may only show a portion of an individual document. Individual document 4115 can therefore be considered in two parts-document areas 4118 and 4120. Document area 4118 is shown on screen whereas document area 4120 is hidden off screen. Similarly, individual document 4127 extends below the bottom edge 4108 of the browser window and can be considered in two parts-document areas 4130 and 4134. Document area 4130 is shown on screen whereas document area 4134 is hidden off screen.

The computer application applies an interval coordinate system to the input so that each point along the input has a location-identifying coordinate or set of coordinates. In the embodiment shown, the interval coordinate system includes vertical interval scale 4160. Vertical interval scale 4160 is measured in units of virtual lines (i.e., display lines), however it is also contemplated that other units of measurement may also be suitable (e.g., pixels, millimeters, inches, etc.).

There are six document separator extenders (4138, 4142, 4146, 4150, 4154, and 4159) depicted between the interval scale and the input. These document separator externs are each shown as having an alternating pattern of narrow-and-wide dashed lines. These reflect the vertical height positions where each individual document of the input begins and ends, and also allows for easier viewing of each relative to the scale 4160. Document separator extenders 4138 and 4142 are the top and bottom of individual document 4115. Document separator extenders 4142 and 4146 are the top and bottom of individual document 4122. Document separator extenders 4146 and 4150 are the top and bottom of individual document 4124. Document separator extenders 4150 and 4154 are the top and bottom of individual document 4126. Document separator extenders 4154 and 4159 are the top and bottom of individual document 4127. Reading the scale, the document separator extenders fall at 0, 113, 174, 207, 240, and 369.

Each individual document has a document identifier (4140, 4144, 4148, 4152, and 4155) associated with that individual document. The document identifier may be a single number or combination of several fields. The document identifiers may or may not appear in the browser window but may be kept associated with the individual documents that make up the input. The association may be as simple as keeping a table of which virtual line numbers of the input are associated with which individual document (as will be shown in transformation table 4162); or alternatively, by showing the individual document identifier in the browser window; or alternatively, by some mechanism to display an individual document but suppress showing the individual document identifier from appearing on the screen. Some or all of the individual documents that make up inputs may be hidden behind buttons, links or other appropriate objects. Those individual documents which are hidden may not be viewable to the display user until after the appropriate object is activated. Individual document 4126 is hidden and only viewable after the appropriate control 4128 is activated to expand the individual document. Metadata may be displayed on the control 4128 such as a date, a document type, author, etc.

The individual documents that make up the input are transformed in transformation table 4162. Line 4164 shows the top and bottom edge of the browser window. Lines 4166 through 4174 transform the beginning and ending of each individual document that make up input 4136. Individual document 4115 is referred to as #101 (i.e., has a document Identifier 4140 of #101) and since the top and bottom edges fall at 0 and 113, individual document 4115 itself runs from 1 to 112 in line 4166. Individual document 4122 is referred to as #102 (i.e., has a document Identifier 4144 of #102) and since the top and bottom edges fall at 113 and 174, individual document 4122 itself runs from 114 to 173 in line 4168. Individual document 4124 is referred to as #103 (i.e., has a document Identifier 4148 of #103) and since the top and bottom edges fall at 174 and 207, individual document 4124 itself runs from 175 to 206 in line 4170. Individual document 4126 is referred to as #104 (i.e., has a document Identifier 4152 of #104) and since the top and bottom edges fall at 207 and 240, individual document 4126 itself runs from 208 to 239 in line 4172. Individual document 4127 is referred to as #105 (i.e., has a document Identifier 4155 of #105) and since the top and bottom edges fall at 240 and 369, individual document 4127 itself runs from 241 to 368 in line 4174.

Viewing history log 4180 is based on transformation table 4162. The viewing history log is a list of user-view indications-a record that a specific user viewed a specific range of vertical coordinates (e.g., line numbers) of a specific document. The user-view indications may also include additional columns such as a timestamp. The UserId column of the viewing history log is an indication of the current user. The DocumentId column is taken from the first column of transformation table 4162. Range Time column indicates the time the individual document was displayed on the screen. Each line of viewing history log 4180 is calculated from the first line of the transformation table 4162 and one other line of the transformation table 4162. The sources for the other lines 4190, 4192, 4194, 4196 and 4198 are lines 4166, 4168, 4170, 4172 and 4174, respectively.

The Virtual Range columns 4182 are taken from the document lines of transformation table 4162 having a start or end value between the reported range of visible line numbers from the browser window 4106 (i.e., line 4164). The values can be expressed (i.e., transformed) by the formulas:

$$VirtualFrom=MAX(BrowserStart, DocumentStart)$$

$$VirtualTo=MIN(BrowserEnd, DocumentEnd)$$

BrowserStart is what the browser window reported as the first virtual line displayed on the screen and is shown in the Start column of line 4164, BrowserEnd is what the browser window reported as the last virtual line number displayed on the screen and is shown in the End column of line 4164, DocumentStart is the Start column for the specific document line and DocumentEnd is the End column for the same document line, MIN is a function that returns the minimum value of two numbers, and MAX is a function that returns the maximum value of two numbers.

The DocumentRange columns 4184 are the specific individual document areas that were viewed at this time. The values can be expressed by the formulas:

$$RangeFrom=1+VirtualFrom-DocumentStart$$

$$RangeTo=1+VirtualTo-DocumentStart$$

VirtualFrom is the corresponding VirtualFrom column of Virtual Range columns 4182, VirtualTo is the corresponding VirtualTo of Virtual Range columns 4182, and DocumentStart is the Start column for the specific document line. Those skilled in the art will appreciate that the columns for VirtualFrom and VirtualTo are not necessary. These columns were left in for the purposes of this initial illustration to better describe this method. The rest of the illustrations will use the following formulas for RangeFrom and RangeTo and not show the VirtualFrom and VirtualTo columns:

$$RangeFrom=1+MAX(BrowserStart, DocumentStart)-DocumentStart$$

$$RangeTo=1+MIN(BrowserEnd, DocumentEnd)-DocumentStart$$

Lastly, the document total lines 4188 is calculated from the formula:

$$DocumentTotalLines=1+DocumentEnd-DocumentStart$$

Those skilled in the art will appreciate that these formulas may vary to accommodate different situations (e.g., how different browser windows handle a partial line height when reporting what is currently displayed or long text areas that extend over multiple lines). It is contemplated that the drawings should be referred to in the event there are any discrepancies between a particular use-case and the examples provided by this disclosure.

Document ranges can be expressed using various techniques. The first is shown in viewing history log 4180 (i.e., having a minimum and a maximum value). Another possibility to express a document range is a starting position and an offset. It would also be possible for ranges to reflect the portions of documents not viewed rather than portions of documents that have been viewed and later use a subtractive process against a list of document line numbers to calculate what was displayed.

Having described the general nature of the solution in FIG. 32A, the present disclosure now turns to a few exemplary example cases. These cases involve inputs having between zero and three document separators appear in the browser window to the display user.

Figure 32B:
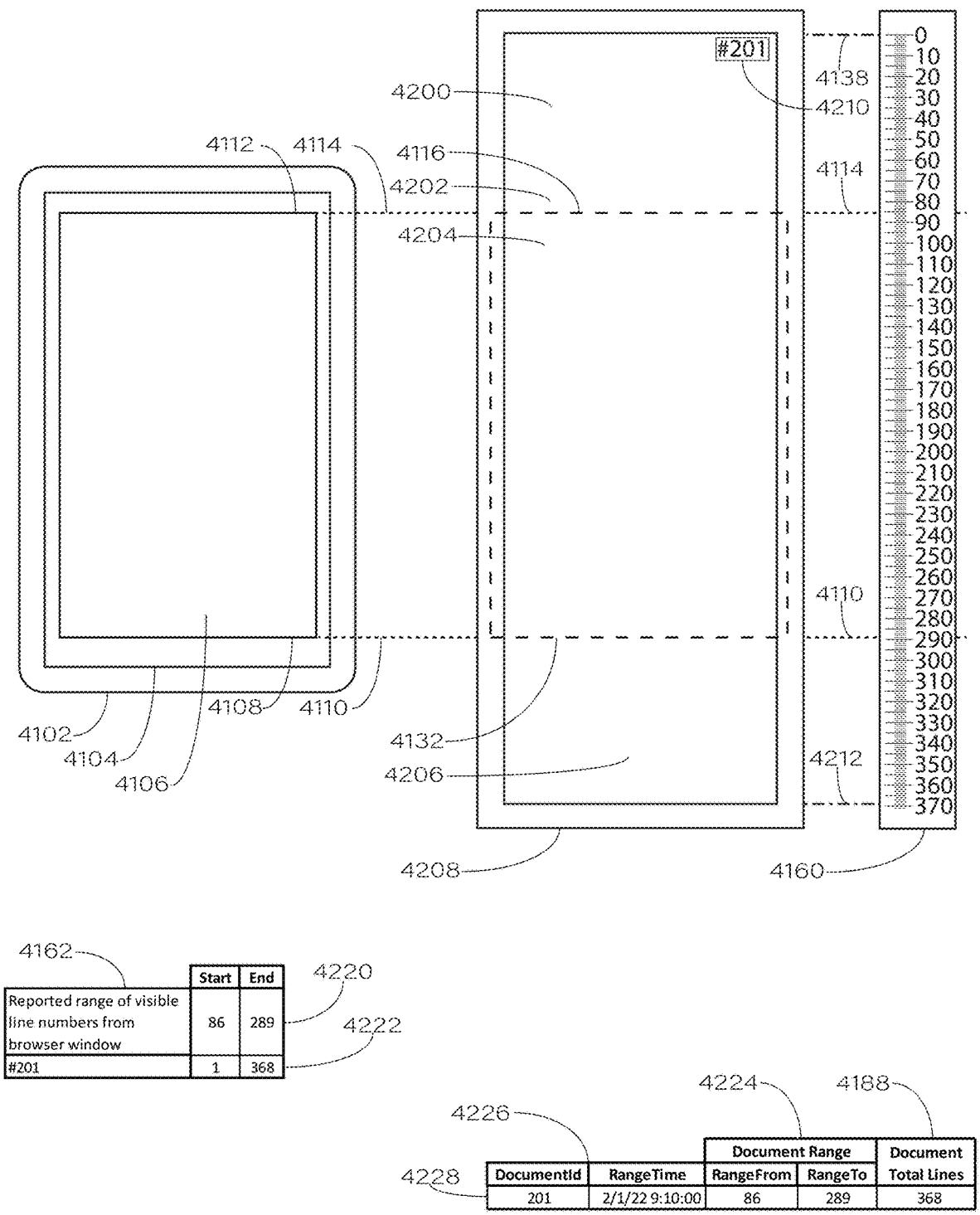
FIG. 32B is an example of calculating a viewing history log when the screen only shows one document.

FIG. 32B shows a way to have zero document separators appear on the screen. For description of label identifiers less than 4200, please refer to FIG. 32A.

Input 4208 includes just one individual document 4200 but can be divided into three parts (document areas 4202, 4204 and 4206). In the browser window 4106 only a portion (document area 4204) of the input is displayed since the vertical dimensions of the input exceeds the vertical dimensions of the browser window 4106. A portion (document area 4202) of the input extends above top edge 4116. Another portion (document area 4206) extends below bottom edge 4132. Individual document 4200 has a document identifier 4210 of "#201".

In this embodiment, whenever the browser window returns offsets relative to the virtual document, the top document separator extender 4138 of the input is located at 0 on scale 4160. In this example, bottom document separator extender 4212 is therefore at 369 on scale 4160.

Transformation table 4162 of FIG. 32B shows that the visible portion of the document runs from 86 to 289 in line 4220 (as it happened to in line 4164 of FIG. 32A). Individual document 4200, with its document Identifier 4210 of #201 and its top and bottom edges falling at 0 and 369 causes individual document 4200 itself to run from 1 to 368 in line 4222.

Viewing history log 4226 of FIG. 32B has been simplified from viewing history log 4180 of FIG. 32A to more accurately depict what it might look like if this was a place where values are accumulated for a single display user session and then put in the viewing verification data set when browser window 4106 is closed. The UserId column has been removed because only a single logged in display user would be responsible for viewing during a single session. If desired, the UserId column can be added when the browser window is closed (because it is just a constant for the current log in session). The Virtual Range columns 4182 have been removed because they are only used to calculate the document range columns 4224. Optionally, column 4188 could also be removed since these numbers are just a constant calculated for each document from the "Start" and "End" columns of transformation table 4162 of FIG. 32B, so this column could also be added, or used, when the browser window is closed. Each user-view indication of the viewing history log qualifies as a record of user-view indications (i.e., entries in the record) because all the lines in the viewing history log were generated during a single session and that single session was initiated by a single user. Calculating from line 4222 according to the method and formulas described in FIG. 32A produces line 4228.

Figure 32C:
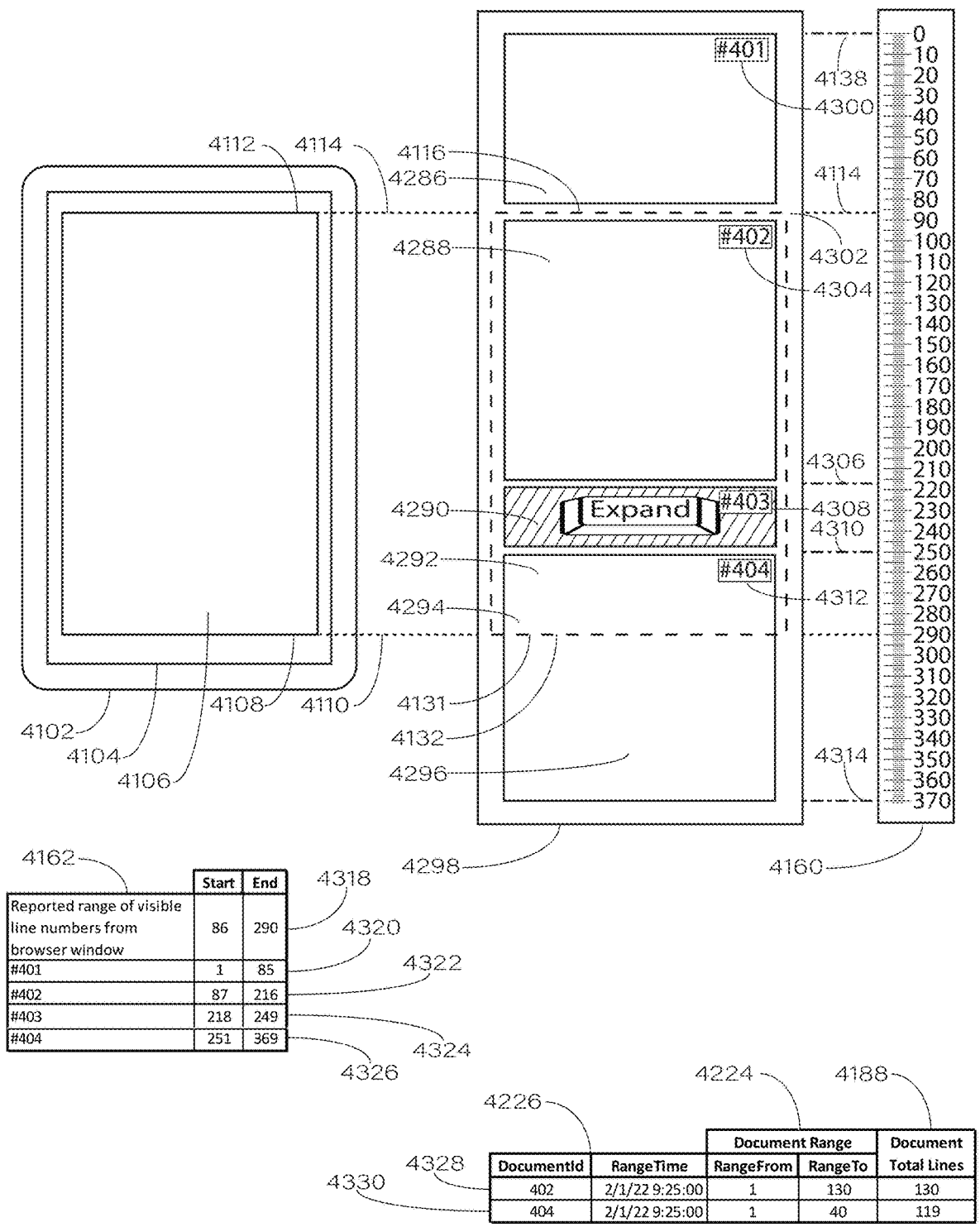
FIG. 32C is an example of calculating a viewing history log when the screen shows three individual document areas.

FIG. 32C shows a way to have three document separators appear on the screen. For description of label identifiers less than 4230, please refer to FIGS. 32A-32B.

Input 4298 is broken up into five parts (individual documents 4286, 4288, and 4290, and individual document areas 4294, and 4296). Input 4298 includes some or all of four different individual documents (individual documents 4286, 4288, 4290, and 4292). In the browser window 4106 appears individual document 4288, individual document 4290 and individual document area 4294 of the input. Individual document 4286 of input 4298 doesn't appear at all in browser window 4106 since the entire individual document is above top edge 4116. Individual document area 4296 is cut off from appearing in browser window 4106 by being below bottom edge 4132. Individual document 4286 has a document identifier 4300 of "#401". Individual document 4288 has a document identifier 4304 of "#402". Individual document 4290 has a document identifier 4308 of "#403", Individual document 4292 has a document identifier 4312 of "#404".

One document separator extender 4302 of input 4298 coincidentally falls at the same place as the line of top edge extension 4114 and is located at 86 on scale 4160. The next document separator extender 4306 is at 217 on scale 4160. The next document separator extender 4310 is located at 250 on scale 4160. The bottom document separator extender 4314 then falls at 370 on scale 4160. The top edge 4116 of browser window 4106 is currently at 86 and the bottom edge 4132 is currently at 290 on scale 4160.

Transformation table 4162 of FIG. 32C contains information for all the individual documents, even if the individual document is hidden (e.g., individual document 4290) in input 4298. This is one alternative, which will be contrasted with FIG. 32D. The top edge 4116 of the browser window currently falls at 86 on scale 4160 and bottom edge falls at 290 on scale 4160 in line 4318. Individual document 4286, with its document Identifier 4300 of "#401" and its top and bottom edges falling at 0 and 86 causes individual document 4286 itself to run from 1 to 85 in line 4320. Individual document 4288, with its document identifier 4304 of "#402" and its top and bottom edges falling at 86 and 217 causes individual document 4288 itself to run from 87 to 216 in line 4322. Individual document 4290, with its document identifier 4308 of "#403" and its top and bottom edges falling at 217 and 250 causes individual document 4290 itself to run from 218 to 249 in line 4324. Individual document 4292, with its top and bottom edges falling at 250 and 370 causes individual document 4292 itself to run from 251 to 369 in line 4326.

Figure 32D:
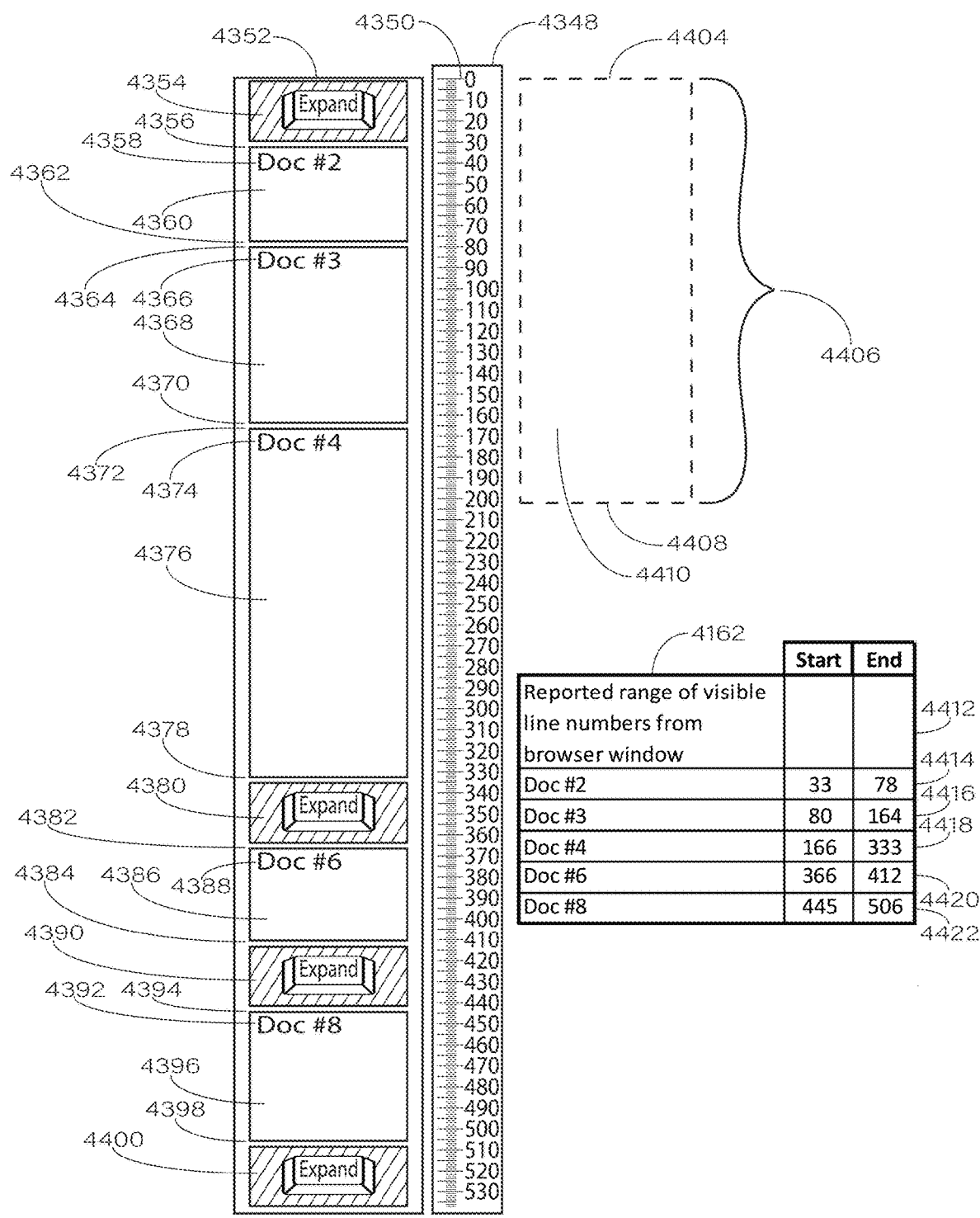
FIG. 32D is the full compound document used in FIGS. 32E and 32F.

Viewing history log 4226 of FIG. 32C only needs to contain information from the individual documents that appeared in the browser window. Therefore, there is no need for information about individual document 4286 in viewing history log 4226. Furthermore, individual document 4290 is hidden behind a link and the individual document itself is not actually shown in browser window 4106. So, there is no need to include information on individual document 4290 in viewing history log 4226. In FIG. 32D, information which may not ultimately appear in the viewing history log may be suppressed from transformation table 4162.

As previously mentioned, individual document 4286 is completely above top edge 4112, so calculations from line 4320 are not included in viewing history log 4226. Calculating from line 4322 according to the method and formulas described in FIG. 32A produces line 4328 of viewing history log 4226. As previously mentioned, individual document 4290 is hidden, so calculations from line 4324 are not included in viewing history log 4226. Calculating from line 4326 according to the method and formulas described in FIG. 32A produces line 4330 in viewing history log 4226.

Figure 32E:
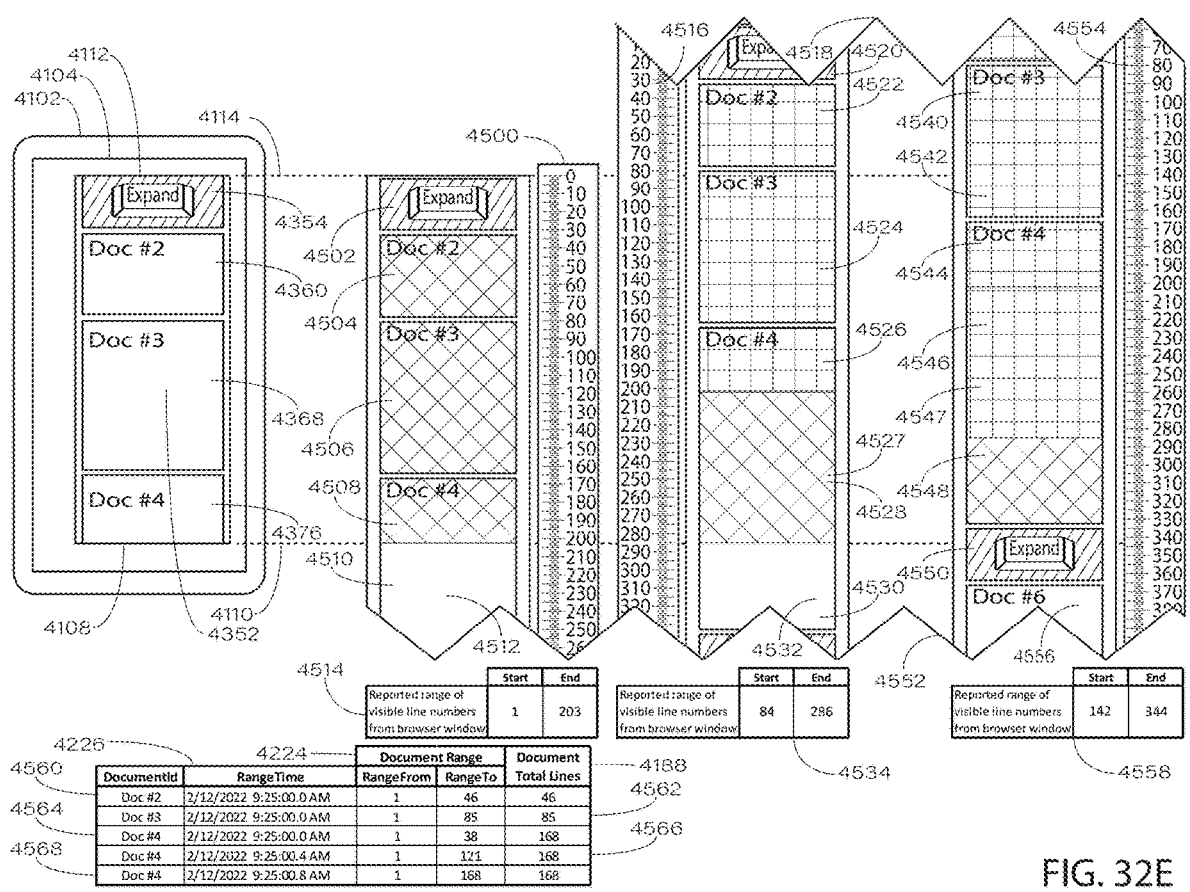
FIG. 32E is an example of creating a viewing history log for a screen slowly scrolled.
Figure 32F:
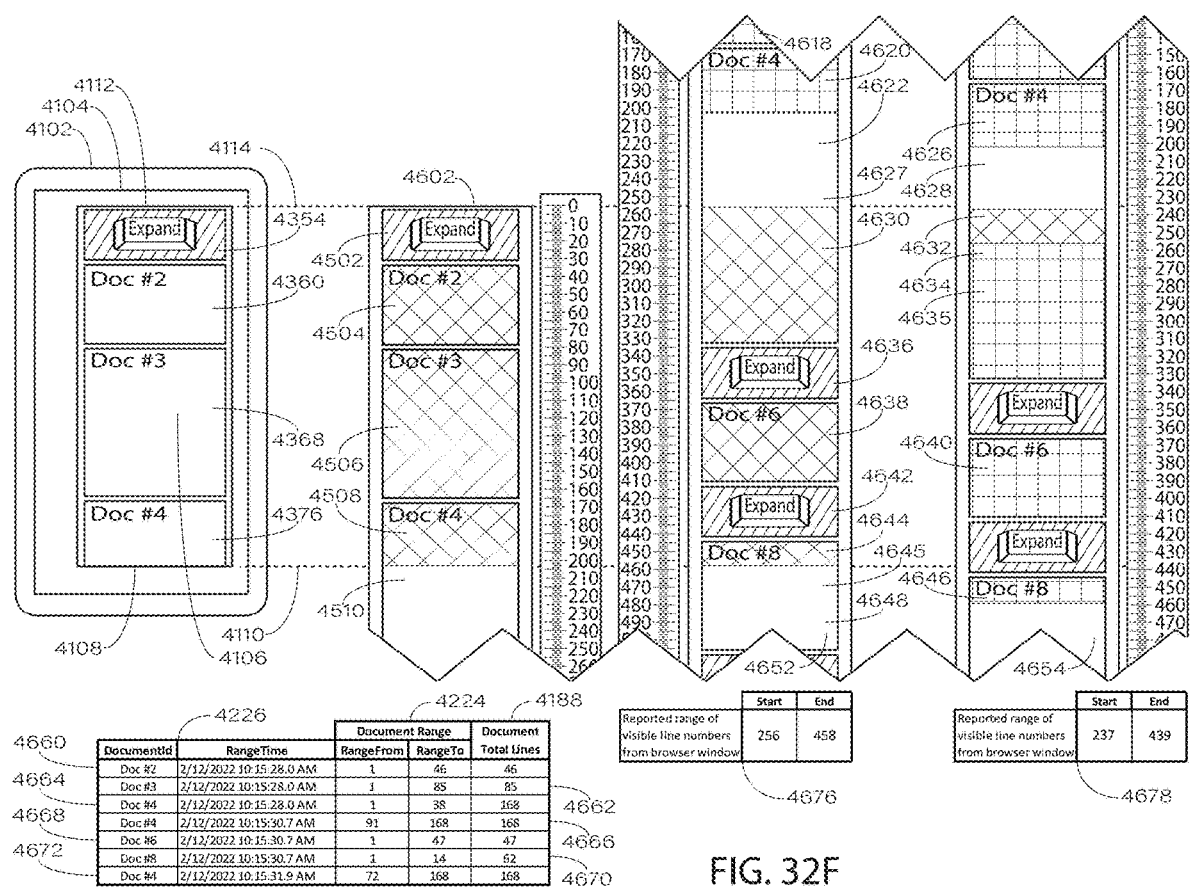
FIG. 32F is an example of creating a viewing history log for a screen quickly scrolled.

Referring to FIG. 32D, shown is input 4352 and its associated transformation table 4162 of FIG. 32D that will be used in FIGS. 32E-32F. Zero point 4350 on scale 4348 aligns with the top edge of compound document 4352. In general, when the browser window returns its values relative to the top of the input (or individual document if only one document is loaded in the browser window), the scale's zero point should (but need not in other embodiments) align with the top of the document.

The first individual document 4354 is hidden, so in the final viewing verification data set, may be ignored. If it will be ignored, the information may also be suppressed from the transformation table 4162.

The second individual document 4360 has a document identifier 4358 of "Doc #2". The start of individual document 4356 falls at 33 on scale 4348. The end of individual document 4362 falls at 78 on scale 4348. This information is recorded on line 4414 of transformation table 4162 of FIG. 32D.

The third individual document 4368 has a document identifier 4366 of "Doc #3". The start of individual document 4364 falls at 80 on scale 4348. The end of individual document 4370 falls at 164 on scale 4348. This information is recorded on line 4416 of transformation table 4162 of FIG. 32D.

The fourth individual document 4376 has a document identifier 4374 of "Doc #4". The start of individual document 4372 falls at 166 on scale 4348. The end of individual document 4378 falls at 333 on scale 4348. This information is recorded on line 4418 of transformation table 4162 of FIG. 32D.

The fifth individual document 4380 is hidden, so may be suppressed from transformation table 4162.

The sixth individual document 4386 has a document identifier 4388 of "Doc #6". The start of individual document 4382 falls at 366 on scale 4348. The end of individual document 4384 falls at 412 on scale 4348. This information is recorded on line 4420 of transformation table 4162 of FIG. 32D.

The seventh individual document 4390 is hidden, so may be suppressed from transformation table 4162.

The eighth individual document 4396 has a document identifier 4392 of "Doc #8". The start of individual document 4394 falls at 445 on scale 4348. The end of the document 4398 falls at 506 on scale 4348. This information is recorded on line 4422 of transformation table 4162 of FIG. 32D.

The ninth individual document 4400 is hidden, so may be suppressed from transformation table 4162.

Also shown is a representation of browser window 4410 of the exact size (but not necessarily position) of the browser window that will be used in FIGS. 32E-32F. The browser window height 4406 is 203. However, at the point in time that input 4352 is built, there is no indication of exactly what portion of the input will be visible and that may change as the display user interacts with the browser window. Therefore, line 4412 is not yet filled in.

Turning to FIG. 32E, shown is a display monitor 4102 with a browser window displaying input 4352 and the effects of slowly scrolling that browser window. Scrolling is demonstrated by three snapshots of input 4352 of FIG. 32D at three different times (inputs 4512, 4532, and 4556). The times are separated by 400 milliseconds. The variable positions of line 4412 of transformation table 4162 in FIG. 32D for each of the three different time appear in transformation table 4514, transformation table 4534 and transformation table 4558, respectively.

Initially, there are areas of four individual documents (4354, 4360, 4368 and 4376) that appear in the browser window. Input 4352 is without the limits of the browser window in input 4512, augmented with additional individual document area 4510 not yet displayed in the browser window, a scale 4500 tied to input 4512, and a transformation table 4514 of the line numbers that appear in the browser window area bounded by top edge extension 4114 and bottom edge extension 4110. Since input 4512 is taller than the useful area of the sheet it is drawn on, it is cut off by dividers 4518 and 4552 to allow for other objects to be displayed on the sheet. The input can be viewed in FIG. 32D.

Note that input 4352, as shown in FIG. 32D, is depicted as how it would appear before being shown on the screen. To show the progression on the screen, an area without any background boxes (as compared to individual document 4360) will mean it has not yet been displayed on the screen. An area filled with diagonal boxes (i.e., hashing, as in individual document 4504) indicates that it is newly shown on the screen at the end of the current step. An area filled with vertically oriented boxes (i.e., hashing, as in individual document 4522) indicates that this information has been displayed in a previous step. So, even though individual documents 4360, 4504 and 4522 all refer to the same individual document, that individual document is shown at three different times (even though the times may vary by a fraction of a second).

Note that transformation table 4514 indicates that the browser window reported input lines 1 through 203 were visible on the screen. Returning to transformation table 4162 in FIG. 32D and looking for any line where the Start and End range overlaps the values 1-203, several documents are found. Line 4414 has Start and End values falling completely in the specified range. So, line 4560 is added to viewing history log 4226 of FIG. 32E from the values in line 4414 indicating that the full individual document 4504 was displayed using the methods and formulas of FIG. 32A. Similarly, line 4416 (i.e., individual document 4506) has Start and End values falling completely in the specified range. So, data from line 4416 is used to calculate line 4562. Finally, only a portion of line 4418 falls in the specified range (indicating only a portion of Individual document 4376 is displayed). This generates line 4564 from line 4418. Individual document 4502 is hidden behind a link, so it is not included in transformation table 4162 and no further processing is required for that individual document.

400 Milliseconds later (according to the RangeTime of viewing history log 4226 of FIG. 32E), the display user had scrolled the input upwards 83 units as indicated by comparing transformation table 4514 with transformation table 4534. The browser window has now changed to show another view of the same input (ref. no. 4532). Now, two individual documents (4520 and 4522) have scrolled up and off the screen. An additional section of individual document 4527 (individual document area 4528) has scrolled onto the browser window from the bottom. Individual document area 4530 of individual document 4527 remains below the browser window. In input 4532, the diagonal hashing of individual document 4504 has been changed to vertical hashing in individual document area 4522 to indicate this individual document area has been seen in a prior step. Similarly, the diagonal hashing of individual document 4506 has been changed to vertical hashing of individual document 4524. Also, the diagonal hashing of individual document area 4508 has been changed to vertical hashing of individual document area 4526. New diagonal hashing appears for individual document area 4528 of individual document 4527 (i.e., individual document 4376) indicating that this portion of the individual document is newly displayed in the browser window.

When calculating what to include in viewing history log 4226 of FIG. 32E, individual document 4524 has already been fully displayed since the DocumentTotalLines 4188 column of line 4562 equals the value calculated from the Document Range columns 4224 of line 4562. So, there is no need to include data from line 4416. Individual document 4527, however, has not been completely displayed (only 38 lines of the 168 total lines appear on line 4564), so the portion of individual document 4376 that is currently displayed is lines 1 through 121 and that is captured in line 4566. Note that an alternative would be to update line 4564 to reflect the new RangeTo number 121 instead of adding new line 4566. Another alternative would have been to only insert the previously unseen line numbers on line 4566, making the "RangeFrom" number for that line to read 39.

Or, the same process, just based on the numbers. Transformation table 4534 indicates the range of virtual line numbers that are visible on the screen are 84 through 286. Looking for all the ranges that overlap these values in transformation table 4162 of FIG. 32D, it becomes apparent that only lines 4416 and 4418 overlap this range. Since line 4562 contained the complete set of lines for individual document 4368, line 4416 can be ignored as redundant. Therefore, the data from line 4418 is used to generate the data in line 4566 according to the methods and formulas of FIG. 32A.

After another 400 Millisecond period of time, the display user scrolled the document upward another "58" units (based on comparing transformation table 4558 with transformation table 4534). Individual document 4368 now has individual document area 4540 that has scrolled above the browser window and individual document area 4542 that still appears in the browser window. Individual document areas 4526 and 4544 are unchanged. The diagonal hashing of individual document area 4528 has now turned to vertical hashing to indicate that view in the browser window was from a previous step (individual document area 4546). The rest of individual document 4547 is now on the screen with diagonal hashing in individual document area 4548. Line 4568 is added to viewing history log 4226 to reflect the portion currently visible on the screen. A portion of individual document 4550 (i.e., individual document 4380) now appears in the browser window, but since it does not appear in transformation table 4162 of FIG. 32D, no line is added to viewing history log 4226 of FIG. 32E for individual document 4550.

Turning to FIG. 32F, shown is a typical sequence where rapid scrolling has occurred such that the display user would not have been able to read a section of individual document 4376 as it was scrolled. In this particular case, the browser window was checked every 300 milliseconds. More discussion on timing is below in FIGS. 32K-32M. FIG. 32F starts at the same place as FIG. 32E, the region of input 4512 of FIG. 32E displayed between top edge 4112 and bottom edge 4108 is identical to the same region of input 4602 of FIG. 32F. With the exception of the times, lines 4560-4564 are identical to lines 4660-4664.

Between the time input 4602 was snapshotted and input 4652 was snapshotted, rapid scrolling occurred which settled on the position shown for input 4652 (i.e., reflected in transformation table 4676). The horizontal hashing of individual document area 4508 is now changed to vertical hashing in individual document area 4620. Two individual documents (4636 and 4642) now shown in the browser window are hidden behind links. The complete individual document 4638 is now displayed on the screen for the first time as shown by the diagonal hashing of individual document 4638 and insertion of line 4668 of viewing history log 4226. Individual document area 4630 of individual document 4627 is displayed in the browser window, still leaving individual document area 4622 of individual document 4627 still un-displayed resulting in line 4666 of viewing history log 4226. Individual document area 4644 of individual document 4645 is displayed in the browser window, leaving individual document area 4648 yet un-displayed resulting in line 4670 of viewing history log 4226. Individual document area 4648 of individual document 4645 does not appear in the browser window since it is below the bottom edge of the window.

Input 4652 was then scrolled to the position shown as input 4654 (i.e., reflected in transformation table 4678). Individual document area 4632 of individual document 4635 is newly displayed in the browser window resulting in line 4672 of the viewing history log 4226. The diagonal hashing of individual document 4638 is changed to vertical hashing in individual document 4640. The diagonal hashing of individual document area 4644 is changed to vertical hashing in individual document area 4646.

Having filled in the viewing history log 4226, the reader may notice that there are three lines for DocumentId "Doc #4", but only two contiguous spaces for the corresponding individual document 4635 filled in (i.e., individual document area 4626, and the pair of individual document areas 4632 and 4634). These three lines have been extracted to table 4686 of FIG. 32G. Line 4664 became line 4680. Line 4666 became line 4682. Line 4672 became line 4684.

Turning to FIG. 32G, a discussion begins about how to handle overlapping ranges. Table 4686 was extracted from viewing history log 4226 of FIG. 32F.

Since the range of line 4682 is completely contained within the range of line 4684, line 4682 may be eliminated as redundant. Table 4688 shows how the same data appears once that line is eliminated. Line 4690 is identical to line 4680 and line 4692 is identical to line 4684.

It is contemplated that there may be a large quantity of overlapping ranges as a result of this method. Thus, there may be a need to create a summary (i.e., a result combining these overlapping, redundant or extended ranges) of viewing history log records at some point prior to when the data collected in the viewing verification data set is useful for finding areas of documents which have not been viewed. There are various alternative methods, but each of them may effectively include combining overlapping, extended or redundant ranges. If a viewing history log is used to accumulate data that is eventually uploaded to the viewing verification data set, the same issues may arise when filling in the viewing verification data set. In other words, there may be a need to summarize two or more different times that different portions of the same document were viewed. If the exact times of each viewing is important, that may be handled by having two separate tables in the viewing verification data set, each representing document view ranges: one with timestamps and another without timestamps.

One alternative method is to update data within the viewing history log if a new range is being added that overlaps rather than add a new line. In this first alternative, trying to add new lines that are already completely contained within the existing data may result in no change to the DocumentRange data. There may be other complications to this alternative that may require deleting a line of data, such as having views from both ends of a single individual document already recorded in the log, then a line is being added for the previously undisplayed portion of the document being displayed on the screen.

Another alternative is to not use the viewing history log at all, just directly update the viewing verification data set as the display user browses the individual document. This has the same complications as the previous alternative, except it happens one fewer times (since there is no loading of the viewing history log into the viewing verification data set).

Still another way to handle summarizing the access history data set is to wait to summarize access history data set data until the summary is needed. For example, if a display user wants to view all the portions of documents for a client that have not been previously viewed, calculate a data set (i.e., an extract table, a query, etc.) at that time of the ranges that have been viewed and use that to calculate which documents or document areas to display to the display user.

SQL statement 4730 combines and summarizes ranges. This statement would, for example, automatically convert table 4686 into table 4688 or table 4770 into table 4786 of FIG. 32H. This SQL statement works by recursively combining overlapping, redundant, or extended ranges to make longer ranges until there are no more overlapping or extended ranges to merge together. In this case, extended ranges are those that occur immediately after the current range (e.g., if one starts with the range one through five and has another range starting at six, that second range can extend the first one because it starts at one more than the ending value of the first range).

Figure 32H:
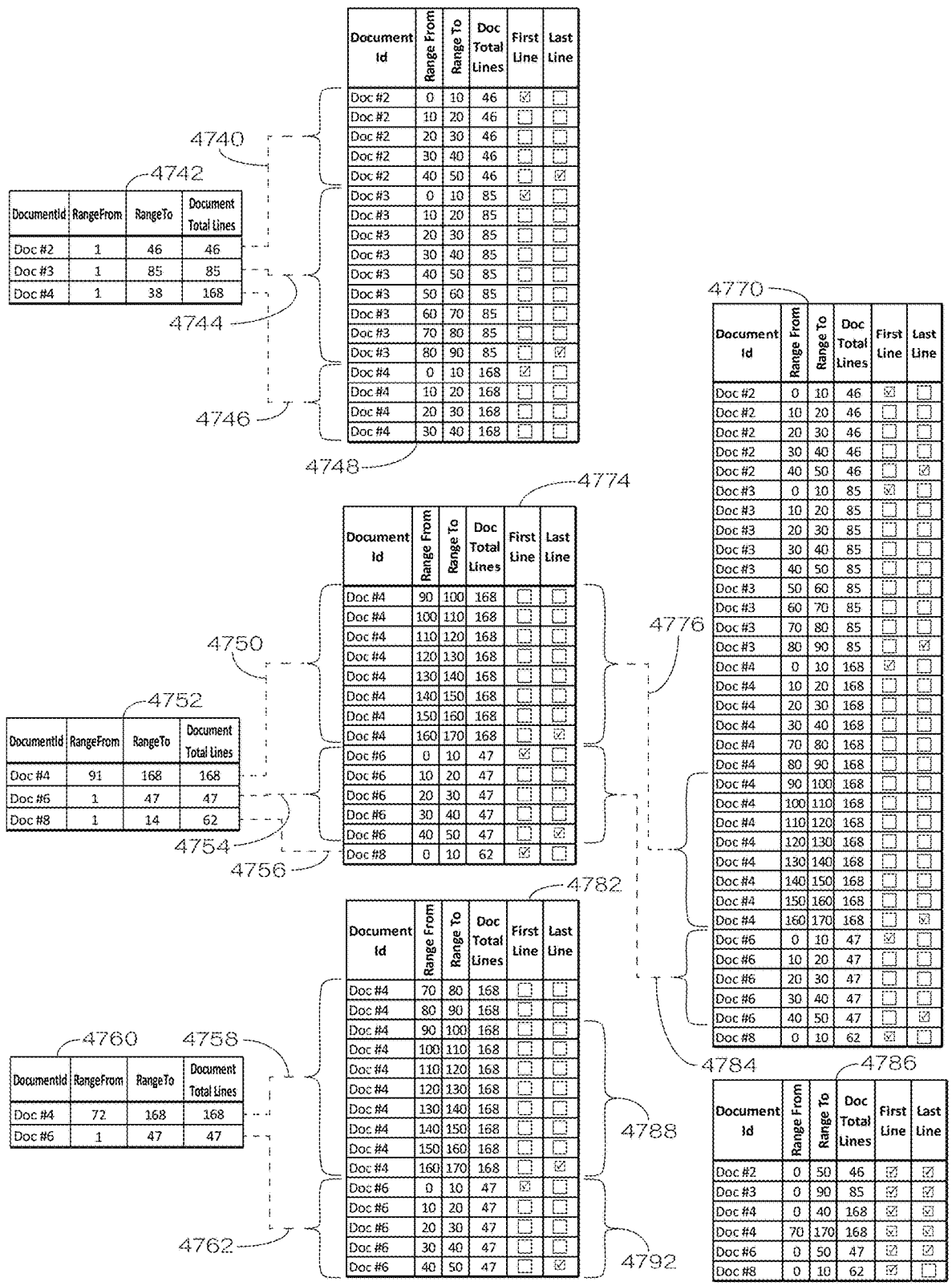
FIG. 32H is an example of the use of a browser-viewing log.

Turning to FIG. 32H, a discussion begins on browser-viewing logs.

A browser-viewing log is a log that may be used on a temporary basis to capture a single user-view indication from the browser window. The user-view indication can then be converted into a plurality of converted user-view indications and then added into an access history data set of longer duration (i.e., either the viewing history log or the viewing verification data set). This adding to the access history data set may occur before the next user-view indication from the browser window is processed and the browser-viewing log is emptied or disappears (to be recreated with the next user-view indication from the browser window). Like the other access history data sets, lines may be summarized and the document area represented by each user-view indication in the browser-viewing log will eventually wind up being reflected in the viewing verification data set.

An embodiment of a browser-viewing log may be created by the following rules:

(1) Convert the range received from the browser window to one or more individual document ranges.

(2) For each converted individual document range, calculate both the starting and ending values from the minimum and maximum lines, respectively, represented by the range received by rounding to the nearest 10. The result from the starting value is rounded down to the nearest 10 (e.g., values 16-25 would be rounded to 20, 26-35 would be rounded to 30, etc.), the result from the ending value is rounded up to the nearest 10 (e.g., values 15-24 would be rounded to 20, 25-34 would be rounded to 30, etc.). Subtract 10 from the ending value. Place the result in the variables StartingWith[ ] and EndingWith[ ].

(3) For each converted individual document range, compute the total lines in each document.

(4) For each converted individual document range, create a FOR loop beginning at StartWith[ ] (calculated in step 2) and ending at EndingWith[ ] (calculated in step 2) that increments by 10 each loop using a LoopVariable that inserts a new line into the browser-viewing log containing: (a) The DocumentId found in step 1; (b) A RangeFrom value equal to the LoopVariable; (c) A RangeTo value equal to 10 plus the LoopVariable; (d) The total lines found in step 3; (e) A bit indicating whether the individual document range (calculated in step 1) indicates the first line of the document was covered by the current range represented by the loop (i.e., this is the first time through the loop for the current document and the first line of the document is being shown on the screen); (f) A bit indicating whether the individual document range (calculated in step 1) indicates the last line of the document (calculated in step 3) was covered by the current range represented by the loop (i.e., this is the last time through the loop for the current document and the last line of the document is being shown on the screen).

(5) Copy each unique individual document range from the browser-viewing log to the access history data set (e.g., a unique constraint on the DocumentId and RangeFrom columns in the access history data set). Note, if the new line has either the FirstLine or LastLine box in the browser-viewing log checked (e.g., a bit column with a non-zero value), the corresponding box in the access history data set needs to be checked, even if the constraint is violated (e.g., a second SQL statement that only sets the FirstLine or LastLine bits).

(6) To use the resulting access history data set, assume all values that can be rounded to any range missing from the access history data set represent ranges not displayed on the screen. Also assume the beginning of the document has not been viewed if the FirstLine box is not checked for the line that includes the first line.

Similarly, assume that the end of the document has not been displayed if the LastLine box is not checked for the line that includes the last line of the document.

Individual document areas 4742 contains values representing the individual document areas calculated from input 4602 of FIG. 32F. Individual document areas 4752 contains values representing the individual document areas calculated from input 4652 of FIG. 32F. Individual document areas 4760 contains values representing the individual document areas calculated from input 4654 of FIG. 32F.

Each of the individual document areas are used to compute a browser-viewing log according to the rules previously outlined for FIG. 32H. Expansion line 4740 creates 5 lines in browser-viewing log 4748 from the single range found in individual document areas 4742. Similarly, expansion lines 4744 and 4746 generate 9 and 4 lines, respectively, in browser-viewing log 4748 from individual document area 4742. Similarly, expansion lines 4750, 4754, and 4756 generate 8, 5 and 1 lines, respectively, in browser-viewing log 4774 from individual document areas 4752. Similarly, expansion lines 4758 and 4762 generate 10 and 5 lines, respectively, in browser-viewing log 4782 from individual document areas 4760.

Every unique line from each of the browser-viewing logs are added to access history data set 4770. As those skilled in the art will appreciate, this allows all of browser-viewing logs 4748 and 4774 to be added to access history data set 4770. Only the first two lines of browser-viewing log 4782 can be added because user-view indications 4788 are identical to the set of user view indications 4776 that have already been added to the access history data set. Similarly, user-view indications 4792 are identical to the set of user view indications 4784 that have already been added to the access history data set.

Finally, access history data set 4770 may be summarized down to transformation table 4786 by combining all the overlapping ranges for each document (i.e., where the RangeTo number is equal to the RangeFrom number for documents having the same DocumentId).

Transformation table 4786 indicates the range 41-69 are missing from DocumentId "Doc #4" and any attempt to show the missing lines from the document should therefore contain line 36-74 since those values would all get rounded to the missing line number range (e.g., to produce that range, at least lines 35 and 75 had to be present in the viewed lines data: if 35 were not present, then the lower reported range missing would have started at 30 or lower and if 75 was not present then the upper reported range would have started at 80 or higher).

Note, it is contemplated that the RangeFrom and RangeTo values can be rounded to a number other than ten. Ten was merely chosen as an example here to demonstrate the method. To change to another number, replace the characters "10" in the rules with a different number. It is contemplated that there may be also a wide variety of other ways to record the ranges. For example, in some embodiments the method may entail combining overlapping ranges automatically (such as by creating a map of predetermined individual document areas by rounding individual document range numbers by a constant and enforcing a unique value constraint). In other embodiments, the method may entail combining overlapping ranges via a dedicated step (e.g., SQL statement 4730 or equivalent). Additional details of scrolling-timing considerations are discussed more in FIGS. 32K-32M.

Figure 32I:
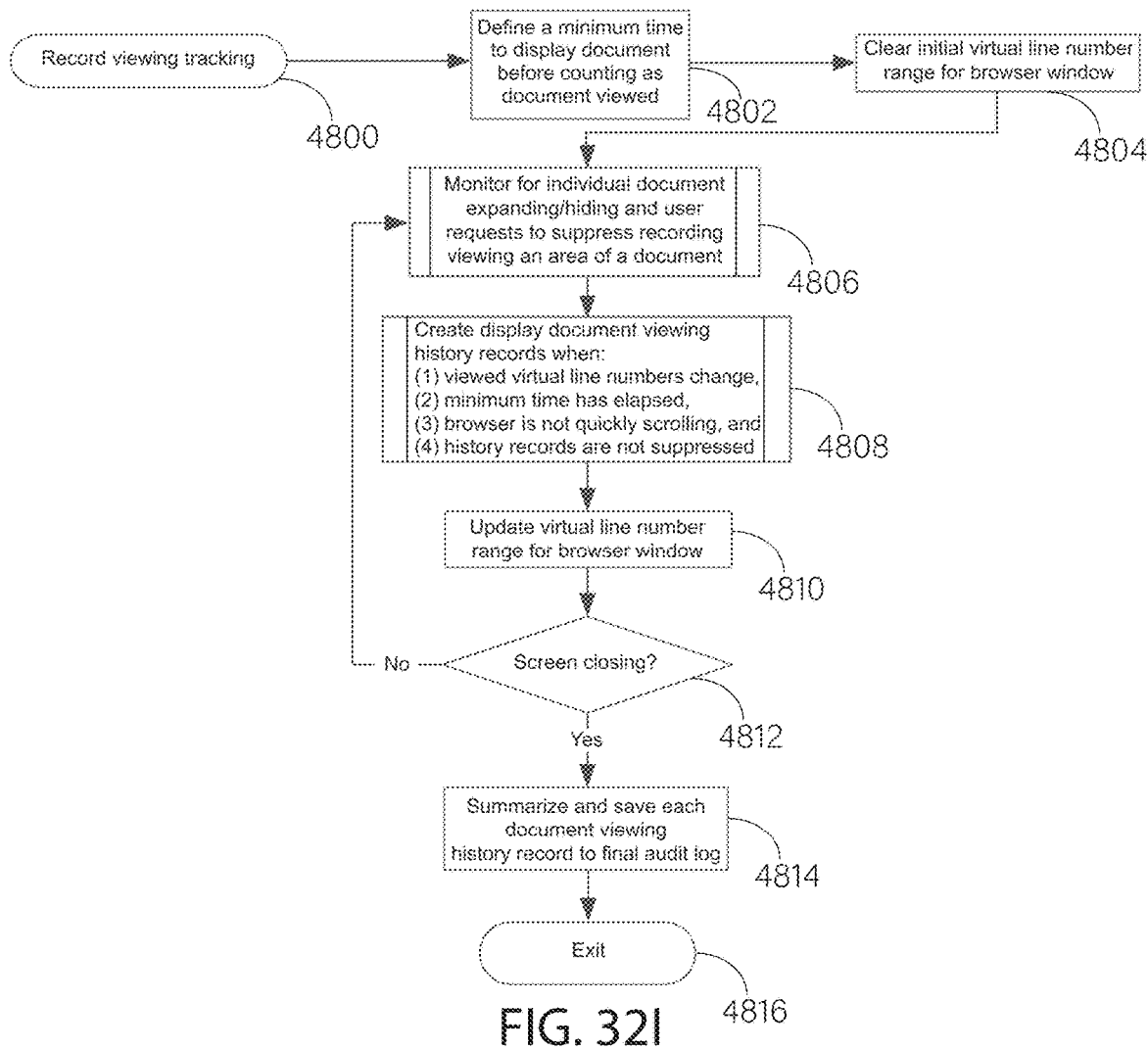
FIG. 32I is a high-level flowchart of calculating an access history data set.

Turning to FIG. 32I, shown is a high-level flowchart of how to track which document areas have been viewed, possibly for the purpose of allowing the display user to later ensure they have been shown all portions of every document of a specific type when the document being viewed is too large for the screen. It may be a trivial case to track viewing portions of a document when individual screens are used for each document area (i.e., just execute whatever subroutine that step 4808 executes, passing it the document area currently visible or individual elements of the screen if the areas come from different parts of the document). The initial step 4800 starts, then a few numbers are initialized, flow proceeds to a loop, and the process ends with summarizing and storing results. Even though the loop is drawn as a polling loop for clarity, it may just as well be an interrupt driven loop or any other suitable structure and remain within the scope of this disclosure. Furthermore, the summary and storing step 4814 could be done within the loop and remain within the scope of this disclosure.

Figure 32J:
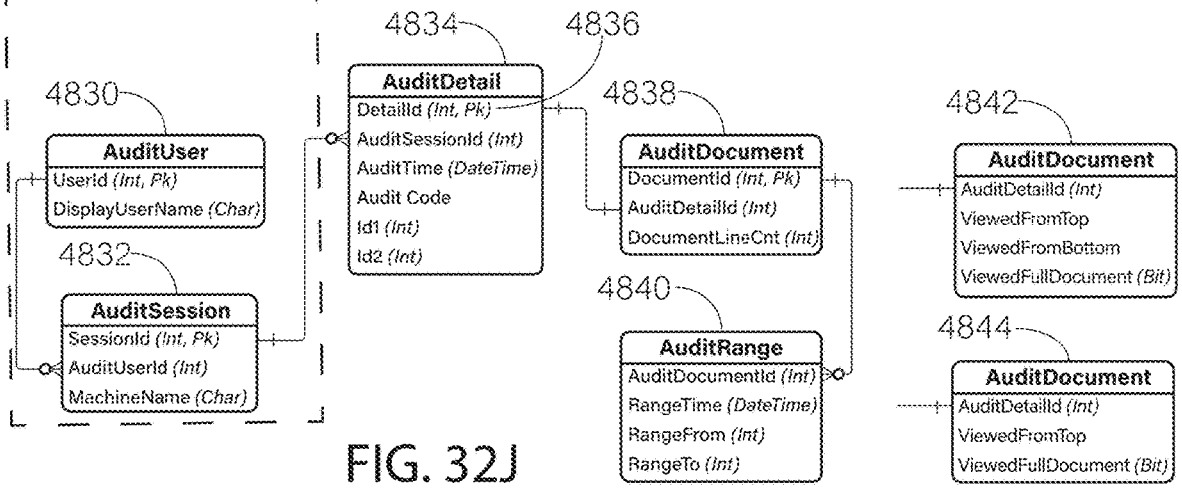
FIG. 32J is an ER diagram of an audit trail that tracks document areas viewed.
Figure 32K:
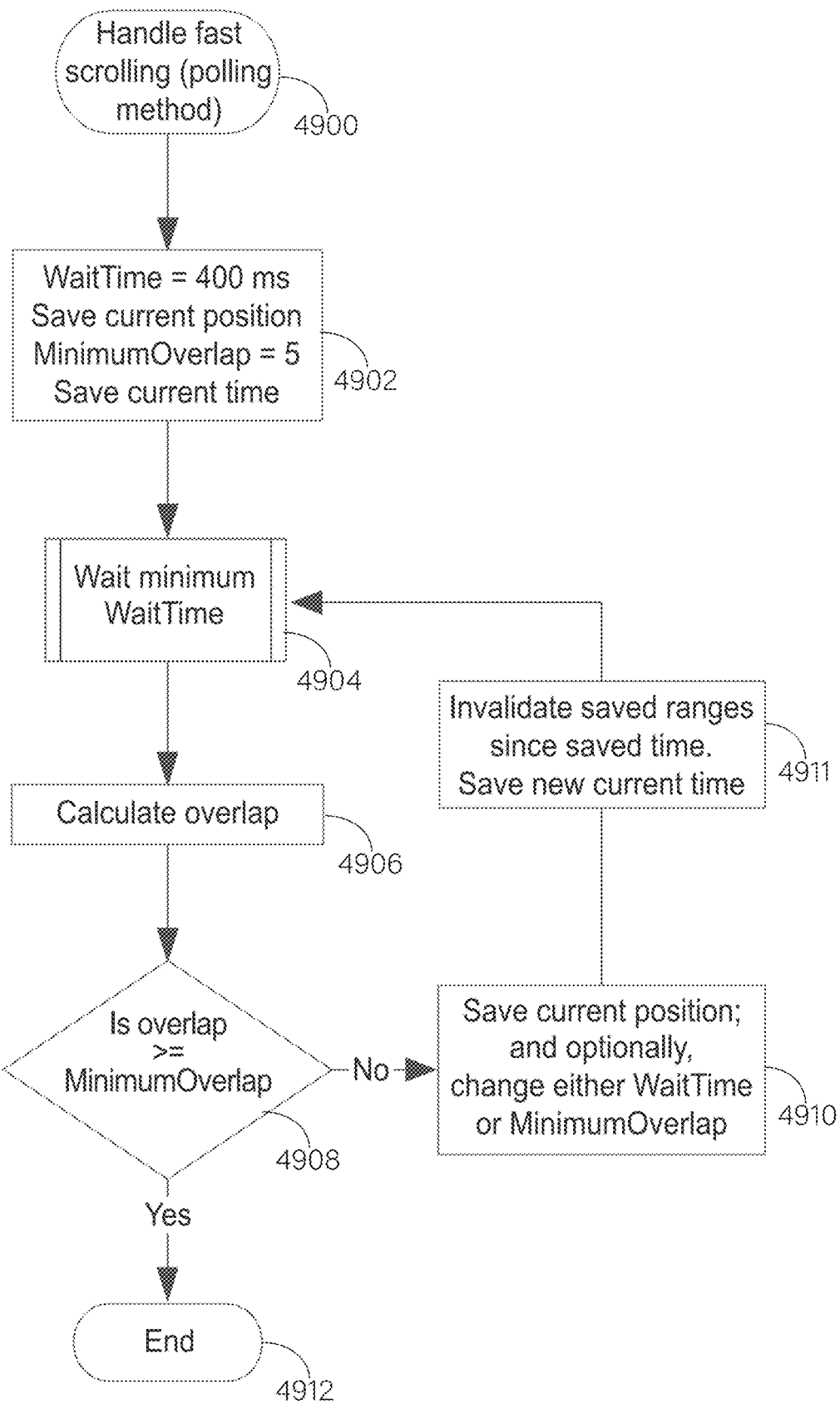
FIG. 32K is a flowchart that demonstrates how to detect, and skip range readings taken from a browser window when the browser window is scrolling quickly by a polling method.

Step 4802 defines some parameters that may be used in step 4902 of FIG. 32K and the explanation of those parameters will occur there.

Step 4804 empties the storage area that may be used to track the last position of the browser window. This storage area may be used in step 4808 to determine if the virtual line numbers are different than before.

Step 4806 monitors for any changes in which individual documents are currently expanded in the input. Typically, the expansion of individual documents is performed by a display user activating onscreen elements, but there is also an initial state each individual document is in when the browser window first displays the document (so recalculating is executed the first time through). When monitoring for individual documents expanding or hiding, recalculation may be required of where each individual document begins and ends. The recalculating itself was demonstrated in calculating transformation table 4162 of FIG. 32D.

Sometimes, it may be helpful for a display user to inactivate recording the fact that some document area was viewed. For example, if a display user knew he only briefly viewed a document and wants to remind himself to later go back and reread that section of the document more carefully. This may include viewed input section(s) (that are already recorded in the viewing history log), the current view shown on the screen, or future view(s) until the display user turns off the recording suppression option. This represents a difference between the invention of the present disclosure and traditional audit logs. Traditional audit logs record each tracked action with no way for a display user to unrecord, block out what has already been recorded, or suppress future recording. As it relates to the invention of the present disclosure, it is contemplated that this feature may be useful. Implementing this feature may entail, for example, popping up a list of input sections which have been viewed in the current session and allow the user to select which ones to have the access history data set keep or invalidate. As a result of invalidating an input section, each user-view indication for that input section in the access history data set may also be invalidated (even if they were not created during the current session). An alternative would be to pop up a list of input sections which have been viewed during the current session and allow the display user to invalidate one or more input sections. If this is handled for the current view only, it may consist of a button or link that allows the user to invalidate tracking the current view. If this is handled for future audit records, it could be handled by a user control that allows suppressing audit tracking (effectively invalidating input sections until the option is turned off, then start tracking with the current or next screen when the suppression is turned off). The process of invalidating an input section may consist of either deleting audit information or augmenting the audit information with an indication that the display user wants to ignore this line of audit information (e.g., a bit column in viewing history log 4226 and/or AuditRange table 4840 of FIG. 32J) for the purposes of this disclosure. Alternatively, the display user might be provided with a button or other link that invalidates all user-view indications for the current display user in the access history data set to allow a user to thereby make a note to review information currently shown on the screen.

In some embodiments, when invalidating a viewing history log record, there may also be a need to invalidate a corresponding document range in the viewing verification data set. For example, if a range has been summarized from several areas of an individual document, the area reflected in the range of the data set may be larger than the viewing area within the browser window. For a user to remind himself to reread some document area that has already been marked by a range in the data set, a single existing row may have to be split into two or three rows (e.g., a single large range becomes (1) the range before the selected range, (2) the selected range, and (3) the range after the selected range) to be able to invalidate just the range shown on the display user's screen.

Step 4808 creates user-view indications of document areas when the browser window is not scrolling too fast for the display user to understand the answer fields displayed on the screen. The whole viewing verification data set could be created in this step, but it may be more efficient to calculate records in a viewing history log and later summarize the viewing history log records (as in SQL 4730 of FIG. 32G) into this portion of the access history data set. For example, if the viewing verification data set records were captured at the time of input 4654 of FIG. 32F, two records would have already been added to the access history data set to reflect the two areas (individual document area 4626 and individual document areas 4632-4634) that had been displayed in the browser window. If the display user scrolls down so that individual area 4628 is visible within the browser window, then the whole individual document 4376 would have been displayed and only one record would be required in the viewing verification data set. Traditional audit logs may have a primary key in the table where user actions are stored as an integrity measure to be able to verify that rows of the audit log have not been deleted. If this summarizing is performed on the viewing history log rather than the viewing verification data set, there may be one fewer deletion(s) in the viewing verification data set and possibly a decreased need to lock tables.

The first condition of step 4808 is that the virtual line number range reported by the browser window changes. While it would be possible to design a system that captures the browser window at constant intervals (such as every second, or 3,600 captures per hour), that information may be more useful (e.g., delaying calculating if the display user was not able to view an onscreen object because of rapid scrolling) once it changes after the initial capture of the document area displayed in the browser window. The program may still eventually have to calculate that rapid onscreen scrolling wasn't occurring to be useful in calculating portions of documents not displayed on the screen, which is the point of step 4808. Note, however, that this raw information may be useful in proving that some portion of a document was never displayed on the screen. So, the purpose of the document range in the viewing verification data set may play a role in how this method is implemented.

The second condition of step 4808 is that some minimum time period has elapsed. This is an option that prevents both different computer hardware from creating different results based on the speed of the hardware and creating large quantities of records that only reflect very minor changes in what is viewed in the browser window.

The third condition of step 4808 is usually the key condition. This prohibits collecting of information if the browser window is scrolling so fast that a display user would not be able to comprehend a portion of what is shown in the browser window. As will be described in FIGS. 32K-32M, there may be two components to this, an amount of time and distance scrolled in the browser window. If the information being collected in this portion of the viewing verification data set is being collected for the purpose of allowing a display user to later determine what individual document areas for a client have not been viewed, this condition is essential. If the information being collected in this portion of the viewing verification data set is being collected to prove some display user did not even scroll an individual document area, even this condition might be optional.

A fourth condition of step 4808 is that the display user has not suppressed creating document viewing history log records (as in step 4806).

Step 4810 updates the virtual line number range initialized in step 4804 and accessed in the first condition of step 4808.

Step 4812 keeps the loop going for steps 4806 through 4810 so that these steps may be executed whenever a change has occurred.

Step 4814 combines overlapping document area ranges, possibly appending session or display user identification, some indication of timestamp and/or an indication that the full document was viewed. One method of combining overlapping ranges is shown in SQL statement 4730 of FIG. 32G. Timestamps could be a first time of viewing the document area, a last time of viewing the document area or a time related to the document or session.

The process ends in step 4816.

FIG. 32J shows an example of how to integrate the current disclosure into an existing audit log. AuditUser table 4830, AuditSession table 4832 and most of AuditDetail table 4834 represent an existing audit log. The one part of AuditDetail table 4834 that may not be a portion of an existing audit log is the primary key. Normally, the primary key 4836 would not be required in an audit log laid out like this. AuditDocument table 4838 and AuditRange table 4840 are new.

AuditUser table 4830 is a table that holds the identification of the various display users that access the system. AuditSession table 4832 holds information about the current time a display user logged in, perhaps with the name of the machine they logged in on, the time they logged in and when that session was terminated. AuditDetail table 4834 holds audit information for various objects that the display user accessed during the time his session was active. The types of columns that such an arrangement might include are a timestamp for when the audit row was entered, a code indicating what type of access the display user did and a few numeric identifiers about the access. For example, if the display user accessed a data form, one numeric identifier might contain a foreign key to the data form type and another numeric identifier might contain a foreign key to the appointment the data form is attached to.

In AuditDocument table 4838, the AuditDetailId serves as a foreign key to the previous existing AuditDetail table. If the AuditDetail table does not have a primary key, another option might be to link the two tables using both AuditSessionId and AuditTime columns as that pair might be unique in this case. The DocumentId column serves to link the AuditRange and AuditDocument tables together. Examples of additional columns that might be appropriate to place in the AuditDocument table would be a column to indicate how many lines are in the individual document (i.e., DocumentLineCnt line), whether the full document had been displayed (not shown) and a foreign key to the actual document (not shown).

AuditRange table 4840 records the individual views ranges and, perhaps, when those occurred. The AuditDocumentId sets up a one-to-many relationship between the AuditDocument and AuditRange tables. The AuditRange table includes an indication of range line numbers in the fields RangeFrom and RangeTo. This table optionally contains a timestamp for when the range was snapshot. An additional column that might appear in this table is a bit indicating the user wanted to invalidate the current line.

AuditDocument table 4842 is an alternative to AuditDocument table 4838 and AuditRange table 4840 that might be appropriate if the browser window has a more limited capability, such as having no capability to browse document starting in the middle of a document, but allows starting the browsing from either end of the document (the top of the individual document and the bottom of the individual document).

AuditDocument table 4844 is another alternative to AuditDocument table 4838 and AuditRange table 4840 that might be appropriate if the browser window has even more limited capability, such as only having the capability to browse individual documents starting at the top of the document.

Of course, it would be possible to have these ranges in the viewing verification data set tables (i.e., any of Audit Range table 4840, AuditDocument table 4842, or AuditDocument table 4844) reflect virtual line numbers of an input rather than ranges of individual documents and still be within the scope of this disclosure, but doing so may require a lot more storage, especially if individual documents can be expanded and hidden. Finally, any virtual line number data from an input may eventually have to be converted (i.e., transformed) to ranges within individual documents, if more than one individual document exists within an input.

In FIG. 32K procedure 4900 shows one possible way to detect rapid scrolling of a browser window.

In step 4902, various variables may be initialized. 400 milliseconds is chosen as the WaitTime limit in this example. The WaitTime limit is a period of time that is the minimum amount of time that must elapse between one reading of the browser window virtual line numbers and the next reading (also referred to as, "minimum time"). If the purpose of the viewing verification data set is to prove a display user might have been able to read some document area on the screen, then the WaitTime should be almost unperceptively short in duration (in the millisecond range). It may also be helpful for the WaitTime to be long enough that different computer hardware speeds do not produce different results when executing the steps of FIG. 32K. If the purpose of the viewing verification data set is for a display user to later review sections of documents they haven't yet read, then the WaitTime may be significantly longer (perhaps several seconds). The MinimumOverlap is the quantity of virtual line numbers in the intersection of two virtual line number ranges. An ideal MinimumOverlap value may be different on different size screens, so this may be a program parameter set for each unique monitor and use the smaller of the values for a workstation with multiple sizes or orientations of monitors.

There are at least two types of scrolling. One type of scrolling is to move the input 4352 in browser window 4410 so fast that none of the information in the browser window can be read as the scrolling continues (e.g., input 4652 of FIG. 32F). The second type of scrolling is slow enough that some text of the document areas on the screen can be read (e.g., FIG. 32E). One method to determine which type of scrolling has occurred is to check if the amount of overlap that is present between one virtual line number range and a subsequent virtual line number range is greater than or equal to a pre-specified minimum overlap, when the subsequent virtual line number range has a minimum amount of time between each virtual line number range.

Step 4904 causes the computer process to sleep for the duration of WaitTime.

Step 4906 obtains the current virtual line number range from the browser window and calculates the current overlap between the newly obtained virtual line number range and the virtual line number range last saved in either steps 4902 or 4910.

Step 4908 compares the value calculated in step 4906 against the MinimumOverlap currently specified (from either steps 4902 or 4910). If the current overlap is less than the MinimumOverlap, control passes to step 4910.

In step 4910, the current virtual line number range obtain from the browser control is saved for use as the prior value the next time step 4906 is executed. There is also the possibility that once it is detected that rapid scrolling is occurring the program may want to adjust how easy it is to get out of the loop that indicates scrolling is continuing, so there is the option to change either the wait time or the minimum overlap. Increasing either the MinimumOverlap or the WaitTime may make it harder to exit the loop. Decreasing either of these values may make it easier to exit the loop.

Step 4911 optionally invalidates any saved ranges since the last time either step 4902 or 4911 was executed for this process. Invalidating may consist of deleting lines from the access history data set (i.e., either the viewing history log or viewing verification data set) since scrolling was occurring too fast for the display user to reasonably have read what appeared in the browser window.

From step 4911, flow continues to step 4904.

The process exits in step 4912, having found a time when the browser window is not scrolling so quickly that information is unreadable on the screen. It is contemplated that either in step 4912 the current position to be saved last stored in either step 4902 or step 4910 may be returned by this step to the process that called procedure 4900.

Figure 32L:
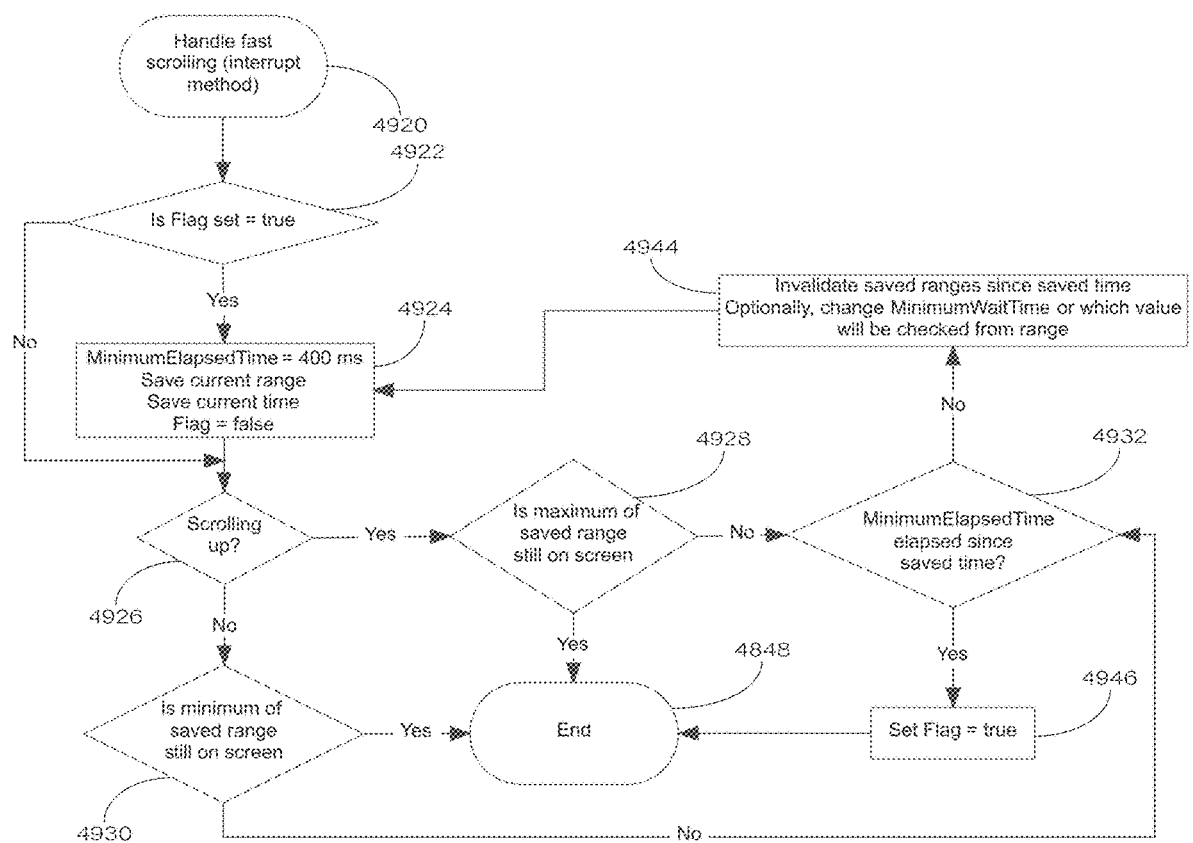
FIG. 32L is a flowchart the demonstrates how to detect, and invalidate range readings taken from a browser window when the browser window is scrolling quickly by an interrupt method.

FIG. 32L is an equivalent of FIG. 32K, except that FIG. 32L is configured for implementation as part of an interrupt driven procedure.

Process 4920 may be passed both the current system time and the current range from the browser window by the calling routine, as will be explained in step 4924. Prior to process 4920 being called the first time, a flag (referred to in steps 4922, 4924, and 4946, and possibly stored in memory accessible to both the current process and the calling routine) is set to True. There may be no need to set the flag manually after the first call.

Step 4922 checks if the flag is set true. If so, flow passes to step 4924, otherwise, step 4924 is skipped.

Step 4924 saves several working variables that the process will be using. A flag is set to indicate that step 4922 should skip executing step 4924 the next time that control reaches step 4922.

Step 4924 also saves the MinimumElapsedTime, which is the minimum amount of time that has to elapse before a predetermined line from the then current range received from the browser window scrolls off the screen. This MinimumElapsedTime is equivalent to the WaitTime of FIG. 32K.

Step 4924 also saves the current range received from the browser window. To prevent problems from rapid scrolling changing the value while the program is executing, the range may be passed to process 4920 each time process 4920 is called. It is contemplated that all that is used from this range during execution of process 4920 is two predetermined points from the range. One point is checked in step 4928 for scrolling up and another point is checked in step 4930 for scrolling down. These two points are equivalent to the MinimumOverlap of FIG. 32K. If the predetermined values are the minimum and maximum values from the range, this is equivalent to having a MinimumOverlap of 1. If the predetermined values are 1 greater than the minimum and 1 less than the maximum values from the range, this is equivalent to having a MinimumOverlap of 2. If the predetermined values are 2 greater than the minimum and 2 less than the maximum values from the range, this is equivalent to having a MinimumOverlap of 3, and so on.

Step 4924 also saves the current system time. To prevent synchronization problems with step 4944 accessing this time, the current system time may be passed to process 4920 each time process 4920 is called.

Step 4926 checks if the net effect of all scrolling since last executing step 4924 is that the input has been scrolled up. This step compares the current range reported by the browser window against the range stored the last time step 4924 was executed. If a scale like scale 4350 is used, as was shown in FIG. 32D and transformation tables 4514, 4534 and 4558 of FIG. 32E, for an input being scrolled up relative to the browser window, the range numbers increase. If the range numbers decrease, then the input is being scrolled down. If the input is being scrolled up, control passes to step 4928, otherwise control passes to step 4930.

In step 4928, a check is made if a value selected from the range saved the last time step 4924 was executed is contained in the current range received from the browser window. If a scale like 4350 is used, this is the maximum of the two predetermined values from the range stored in step 4924.

Similarly, step 4930 checks if a value selected from the range saved the last time step 4924 was executed is contained in the current range received from the browser window. If a scale like 4350 is used, this is the minimum value of the two predetermined values from the range stored in step 4924. Both steps 4928 and 4930 are equivalent to steps 4906 and 4908 of FIG. 32K since they calculate when the predetermined overlap is scrolled off the screen.

If either step 4928 or step 4930 determines that the respective value from the saved range is still on the screen, processing exits in step 4848, having found no reason not to store the current range yet (the saved ranges may later be invalidated in step 4944). Otherwise processing continues to step 4932 where a check is made if the MinimumElapsedTime has elapsed. If it has elapsed, range values that have been saved elsewhere in the system have not scrolled too fast to view portions of the text in the browser window and step 4946 prepares for the next range series to start by setting up to execute step 4924 the next time process 4920 is called.

If step 4932 determines sufficient time has not elapsed, then step 4944 invalidates each of the ranges saved by other portions of the system between the saved time and the current time as the scrolling has been too fast for a display user to have reasonably read the material. Invalidating here may consist of deleting lines from the viewing history log. Alternatively, invalidating may involve setting a bit to indicate that fast scrolling was occurring. This bit can later be used to separate the lines in the access history data set (i.e., the viewing history log or the viewing verification data set) into two categories: (1) lines which were scrolled slow enough to read the material in the browser window, and (2) lines which were scrolled, regardless of the speed of scrolling. In step 4944, as in step 4910, default parameters for MinimumElapsedTime and which values to use from the saved current range may be altered to either make it easier or harder to exit the loop now that rapid scrolling has been detected. Processing continues with step 4924.

Figure 32M:
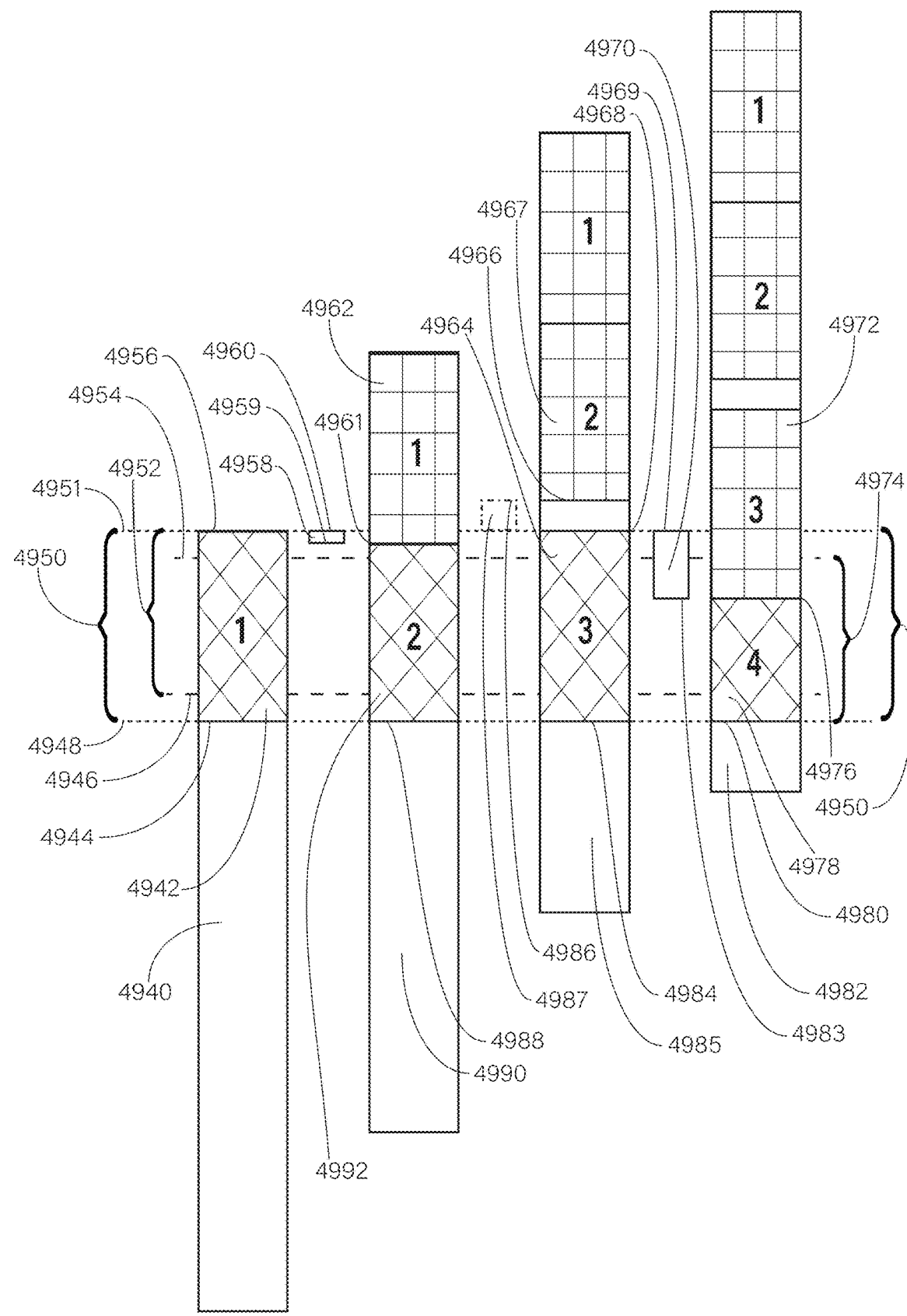
FIG. 32M is an example of a browser window quickly scrolling to demonstrate the use of the flowchart in FIGS. 32K-32L.

FIG. 32M is an illustration of what happens when a display user is scrolling the browser window fast. The illustration shows the same input at 4 different points in time (as indicated by inputs 4940, 4990, 4985, and 4982). The input is being scrolled up relative to the browser window. The input may be either a compound document or an individual document. Browser window 4950 initially shows viewable portion of document area 4942 and is hashed diagonally to indicate that this is the first time that document area is shown in the browser window. The top and bottom edge of browser window 4950 are extended by narrow dashed lines 4951 and 4948.

Allowable overlap scrolling up 4974 (and the minimum allowable overlap scrolling up 4954) shows the limits that bottom margin 4944 is allowed to fall within after the input is scrolled up for the next range received from the browser window after the WaitTime. Similarly, allowable overlap scrolling down 4952 (and the minimum allowable overlap scrolling down 4946) shows the limits that top visible margin 4956 is allowed to fall within after the input is scrolled down for the next range received from the browser window after the WaitTime. If the top or bottom margin falls within the corresponding allowable range, then the input is not being scrolled too fast for the user to possibly view it or read it in depth (depending on the purpose of the viewing verification data set). If the purpose of the viewing verification data set is to allow the user to ensure they have reviewed all documents for the client, then the WaitTime may be somewhat longer. If the purpose of the viewing verification data set is to prove a user never accessed a document area, then the WaitTime may be shorter (or even zero).

After the WaitTime has elapsed, input 4940 has now scrolled to the vertical position shown for (and is renumbered to) input 4990. Notice that the bottom visible margin 4944 has been renumbered to previous bottom margin 4961 which is above the minimum allowable overlap scrolling up 4954 height. Input 4990 now has bottom visible margin 4988. Also notice, the input has been scrolled up (since a lower document area is shown on the screen, and the virtual line numbers received from the browser window are getting larger, if a scale like scale 4348 of FIG. 32D is used). That is equivalent to taking the "No" option from step 4908 of FIG. 32K. Notice the hashing of document area 4962 has been changed to vertical from document area 4942 because the document area is no longer the first time seen on the browser screen. The hashing of document area 4992 is now diagonal, since it is the first time seen in the browser window.

When the input is scrolling up, overlap 4958 is the area shown in the browser window between narrow dashed line 4951 (i.e., screen boundary side of overlap 4960) and a line inline with previous bottom margin 4961 (i.e., inside boundary side of overlap 4959). If the input had been scrolled down, the overlap would run from narrow dashed line 4948 toward the minimum allowable overlap scrolling down 4946. Note the total height of overlap 4958 does not reach the minimum allowable overlap scrolling up 4954.

As the input is scrolled even farther up, input 4990 becomes input 4985, bottom visible margin 4988 becomes previous bottom margin 4966, and a new bottom visible margin 4984 appears. The diagonal hashing of document area 4992 becomes vertical in document area 4967. Document area 4964 is the new portion visible in the browser window, so it gets diagonal hashing. Since input 4985 is scrolling up, and previous bottom margin 4966 is above the minimum allowable overlap scrolling up 4954 height, the loop continues at step 4908 in FIG. 32K.

Attempting to draw overlap 4987 by creating a line segment inline with previous bottom margin 4966 (i.e., inside boundary side of overlap 4986), the reader will notice that overlap 4987 is heading away from minimum allowable overlap scrolling up 4954. In fact, the overlap between input 4990 and input 4985 for the browser window 4950 is a negative value.

Finally, scrolling slows down at the next WaitTime. Input 4985 becomes input 4982, bottom visible margin 4984 becomes previous bottom margin 4976 and a new bottom margin 4980 appears. The diagonal hashing of document area 4964 becomes vertical in document area 4972. Document area 4978 is now visible in the browser window, so it gets diagonal hashing. Now, the height of previous bottom margin 4976 falls within allowable overlap scrolling up 4974 range, at step 4908 of FIG. 32K, the "yes" option is taken the process has now skipped storing ranges during rapid scrolling.

Overlap 4970 starts at screen boundary side of overlap 4969 (i.e., narrow dashed line 4951) and extends to inside boundary side of overlap 4983 (i.e., a line inline with previous bottom margin 4976) and it extends over minimum allowable overlap scrolling up 4954. So, this scrolling was slow enough to possibly view the material in the browser window.

Figure 33:
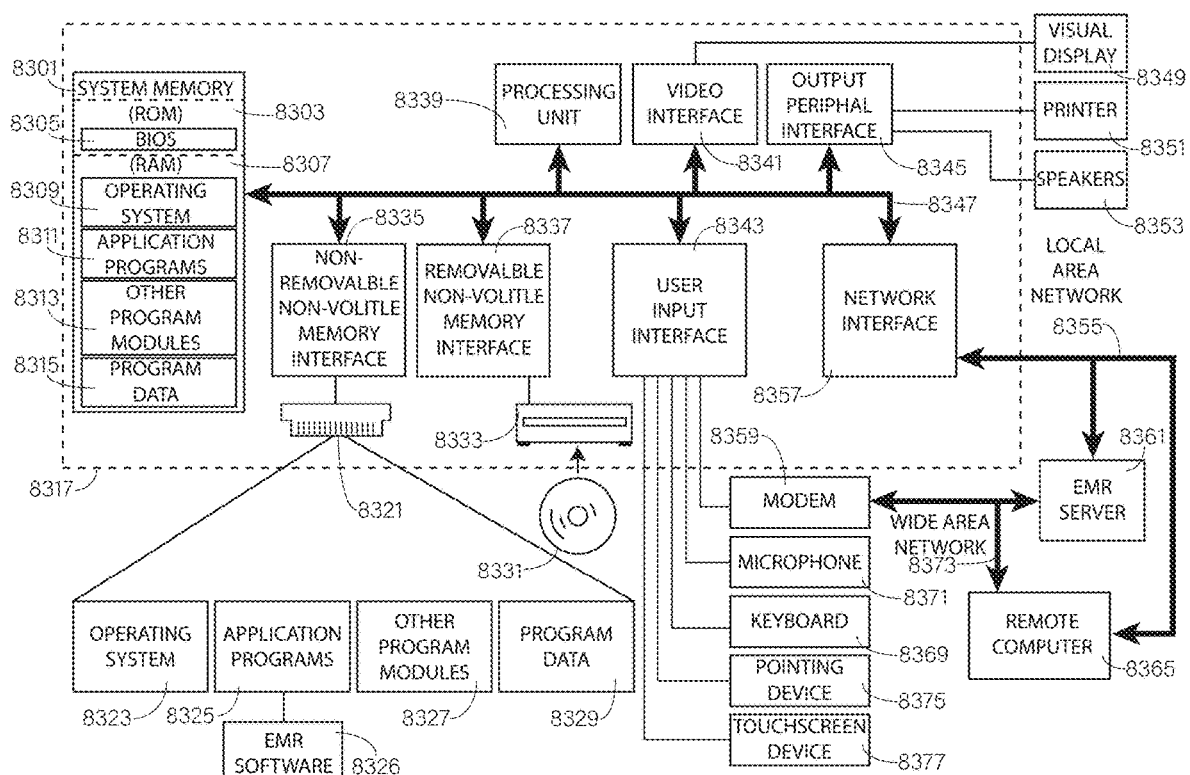
FIG. 33 shows a block diagram of one example of a computing environment.

FIG. 33 is one embodiment of a computing environment in which system 75, or parts of it, (for example) can be deployed. With reference to FIG. 33, an exemplary system for implementing some embodiments includes a general-purpose computing device in the form of a computer 8317. Components of computer 8317 may include, but are not limited to, a processing unit 8339 (which can comprise processor 42), a system memory 8301, and a system bus 8347 that couples various system components including the system memory to the processing unit 8339. The system bus 8347 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described with respect to FIG. 1 can be deployed in corresponding portions of FIG. 33.

Computer 8317 typically includes a variety of computer readable media. Computer readable media can be any available media that can be accessed by computer 8317 (e.g., for storing and retrieving one or more document criterion) and includes both volatile and nonvolatile media, removable and non-removable media. By way of example, and not limitation, computer readable media may include hardware storage media including both volatile and nonvolatile, removable and non-removable media implemented in any method or technology for storage of information such as computer readable instructions, data structures, program modules or other data.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer 8317. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a web site, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

The system memory 8301 includes computer storage media in the form of volatile and/or nonvolatile memory such as read only memory (ROM) 8303 and random-access memory (RAM) 8307. A basic input/output system 8305 (BIOS), containing the basic routines that help to transfer information between elements within computer 8317, such as during start-up, is typically stored in ROM 8303. RAM 8307 typically contains data and/or program modules that are immediately accessible to and/or presently being operated on by processing unit 8339. By way of example, and not limitation, FIG. 33 illustrates operating system 8309, application programs 8311, other program modules 8313, and program data 8315.

The system memory 8301 includes computer storage media in the form of volatile and/or nonvolatile memory such as read only memory (ROM) 8303 and random-access memory (RAM) 8307. A basic input/output system 8305 (BIOS), containing the basic routines that help to transfer information between elements within computer 8317, such as during start-up, is typically stored in ROM 8303. RAM 8307 typically contains data and/or program modules that are immediately accessible to and/or presently being operated on by processing unit 8339. By way of example, and not limitation, FIG. 33 illustrates operating system 8309, application programs 8311, other program modules 8313, and program data 8315.

The computer 8317 may also include other removable/non-removable volatile/nonvolatile computer storage media. By way of example only, FIG. 33 illustrates a solid-state RAM drive 8321 that reads from or writes to non-removable, nonvolatile magnetic media, and an optical disk drive 8333 that reads from or writes to a removable, nonvolatile optical disk 8331 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, hard drive, solid state ROM, and the like. The solid-state RAM drive (SSD) 8321 is typically connected to the system bus 8347 through a non-removable memory interface such as interface 8335, and optical disk drive 8333 are typically connected to the system bus 8347 by a removable memory interface, such as interface 8337.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The drives and their associated computer storage media discussed above and illustrated in FIG. 33, provide storage of computer readable instructions, data structures, program modules and other data for the computer 8317. In FIG. 33, for example, solid state RAM drive 8321 is illustrated as storing operating system 8323, application programs 8325, other program modules 8327, and program data 8329. Note that these components can either be the same as or different from operating system 8309, application programs 8311, other program modules 8313, and program data 8315. Operating system 8323, application programs 8325, other program modules 8327, and program data 8329 are given different numbers here to illustrate that, at a minimum, they are different copies. FIG. 33 illustrates EMR software programs 8326 as residing on local computer 8317 by way of illustration, and not as a limitation.

A display or data entry user may enter commands and information into the computer 8317 through input devices such as a keyboard 8369, a microphone 8371, a pointing device 8375 such as a mouse, trackball or touch pad, and a touchscreen 8377. Other input devices (not shown) may include a joystick, game pad, satellite dish, scanner, or the like. These and other input devices are often connected to the processing unit 8339 through a user input interface 8343 that is coupled to the system bus, but may be connected by other interface and bus structures, such as a parallel port, game port or a universal serial bus (USB). A visual display 8349 or other type of display device is also connected to the system bus 8347 via an interface, such as a video interface 8341. In addition to the monitor, computers may also include other peripheral output devices such as speakers 8353 and printer 8351, which may be connected through an output peripheral interface 8345.

The computer 8317 is operated in a networked environment using logical connections to one or more remote computers, such as a remote computer 8365 and an EMR Server 8361. The remote computer 8365 may be a personal computer, a hand-held device, a server, a router, a network PC, a peer device or other common network node, and typically includes many or all of the elements described above relative to the computer 8317. The EMR server 8361 is an example of the remote computer 8365. The logical connections depicted in FIG. 33 include a local area network (LAN) 8355 and a wide area network (WAN) 8373, but may also include other networks. Such networking environments are commonplace in offices, enterprise-wide computer networks, intranets and the Internet.

When used in a LAN networking environment, the computer 8317 is connected to the LAN 8355 through a network interface or adapter 8357. When used in a WAN networking environment, the computer 8317 typically includes a modem 8359 or other means for establishing communications over the WAN 8373, such as the Internet. The modem 8359, which may be internal or external, may be connected to the system bus 8347 via the user input interface 8343, or other appropriate mechanism. In a networked environment, program modules depicted relative to the computer 8317, or portions thereof, may be stored in the remote memory storage device. By way of example, and not limitation, FIG. 33 illustrates EMR software 8326 as residing on the computer 8317. It will be appreciated that the network connections shown are exemplary and other means of establishing a communications link between the computers may be used.

Figure 34:
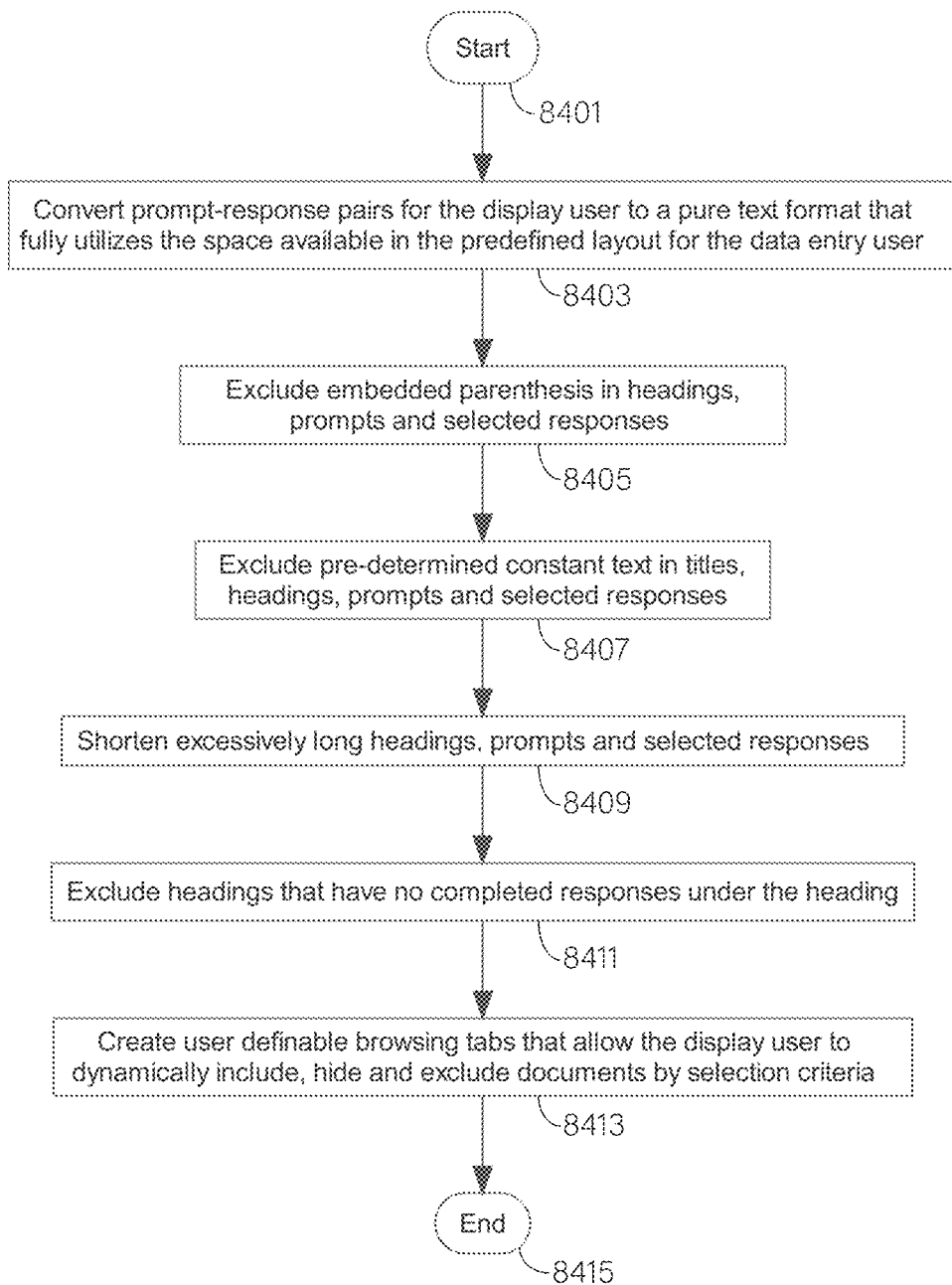
FIG. 34 is a flow diagram depicting the various methods of the present

FIG. 34 is an example overview of some embodiments of the invention. This invention disclosure was written with the idea that most of these techniques are able to stand independently, but more powerful work can be done by combining the techniques. The process starts with step 8401.

Step 8403 is the most basic technique and it involves converting the answer entity to a formatted converted text (e.g., a converted answer value), combining converted answer value with the prompt text using a user defined combining string. It also involves applying user defined attributes to the texts of title, heading, and prompt entities and answer values, then placing the combined prompt text and converted answer value back on the screen within the same horizontal width allowed and defined by the furthest-left and furthest-right boundaries of the prompt-answer pair. This is covered in FIGS. 3-8, 31B, 31G and 31H.

Step 8405 excludes parenthetical comments in texts of heading entities, texts of prompt entities and converted values of selected answer entities. The selected answers eligible for this technique are any other than those typed by the data entry user and those which are computed answers. This is covered in FIGS. 9-11, 31B, 31D and 31G.

Step 8407 excludes certain constant text that is predetermined to never be useful to the display user, such as a prefix "OBSOLETE:" to mark in certain titles, texts of heading entities, texts of prompt entities and converted values of selected answer entities. This is covered in step 904 of FIG. 11 and FIG. 31G.

Step 8409 shortens excessively long text of heading entities, prompt entities and selected answer entities. The selected answers eligible for this technique are any other than those typed by the data entry user and those which are computed answers. This is covered in FIGS. 12-18, 31B, 31D and 31G.

Step 8411 excludes unanswered prompt and various heading entities that are no longer necessary based on which answers the data entry user did not complete, and which heading entities are classified as repeat heading series entities or terminal heading entities. The specific heading entities include those where there is no answered prompt entities between the heading entity of interest entity and the first occurrence of (1) a heading entity of the same or substitute classification, (2) a next top repeat heading entity, or (3) the next end of document marker. Further, the use of alternate text for repeat heading series entities can decrease the vertical height of any heading entities which are displayed. This is covered in FIGS. 19-23 and 31G.

Step 8413 separates the documents that make up a client chart into separate user definable tabs so that the information sought by the display user may be easier to find considering that documents are typically not presented all on a single tab. Configuring the tabs is covered in FIGS. 25A-25H. Browsing the tabs is covered in FIGS. 24, and 26-31A.

Step 8415 allows the display user to create custom subsets of headings and prompts from a document (e.g., data form) by allowing the user to pick individual heading and prompt entities to include or exclude. Then every time that document is displayed on the current tab, only the portion of the document specified will display (and then only those portions that meet other criteria will display, e.g., unanswered prompts will not display if the tab is set to hide unanswered prompts). Statically hiding sub-leaves is further covered in FIGS. 27A-C and 29E.

The process ends with step 8417.

It is contemplated that any of the methods of the present disclosure may be applied to any suitable collection of documents (i.e., a "document group"). This may include, for example, the documents contained in an EMR or some other database of documents, including subsects of documents (i.e., contained in the EMR or database) such as those grouped by a particular topic.

What is claimed is:

1. A tangible, non-transitory, computer readable medium comprising program instructions that causes a computer to execute a method of utilizing a document group stored in a data store to generate an output document that is formatted for a peripheral output device;

wherein each document of the document group comprises at least one of:
  a heading; and
  a prompt field and a corresponding answer field, the prompt field and the corresponding answer field defining a set theory union;
wherein the answer field of each union comprises an answer status that is either unanswered if the answer field is empty or answered if the answer field is not empty;
wherein the answer field of each union comprises at least one of:
  data entry user-supplied text that constitutes an answer; and
  a selectable answer that has been selected by a data entry user, wherein the selectable answer comprises a text label and a corresponding means for receiving a user selection;
wherein each union defines a left boundary, a right boundary, and a width equal to the amount of horizontal space between the left boundary and the right boundary;
wherein the width of each union is constant relative to the window width;
wherein the data store comprises a specification that comprises column position values from which the width of each union may be calculated;
the method comprising:
  generating an output document that comprises a plurality of horizontal text lines;
  reproducing the prompt field of a union to yield a reproduced prompt;
  converting the answer field of the same union into pure text to yield a converted answer;

creating a prompt-answer pair by combining the reproduced prompt and the converted answer into a single text string;
including the prompt-answer pair in a text line of the output document;
copying a heading from a document onto the output document;
sending the output document to the peripheral output device;
calculating the width of the union from which the prompt-answer pair was created; and
paragraph-formatting the prompt-answer pair so that it is not wider than the calculated union width, the paragraph-formatting being performed by moving at least a portion of the pure text of the converted answer to adjacent text lines on the output document.

2. The computer-readable medium of claim 1, wherein:
the document group comprises a subset of documents, the subset of documents comprising a first document and a second document;
the computer readable medium further comprises an access history data set that comprises user-view indications related to the first and second documents;
the access history data set comprises one or more user-view indications indicating that the entire first document has been displayed;
the access history data set is devoid of any user-view indications indicating that the second document, or any parts thereof, has been displayed;
the method further comprises:
concatenating the documents of the subset of documents, wherein the concatenating excludes the first document and includes the second document; and
including the concatenated documents in the output.

3. The computer-readable medium of claim 1, wherein:
the document group comprises a subset of documents, the subset of documents comprising a first document and a second document;
the computer readable medium further comprises an access history data set that comprises user-view indications related to the first and second documents;
the access history data set comprises one or more user-view indications indicating that the entire first document has been displayed;
the access history data set comprises a user-view indication indicating that a part of the second document has been displayed;
the access history data set is devoid of any user-view indications indicating that the entire second document has been displayed;
the method further comprises:
concatenating the documents of the subset of documents, wherein the concatenating excludes the first document and includes the second document; and
including the concatenated documents in the output.

4. The computer-readable medium of claim 1, wherein the method further comprises:
determining the total height of the prompt-answer pair as measured by the total number of text lines that it occupies;
inserting a carriage return between the reproduced prompt and the converted answer;
determining the total height of the prompt-answer pair with the carriage return; and
removing the carriage return if the total height of the prompt-answer pair is greater with the carriage return than it is without it.

5. The computer-readable medium of claim 1, wherein:
a document of the document group comprises a plurality of elements arranged in a sequential order on the document;
the first element of the sequential order comprises a start of document marker and the last element of the sequential order comprises an end of document marker;
the plurality of elements further comprising a plurality of headings and a plurality of prompt-answer pairs in-between the start of document marker and the end of document marker in the sequential order; and
the method further comprises:
selecting a heading from the plurality of headings;
defining a heading scope for the selected heading, the heading scope comprising all headings and prompt-answer pairs in-between the selected heading and a subsequent element in the sequential order, excluding both the selected heading and the subsequent element, and wherein the subsequent element is another heading or an element comprising the end of document marker; and
excluding an element within the heading scope of the selected heading if: (a) the heading scope of the selected heading only includes unanswered prompt-answer pairs or (b) the heading scope of the selected heading has at least one answered prompt-answer pair.

6. The computer-readable medium of claim 1, wherein:
a document of the document group comprises a plurality of elements arranged in a sequential order on the document;
the first element of the sequential order comprises a start of document marker and the last element of the sequential order comprises an end of document marker;
the plurality of elements further comprising a plurality of headings and a plurality of prompt-answer pairs in-between the element comprising the start of document marker and the element comprising the end of document marker in the sequential order;
the method further comprises:
selecting a heading from the plurality of headings;
defining a heading scope for the selected heading, the heading scope comprising the selected heading plus all headings and prompt-answer pairs in-between the selected heading and a subsequent element in the sequential order, the subsequent element being another heading or the element comprising the end of document marker, wherein the heading scope excludes the subsequent element; and
augmenting the selected heading with a text recapping all elements within the heading scope of the selected heading.

7. The computer-readable medium of claim 6, wherein the text recapping all headings within the heading scope comprises at least one of:
a count of the unanswered prompts under the heading;
a count of the answered prompts under the heading;
a statistic comparing the unanswered prompts under the heading with all prompts under the heading; and
a statistic comparing the answered prompts under the heading with all prompts under the heading.

8. The computer-readable medium of claim 1, wherein a document of the document group comprises a plurality of headings and the method further comprises:
classifying each heading of the plurality of headings as being of a heading type, selecting a replacement heading for the headings of the heading type,
including the replacement heading on the output document.

9. The computer-readable medium of claim 1, wherein:
the peripheral output device is an output screen,
the peripheral output device is configured to display tabs on the output screen;
each document of the first group of documents comprises a selection attribute;
the method further comprises:
    selecting a document criterion;
    storing the document criterion on a non-volatile memory;
    retrieving the document criterion from the non-volatile memory;
    identifying documents from the document groups that have a selection attribute that matches the document criterion;
    including the identified documents in the output; and
    displaying the identified documents on a tab that is displayed on the output screen.

10. The computer-readable medium of claim 1, wherein:
the document group comprises a document that comprises a heading and a union, the answer field of the union comprising an answer that can be converted to text, and wherein the document further includes candidate text that comprises at least one of the heading, the answer of the union converted to text, and the prompt of the union;
the document group comprises a document that comprises text comprising a parenthetical comment defined by an open parenthesis and a corresponding close parenthesis; and
the method further comprises excluding at least a portion of the parenthetical comment if the candidate text comprises data form design text.

11. The computer-readable medium of claim 1, wherein:
the document group comprises a document that comprises a heading and a union, the answer field of the union comprising an answer that can be converted to text, and wherein the document further includes candidate text that comprises at least one of the heading, the answer of the union converted to text, and the prompt of the union;
the method further comprises:
    defining a pre-determined constant text;
    identifying the candidate text from the document comprising said pre-determined constant text; and
    excluding at least a portion of the pre-determined constant text from the candidate text.

12. The computer-readable medium of claim 1, wherein:
the document group comprises a document that comprises a heading and a union, the answer field of the union comprising an answer that can be converted to text;
the document comprises a candidate text that comprises a string of text; and
the method further comprises excluding a plurality of characters from a furthest right portion of said candidate text if the candidate text comprises data form design text.

13. The computer-readable medium of claim 1, wherein:
the document group is stored within an electronic records system;
a document of the document group comprises a selection attribute that defines a root node; and
the document comprises a plurality of sub-leaves that each comprise a sub-leaf selection attribute;
the method further comprises:
    creating a selection criterion that comprises a sub-leaf selection attribute;
    storing the selection criterion on non-volatile memory;
    retrieving the selection criterion from the non-volatile memory;
    selecting sub-leaves from the document by comparing a selection attribute from each sub-leaf against the selection criterion; and
    including the selected sub-leaves on an output document.

14. The computer-readable medium of claim 1, wherein the method further comprises:
selecting an answer status of interest between either answered or unanswered; and
excluding the prompt-answer pair from the output document if the prompt-answer pair comprises an answer status that matches the answer status of interest.

15. A method of utilizing a document group stored in a data store to generate an output document that is formatted for a peripheral output device;
wherein each document of the document group comprises at least one of:
    a heading; and
    a prompt field and a corresponding answer field, the prompt field and the corresponding answer field defining a set theory union;
wherein the answer field of each union comprises an answer status that is either unanswered if the answer field is empty or answered if the answer field is not empty;
wherein the answer field of each union comprises at least one of:
    data entry user-supplied text that constitutes an answer; and
    a selectable answer that has been selected by a data entry user, wherein the selectable answer comprises a text label and a corresponding means for receiving a user selection;
wherein each union defines a left boundary, a right boundary, and a width equal to the amount of horizontal space between the left boundary and the right boundary;
wherein the width of each union is constant relative to the window width;
wherein the data store comprises a specification that comprises column position values from which the width of each union may be calculated;
the method comprising:
    generating an output document that comprises a plurality of horizontal text lines;
    reproducing the prompt field of a union from a document of the plurality of documents to yield a reproduced prompt;
    converting the answer field of the same union into pure text to yield a converted answer;
    creating a prompt-answer pair by combining the reproduced prompt and the converted answer into a single text string;
    including the prompt-answer pair in a text line of the output document;
    copying a heading from a document of the plurality of documents onto the output document;
    sending the output document to the peripheral output device;

calculating the width of the union from which the prompt-answer pair was created; and paragraph-formatting the prompt-answer pair so that it is not wider than the calculated union width, the paragraph-formatting being performed by moving at least a portion of the pure text of the converted answer to adjacent text lines on the output document.

16. The method of claim 15, wherein:

the document group comprises a subsect of documents, the subsect of documents comprising a first document and a second document;

the computer readable medium further comprises an access history data set that comprises user-view indications related to the first and second documents;

the access history data set comprises one or more user-view indications indicating that the entire first document has been displayed;

the access history data set is devoid of any user-view indications indicating that the second document, or any parts thereof, has been displayed;

the method further comprises:

concatenating the documents of the subsect of documents, wherein the concatenating excludes the first document and includes the second document; and including the concatenated documents in the output.

17. The method of claim 15, wherein:

the document group comprises a subsect of documents, the subsect of documents comprising a first document and a second document;

the computer readable medium further comprises an access history data set that comprises user-view indications related to the first and second documents;

the access history data set comprises one or more user-view indications indicating that the entire first document has been displayed;

the access history data set comprises a user-view indication indicating that a part of the second document has been displayed;

the access history data set is devoid of any user-view indications indicating that the entire second document has been displayed;

the method further comprises:

concatenating the documents of the subsect of documents, wherein the concatenating excludes the first document and includes the second document; and including the concatenated documents in the output.

18. The method of claim 15, wherein the method further comprises:

determining the total height of the prompt-answer pair as measured by the total number of text lines that it occupies;

inserting a carriage return between the reproduced prompt and the converted answer;

determining the total height of the prompt-answer pair with the carriage return; and removing the carriage return if the total height of the prompt-answer pair is greater with the carriage return than it is without it.

19. The method of claim 15, wherein:

a document of the document group comprises a plurality of elements arranged in a sequential order on the document;

the first element of the sequential order comprises a start of document marker and the last element of the sequential order comprises an end of document marker;

the plurality of elements further comprising a plurality of headings and a plurality of prompt-answer pairs in-between the start of document marker and the end of document marker in the sequential order; and the method further comprises:

selecting a heading from the plurality of headings;

defining a heading scope for the selected heading, the heading scope comprising all headings and prompt-answer pairs in-between the selected heading and a subsequent element in the sequential order, excluding both the selected heading and the subsequent element, and wherein the subsequent element is another heading or an element comprising the end of document marker; and excluding all the elements within the heading scope of the selected heading if: (a) the heading scope of the selected heading only includes unanswered prompt-answer pairs or (b) the heading scope of the selected heading has at least one answered prompt-answer pair.

20. The method of claim 15, wherein:

a document of the document group comprises a plurality of elements arranged in a sequential order on the document;

the first element of the sequential order comprises a start of document marker and the last element of the sequential order comprises an end of document marker;

the plurality of elements further comprising a plurality of headings and a plurality of prompt-answer pairs in-between the element comprising the start of document marker and the element comprising the end of document marker in the sequential order;

the method further comprises:

selecting a heading from the plurality of headings;

defining a heading scope for the selected heading, the heading scope comprising the selected heading plus all headings and prompt-answer pairs in-between the selected heading and a subsequent element in the sequential order, the subsequent element being another heading or the end of document marker, wherein the heading scope excludes the subsequent element; and augmenting the selected heading with a text recapping all headings within the heading scope of the selected heading.

21. The method of claim 20, wherein the text recapping all headings within the heading scope comprises at least one of:

a count of the unanswered prompts under the heading;

a count of the answered prompts under the heading;

a statistic comparing the unanswered prompts under the heading with all prompts under the heading; and a statistic comparing the answered prompts under the heading with all prompts under the heading.

22. The method of claim 15, wherein a document of the document group comprises a plurality of headings and the method further comprises:

classifying each heading of the plurality of headings as being of a heading type, selecting a replacement heading for the headings of the heading type, including the replacement heading on the output document.

23. The method of claim 15, wherein:

the peripheral output device is an output screen, the peripheral output device is configured to display tabs on the output screen;

each document of the first group of documents comprises a selection attribute;

the method further comprises:

selecting a document criterion;
storing the document criterion on a non-volatile memory;
retrieving the document criterion from the non-volatile memory;
identifying documents from the document groups that have a selection attribute that matches the document criterion;
including the identified documents in the output; and
displaying the identified documents on a tab that is displayed on the output screen.

24. The method of claim 15, wherein:
the first group of documents comprises a document that comprises a heading and a union, the answer field of the union comprising an answer that can be converted to text, and wherein the document further includes candidate text that comprises at least one of the heading, the answer of the union converted to text, and the prompt of the union;
the document group comprises a document that comprises text comprising a parenthetical comment defined by an open parenthesis and a corresponding close parenthesis; and
the method further comprises excluding at least a portion of the parenthetical comment if the candidate text comprises data form design text.

25. The method of claim 15, wherein
the first group of documents comprises a document that comprises a heading and a union, the answer field of the union comprising an answer that can be converted to text, and wherein the document further includes candidate text that comprises at least one of the heading, the answer of the union converted to text, and the prompt of the union;
the method further comprises:
defining a pre-determined constant text;
identifying the candidate text from the document comprising said pre-determined constant text; and
excluding at least a portion of the pre-determined constant text from the candidate text.

26. The method of claim 15, wherein:
the first group of documents comprises a document that comprises a heading and a union, the answer field of the union comprising an answer that can be converted to text,
the document comprises a candidate text that comprises a string of text, and
the method further comprises excluding a plurality of characters from a furthest right portion of said candidate text if the candidate text comprises data form design text.

27. The method of claim 15, wherein:
the document group is stored within an electronic records system;
a document of the document group comprises a selection attribute that defines a root node; and
the document comprises a plurality of sub-leaves that each comprise a sub-leaf selection attribute;
the method further comprises:
creating a selection criterion that comprises a sub-leaf selection attribute;
storing the selection criterion on non-volatile memory;
retrieving the selection criterion from the non-volatile memory;
selecting sub-leaves from the document by comparing a selection attribute from each sub-leaf against the selection criterion; and
including the selected sub-leaves on an output document.

* * * * *